US011475981B2

(12) United States Patent
Tell et al.

(10) Patent No.: US 11,475,981 B2
(45) Date of Patent: Oct. 18, 2022

(54) METHODS AND SYSTEMS FOR DYNAMIC VARIANT THRESHOLDING IN A LIQUID BIOPSY ASSAY

(71) Applicant: Tempus Labs, Inc., Chicago, IL (US)

(72) Inventors: Robert Tell, Chicago, IL (US); Wei Zhu, Naperville, IL (US); Justin David Finkle, Chicago, IL (US); Christine Lo, Chicago, IL (US); Terri M. Driessen, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/179,086

(22) Filed: Feb. 18, 2021

(65) Prior Publication Data

US 2021/0343372 A1    Nov. 4, 2021

Related U.S. Application Data

(60) Provisional application No. 63/041,293, filed on Jun. 19, 2020, provisional application No. 62/978,130, filed on Feb. 18, 2020.

(51) Int. Cl.
*G16B 30/10* (2019.01)
*G16B 20/40* (2019.01)
*G16B 20/20* (2019.01)

(52) U.S. Cl.
CPC .............. *G16B 30/10* (2019.02); *G16B 20/20* (2019.02); *G16B 20/40* (2019.02)

(58) Field of Classification Search
None
See application file for complete search history.

(56) References Cited

U.S. PATENT DOCUMENTS

| | | |
|---|---|---|
| 6,753,137 B2 | 6/2004 | Lo et al. |
| 7,163,789 B2 | 1/2007 | Chen et al. |
| 7,294,468 B2 | 11/2007 | Bell |
| 7,700,286 B2 | 4/2010 | Stroun et al. |
| 7,727,720 B2 | 6/2010 | Shallan |
| 7,888,017 B2 | 2/2011 | Quake et al. |
| 7,899,626 B2 | 3/2011 | Kruglyak et al. |
| 8,076,063 B2 | 12/2011 | Fan et al. |
| 8,105,769 B2 | 1/2012 | Bell |
| 8,110,358 B2 | 2/2012 | Liew |
| 8,150,626 B2 | 4/2012 | Fan et al. |
| 8,168,385 B2 | 5/2012 | Brenner |
| 8,216,784 B2 | 7/2012 | Taylor et al. |
| 8,318,433 B2 | 11/2012 | Brenner |
| 8,383,338 B2 | 2/2013 | Kitzman et al. |
| 8,481,292 B2 | 7/2013 | Casbon et al. |
| 8,486,626 B2 | 7/2013 | Umansky et al. |
| 8,541,207 B2 | 9/2013 | Kester |
| 8,566,039 B2 | 10/2013 | Li |
| RE44,596 E | 11/2013 | Stroun et al. |
| 8,583,380 B2 | 11/2013 | Stephan et al. |
| 8,597,892 B2 | 12/2013 | Shelton et al. |
| 8,637,254 B2 | 1/2014 | Taylor et al. |
| 8,685,889 B2 | 4/2014 | Eijk et al. |
| 8,688,388 B2 | 4/2014 | Dzakula et al. |
| 8,712,697 B2 | 4/2014 | Struble et al. |
| 8,728,764 B2 | 5/2014 | Boutell |
| 8,735,074 B2 | 5/2014 | Mambo et al. |
| 8,741,811 B2 | 6/2014 | Lo et al. |
| 8,785,353 B2 | 7/2014 | Eijk et al. |
| 8,835,358 B2 | 9/2014 | Fodor et al. |
| 8,865,410 B2 | 10/2014 | Shendure et al. |
| 8,880,350 B2 | 11/2014 | Von Hoff et al. |
| 8,956,817 B2 | 2/2015 | Goel et al. |
| 9,023,768 B2 | 5/2015 | Eijk et al. |
| 9,080,210 B2 | 7/2015 | Eijk et al. |
| 9,085,798 B2 | 7/2015 | Chee |
| 9,109,256 B2 | 8/2015 | Shuber |
| 9,121,069 B2 | 9/2015 | Lo et al. |
| 9,218,449 B2 | 12/2015 | Lo et al. |
| 9,260,745 B2 | 2/2016 | Rava et al. |
| 9,260,753 B2 | 2/2016 | Xie et al. |
| 9,315,857 B2 | 4/2016 | Fu et al. |
| 9,328,383 B2 | 5/2016 | Eijk et al. |
| 9,334,536 B2 | 5/2016 | Eijk et al. |
| 9,340,830 B2 | 5/2016 | Lipson et al. |
| 9,361,426 B2 | 6/2016 | Akmaev et al. |

(Continued)

FOREIGN PATENT DOCUMENTS

| | | |
|---|---|---|
| EP | 1504120 B1 | 8/2009 |
| EP | 2898100 B1 | 11/2017 |
| EP | 2825675 B1 | 12/2017 |
| EP | 3218523 B1 | 2/2020 |
| EP | 2971168 A1 | 5/2021 |
| WO | WO 2013/060762 A1 | 5/2013 |
| WO | WO 2013/109981 A1 | 7/2013 |
| WO | WO 2016/028316 A1 | 2/2016 |
| WO | WO 2016/071369 A1 | 5/2016 |

(Continued)

OTHER PUBLICATIONS

Jennigs et al. Guidelines for Validation of Next-Generation Sequencing-Based Oncology Panels, J Mol Diagn. May 2017 ; 19(3): 341-365. doi:10.1016/j.jmoldx.2017.01.011.*

(Continued)

*Primary Examiner* — Joseph Woitach
(74) *Attorney, Agent, or Firm* — Morgan, Lewis & Bockius LLP

(57) ABSTRACT

Methods, systems, and software are provided for validating a somatic sequence variant in a subject having a cancer condition. Sequence reads are obtained from sequencing cell-free DNA fragments in a liquid biopsy sample of the subject. Sequence reads are aligned to a reference sequence. A variant allele fragment count and locus fragment count are identified for a candidate variant that maps to a locus in the reference sequence. The variant allele fragment count is compared against a dynamic variant count threshold for the locus. The threshold is based on a pre-test odds of a positive variant call for the locus, based on the prevalence of variants in a genomic region including the locus in a cohort of subjects having the cancer condition. The somatic sequence variant in the subject is validated, or rejected, when the variant allele fragment count for the candidate variant satisfies, or does not satisfy, the threshold.

29 Claims, 49 Drawing Sheets

(56) References Cited

U.S. PATENT DOCUMENTS

| | | |
|---|---|---|
| 9,404,156 B2 | 8/2016 | Hicks et al. |
| 9,422,598 B2 | 8/2016 | Ye et al. |
| 9,447,459 B2 | 9/2016 | Eijk et al. |
| 9,453,256 B2 | 9/2016 | Eijk et al. |
| 9,463,223 B2 | 10/2016 | Genkin et al. |
| 9,476,095 B2 | 10/2016 | Vogelstein et al. |
| 9,487,829 B2 | 11/2016 | Vogelstein et al. |
| 9,493,820 B2 | 11/2016 | Eijk et al. |
| 9,499,870 B2 | 11/2016 | Babiarz et al. |
| 9,598,731 B2 | 3/2017 | Talasaz |
| 9,646,134 B2 | 5/2017 | Sanborn |
| 9,670,530 B2 | 6/2017 | Kostem et al. |
| 9,689,041 B2 | 6/2017 | Ye et al. |
| 9,702,004 B2 | 7/2017 | Eijk et al. |
| 9,721,062 B2 | 8/2017 | Sanborn |
| 9,732,390 B2 | 8/2017 | Lo et al. |
| 9,745,627 B2 | 8/2017 | Van Eijk |
| 9,752,188 B2 | 9/2017 | Schmitt et al. |
| 9,758,814 B2 | 9/2017 | Fehr et al. |
| 9,771,621 B2 | 9/2017 | Ye et al. |
| 9,777,324 B2 | 10/2017 | Eijk et al. |
| 9,783,847 B2 | 10/2017 | Chee |
| 9,834,822 B2 | 12/2017 | Talasaz |
| 9,840,743 B2 | 12/2017 | Talasaz |
| 9,850,523 B1 | 12/2017 | Chudova et al. |
| 9,862,995 B2 | 1/2018 | Patel |
| 9,879,312 B2 | 1/2018 | Steemers et al. |
| 9,890,425 B2 | 2/2018 | Domanus et al. |
| 9,892,230 B2 | 2/2018 | Lo et al. |
| 9,896,721 B2 | 2/2018 | Eijk et al. |
| 9,898,576 B2 | 2/2018 | Eijk et al. |
| 9,898,577 B2 | 2/2018 | Eijk et al. |
| 9,902,992 B2 | 2/2018 | Talasaz et al. |
| 9,920,366 B2 | 3/2018 | Eltoukhy et al. |
| 9,957,572 B2 | 5/2018 | Vogelstein et al. |
| 10,000,800 B2 | 6/2018 | Chee |
| 10,023,907 B2 | 7/2018 | Eijk et al. |
| 10,041,127 B2 | 8/2018 | Talasaz |
| 10,095,832 B2 | 10/2018 | Eijk et al. |
| 10,106,850 B2 | 10/2018 | Eijk et al. |
| 10,235,494 B2 | 3/2019 | Eijk et al. |
| 10,240,209 B2 | 3/2019 | Lo et al. |
| 10,266,883 B2 | 4/2019 | Chee |
| 10,266,884 B2 | 4/2019 | Chee |
| 10,287,631 B2 | 5/2019 | Salk et al. |
| 2006/0094016 A1 | 5/2006 | Gormley |
| 2013/0116127 A1 | 5/2013 | Schuetz et al. |
| 2014/0024537 A1 | 1/2014 | Rigatti |
| 2014/0045181 A1 | 2/2014 | Lo |
| 2014/0100121 A1 | 4/2014 | Lo |
| 2014/0227712 A1 | 8/2014 | Horlitz et al. |
| 2014/0274740 A1 | 9/2014 | Srinivasan et al. |
| 2014/0274752 A1 | 9/2014 | Blume et al. |
| 2015/0011403 A1 | 1/2015 | Lo |
| 2015/0038335 A1 | 2/2015 | Skog et al. |
| 2015/0159212 A1 | 6/2015 | Pantoja et al. |
| 2015/0197798 A1 | 7/2015 | Xu |
| 2015/0211070 A1 | 7/2015 | Seligson et al. |
| 2015/0302143 A1 | 10/2015 | Ma et al. |
| 2015/0344970 A1 | 12/2015 | Vogelstein et al. |
| 2015/0368708 A1 | 12/2015 | Talasaz |
| 2016/0002739 A1 | 1/2016 | Schuetz et al. |
| 2016/0017396 A1 | 1/2016 | Cann et al. |
| 2016/0017419 A1 | 1/2016 | Chiu et al. |
| 2016/0032396 A1 | 2/2016 | Alizadeh et al. |
| 2016/0040229 A1 | 2/2016 | Talasaz et al. |
| 2016/0046979 A1 | 2/2016 | Leamon et al. |
| 2016/0046986 A1 | 2/2016 | Eltoukhy et al. |
| 2016/0144378 A1 | 5/2016 | Huang |
| 2016/0168643 A1 | 6/2016 | Ahlquist |
| 2016/0201142 A1 | 7/2016 | Lo |
| 2016/0210403 A1 | 7/2016 | Zhang et al. |
| 2016/0222463 A1 | 8/2016 | Baker |
| 2016/0232290 A1 | 8/2016 | Rava |
| 2016/0237505 A1 | 8/2016 | Nonn et al. |
| 2016/0239604 A1 | 8/2016 | Chudova et al. |
| 2016/0265027 A1 | 9/2016 | Sanches-Kuiper et al. |
| 2016/0275239 A1 | 9/2016 | Devogelaere et al. |
| 2016/0281154 A1 | 9/2016 | So et al. |
| 2016/0292356 A1 | 10/2016 | Kim et al. |
| 2016/0304936 A1 | 10/2016 | Ji |
| 2016/0319345 A1 | 11/2016 | Gnerre et al. |
| 2016/0333417 A1 | 11/2016 | Talasaz |
| 2016/0333420 A1 | 11/2016 | Stern et al. |
| 2016/0340740 A1 | 11/2016 | Zhang |
| 2017/0016054 A1 | 1/2017 | Southern et al. |
| 2017/0024513 A1 | 1/2017 | Lo et al. |
| 2017/0061072 A1 | 3/2017 | Kermani et al. |
| 2017/0073774 A1 | 3/2017 | Lo |
| 2017/0101681 A1 | 4/2017 | Jacob et al. |
| 2017/0107576 A1 | 4/2017 | Babiarz et al. |
| 2017/0145509 A1 | 5/2017 | Koh et al. |
| 2017/0145516 A1 | 5/2017 | Kopetz et al. |
| 2017/0175205 A1 | 6/2017 | Toung et al. |
| 2017/0211143 A1 | 7/2017 | Shendure et al. |
| 2017/0211153 A1 | 7/2017 | Kohli et al. |
| 2017/0218459 A1 | 8/2017 | Talasaz et al. |
| 2017/0226590 A1 | 8/2017 | Mortimer |
| 2017/0240972 A1 | 8/2017 | Mokhtari et al. |
| 2017/0240973 A1 | 8/2017 | Eltoukhy et al. |
| 2017/0249421 A1 | 8/2017 | Eberle |
| 2017/0260590 A1 | 9/2017 | Eltoukhy et al. |
| 2017/0327869 A1 | 11/2017 | Schutz |
| 2017/0342477 A1 | 11/2017 | Jensen et al. |
| 2017/0342500 A1 | 11/2017 | Marquard et al. |
| 2017/0356053 A1 | 12/2017 | Otto |
| 2017/0362638 A1 | 12/2017 | Chudova et al. |
| 2018/0010176 A1 | 1/2018 | Patel |
| 2018/0023125 A1 | 1/2018 | Talasaz et al. |
| 2018/0032666 A1 | 2/2018 | Sun et al. |
| 2018/0032671 A1 | 2/2018 | Mazloom et al. |
| 2018/0045727 A1 | 2/2018 | Spetzler et al. |
| 2018/0082012 A1 | 3/2018 | Jiang et al. |
| 2018/0087114 A1 | 3/2018 | Melnikova et al. |
| 2018/0119230 A1 | 5/2018 | Velculescu et al. |
| 2018/0120291 A1 | 5/2018 | Eltoukhy et al. |
| 2018/0148777 A1 | 5/2018 | Kirkizlar et al. |
| 2018/0149660 A1 | 5/2018 | Anekella |
| 2018/0203974 A1 | 7/2018 | Venn |
| 2018/0211002 A1 | 7/2018 | Devogelaere et al. |
| 2018/0237863 A1 | 8/2018 | Namsaraev et al. |
| 2018/0251848 A1 | 9/2018 | Alizadeh |
| 2018/0363053 A1 | 12/2018 | Schmitt et al. |
| 2019/0005194 A1 | 1/2019 | Eltoukhy et al. |
| 2019/0040382 A1 | 2/2019 | Steemers et al. |
| 2019/0078164 A1 | 3/2019 | Talasaz |
| 2019/0078232 A1 | 3/2019 | Ha et al. |
| 2019/0085406 A1 | 3/2019 | Mortimer |
| 2019/0169685 A1 | 6/2019 | Georgiadis et al. |
| 2019/0172550 A1 | 6/2019 | Ghosh |
| 2019/0218625 A1 | 7/2019 | Lo et al. |
| 2020/0087710 A1 | 3/2020 | McCullough |
| 2020/0299760 A1 | 9/2020 | Song et al. |
| 2021/0102262 A1 | 4/2021 | Valouev et al. |

FOREIGN PATENT DOCUMENTS

| | | |
|---|---|---|
| WO | WO 2017/020024 A2 | 2/2017 |
| WO | WO 2017/027391 A2 | 2/2017 |
| WO | WO 2017/062867 A2 | 4/2017 |
| WO | WO 2017/181079 A2 | 10/2017 |
| WO | WO 2017/181111 A2 | 10/2017 |
| WO | WO 2017/181134 A2 | 10/2017 |
| WO | WO 2017/181146 A1 | 10/2017 |
| WO | WO 2017/181202 A2 | 10/2017 |
| WO | WO 2017/194668 A1 | 11/2017 |
| WO | WO 2017/201102 A1 | 11/2017 |
| WO | WO 2017/205823 A1 | 11/2017 |
| WO | WO 2017/205827 A1 | 11/2017 |
| WO | WO 2017/212428 A1 | 12/2017 |
| WO | WO 2018/005983 A1 | 1/2018 |
| WO | WO 2018/039463 A1 | 3/2018 |

(56) References Cited

FOREIGN PATENT DOCUMENTS

| WO | WO 2018/081130 A1 | 5/2018 |
|---|---|---|
| WO | WO 2019/079624 A2 | 4/2019 |

OTHER PUBLICATIONS

Kaseniit et al. "Strategies to minimize false positives and interpret novel microdeletions based on maternal copy-number variants in 87,000 noninvasive prenatal screens", BMC Medical Genomics, vol. 11, Article 90 (2018), pp. 1-13.
Cancer Genome Analysis, Home | www.broadinstitute.org/cancer/CGA, https://software.broadinstitute.org/cancer/cga/, Sep. 14, 2020, p. 1.
Scikit-learn: machine learning in Python—scikit-learn 0.23.2 documentation, https://scikit-learn.org/stable/, pp. 1-2.
What is Firehose? Firehose | www.broadinstitute.org/cancer/CGA, https://software.broadinstitute.org/cancer/cga/Firehose, Sep. 14, 2020, p. 1.
Abbosh, Christopher et al, "Early stage NSCLC—challenges to implementing ctDNA-based screening and MRD detection," Perspectives, Nature Reviews | Clinical Oncology, vol. 15, Sep. 2018, pp. 577-588.
Adalsteinsson, Viktor A. et al. "Scalable whole-exome sequencing of cell-free DNA reveals high concordance with metastatic tumors," nature communications, 8:1324, pp. 1-13.
Aggarwal, Charu et al. "Clinical Implications of Plasma-Based Genotyping With the Delivery of Personalized Therapy in Metastatic Non-Small Cell Lung Cancer," JAMA Oncology | Original Investigation, Oct. 11, 2018, 5(2), pp. 173-180.
Artyomenko, A. et al., "Microsatellite instability detection by targeted sequencing of cell-free DNA," Abstract, Annals of Oncology, vol. 29, Supplement 8, Oct. 2019, p. 1.
Ashford, Molika, "Lexent Bio Details Liquid Biopsy Monitoring Method, Expects Clinical Launch Next Year", GenomeWeb, Aug. 16, 2019, pp. 1-4.
Beaubier, Nike, et al. "Integrated genomic profiling expands clinical options for patients with cancer", Nature Biotechnology, 2019, 37, pp. 1351-1360.
Bettegowda, Chetan et al. "Detection of Circulating Tumor DNA in Early- and Late-Stage Human Malignancies," www.ScienceTranslationalMedicine.org, Feb. 19, 2014, vol. 6 Issue 224, pp. 1-13.
Chabon, Jacob J., et al. "Integrating genomic features for non-invasive early lung cancer detection", Nature, vol. 580, Apr. 9, 2020, pp. 245-278.
Chen, Ming et al., "Next-generation sequencing in liquid biopsy: cancer screening and early Detection," Human Genomics, 2019, pp. 1-10.
Cheng, Fiona Tsui-Fen, et al. "Liquid Biopsy Detects Relapse Five Months Earlier than Regular Clinical Follow-Up and Guides Targeted Treatment in Breast Cancer", Hindawi, Case Reports in Oncological Medicine, vol. 2019, pp. 4.
Cheng, Ju et al., "Clinical Validation of a Cell-Free DNA Gene Panel," The Journal of Molecular Diagnostics, vol. 21, No. 4, Jul. 2019, pp. 632-645.
Chera, Bhishamjit S. et al., "Plasma Circulating Tumor HPV DNA for the Surveillance of Cancer Recurrence in HPV-Associated Oropharyngeal Cancer," Journal of Clinical Oncology, 2020, vol. 38, Issue 10, pp. 1050-1060.
Chiang, Colby et al., "SpeedSeq: ultra-fast personal genome analysis and interpretation," Nature Methods, vol. 12, No. 10, Oct. 2015, pp. 966-970.
Choudhury, Atish D. et al., "Tumor fraction in cell-free DNA as a biomarker in prostate cancer," Clinical Medicine, 2018, pp. 1-13.
Christensen, Emil et al. "Early Detection of Metastatic Relapse and Monitoring of Therapeutic Efficacy by Ultra-Deep Sequencing of Plasma Cell-Free DNA in Patients With Urothelial Bladder Carcinoma," Journal of Clinical Oncology, vol. 37, Issue 18, pp. 1547-1558.
Clark, Travis A. et al., "Analytical Validation of a Hybrid Capture-Based Next-Generation Sequencing Clinical Assay for Genomic Profiling of Cell-Free Circulating Tumor DNA," The Journal of Molecular Diagnostics, vol. 20, No. 5, Sep. 2018, pp. 686-702.
Colleoni, Marco et al. "Annual Hazard Rates of Recurrence for Breast Cancer During 24 Years of Follow-Up: Results From the International Breast Cancer Study Group Trials I to V," Journal of Clinical Oncology, vol. 34, No. 9, Mar. 20, 2016, pp. 927-935.
Coombes, Raoul Charles et al., "Personalized Detection of Circulating Tumor DNA Antedates Breast Cancer Metastatic Recurrence," Clinical Cancer Research, 25(14), Jul. 15, 2019, pp. 4255-4263.
Cristiano, Stephen et al., "Genome-wide cell-free DNA fragmentation in patients with cancer," Nature, Jun. 2019, pp. 1-35.
Davis, Andrew A. et al., "Early detection of molecular disease progression by whole-genome circulating tumor DNA in advanced solid tumors," medRxiv reprint, 2019, pp. 1-20.
Deng, Shibing et al., "TNER: a novel background error suppression method for mutation detection in circulating tumor DNA," BMC Bioinformatics, Methodology Article, 2018, pp. 1-7.
Georgiadis, Andrew et al., "Noninvasive Detection of Microsatellite Instability and High Tumor Mutation Burden in Cancer Patients Treated with PD-1 Blockade," Clinical Cancer Research, 25(23), Dec. 1, 2019, pp. 7024-7035.
Han, Andrew P. "Personal Genome Diagnostics Alleges Patent Fraud by Guardant Health in Countersuit," GenomeWeb, May 16, 2019, pp. 1-3.
Hanibuchi, Masaki et al., "Development, validation, and comparison of gene analysis methods for detecting EGFR mutation from non-small cell lung cancer patients-derived circulating free DNA," Oncotarget, 2019, vol. 10, No. 38, pp. 3654-3666.
Haque, Imran, "2019 Early Detection Mid-YearRoundup, Part II: Technology," ihaque.org, Jul. 8, 2019, pp. 1-13.
Van Heiden, Erik J. "RAS and BRAF mutations in cell-free DNA are predictive for outcome of cetuximab monotherapy in patients with tissue-tested RAS wild-type advanced colorectal cancer", Molecular Oncology, 13, 2019, pp. 2361-2374.
Hennigan, Thomas S., et al. "Low Abundance of Circulating Tumor DNA in Localized Prostate Cancer", American Society of Clinical Oncology, 2019, pp. 1-13.
Houseman, Eugene Andres et al. "DNA methylation arrays as surrogate measures of cell mixture distribution," BMC Bioinformatics, 2012, 13, pp. 1-16.
Hu, Yuebi et al., "False-Positive Plasma Genotyping Due to Clonal Hematopoiesis," Clinical Cancer Research, 24(18), Sep. 15, 2018, pp. 4437-4444.
Hubbell, Earl et al., "Cell-free DNA (cfDNA) Fragment Length Patterns of Tumor- and Blood-derived Variants in Participants With and Without Cancer," Abstract 3372, Mar. 29-Apr. 3, 2019 AACR Meeting, p. 1.
Hyun, Myung Han et al., "Clinical implications of circulating cell-free DNA quantification and metabolic tumor burden in advanced non-small cell lung cancer," Elsevier, Lung Cancer, 134, 2019, pp. 158-166.
Isaksson, Sofi et al., "Pre-operative plasma cell-free circulating tumor DNA and serum protein tumor markers as predictors of lung adenocarcinoma recurrence," Acta Oncologica, vol. 58, No. 8, pp. 1079-1086.
Jensen, Taylor J. et al., "Genome-Wide Sequencing of Cell-Free DNA Identifies Copy-Number Alterations That Can Be Used for Monitoring Response to Immunotherapy in Cancer Patients," Molecular Cancer Therapeutics, 18,(2), Feb. 2019, pp. 448-459.
Kalia, Sarah S. et al. "Recommendations for reporting of secondary findings in clinical exome and genome sequencing, 2016 update (ACMG SF v2.0): a policy statement of the American College of Medical Genetics and Genomics," Genetics in Medicine, vol. 19, No. 2, Feb. 2017, pp. 249-255.
Kato, Shumei et al., "Revisiting Epidermal Growth Factor Receptor (EGFR) Amplification as a Target for Anti-EGFR Therapy: Analysis of Cell-Free Circulating Tumor DNA in Patients With Advanced Malignancies," American Society of Clinical Oncology, 2019, pp. 1-14.
Keup, Corinna et al., "Targeted deep sequencing revealed variants in cell-free DNA of hormone receptor-positive metastatic breast cancer patients," Cellular and Molecular Life Sciences (2020) 77, pp. 497-509.

(56) References Cited

OTHER PUBLICATIONS

Koch, Alexander et al., "Analysis of DNA methylation in cancer: location revisited," Perspectives, Nature Reviews, Clinical Oncology, vol. 15, Jul. 2018, pp. 459-466.
Kuderer, Nicole M. et al., "Comparison of 2 Commercially Available Next-Generation Sequencing Platforms in Oncology," JAMA Oncology, vol. 3 No. 7, Jul. 2017, pp. 996-998.
Kurtz, David M. et al., "Circulating Tumor DNA Measurements as Early Outcome Predictors in Diffuse Large B-Cell Lymphoma," Journal of Clinical Oncology, vol. 36, No. 28, Oct. 1, 2018, pp. 19.
Lai, Zhongwu et al., "VarDict: a novel and versatile variant caller for next-generation sequencing in cancer research," Nucleic Acids Research, 2016, vol. 44, No. 11, pp. 1-11.
Lapin, Morten et al., "Fragment size and level of cell-free DNA provide prognostic information in patients with advanced pancreatic cancer," Journal of Translational Medicine, 2018, pp. 1-10.
Layer, Ryan M. et al., "LUMPY: a probabilistic framework for structural variant discovery," Genome Biology, 2014, pp. 1-19.
Leal, Alessandro, et al. "White blood cell and cell-free DNA analyses for detection of residual disease in gastric cancer", Nature Communications, (2020) 11:525, pp. 1-11.
Lee, Jeeyun et al., "Detection of ERBB2 (HER2) Gene Amplification Events in Cell-Free DNA and Response to Anti-HER2 Agents in a Large Asian Cancer Patient Cohort," frontiers in Oncology, vol. 9, Article 212, Apr. 2019, pp. 1-10.
Leighl, Natasha B. et al., "Clinical Utility of Comprehensive Cell-free DNA Analysis to Identify Genomic Biomarkers in Patients with Newly Diagnosed Metastatic Non-small Cell Lung Cancer," Clinical Cancer Research, 2019, 25, pp. 4691-4700.
Li, Gerald et al., "Genomic profiling of cell-free circulating tumor DNA in patients with colorectal cancer and its fidelity to the genomics of the tumor biopsy," Journal of Gastrointestinal Oncology, 2019, 10, pp. 831-840.
Li, Heng et al., "Fast and accurate short read alignment with Burrows-Wheeler transform," Bioinformatics, vol. 25, No. 14, 2009, pp. 1754-1760.
Li, Marilyn M. et al., "Standards and Guidelines for the Interpretation and Reporting of Sequence Variants in Cancer," The Journal of Molecular Diagnostics, vol. 19, No. 1, Jan. 2017, pp. 1-20.
Li, Yuanyuan et al., "DNA methylation detection: Bisulfite genomic sequencing analysis," Methods of Molecular Biology, 2011, pp. 1-10.
Liu, M. C., et al. "Sensitive and specific multi-cancer detection and localization using methylation signatures in cell-free DNA", Annals of Oncology, vol. 31, Issue 6, 2020, pp. 745-759.
Maruvka, Yosef E. et al., "Abstract 2677: MSIClass—Identification and classification of microsatellite unstable using cell-free DNA from ultralow-pass sequencing," Cancer Research, 2019, pp. 1-4.
Mayrhofer, Markus et al., "Cell-free DNA profiling of metastatic prostate cancer reveals microsatellite instability, structural rearrangements and clonal hematopoiesis," Genome Medicine, 2018, pp. 1-13.
McEvoy, Ashleigh C. et al., "Monitoring melanoma recurrence with circulating tumor DNA: a proof of concept from three case studies," Oncotarget, 2019, vol. 10, No. 2, pp. 113-122.
Michalak, Ewa M., et al. "The roles of DNA, RNA and histone methylation in ageing and cancer", Methylation in Biology, Nature Reviews, Molecular Cell Biology, vol. 20, Oct. 2019, pp. 573-589.
Moss, Joshua et al., "Comprehensive human cell-type methylation atlas reveals origins of circulating cell-free DNA in health and disease," nature communications, 2018, 9:5068, pp. 1-12.
Mouliere, Florent et al., "Enhanced detection of circulating tumor DNA by fragment size analysis," Sci Transl Med., Nov. 7, 2018, pp. 1-28.
Newman, Aaron M. et al., "Integrated digital error suppression for improved detection of circulating tumor DNA," Nat. Biotechnol. May 2016, pp. 1-35.
Newman, Aaron M. et al., "An ultrasensitive method for quantitating circulating tumor DNA with broad patient coverage," nature medicine, vol. 20, No. 5, May 2014, pp. 548-556.
Odegaard, Justin I. et al., "Validation of a Plasma-Based Comprehensive Cancer Genotyping Assay Utilizing Orthogonal Tissue- and Plasma-Based Methodologies," Clinical Cancer Research, 2018, 24, pp. 3539-3549.
Olshen, Adam B. et al., "Circular binary segmentation for the analysis of array-based DNA copy number data," Biostatistics, Oxford University Press, 2004, vol. 5, No. 4, pp. 557-572.
Pailler, Emma, et al. "Acquired Resistance Mutations to ALK Inhibitors Identified by Single Circulating Tumor Cell Sequencing in ALK-Rearranged Non-Small-Cell Lung Cancer", Clinical Cancer Research, 25(22), Nov. 25, 2019, pp. 6671-6682.
Parikh, Aparna R., et al. "Liquid versus tissue biopsy for detecting acquired resistance and tumor heterogeneity in gastrointestinal cancers", Nature Medicine, vol. 25, Sep. 2019, pp. 1415-1421.
Plagnol, Vincent et al., "Analytical validation of a next generation sequencing liquid biopsy assay for high sensitivity broad molecular profiling," PLOS One, Mar. 15, 2018, pp. 1-18.
Qin, Zhen et al., "Cell-free circulating tumor DNA in cancer," Chinese Journal of Cancer, BioMed Central, 2016, pp. 1-9.
Roy, Somak et al., "Standards and Guidelines for Validating Next-Generation Sequencing Bioinformatics Pipelines," The Journal of Molecular Diagnostics, Jan. 2018, vol. 20, No. 1, pp. 1-27.
Savli, Hakan et al., "TP53, EGFR and PIK3CA gene variations observed as prominent biomarkers in breast and lung cancer by plasma cell-free DNA genomic testing," Journal of Biotechnology 300, 2019, pp. 87-93.
Shen, Ronglai et al., "FACETS: allele-specific copy number and clonal heterogeneity analysis tool for high-throughput DNA sequencing," Nucleic Acids Research, 2016, vol. 44, No. 16, pp. 1-9.
Shen, Shu Yi et al., "Sensitive tumour detection and classification using plasma cell-free DNA methylomes," Springer Nature Limited, Nov. 22, 2018, vol. 563, pp. 579-599.
Stover, Daniel G. et al., "Association of Cell-Free DNA Tumor Fraction and Somatic Copy Number Alterations With Survival in Metastatic Triple-Negative Breast Cancer," Journal of Clinical Oncology, vol. 36, No. 6, Feb. 20, 2018, pp. 1-21.
Talevich, Eric et al., "CNVkit: Genome-Wide Copy Number Detection and Visualization from Targeted DNA Sequencing," PLOS Computational Biology, Apr. 21, 2016, pp. 1-18.
Taunk, Neil K. et al., "Immunotherapy and radiation therapy for operable early stage and locally advanced non-small cell lung cancer," Translational Lung Cancer Research, 2017, pp. 178-185.
Tie, Jeanne et al. "Circulating Tumor DNA Analyses as Markers of Recurrence Risk and Benefit of Adjuvant Therapy for Stage III Colon Cancer", JAMA Oncology | Original Investigation, vol. 5, No. 12, Dec. 2019, pp. 1710-1717.
Uramoto, Hidetaka et al., "Recurrence after surgery in patients with NSCLC," Translational Lung Cancer Research, 2014, pp. 242-249.
Van Laar, Ryan et al., "Development and validation of a plasma-based melanoma biomarker suitable for clinical use," British Journal of Cancer, 2018, 118, pp. 857-866.
Versel, Neil, "Illumina Looking to Raise Profile in Genome Informatics," GenomeWeb, Oct. 4, 2018, pp. 1-3.
Voet, Douglas et al. "Firehose: An Analysis Infrastructure," Firehose Broad GDAC, Broad Institute, p. 1.
Wan, Jonathan C.M. et al., "High-sensitivity monitoring of ctDNA by patient-specific sequencing panels and integration of variant reads," bioRxiv preprint doi: https://doi.org/10.1101/759399, Sep. 2019, pp. 1-37.
Wan, Jonathan C.M. et al., "ctDNA monitoring using patient-specific sequencing and integration of variant reads," Science Translational Medicine | Research Article, 12, Jun. 17, 2020, pp. 1-16.
Willis, Jason et al., "Validation of Microsatellite Instability Detection Using a Comprehensive Plasma-Based Genotyping Panel," Clinical Cancer Research, Aug. 4, 2019, pp. 1-12.
Xue, Vivian Weiwen et al., "Early detection and monitoring of cancer in liquid biopsy: advances and challenges," Expert Review of Molecular Diagnostics, 2019, pp. 273-276.
Yates, Lucy R. et al., "Genomic Evolution of Breast Cancer Metastasis and Relapse," Cancer Cell 32, 2017, pp. 169-184.
Diagnostics and Likelihood Ratios, Explained—The NNT, 4 pages, [online] [retrieved on Mar. 1, 2021] Retrieved from the Internet: <URL: https://www.thennt.com/diagnostics-and-likelihood-ratios-explained/.

(56) References Cited

OTHER PUBLICATIONS

AWS Command Line Interface, 5 pages, [online], [retrieved on Mar. 1, 2021], Retrieved from the Internet: <URL: https://aws.amazon.com/cli/.
Babraham Bioinformatics, A tool to map bisulfite converted sequence reads and determine cytosine methylation states, 22 pages, [online] [retrieved on Mar. 1, 2021] Retrieved from the Internet: <URL: https://www.bioinformatics.babraham.ac.uk/projects/bismark/.
Babraham Bioinformatics, A quality control tool for high throughput sequence data, 6 pages, [online] [retrieved on Mar. 1, 2021] Retrieved from the Internet: <URL: https://www.bioinformatics.babraham.ac.uk/projects/fastqc/.
GNU Bash, 2 pages, [online] [retrieved on Mar. 1, 2021] Retrieved from the Internet: <URL: https://www.gnu.org/software/bash/.
Bcl2fastq and bcl2fastq2 Conversion Software, 3 pages, [online] [retrieved on Mar. 1, 2021] Retrieved from the Internet: <URL: https://support.illumina.com/sequencinq/sequencing_software/bcl2fastg-conversion-software.html.
Bedtools: a powerful toolset for genome arithmetic, 5 pages, [online] [retrieved on Mar. 1, 2021] Retrieved from the Internet: <URL: https://bedtools.readthedocs.io/en/latest/.
Bgzip—Block compression/decompression utility, 3 pages, [online] [retrieved on Mar. 1, 2021] Retrieved from the Internet: <URL: http://www.htslib.org/doc/bgzip.html.
Minfi, Analyze Illumina Infinium DNA methylation arrays, 4 pages, [online] [retrieved on Mar. 1, 2021] Retrieved from the Internet: <URL: http://bioconductor.org/packages/release/bioc/html/minfi.html.
Bowtie 2, Fast and sensitive read alignment, 5 pages, [online] [retrieved on Mar. 1, 2021] Retrieved from the Internet: <URL: http://bowtie-bio.sourceforge.net/bowtie2/index.shtml.
Burrows—Wheeler Aligner, 3 pages, [online] [retrieved on Mar. 1, 2021] Retrieved from the Internet: <URL: http://bio-bwa.sourceforge.net/.
CNVkit: Genome-wide copy number from high-throughput sequencing, 5 pages, [online] [retrieved on Mar. 1, 2021] Retrieved from the Internet: <URL: https://cnvkit.readthedocs.io/en/stable/.
Coreutils—GNU core utilities, 3 pages, [online] [retrieved on Mar. 1, 2021] Retrieved from the Internet: <URL: https://www.gnu.org/software/coreutils/.
Cutadapt, 4 pages, [online] [retrieved on Mar. 1, 2021] Retrieved from the Internet: <URL: https://cutadapt.readthedocs.io/en/stable/.
Get Started with Docker, 4 pages, [online] [retrieved on Mar. 1, 2021] Retrieved from the Internet: <URL: https://www.docker.com/.
Fgbio | Tools for working with genomic and high throughput sequencing data, 2 pages, [online] [retrieved on Mar. 1, 2021] Retrieved from the Internet: <URL: http://fulcrumgenomics.github.io/fgbio/.
GitHub—AstraZeneca-NGS/VarDictJava: VarDict Java port, 23 pages, [online] [retrieved on Mar. 1, 2021] Retrieved from the Internet: <URL: https://github.com/AstraZeneca-NGS/VarDictJava.
GitHub—cancer-genomics/delfi_scripts, 1 page, [online] [retrieved on Mar. 1, 2021] Retrieved from the Internet: <URL: https://github.com/cancer-genomics/delfi_scripts.
GitHub—broadinstitute/ichorCNA: Estimating tumor fraction in cell-free DNA from ultra-low-pass whole genome sequencing, 3 pages, [online] [retrieved on Mar. 1, 2021] Retrieved from the Internet: <URL: https://github.com/broadinstitute/ichorCNA.
GATK—Genome Analysis Toolkit, Variant Discovery in High-Throughput Sequencing Data, 3 pages, [online] [retrieved on Mar. 1, 2021] Retrieved from the Internet: <URL: https://gatk.broadinstitute.org/hc/en-us.
GitHub—hall-lab/speedseq: A flexible framework for rapid genome analysis and interpretation, 22 pages, [online] [retrieved on Mar. 1, 2021] Retrieved from the Internet: <URL: https://github.com/hall-lab/speedseq.
GitHub—parklab/NGSCheckMate: Software program for checking sample matching for NGS data, 12 pages, [online] [retrieved on Mar. 1, 2021] Retrieved from the Internet: <URL: https://github.com/parklab/NGSCheckMate.
GitHub—shahcompbio/hmmcopy_utils: Tools for extracting read counts and gc and mappability statistics in preparation for running HMMC . . . , 4 pages, [online] [retrieved on Mar. 1, 2021] Retrieved from the Internet: <URL: https://github.com/shahcompbio/hmmcopy_utils.
GitHub—vcflib/vcflib: C++ library and cmdline tools for parsing and manipulating VCF files, 16 pages, [online] [retrieved on Mar. 1, 2021] Retrieved from the Internet: <URL: https://github.com/vcflib/vcflib.
Home—SnpEff & SnpSift Documentation, 3 pages, [online] [retrieved on Mar. 1, 2021] Retrieved from the Internet: <URL: https://pcingola.github.io/SnpEff/.
Java+You, Download Today!, 1 page, [online] [retrieved on Mar. 1, 2021] Retrieved from the Internet: <URL: https://www.java.com/en/.
MultiQC, Aggregate results from bioinformatics analyses across many samples into a single report, 9 pages, [online] [retrieved on Mar. 1, 2021] Retrieved from the Internet: <URL: https://multiqc.info/.
Picard Tools—By Broad Institute, 5 pages, [online] [retrieved on Mar. 1, 2021] Retrieved from the Internet: <URL: https://broadinstitute.github.io/picard/.
Pigz—Parallel gzip, 1 page, [online] [retrieved on Mar. 1, 2021] Retrieved from the Internet: <URL: https://zlib.net/pigz/.
R: The R Project for Statistical Computing, 2 pages, [online] [retrieved on Mar. 1, 2021] Retrieved from the Internet: <URL: https://www.r-project.org/.
Samtools, 2 pages, [online] [retrieved on Mar. 1, 2021] Retrieved from the Internet: <URL: http://www.htslib.org/.
Tabix(1) manual page, tabix—Generic indexer for TAB-delimited genome position files, 3 pages, [online] [retrieved on Mar. 1, 2021] Retrieved from the Internet: <URL: http://www.htslib.org/doc/tabix.html.
The Perl Programming Language, 4 pages, [online] [retrieved on Mar. 1, 2021] Retrieved from the Internet: <URL: https://www.perl.org/.
Home of Variant Tools, 8 pages, [online] [retrieved on Mar. 1, 2021] Retrieved from the Internet: <URL: https://vatlab.github.io/vat-docs/.
Python 3.9.2 documentation, 3 pages, [online] [retrieved on Mar. 1, 2021] Retrieved from the Internet: <URL: https://docs.python.org/3/.
Chen, Shinan et al. "FGFR1 and HER1 or HER2 co-amplification in breast cancer indicate poor prognosis", Oncology Letters, 2018, 15, pp. 8206-8214.
Falzone, Luca et al. "Evolution of Cancer Pharmacological Treatments at the Turn of the Third Millennium", Frontiers in Pharmacology, Nov. 2018, vol. 9, Article 1300, pp. 1-26.
Huang, Chiang-Ching et al. "Bioinformatics Analysis for Circulating Cell-Free DNA in Cancer", Cancers, 2019, 11, 805, pp. 1-15.
Li, Heng et al. "A survey of sequence alignment algorithms for next-generation sequencing", Briefings in Bioinformatics, vol. 11, No. 5, May 11, 2010, pp. 473-483.
Raman, Lennart et al. "WisecondorX: improved copy number detection for routine shallow whole-genome sequencing", Nucleic Acids Research, 2019, vol. 47, No. 4, pp. 1605-1614.
Molparia, Bhuvan et al. "Assessment of circulating copy number variant detection for cancer screening", PLOS One, Jul. 7, 2017, pp. 1-18.
Xu, Xinjie et al. "Assessing copy number abnormalities and copy-neutral loss-of-heterozygosity across the genome as best practice in diagnostic evaluation of acute myeloid leukemia: An evidence-based review from the cancer genomics consortium (CGC) myeloid neoplasms working group", Cancer Genetics, 2018, pp. 218-235.

* cited by examiner

| Test patient data store 120 |
|---|
| Patient 1 121-1 |
|     Sequencing data 122-1 |
|         Sequencing run 1 122-1-1 |
|             Sequence read 1 123-1-1-1 |
|             ⋮ |
|             Sequence read K 123-1-1-K |
|             Aligned sequences (e.g., BAM file) 124-1-1 |
|         ⋮ |
|         Sequencing run L 122-1-L |
|     Feature data 125-1 |
|         Personal characteristics 126-1 |
|         Medical history 127-1 |
|         Clinical features 128-1 |
|             Pathology data 128-1-1 |
|             Imaging data 128-2-1 |
|             Tissue culture / organoid data 128-3-1 |
|         Genomic features 131-1 |
|             Allelic states 132-1 |
|             Variant allele fractions 133-1 |
|             Methylation states 132-1 |
|             Genomic copy numbers 135-1 |
|             Tumor mutational burden 136-1 |
|             Microsatellite instability status 137-1-1 |
|             Tumor ploidy 137-1-2 |
|             HRD status 137-1-3 |
|         Other -omics data 138-1 |
|     Clinical assessment 139-1 |
|         Actionable variants and characteristics 139-1-1 |
|         Matched therapies 139-1-2 |
|         Clinical reports 139-1-3 |
| ⋮ |
| Patient M 121-M |

Non-persistent memory 111

Fig. 1B

Non-persistent memory 111

| Genomic features 131 |
| Allelic states 132 |
| Candidate sequence variants 132-c |
| Candidate 1 132-c-1 |
| Variant allele fragment count 132-c-1-ac |
| Variant allele locus count 132-c-1-lc |
| Variant allele fraction 132-c-1-vf |
| Candidate 2 132-c-2 |
| Variant allele fragment count 132-c-2-ac |
| Variant allele locus count 132-c-2-lc |
| Variant allele fraction 132-c-2-vf |
| ⋮ |
| Candidate W 132-c-W |
| Variant allele fragment count 132-c-W-ac |
| Variant allele locus count 132-c-W-lc |
| Variant allele fraction 132-c-W-vf |
| Validated sequence variants 132-v |
| Variant 1 132-v-1 |
| Variant 2 132-v-1 |
| ⋮ |
| Variant X 132-v-X |

Fig. 1C

Sensitivity distribution training data 180

- Training sample 1 181-1
  - Cancer type 182-1
  - Locus 1 183-1-1
    - Variant allele fraction 184-1-1
    - Detection status in matched sequencing assay 185-1-1
  - Locus 2 183-1-2
    - Variant allele fraction 184-1-2
    - Detection status in matched sequencing assay 185-1-2
  - ⋮
  - Locus Q 183-1-Q
    - Variant allele fraction 184-1-Q
    - Detection status in matched sequencing assay 185-1-Q
- Training sample 2 181-2
  - Cancer type 182-2
  - Locus 1 183-2-1
    - Variant allele fraction 184-2-1
    - Detection status in matched sequencing assay 185-2-1
  - Locus 2 183-2-2
    - Variant allele fraction 184-2-2
    - Detection status in matched sequencing assay 185-2-2
  - ⋮
  - Locus Q 183-2-Q
    - Variant allele fraction 184-2-Q
    - Detection status in matched sequencing assay 185-2-Q
- ⋮
- Training sample R 181-R Non-persistent memory 111

Fig. 1E

| | Variant prevalence training data 192 | |
|---|---|---|
| Non-persistent memory 111 | Reference subject 1 193-1 | |
| | | Cancer type 194-1 |
| | | Somatic sequence variants 195-1 |
| | | Variant 1 196-1-1 |
| | | Variant 2 196-1-2 |
| | | ⋮ |
| | | Variant S 196-1-S |
| | Reference subject 2 193-2 | |
| | | Cancer type 194-2 |
| | | Somatic sequence variants 195-2 |
| | | Variant 1 196-2-1 |
| | | Variant 2 196-2-2 |
| | | ⋮ |
| | | Variant T 196-2-T |
| | ⋮ | |
| | Reference subject U 193-U | |
| | | Cancer type 194-U |
| | | Somatic sequence variants 195-U |
| | | Variant 1 196-U-1 |
| | | Variant 2 196-U-2 |
| | | ⋮ |
| | | Variant V 196-U-V |

Fig. 1F

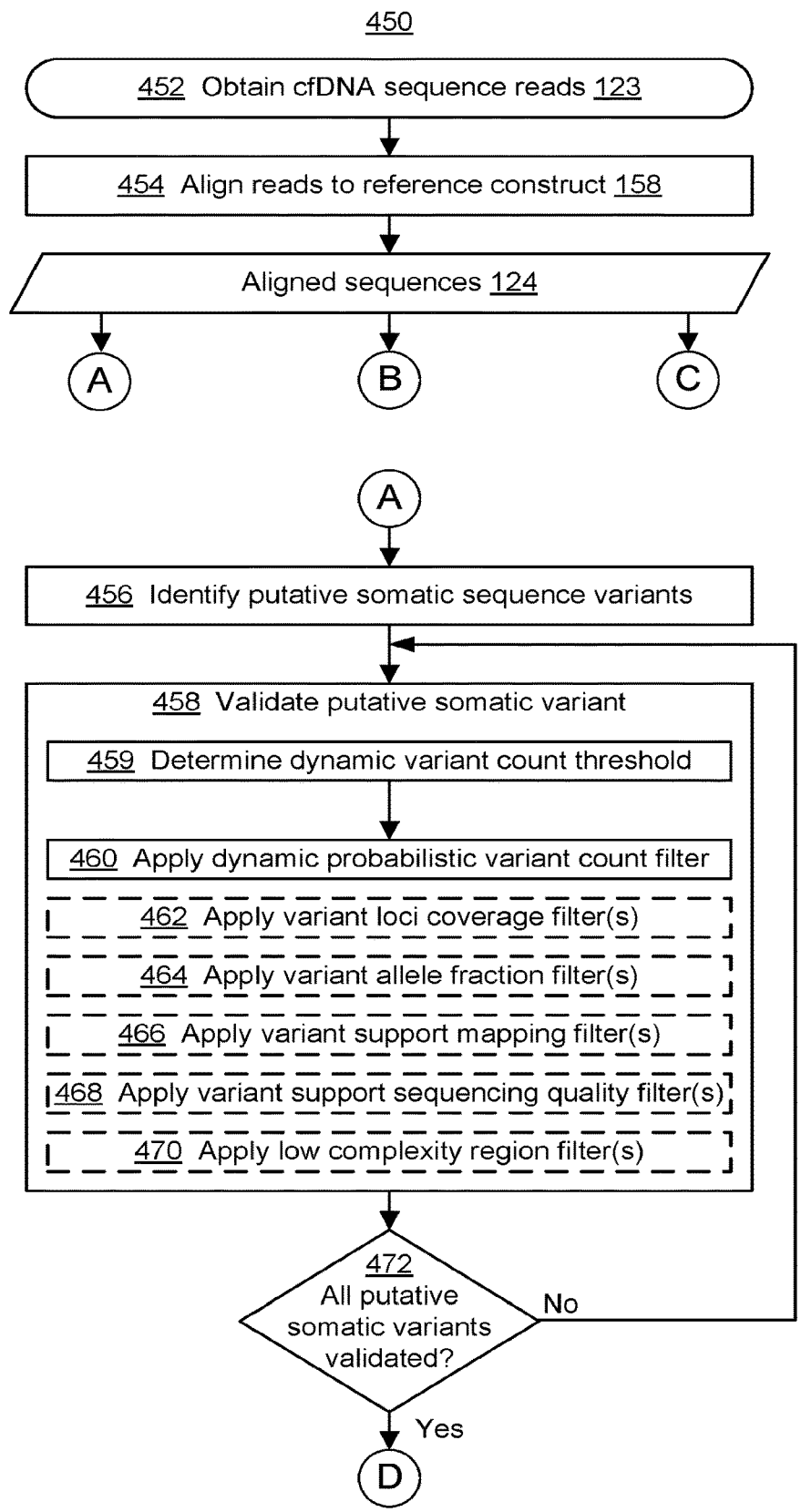
Fig. 4G1

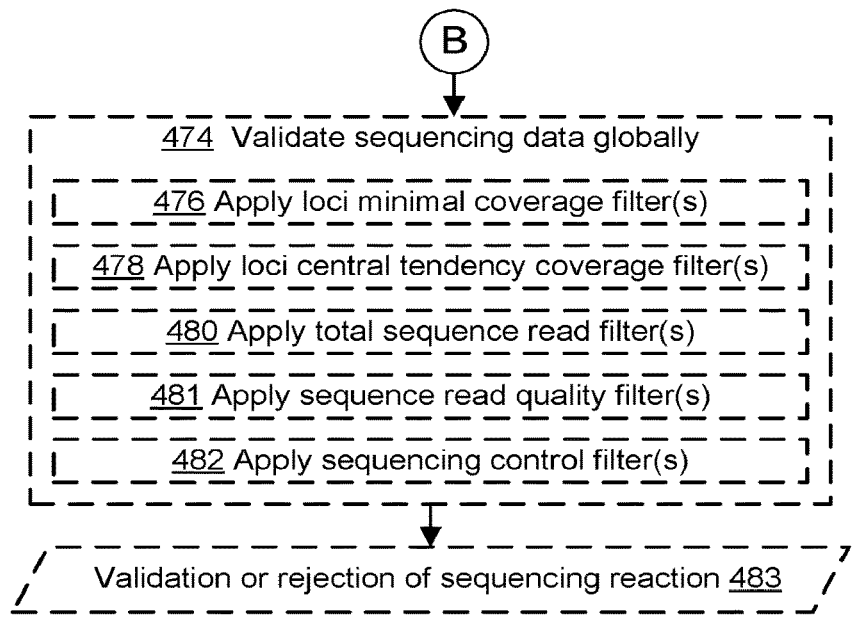
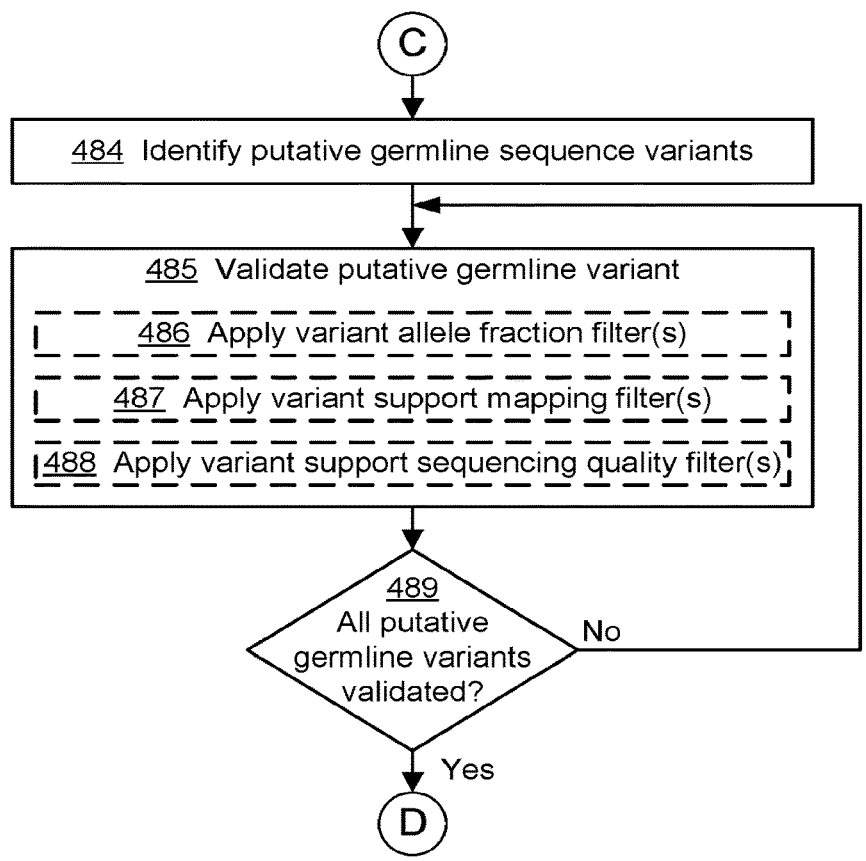
Fig. 4G2

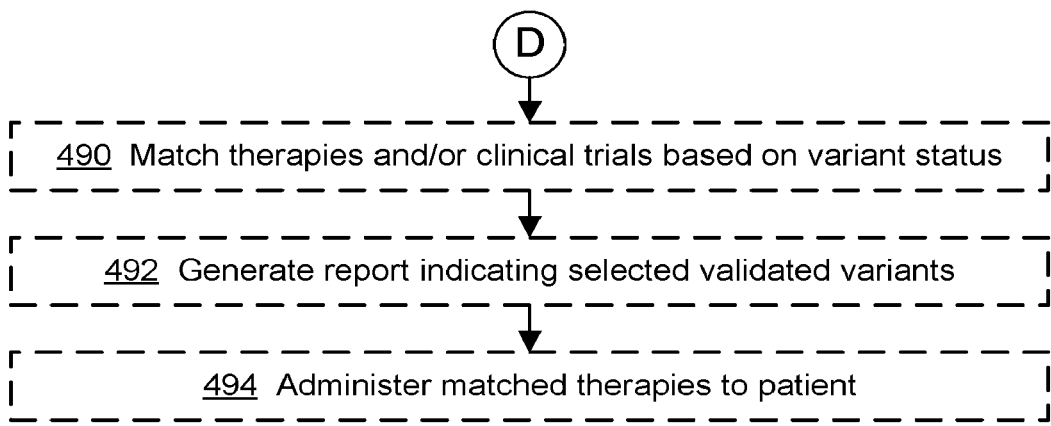
Fig. 4G3

500

| A method of validating a somatic sequence variant in a test subject having a cancer condition. |

↓

| 502 Obtain from a first sequencing reaction, a corresponding sequence of each cell-free DNA fragment in a first plurality of cell-free DNA fragments in a liquid biopsy sample of the test subject, thus obtaining a first plurality of sequence reads. |

↓

| 504 Align each respective sequence read in the first plurality of sequence reads to a reference sequence for the species of the subject, thus identifying (i) a variant allele fragment count for a candidate variant, where the candidate variant maps to a locus in the reference sequence, and (ii) a locus fragment count for the locus encompassing the candidate variant. |

↓

| 506 Compare the variant allele fragment count for the candidate variant against a dynamic variant count threshold for the locus in the reference sequence that the candidate variant maps to.<br>The dynamic variant count threshold is based upon a pre-test odds of a positive variant call for the locus based upon the prevalence of variants in a genomic region that includes the locus from a first set of nucleic acids obtained from a cohort of subjects having the cancer condition. |

↓

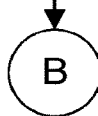

Fig. 5A

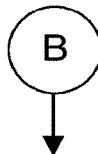

506 (cont)

508 Obtain a distribution of variant detection sensitivities as a function of circulating variant allele fraction from the cohort of subjects.
   The distribution of variant detection sensitivities is based on the circulating variant allele fraction of a second set of nucleic acids collected from the cohort of subjects relative to variant alleles detected in the first set of nucleic acids collected from the cohort of subjects.
   The first set of nucleic acids are from solid tumor biopsies of the cohort of subjects. The second set of nucleic acids are cell-free nucleic acids from liquid biopsies of the cohort of subjects.

Estimate a circulating variant fraction for the candidate variant, where the dynamic threshold for the locus is set based upon a desired variant detection specificity determined by the relationship:

$$\text{specificity} = 1 - ( (\text{sensitivity}) \times ( \text{odds(pre-test)}/\text{odds(post-test)} ) )$$

Sensitivity is the variant detection sensitivity in the distribution of variant detection sensitivities that corresponds to the circulating variant fraction for the candidate variant.
odds(post-test) is the post-test odds of a positive variant call for the locus.
odds(pre-test) is the pre-test odds of the positive variant call for the locus.

510 When the variant allele fragment count for the candidate variant satisfies the dynamic variant count threshold for the locus, validate the presence of the somatic sequence variant in the test subject.

When the variant allele fragment count for the candidate variant does not satisfy the dynamic variant count threshold for the locus, reject the presence of the somatic sequence variant in the test subject.

A method of obtaining a distribution of variant detection sensitivities as a function of circulating variant allele fraction from a cohort of subjects.

602 Obtain matched liquid biopsy and solid tumor samples from a set of training subjects.

604 Sequence the solid tumor sample, thus detecting one or more variants in the solid tumor sample.

606 Sequence the liquid biopsy sample, thus detecting one or more variants in the liquid biopsy sample.

608 Compare the one or more variants detected in the liquid biopsy sample against the one or more variants detected in the solid tumor sample, thus determining a variant detection sensitivity for each variant in the liquid biopsy sample.

610 Bin each variant detection sensitivity into a plurality of bins with respect to the variant allele fraction in the liquid sample, thus obtaining a distribution of variant detection sensitivities.

Fig. 6

Liquid Biopsy Assay Sensitivity

| Variant Type | DNA quantity | 0.1% VAF Sensitivity, % (detected/ total variants) | 0.25% VAF Sensitivity, % (detected/ total variants) | 0.5% VAF Sensitivity, % (detected/ total variants) | 1% VAF Sensitivity, % (detected/ total variants) | 5% VAF Sensitivity, % (detected/ total variants) |
|---|---|---|---|---|---|---|
| SNVs | 10 ng | 25.93 (14/54) | 65.00 (39/60) | 79.63 (43/54) | 100.00 (39/39) | 100.00 (60/60) |
|  | 30 ng | 66.67 (40/60) | 93.75 (45/48) | 100.00 (54/54) | 100.00 (51/51) | 100.00 (48/48) |
|  | 50 ng | 75.00 (36/48) | 100 (51/51) | 100.00 (60/60) | 100.00 (42/42) | 100.00 (60/60) |
| Indels | 10 ng | 33.33 (8/24) | 46.15 (12/26) | 86.36 (19/22) | 100.00 (18/18) | 100.00 (26/26) |
|  | 30 ng | 46.15 (12/26) | 75 (15/20) | 95.83 (23/24) | 100.00 (22/22) | 100.00 (20/20) |
|  | 50 ng | 45.00 (9/20) | 86.36 (19/22) | 96.15 (25/26) | 94.44 (17/18) | 100.00 (26/26) |
| CNVs | 10 ng | 0.00 (0/12) | 0.00 (0/12) | 100.00 (8/8) | 100.00 (10/10) | 100.00 (12/12) |
|  | 30 ng | 0.00 (0/12) | 25 (2/8) | 100.00 (12/12) | 100.00 (10/10) | 100.00 (8/8) |
|  | 50 ng | 12.50 (1/8) | 20 (2/10) | 100.00 (12/12) | 100.00 (8/8) | 100.00 (12/12) |
| Fusions | 10 ng | 0.00 (0/12) | 8.33 (1/12) | 37.50 (3/8) | 40.00 (4/10) | 100.00 (12/12) |
|  | 30 ng | 16.67 (2/12) | 37.50 (3/8) | 75.00 (9/12) | 90.00 (9/10) | 100.00 (8/8) |
|  | 50 ng | 0.00 (0/8) | 50.00 (5/10) | 66.67 (8/12) | 100.00 (8/8) | 100.00 (12/12) |

Figure 13

Liquid Biopsy Assay Analytical Specificity

| Variant Type | Percent | TN/(TN+FP) |
|---|---|---|
| SNVs | 100% | 264/264 |
| Indels | 100% | 88/88 |
| CNVs | 96.2% | 176/183 |
| Rearrangements | 100% | 1848/1848 |

TN: true negative; FP: false positive

Figure 14

Liquid Biopsy Assay Accuracy Compared to
Conventional Methods (Avenio)

| Sample Size | Variant Type | Percent | Variants Called |
|---|---|---|---|
| 30 ng | SNVs | 94.8% | 110/116 |
| | Indels | 100% | 8/8 |
| | CNVs | 100% | 5/5 |
| | Rearrangements | 100% | 3/3 |
| 10 ng | SNVs | 91.9% | 79/86 |
| | Indels | 100% | 3/3 |
| | CNVs | 80% | 4/5 |
| | Rearrangements | 100% | 1/1 |

Figure 15

Variants Detected by Liquid Biopsy Assay

| Gene | SNV / Indel | Rearrangement | CNV |
|---|---|---|---|
| AKT1 | * | | |
| AKT2 | * | | |
| ALK | * | * | |
| APC | * | | |
| AR | * | | |
| ARAF | * | | |
| ARID1A | * | | |
| ATM | * | | |
| ATR | * | | |
| B2M | * | | |
| BAP1 | * | | |
| BRAF | * | * | |
| BRCA1 | * | | |
| BRCA2 | * | | |
| BTK | * | | |
| CCND1 | * | | |
| CCND2 | * | | |
| CCND3 | * | | |
| CCNE1 | * | | * |
| CD274 | * | | * |
| CDH1 | * | | |
| CDK4 | * | | |
| CDK6 | * | | |
| CDKN2A | * | | |
| CTNNB1 | * | | |
| DDR2 | * | | |
| DPYD | * | | |
| EGFR | * | | * |
| ERBB2 | * | | * |
| ERRFI1 | * | | |
| ESR1 | * | | |
| EZH2 | * | | |
| FBXW7 | * | | |
| FGFR1 | * | | |
| FGFR2 | * | * | |
| FGFR3 | * | * | |
| FGFR4 | * | | |
| FLT3 | * | | |
| FOXL2 | * | | |

Figure 16A

| Gene | SNV / Indel | Rearrangement | CNV |
|---|---|---|---|
| GATA3 | * | | |
| GNA11 | * | | |
| GNAQ | * | | |
| GNAS | * | | |
| HNF1A | * | | |
| HRAS | * | | |
| IDH1 | * | | |
| IDH2 | * | | |
| JAK1 | * | | |
| JAK2 | * | | |
| JAK3 | * | | |
| KDR | * | | |
| KEAP1 | * | | |
| KIT | * | | |
| KMT2A | * | | |
| KRAS | * | | |
| MAP2K1 | * | | |
| MAP2K2 | * | | |
| MAPK1 | * | | |
| MET | * | | * |
| MLH1 | * | | |
| MPL | * | | |
| MSH2 | * | | |
| MSH3 | * | | |
| MSH6 | * | | |
| MTOR | * | | |
| MYC | * | | * |
| MYCN | * | | |
| NF1 | * | | |
| NF2 | * | | |
| NFE2L2 | * | | |
| NOTCH1 | * | | |
| NPM1 | * | | |
| NRAS | * | | |
| NTRK1 | * | * | |
| PALB2 | * | | |
| PBRM1 | * | | |
| PDCD1LG2 | * | | |
| PDGFRA | * | | |
| PDGFRB | * | | |
| PIK3CA | * | | |
| PIK3R1 | * | | |

Figure 16B

| Gene | SNV / Indel | Rearrangement | CNV |
|---|---|---|---|
| PMS2 | * | | |
| PTCH1 | * | | |
| PTEN | * | | |
| PTPN11 | * | | |
| RAD51C | * | | |
| RAF1 | * | | |
| RB1 | * | | |
| RET | * | * | |
| RHEB | * | | |
| RHOA | * | | |
| RIT1 | * | | |
| RNF43 | * | | |
| ROS1 | * | * | |
| SDHA | * | | |
| SMAD4 | * | | |
| SMO | * | | |
| SPOP | * | | |
| STK11 | * | | |
| TERT | * | | |
| TP53 | * | | |
| TSC1 | * | | |
| TSC2 | * | | |
| UGT1A1 | * | | |
| VHL | * | | |

Figure 16C

Probabilistic noise filtering methodology improves variant calling

| | Current Filtering Method | Dynamic Filtering Method | % Improvement Relative to Reference Samples |
|---|---|---|---|
| False Positive Variant Count | 226 | 200 | 11.45% |
| True Positive Variant Count | 164 | 162 | -1.22% |

Figure 17

Cancer groups included in clinical profiling analysis

| Cancer Group | Count |
|---|---|
| Breast | 254 |
| Lung | 241 |
| Colorectal | 98 |
| Prostate | 96 |
| Pancreatic | 83 |
| Tumor of unknown origin | 28 |
| Hepatobiliary | 26 |
| Ovarian | 23 |
| Melanoma | 21 |
| Head and neck | 19 |
| Bladder | 18 |
| Gastric | 18 |
| Kidney | 18 |
| Sarcoma | 14 |
| Esophageal | 10 |
| Endometrial | 8 |
| Thyroid | 6 |
| Endocrine | 6 |
| Skin | 4 |
| Thymoma | 3 |
| Cervical | 2 |
| Testicular | 2 |
| Glioma | 1 |
| Mesothelioma | 1 |

Figure 18

METHODS AND SYSTEMS FOR DYNAMIC VARIANT THRESHOLDING IN A LIQUID BIOPSY ASSAY

CROSS REFERENCE TO RELATED APPLICATIONS

This application claims priority to U.S. Provisional Patent Application No. 63/041,293, filed Jun. 19, 2020, and U.S. Provisional Patent Application No. 62/978,130, filed Feb. 18, 2020, the contents of which are hereby incorporated by reference, in their entireties, for all purposes.

FIELD OF THE INVENTION

The present disclosure relates generally to the use of cell-free DNA sequencing data to provide clinical support for personalized treatment of cancer.

BACKGROUND

Precision oncology is the practice of tailoring cancer therapy to the unique genomic, epigenetic, and/or transcriptomic profile of an individual's cancer. Personalized cancer treatment builds upon conventional therapeutic regimens used to treat cancer based only on the gross classification of the cancer, e.g., treating all breast cancer patients with a first therapy and all lung cancer patients with a second therapy. This field was borne out of many observations that different patients diagnosed with the same type of cancer, e.g., breast cancer, responded very differently to common treatment regimens. Over time, researchers have identified genomic, epigenetic, and transcriptomic markers that improve predictions as to how an individual cancer will respond to a particular treatment modality.

There is growing evidence that cancer patients who receive therapy guided by their genetics have better outcomes. For example, studies have shown that targeted therapies result in significantly improved progression-free cancer survival. See, e.g., Radovich M. et al., Oncotarget, 7(35): 56491-500 (2016). Similarly, reports from the IMPACT trial—a large (n=1307) retrospective analysis of consecutive, prospectively molecularly profiled patients with advanced cancer who participated in a large, personalized medicine trial—indicate that patients receiving targeted therapies matched to their tumor biology had a response rate of 16.2%, as opposed to a response rate of 5.2% for patients receiving non-matched therapy. Tsimberidou A M et al., ASCO 2018, Abstract LBA2553 (2018).

In fact, therapy targeted to specific genomic alterations is already the standard of care in several tumor types, e.g., as suggested in the National Comprehensive Cancer Network (NCCN) guidelines for melanoma, colorectal cancer, and non-small cell lung cancer. In practice, implementation of these targeted therapies requires determining the status of the diagnostic marker in each eligible cancer patient. While this can be accomplished for the few, well known mutations associated with treatment recommendations in the NCCN guidelines using individual assays or small next generation sequencing (NGS) panels, the growing number of actionable genomic alterations and increasing complexity of diagnostic classifiers necessitates a more comprehensive evaluation of each patient's cancer genome, epigenome, and/or transcriptome.

For instance, some evidence suggests that use of combination therapies where each component is matched to an actionable genomic alteration holds the greatest potential for treating individual cancers. To this point, a retroactive study of cancer patients treated with one or more therapeutic regimens revealed that patients who received therapies matched to a higher percentage of their genomic alterations experienced a greater frequency of stable disease (e.g., a longer time to recurrence), longer time to treatment failure, and greater overall survival. Wheeler J J et al., Cancer Res., 76:3690-701 (2016). Thus, comprehensive evaluation of each cancer patient's genome, epigenome, and/or transcriptome should maximize the benefits provided by precision oncology, by facilitating more fine-tuned combination therapies, use of novel off-label drug indications, and/or tissue agnostic immunotherapy. See, for example, Schwaederle M. et al., J Clin Oncol., 33(32):3817-25 (2015); Schwaederle M. et al., JAMA Oncol., 2(11):1452-59 (2016); and Wheler J J et al., Cancer Res., 76(13):3690-701 (2016). Further, the use of comprehensive next generation sequencing analysis of cancer genomes facilitates better access and a larger patient pool for clinical trial enrollment. Coyne G O et al., Curr. Probl. Cancer, 41(3):182-93 (2017); and Markman M., Oncology, 31(3):158, 168.

The use of large NGS genomic analysis is growing in order to address the need for more comprehensive characterization of an individual's cancer genome. See, for example, Fernandes G S et al., Clinics, 72(10):588-94. Recent studies indicate that of the patients for which large NGS genomic analysis is performed, 30-40% then receive clinical care based on the assay results, which is limited by at least the identification of actionable genomic alterations, the availability of medication for treatment of identified actionable genomic alterations, and the clinical condition of the subject. See, Ross J S et al., JAMA Oncol., 1(1):40-49 (2015); Ross J S et al., Arch. Pathol. Lab Med., 139:642-49 (2015); Hirshfield K M et al., Oncologist, 21(11):1315-25 (2016); and Groisberg R. et al., Oncotarget, 8:39254-67 (2017).

However, these large NGS genomic analyses are conventionally performed on solid tumor samples. For instance, each of the studies referenced in the paragraph above performed NGS analysis of FFPE tumor blocks from patients. Solid tissue biopsies remain the gold standard for diagnosis and identification of predictive biomarkers because they represent well-known and validated methodologies that provide a high degree of accuracy. Nevertheless, there are significant limitations to the use of solid tissue material for large NGS genomic analyses of cancers. For example, tumor biopsies are subject to sampling bias caused by spatial and/or temporal genetic heterogeneity, e.g., between two regions of a single tumor and/or between different cancerous tissues (such as between primary and metastatic tumor sites or between two different primary tumor sites). Such intertumor or intratumor heterogeneity can cause sub-clonal or emerging mutations to be overlooked when using localized tissue biopsies, with the potential for sampling bias to be exacerbated over time as sub-clonal populations further evolve and/or shift in predominance.

Additionally, the acquisition of solid tissue biopsies often requires invasive surgical procedures, e.g., when the primary tumor site is located at an internal organ. These procedures can be expensive, time consuming, and carry a significant risk to the patient, e.g., when the patient's health is poor and may not be able to tolerate invasive medical procedures and/or the tumor is located in a particularly sensitive or inoperable location, such as in the brain or heart. Further, the amount of tissue, if any, that can be procured depends on multiple factors, including the location of the tumor, the size of the tumor, the fragility of the patient, and the risk of comorbidities related to biopsies, such as bleeding and infections. For instance, recent studies report that tissue samples in a majority of advanced non-small cell lung cancer patients are limited to small biopsies and cannot be obtained at all in up to 31% of patients. Ilie and Hofman, Transl. Lung Cancer Res., 5(4):420-23 (2016). Even when a tissue biopsy is obtained, the sample may be too scant for comprehensive testing.

Further, the method of tissue collection, preservation (e.g., formalin fixation), and/or storage of tissue biopsies can result in sample degradation and variable quality DNA. This, in turn, leads to inaccuracies in downstream assays and analysis, including next-generation sequencing (NGS) for the identification of biomarkers. Ilie and Hofman, Transl Lung Cancer Res., 5(4):420-23 (2016).

In addition, the invasive nature of the biopsy procedure, the time and cost associated with obtaining the sample, and the compromised state of cancer patients receiving therapy render repeat testing of cancerous tissues impracticable, if not impossible. As a result, solid tissue biopsy analysis is not amenable to many monitoring schemes that would benefit cancer patients, such as disease progression analysis, treatment efficacy evaluation, disease recurrence monitoring, and other techniques that require data from several time points.

Cell-free DNA (cfDNA) has been identified in various bodily fluids, e.g., blood serum, plasma, urine, etc. Chan et al., Ann. Clin. Biochem., 40(Pt 2):122-30 (2003). This cfDNA originates from necrotic or apoptotic cells of all types, including germline cells, hematopoietic cells, and diseased (e.g., cancerous) cells. Advantageously, genomic alterations in cancerous tissues can be identified from cfDNA isolated from cancer patients. See, e.g., Stroun et al., Oncology, 46(5):318-22 (1989); Goessl et al., Cancer Res., 60(21):5941-45 (2000); and Frenel et al., Clin. Cancer Res. 21(20):4586-96 (2015). Thus, one approach to overcoming the problems presented by the use of solid tissue biopsies described above is to analyze cell-free nucleic acids (e.g., cfDNA) and/or nucleic acids in circulating tumor cells present in biological fluids, e.g., via a liquid biopsy.

Specifically, liquid biopsies offer several advantages over conventional solid tissue biopsy analysis. For instance, because bodily fluids can be collected in a minimally invasive or non-invasive fashion, sample collection is simpler, faster, safer, and less expensive than solid tumor biopsies. Such methods require only small amounts of sample (e.g., 10 mL or less of whole blood per biopsy) and reduce the discomfort and risk of complications experienced by patients during conventional tissue biopsies. In fact, liquid biopsy samples can be collected with limited or no assistance from medical professionals and can be performed at almost any location. Further, liquid biopsy samples can be collected from any patient, regardless of the location of their cancer, their overall health, and any previous biopsy collection. This allows for analysis of the cancer genome of patients from which a solid tumor sample cannot be easily and/or safely obtained. In addition, because cell-free DNA in the bodily fluids arise from many different types of tissues in the patient, the genomic alterations present in the pool of cell-free DNA are representative of various different clonal sub-populations of the cancerous tissue of the subject, facilitating a more comprehensive analysis of the cancerous genome of the subject than is possible from one or more sections of a single solid tumor sample.

Liquid biopsies also enable serial genetic testing prior to cancer detection, during the early stages of cancer progression, throughout the course of treatment, and during remission, e.g., to monitor for disease recurrence. The ability to conduct serial testing via non-invasive liquid biopsies throughout the course of disease could prove beneficial for many patients, e.g., through monitoring patient response to therapies, the emergence of new actionable genomic alterations, and/or drug-resistance alterations. These types of information allow medical professionals to more quickly tailor and update therapeutic regimens, e.g., facilitating more timely intervention in the case of disease progression. See, e.g., Ilie and Hofman, Transl. Lung Cancer Res., 5(4):420-23 (2016).

Nevertheless, while liquid biopsies are promising tools for improving outcomes using precision oncology, there are significant challenges specific to the use of cell-free DNA for evaluation of a subject's cancer genome. For instance, there is a highly variable signal-to-noise ratio from one liquid biopsy sample to the next. This occurs because cfDNA originates from a variety of different cells in a subject, both healthy and diseased. Depending on the stage and type of cancer in any particular subject, the fraction of cfDNA fragments originating from cancerous cells (the "tumor fraction" or "ctDNA fraction" of the sample/subject) can range from almost 0% to well over 50%. Other factors, including tumor type and mutation profile, can also impact the amount of DNA released from cancerous tissues. For instance, cfDNA clearance through the liver and kidneys is affected by a variety of factors, including renal dysfunction or other tissue damaging factors (e.g., chemotherapy, surgery, and/or radiotherapy).

This, in turn, leads to problems detecting and/or validating cancer-specific genomic alterations in a liquid sample. This is particularly true during early stages of the disease—when cancer therapies have much higher success rates—because the tumor fraction in the patient is lowest at this point. Thus, early stage cancer patients can have ctDNA fractions below the limit of detection (LOD) for one or more informative genomic alterations, limiting clinical utility because of the risk of false negatives and/or providing an incomplete picture of the cancer genome of the patient. Further, because cancers, and even individual tumors, can be clonally diverse, actionable genomic alterations that arise in only a subset of clonal populations are diluted below the overall tumor fraction of the sample, further frustrating attempts to tailor combination therapies to the various actionable mutations in the patient's cancer genome. Consequently, most studies using liquid biopsy samples to date have focused on late stage patients for assay validation and research.

Another challenge associated with liquid biopsies is the accurate determination of tumor fraction in a sample. This difficulty arises from at least the heterogeneity of cancers and the increased frequency of large chromosomal duplications and deletions found in cancers. As a result, the frequency of genomic alterations from cancerous tissues varies from locus to locus based on at least (i) their prevalence in different sub-clonal populations of the subject's cancer, and (ii) their location within the genome, relative to large chromosomal copy number variations. The difficulty in accurately determining the tumor fraction of liquid biopsy samples affects accurate measurement of various cancer features shown to have diagnostic value for the analysis of solid tumor biopsies. These include allelic ratios, copy number variations, overall mutational burden, frequency of abnormal methylation patterns, etc., all of which are correlated with the percentage of DNA fragments that arise from cancerous tissue, as opposed to healthy tissue.

Altogether, these factors result in highly variable concentrations of ctDNA—from patient to patient and possibly from locus to locus—that confound accurate measurement of disease indicators and actionable genomic alterations. Further, the quantity and quality of cfDNA obtained from liquid biopsy samples are highly dependent on the particular methodology for collecting the samples, storing the samples, sequencing the samples, and standardizing the sequencing data.

While validation studies of existing liquid biopsy assays have shown high sensitivity and specificity, few studies have corroborated results with orthogonal methods, or between particular testing platforms, e.g., different NGS technologies and/or targeted panel sequencing versus whole genome/exome sequence. Reports of liquid biopsy-based studies are limited by comparison to non-comprehensive tissue testing algorithms including Sanger sequencing, small NGS hotspot panels, polymerase chain reaction (PCR), and fluorescent in situ hybridization (FISH), which may not contain all NCCN guideline genes in their reportable range, thus suffering in comparison to a more comprehensive liquid biopsy assay.

As an example, conventional liquid biopsy assays do not provide a method for accurately detecting variants (e.g., variant alleles) in ctDNA NGS assays. As described above, many patients may not have abundant ctDNA in early stage disease and may shed variants below the limit of detection (LOD) for ctDNA assays, resulting in false negatives. Detecting these variants at low circulating fractions is also technically challenging due to constraints of sequencing by synthesis. Additionally, differentiating between germline and somatic variants in ctDNA is difficult, as is differentiating between mutations derived from clonal hematopoiesis (CH) and the solid tumor being assayed. In such cases, mutations in hematopoietic lineage cells may be mistaken for tumor-derived mutations. Indeed, researchers have identified several genes frequently mutated in CH with potential importance in cancer, such as JAK2, TP53, GNAS, IDH2, and KRAS. Mayrhofer et al., 2018, "Cell-free DNA profiling of metastatic prostate cancer reveals microsatellite instability, structural rearrangements and clonal hematopoiesis," Genome Med, (10), pg. 85; Hu et al., 2018, "False-Positive Plasma Genotyping Due to Clonal Hematopoiesis," Clin Cancer Res, (24), pg. 4437.

The information disclosed in this Background section is only for enhancement of understanding of the general background of the invention and should not be taken as an acknowledgement or any form of suggestion that this information forms the prior art already known to a person skilled in the art.

SUMMARY

Given the above background, there is a need in the art for improved methods and systems for supporting clinical decisions in precision oncology using liquid biopsy assays. In particular, there is a need in the art for improved methods and systems for identifying somatic tumor mutations in cell-free DNA, particularly where the sample has low tumor fractions. Advantageously, the present disclosure solves this and other needs in the art by providing improved somatic variant identification methodology that better accounts for locus-specific and/or sample specific considerations to more accurately identify true somatic mutations in a liquid biopsy sample. For example, by using an application of Bayes theorem to account for one or more of (i) the prevalence of variants at a specific locus in a specific cancer type, (ii) the variant allele fraction for the variant being evaluated, (iii) the prevalence of sequencing errors at a particular locus, and (iv) the actual sequencing error rate of a particular reaction, the variant filter methodologies described herein tune the specificity and sensitivity of variant count thresholds in a locus-specific fashion to achieve higher accuracy of true somatic variant calling in a liquid biopsy assay.

For example, in one aspect, the present disclosure provides a method of validating a somatic sequence variant in a test subject having a cancer condition. The method is performed at a computer system having one or more processors, and memory storing one or more programs for execution by the one or more processors.

The method includes obtaining, from a first sequencing reaction, a corresponding sequence of each cell-free DNA fragment in a first plurality of cell-free DNA fragments in a liquid biopsy sample of the test subject, thus obtaining a first plurality of sequence reads. Each respective sequence read in the first plurality of sequence reads is aligned to a reference sequence for the species of the subject, thus identifying a variant allele fragment count for a candidate variant that maps to a locus in the reference sequence, and a locus fragment count for the locus encompassing the candidate variant.

The method further includes comparing the variant allele fragment count for the candidate variant against a dynamic variant count threshold for the locus in the reference sequence that the candidate variant maps to. The dynamic variant count threshold is based upon a pre-test odds of a positive variant call for the locus based on the prevalence of variants in a genomic region that includes the locus from a first set of nucleic acids obtained from a cohort of subjects having the cancer condition.

The method then includes rejecting or validating the variant as a true somatic variant based upon the dynamic variant count threshold. For instance, when the variant allele fragment count for the candidate variant satisfies the dynamic variant count threshold for the locus, the presence of the somatic sequence variant in the test subject is validated. And when the variant allele fragment count for the candidate variant does not satisfy the dynamic variant count threshold for the locus, the presence of the somatic sequence variant in the test subject is rejected.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIGS. 1A, 1B, 1C, 1D, 1E, and 1F collectively illustrate a block diagram of an example computing device for validating a somatic sequence variant in a test subject having a cancer condition, in accordance with some embodiments of the present disclosure.

FIG. 4A provides an overview flow chart of processes and features in a bioinformatics pipeline, in accordance with some embodiments of the present disclosure.

FIG. 4B provides an overview of a bioinformatics pipeline executed with either a liquid biopsy sample alone or a liquid biopsy sample and a matched normal sample. FIG. 4C illustrates that paired end reads from tumor and normal isolates are zipped and stored separately under the same order identifier, in accordance with some embodiments of the present disclosure. FIG. 4D illustrates quality correction for FASTQ files, in accordance with some embodiments of the present disclosure. FIG. 4E illustrates processes for obtaining tumor and normal BAM alignment files, in accordance with some embodiments of the present disclosure. FIG. 4F provides a flow chart of a method for validating a somatic sequence variant in a test subject having a cancer condition, in which dashed boxes represent optional portions of the method, in accordance with some embodiments of the present disclosure.

FIGS. 4G1, 4G2, and 4G3 collectively illustrate an example bioinformatics pipeline for precision oncology, in accordance with various embodiments of the present disclosure. Specifically, these figures provide a flow chart of a method for validating a somatic sequence variant in a test subject having a cancer condition, in which dashed boxes represent optional portions of the method, in accordance with some embodiments of the present disclosure.

FIGS. 5A and 5B collectively provide a flow chart of processes and features for validating a somatic sequence variant in a test subject having a cancer condition, in which dashed boxes represent optional portions of the method, in accordance with some embodiments of the present disclosure.

FIG. 6 illustrates a flow chart of a method for obtaining a distribution of variant detection sensitivities as a function of circulating variant allele fraction from a cohort of subjects, in accordance with some embodiments of the present disclosure.

FIG. 13 illustrates a first table describing sensitivity for all SNVs, indels, CNVs, and rearrangements targeted in reference samples, in accordance with various embodiments of the present disclosure.

FIG. 14 illustrates a second table describing sensitivity for all SNVs, indels, CNVs, and rearrangements targeted in reference samples, in accordance with various embodiments of the present disclosure.

FIG. 15 illustrates a third table describing comparisons between the presently disclosed liquid biopsy assay and a commercial liquid biopsy kit, in accordance with various embodiments of the present disclosure.

FIGS. 16A, 16B, and 16C collectively illustrate a fourth table describing variants detected by a liquid biopsy assay, in accordance with various embodiments of the present disclosure.

FIG. 17 illustrates a fifth table describing dynamic filtering methodology to further reduced discordance, in accordance with various embodiments of the present disclosure.

FIG. 18 illustrates a sixth table describing cancer groups included in clinical profiling analysis, in accordance with various embodiments of the present disclosure.

Like reference numerals refer to corresponding parts throughout the several views of the drawings.

DETAILED DESCRIPTION

Introduction

Figure 1A:
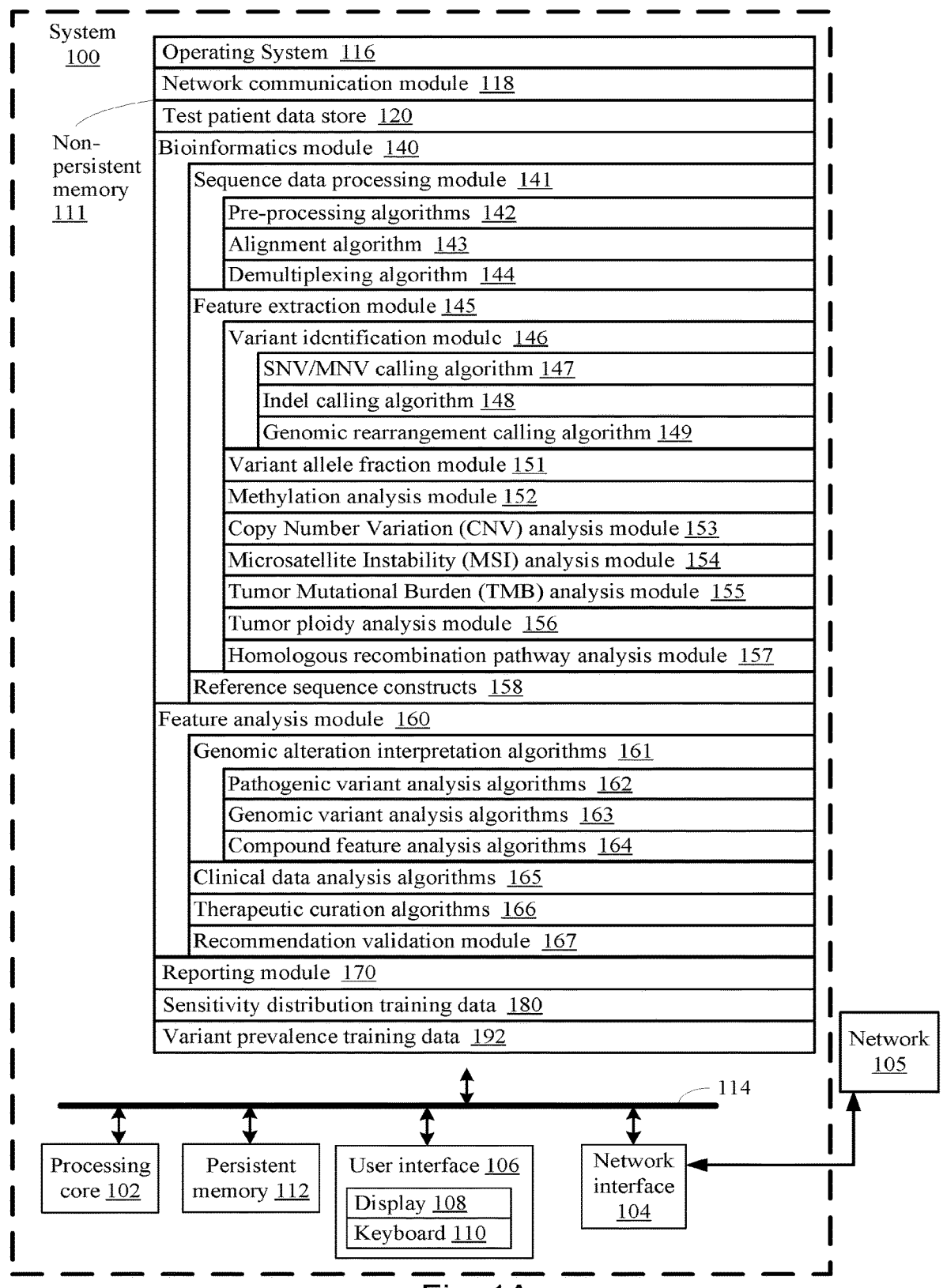

As described above, conventional liquid biopsy assays do not provide accurate determination of variants (e.g., somatic variants), particularly at low circulating variant fractions. This is due, in large part, to the use of static variant count filters that require a common amount of support to call a variant positively as a somatic variant in sequencing data, regardless of the identity of the variant and its position within the genome. That is, conventional methods require that at least X number of unique sequence reads (e.g., 8 sequence reads) provide support for (e.g., encompass) a particular variant in order for that variant to be confirmed as a true somatic variant. While this may be fine for liquid biopsy samples having a high tumor fraction, where more copies of each somatic variant would be expected to be found, it results in a high number of false negatives when samples with lower tumor fractions are analyzed. On the other hand, simply lowering the threshold to allow calling of variants with lower support for a particular variant will increase the number of false positives, that is the number of untrue positive somatic variant calls, which are actually sequencing errors.

While there are many methods of performing noise suppression on ultra-high depth sequencing data commonly generated for liquid biopsy assays, there remains the fundamental fidelity boundary of sequencing by synthesis that cannot be overcome. Along with this, there are a variety of complexities and non-linearities within the ability to map reads across complex sets of genomic features and from these data, successfully call a variant. While it is possible to filter very stringently, one of the goals of liquid biopsy assays is to detect alterations at very low circulating fractions. This requires that low levels of support be sufficient to make a positive alteration call given that at 0.1% circulating fraction and an average depth of 5000×, only 5 reads containing alternate alleles will be present. Because of this, it is impossible to have a consistent set of thresholds that will be used to filter variants as any filter will either be too stringent or too permissive depending on the variant context and local sequence specific error generation models.

Advantageously, the present disclosure provides methods and systems that more accurately call somatic variants by adjusting the variant count threshold in a locus-by-locus fashion, e.g., by lowering the variant count threshold when there is an increased likelihood (orthogonal to the variant count in the sequencing reaction) that a variant at a particular locus is a true somatic variant and/or by raising the variant count threshold when there is an increased likelihood (orthogonal to the variant count in the sequencing reaction) that a variant at a particular locus is a result of a sequencing error, rather than a true somatic variant.

For example, in some embodiments, the methods and systems described herein employ a generalized application of Bayes' Theorem through the likelihood ratio test that allows dynamic calibration of filtering threshold for diagnostic assays. These thresholds are based on one or more of a sample-specific error rate, a methodology-specific sequencing error rate (e.g., from a pool of process matched healthy control samples), an estimate of the variant allele fraction for the variant being evaluated, and a historical likelihood that a variant would be present at a particular locus in a particular cancer (e.g., derived from an extensive cohort of human solid tumor tissue samples to inform probability models). This results in high sensitivity and specificity in variant detection, allowing identification of actionable oncologic targets, as well as determination of a precise limit of detection to reduce the occurrence of false negatives.

For instance, in some embodiments, the dynamic variant filtering methodology described herein uses an application of Bayes theorem to dynamically tune a variant count threshold for calling a somatic variant at a particular genomic region based on the prevalence of similar mutations within that genomic regions in similar cancers. For instance, where there is a high prevalence of a somatic variant in a given gene for a particular cancer, (e.g., BRCA1 mutations are common in breast cancers), the dynamic filtering method accounts for this prior (e.g., the prior knowledge that BRCA mutations are commonly found in breast cancers) by setting a lower variant count threshold to call somatic variants in the BRCA1 gene for a breast cancer. That is, the dynamic filtering methodology requires less evidence in order to call a variant in the BRCA1 gene when the subject has breast cancer than when the subject has a different cancer that is not associated with a high prevalence of BRCA1 mutations.

In some embodiments, the dynamic variant filtering methodology described herein uses an application of Bayes theorem to dynamically tune a variant count threshold for calling a somatic variant based on an estimated variant allele fraction for the variant being evaluated. That is, the dynamic filtering methodology takes into account the fact that in a sample having a lower tumor fraction, and therefore a lower variant allele fraction, a fewer number of sequences encompassing a somatic variant would be expected than in a sample having a higher tumor fraction, and therefore a higher variant allele fraction. Accordingly, the sensitivity and specificity of the dynamic filter are tuned to account for the expectation that a higher percentage of variant sequences with low sequence counts (e.g., lower support) represent true somatic variants in a sample with a low tumor fraction than in a sample with a high tumor fraction, for which a higher percentage of variant sequences with low sequence counts represent sequencing errors.

In some embodiments, the dynamic variant filtering methodology described herein used an application of Bayes theorem to dynamically tune a variant count threshold for calling a somatic variant at a particular genomic locus based on a historical sequencing error rate for the locus. That is, the dynamic filtering methodology takes into account the fact that at genomic loci that are more prone to sequencing errors, such as loci with short nucleotide repeat sequences (e.g., di-nucleotide or tri-nucleotide repeats), there is a higher likelihood that a particular variant is a product of a sequencing error, rather than a true somatic mutation, than at a locus that is not prone to sequencing errors.

Similarly, in some embodiments, the dynamic variant filtering methodology described herein used an application of Bayes theorem to dynamically tune a variant count threshold for calling a somatic variant at a particular genomic locus based on a reaction-specific sequencing error rate. That is, the dynamic filtering methodology takes into account the fact that in reactions with higher sequencing rates there is a higher likelihood that a particular variant is a product of a sequencing error, rather than a true somatic mutation.

The present disclosure provides improved systems and methods for precision oncology based on improved variant calling in liquid biopsy data. The various improvements described herein, e.g., improved variant detection at low circulating fractions, are embodied in an example liquid biopsy workflow described in Examples 2 and 3. These examples describe an example liquid biopsy assay employing a 105-gene hybrid-capture next-generation sequencing (NGS) panel spanning 270 kb of the human genome, configured to detect targets in four variant classes, including single nucleotide variants (SNVs), insertions and/or deletions (indels), copy number variants (CNVs), and gene rearrangements. To establish robust clinical performance, extensive validation studies were conducted that demonstrated high sensitivity and specificity. Accordingly, the example liquid biopsy assay detected actionable variants with high accuracy in comparison to a commercial ctDNA NGS kit, commercial solid tumor biopsy-based assays, such as a solid tumor biopsy NGS tissue assay, and digital droplet PCR (ddPCR). As shown in the results of FIG. 17, the methods and systems disclosed herein reduced false positive variant calling by 11.45% compared to conventional variant detection methods.

The identification of actionable genomic alterations in a patient's cancer genome is a difficult and computationally demanding problem. For instance, the determination of various prognostic metrics useful for precision oncology, such as variant allelic ratio, copy number variation, tumor mutational burden, microsatellite instability status, etc., requires analysis of hundreds of millions to billions, of sequenced nucleic acid bases. An example of a typical bioinformatics pipeline established for this purpose includes at least five stages of analysis: assessment of the quality of raw next generation sequencing data, generation of collapsed nucleic acid fragment sequences and alignment of such sequences to a reference genome, detection of structural variants in the aligned sequence data, annotation of identified variants, and visualization of the data. See, Wadapurkar and Vyas, Informatics in Medicine Unlocked, 11:75-82 (2018), the content of which is hereby incorporated by reference, in its entirety, for all purposes. Each one of these procedures is computationally taxing in its own right.

For instance, the overall temporal and spatial computation complexity of simple global and local pairwise sequence alignment algorithms are quadratic in nature (e.g., second order problems), that increase rapidly as a function of the size of the nucleic acid sequences (n and m) being compared. Specifically, the temporal and spatial complexities of these sequence alignment algorithms can be estimated as O(mn), where O is the upper bound on the asymptotic growth rate of the algorithm, n is the number of bases in the first nucleic acid sequence, and m is the number of bases in the second nucleic acid sequence. See, Baichoo and Ouzounis, BioSystems, 156-157:72-85 (2017), the content of which is hereby incorporated by reference, in its entirety, for all purposes. Given that the human genome contains more than 3 billion bases, these alignment algorithms are extremely computationally taxing, especially when used to analyze next generation sequencing (NGS) data, which can generate more than 3 billion sequence reads per reaction.

This is particularly true when performed in the context of a liquid biopsy assay, because liquid biopsy samples contain a complex mixture of short DNA fragments originating from many different germline (e.g., healthy) and diseased (e.g., cancerous) tissues. Thus, the cellular origins of the sequence reads are unknown, and the sequence signals originating from cancerous cells, which may constitute multiple sub-clonal populations, must be computationally deconvoluted from signals originating from germline and hematopoietic origins, in order to provide relevant information about the subject's cancer. Thus, in addition to the computationally taxing processes required to align sequence reads to a human genome, there is a computation problem of determining whether a particular abnormal signal, e.g., one or more sequence reads corresponding to a genomic alteration, (i) is not an artifact, and (ii) originated from a cancerous source in the subject. This is increasingly difficult during the early stages of cancer—when treatment is presumably most effective—when only small amounts of ctDNA are diluted by germline and hematopoietic DNA.

Advantageously, the present disclosure provides various systems and methods that improve the computational elucidation of actionable genomic alterations from a liquid biopsy sample of a cancer patient. Specifically, the present disclosure improves a method for identifying variants in ctDNA using a dynamic thresholding approach. As described above, the disclosed methods and systems are necessarily computer-implemented due to their complexity and heavy computational requirements, and thus solve a problem in the computing art.

Advantageously, the methods and systems described herein provide an improvement to the abovementioned technical problem (e.g., performing complex computer-implemented methods for identifying variants in ctDNA using a dynamic thresholding approach). The methods described herein therefore solve a problem in the computing art by improving upon conventional methods for identifying variants (e.g., actionable oncologic targets) for cancer diagnosis and treatment. For example, the application of Bayes' Theorem through the likelihood ratio test provides a means for improving detection of true positive variants and reducing detection of false positive variants for clinically relevant biomarkers, thus improving the accuracy and precision of genomic alteration detection in precision oncology.

The methods and systems described herein also improve precision oncology methods for assigning and/or administering treatment because of the improved accuracy of variation detection. The identification of therapeutically actionable variants that can be included in a clinical report for patient and/or clinician review, and/or matched with appropriate therapies and/or clinical trials for treatment and/or monitoring, allows for more accurate assignment of treatments. Furthermore, the removal of false positive variant detection reduces the risk of patients undergoing unnecessary or potentially harmful regimens due to misdiagnoses.

Definitions

As used herein, the term "subject" refers to any living or non-living organism including, but not limited to, a human (e.g., a male human, female human, fetus, pregnant female, child, or the like), a non-human mammal, or a non-human animal. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. In some embodiments, a subject is a male or female of any age (e.g., a man, a woman, or a child).

As used herein, the terms "control," "control sample," "reference," "reference sample," "normal," and "normal sample" describe a sample from a non-diseased tissue. In some embodiments, such a sample is from a subject that does not have a particular condition (e.g., cancer). In other embodiments, such a sample is an internal control from a subject, e.g., who may or may not have the particular disease (e.g., cancer), but is from a healthy tissue of the subject. For example, where a liquid or solid tumor sample is obtained from a subject with cancer, an internal control sample may be obtained from a healthy tissue of the subject, e.g., a white blood cell sample from a subject without a blood cancer or a solid germline tissue sample from the subject. Accordingly, a reference sample can be obtained from the subject or from a database, e.g., from a second subject who does not have the particular disease (e.g., cancer).

As used herein the term "cancer," "cancerous tissue," or "tumor" refers to an abnormal mass of tissue in which the growth of the mass surpasses, and is not coordinated with, the growth of normal tissue, including both solid masses (e.g., as in a solid tumor) or fluid masses (e.g., as in a hematological cancer). A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" refers to a biological sample obtained or derived from a tumor of a subject, as described herein.

Non-limiting examples of cancer types include ovarian cancer, cervical cancer, uveal melanoma, colorectal cancer, chromophobe renal cell carcinoma, liver cancer, endocrine tumor, oropharyngeal cancer, retinoblastoma, biliary cancer, adrenal cancer, neural cancer, neuroblastoma, basal cell carcinoma, brain cancer, breast cancer, non-clear cell renal cell carcinoma, glioblastoma, glioma, kidney cancer, gastrointestinal stromal tumor, medulloblastoma, bladder cancer, gastric cancer, bone cancer, non-small cell lung cancer, thymoma, prostate cancer, clear cell renal cell carcinoma, skin cancer, thyroid cancer, sarcoma, testicular cancer, head and neck cancer (e.g., head and neck squamous cell carcinoma), meningioma, peritoneal cancer, endometrial cancer, pancreatic cancer, mesothelioma, esophageal cancer, small cell lung cancer, Her2 negative breast cancer, ovarian serous carcinoma, HR+ breast cancer, uterine serous carcinoma, uterine corpus endometrial carcinoma, gastroesophageal junction adenocarcinoma, gallbladder cancer, chordoma, and papillary renal cell carcinoma.

As used herein, the terms "cancer state" or "cancer condition" refer to a characteristic of a cancer patient's condition, e.g., a diagnostic status, a type of cancer, a location of cancer, a primary origin of a cancer, a cancer stage, a cancer prognosis, and/or one or more additional characteristics of a cancer (e.g., tumor characteristics such as morphology, heterogeneity, size, etc.). In some embodiments, one or more additional personal characteristics of the subject are used further describe the cancer state or cancer condition of the subject, e.g., age, gender, weight, race, personal habits (e.g., smoking, drinking, diet), other pertinent medical conditions (e.g., high blood pressure, dry skin, other diseases), current medications, allergies, pertinent medical history, current side effects of cancer treatments and other medications, etc.

As used herein, the term "liquid biopsy" sample refers to a liquid sample obtained from a subject that includes cell-free DNA. Examples of liquid biopsy samples include, but are not limited to, blood, whole blood, plasma, serum, urine, cerebrospinal fluid, fecal material, saliva, sweat, tears, pleural fluid, pericardial fluid, or peritoneal fluid of the subject. In some embodiments, a liquid biopsy sample is a cell-free sample, e.g., a cell free blood sample. In some embodiments, a liquid biopsy sample is obtained from a subject with cancer. In some embodiments, a liquid biopsy sample is collected from a subject with an unknown cancer status, e.g., for use in determining a cancer status of the subject. Likewise, in some embodiments, a liquid biopsy is collected from a subject with a non-cancerous disorder, e.g., a cardiovascular disease. In some embodiments, a liquid biopsy is collected from a subject with an unknown status for a non-cancerous disorder, e.g., for use in determining a non-cancerous disorder status of the subject.

As used herein, the term "cell-free DNA" and "cfDNA" interchangeably refer to DNA fragments that circulate in a subject's body (e.g., bloodstream) and originate from one or more healthy cells and/or from one or more cancer cells. These DNA molecules are found outside cells, in bodily fluids such as blood, whole blood, plasma, serum, urine, cerebrospinal fluid, fecal material, saliva, sweat, sweat, tears, pleural fluid, pericardial fluid, or peritoneal fluid of a subject, and are believed to be fragments of genomic DNA expelled from healthy and/or cancerous cells, e.g., upon apoptosis and lysis of the cellular envelope.

As used herein, the term "locus" refers to a position (e.g., a site) within a genome, e.g., on a particular chromosome. In some embodiments, a locus refers to a single nucleotide position, on a particular chromosome, within a genome. In some embodiments, a locus refers to a group of nucleotide positions within a genome. In some instances, a locus is defined by a mutation (e.g., substitution, insertion, deletion, inversion, or translocation) of consecutive nucleotides within a cancer genome. In some instances, a locus is defined by a gene, a sub-genic structure (e.g., a regulatory element, exon, intron, or combination thereof), or a pre-defined span of a chromosome. Because normal mammalian cells have diploid genomes, a normal mammalian genome (e.g., a human genome) will generally have two copies of every locus in the genome, or at least two copies of every locus located on the autosomal chromosomes, e.g., one copy on the maternal autosomal chromosome and one copy on the paternal autosomal chromosome.

As used herein, the term "allele" refers to a particular sequence of one or more nucleotides at a chromosomal locus. In a haploid organism, the subject has one allele at every chromosomal locus. In a diploid organism, the subject has two alleles at every chromosomal locus.

As used herein, the term "base pair" or "bp" refers to a unit consisting of two nucleobases bound to each other by hydrogen bonds. Generally, the size of an organism's genome is measured in base pairs because DNA is typically double stranded. However, some viruses have single-stranded DNA or RNA genomes.

As used herein, the terms "genomic alteration," "mutation," and "variant" refer to a detectable change in the genetic material of one or more cells. A genomic alteration, mutation, or variant can refer to various type of changes in the genetic material of a cell, including changes in the primary genome sequence at single or multiple nucleotide positions, e.g., a single nucleotide variant (SNV), a multi-nucleotide variant (MNV), an indel (e.g., an insertion or deletion of nucleotides), a DNA rearrangement (e.g., an inversion or translocation of a portion of a chromosome or chromosomes), a variation in the copy number of a locus (e.g., an exon, gene, or a large span of a chromosome) (CNV), a partial or complete change in the ploidy of the cell, as well as in changes in the epigenetic information of a genome, such as altered DNA methylation patterns. In some embodiments, a mutation is a change in the genetic information of the cell relative to a particular reference genome, or one or more 'normal' alleles found in the population of the species of the subject. For instance, mutations can be found in both germline cells (e.g., non-cancerous, 'normal' cells) of a subject and in abnormal cells (e.g., pre-cancerous or cancerous cells) of the subject. As such, a mutation in a germline of the subject (e.g., which is found in substantially all 'normal cells' in the subject) is identified relative to a reference genome for the species of the subject. However, many loci of a reference genome of a species are associated with several variant alleles that are significantly represented in the population of the subject and are not associated with a diseased state, e.g., such that they would not be considered 'mutations.' By contrast, in some embodiments, a mutation in a cancerous cell of a subject can be identified relative to either a reference genome of the subject or to the subject's own germline genome. In certain instances, identification of both types of variants can be informative. For instance, in some instances, a mutation that is present in both the cancer genome of the subject and the germline of the subject is informative for precision oncology when the mutation is a so-called 'driver mutation,' which contributes to the initiation and/or development of a cancer. However, in other instances, a mutation that is present in both the cancer genome of the subject and the germline of the subject is not informative for precision oncology, e.g., when the mutation is a so-called 'passenger mutation,' which does not contribute to the initiation and/or development of the cancer. Likewise, in some instances, a mutation that is present in the cancer genome of the subject but not the germline of the subject is informative for precision oncology, e.g., where the mutation is a driver mutation and/or the mutation facilitates a therapeutic approach, e.g., by differentiating cancer cells from normal cells in a therapeutically actionable way. However, in some instances, a mutation that is present in the cancer genome but not the germline of a subject is not informative for precision oncology, e.g., where the mutation is a passenger mutation and/or where the mutation fails to differentiate the cancer cell from a germline cell in a therapeutically actionable way.

As used herein, the term "reference allele" refers to the sequence of one or more nucleotides at a chromosomal locus that is either the predominant allele represented at that chromosomal locus within the population of the species (e.g., the "wild-type" sequence), or an allele that is predefined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference sequence construct (e.g., a reference genome or set of reference genomes) for the species. In some instances, sequence isoforms found within the population of a species that do not affect a change in a protein encoded by the genome, or that result in an amino acid substitution that does not substantially affect the function of an encoded protein, are not variant alleles.

As used herein, the term "variant allele fraction," "VAF," "allelic fraction," or "AF" refers to the number of times a variant or mutant allele was observed (e.g., a number of reads supporting a candidate variant allele) divided by the total number of times the position was sequenced (e.g., a total number of reads covering a candidate locus).

As used herein, the terms "variant fragment count" and "variant allele fragment count" interchangeably refer to a quantification, e.g., a raw or normalized count, of the number of sequences representing unique cell-free DNA fragments encompassing a variant allele in a sequencing reaction. That is, a variant fragment count represents a count of sequence reads representing unique molecules in the liquid biopsy sample, after duplicate sequence reads in the raw sequencing data have been collapsed, e.g., through the use of unique molecular indices (UMI) and bagging, etc. as described herein.

As used herein, the term "germline variants" refers to genetic variants inherited from maternal and paternal DNA. Germline variants may be determined through a matched tumor-normal calling pipeline.

As used herein, the term "somatic variants" refers to variants arising as a result of dysregulated cellular processes associated with neoplastic cells, e.g., a mutation. Somatic variants may be detected via subtraction from a matched normal sample.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "insertions and deletions" or "indels" refers to a variant resulting from the gain or loss of DNA base pairs within an analyzed region.

As used herein, the term "copy number variation" or "CNV" refers to the process by which large structural changes in a genome associated with tumor aneuploidy and other dysregulated repair systems are detected. These processes are used to detect large scale insertions or deletions of entire genomic regions. CNV is defined as structural insertions or deletions greater than a certain base pair ("bp") in size, such as 500 bp.

As used herein, the term "gene fusion" refers to the product of large-scale chromosomal aberrations resulting in the creation of a chimeric protein. These expressed products can be non-functional, or they can be highly over or underactive. This can cause deleterious effects in cancer such as hyper-proliferative or anti-apoptotic phenotypes.

As used herein, the term "loss of heterozygosity" refers to the loss of one copy of a segment (e.g., including part or all of one or more genes) of the genome of a diploid subject (e.g., a human) or loss of one copy of a sequence encoding a functional gene product in the genome of the diploid subject, in a tissue, e.g., a cancerous tissue, of the subject. As used herein, when referring to a metric representing loss of heterozygosity across the entire genome of the subject, loss of heterozygosity is caused by the loss of one copy of various segments in the genome of the subject. Loss of heterozygosity across the entire genome may be estimated without sequencing the entire genome of a subject, and such methods for such estimations based on gene panel targeting-based sequencing methodologies are described in the art. Accordingly, in some embodiments, a metric representing loss of heterozygosity across the entire genome of a tissue of a subject is represented as a single value, e.g., a percentage or fraction of the genome. In some cases, a tumor is composed of various sub-clonal populations, each of which may have a different degree of loss of heterozygosity across their respective genomes. Accordingly, in some embodiments, loss of heterozygosity across the entire genome of a cancerous tissue refers to an average loss of heterozygosity across a heterogeneous tumor population. As used herein, when referring to a metric for loss of heterozygosity in a particular gene, e.g., a DNA repair protein such as a protein involved in the homologous DNA recombination pathway (e.g., BRCA1 or BRCA2), loss of heterozygosity refers to complete or partial loss of one copy of the gene encoding the protein in the genome of the tissue and/or a mutation in one copy of the gene that prevents translation of a full-length gene product, e.g., a frameshift or truncating (creating a premature stop codon in the gene) mutation in the gene of interest. In some cases, a tumor is composed of various sub-clonal populations, each of which may have a different mutational status in a gene of interest. Accordingly, in some embodiments, loss of heterozygosity for a particular gene of interest is represented by an average value for loss of heterozygosity for the gene across all sequenced sub-clonal populations of the cancerous tissue. In other embodiments, loss of heterozygosity for a particular gene of interest is represented by a count of the number of unique incidences of loss of heterozygosity in the gene of interest across all sequenced sub-clonal populations of the cancerous tissue (e.g., the number of unique frame-shift and/or truncating mutations in the gene identified in the sequencing data).

As used herein, the term "microsatellites" refers to short, repeated sequences of DNA. The smallest nucleotide repeated unit of a microsatellite is referred to as the "repeated unit" or "repeat unit." In some embodiments, the stability of a microsatellite locus is evaluated by comparing some metric of the distribution of the number of repeated units at a microsatellite locus to a reference number or distribution.

As used herein, the term "microsatellite instability" or "MSI" refers to a genetic hypermutability condition associated with various cancers that results from impaired DNA mismatch repair (MMR) in a subject. Among other phenotypes, MSI causes changes in the size of microsatellite loci, e.g., a change in the number of repeated units at microsatellite loci, during DNA replication. Accordingly, the size of microsatellite repeats is varied in MSI cancers as compared to the size of the corresponding microsatellite repeats in the germline of a cancer subject. The term "Microsatellite Instability-High" or "MSI-H" refers to a state of a cancer (e.g., a tumor) that has a significant MMR defect, resulting in microsatellite loci with significantly different lengths than the corresponding microsatellite loci in normal cells of the same individual. The term "Microsatellite Stable" or "MSS" refers to a state of a cancer (e.g., a tumor) without significant MMR defects, such that there is no significant difference between the lengths of the microsatellite loci in cancerous cells and the lengths of the corresponding microsatellite loci in normal (e.g., non-cancerous) cells in the same individual. The term "Microsatellite Equivocal" or "MSE" refers to a state of a cancer (e.g., a tumor) having an intermediate microsatellite length phenotype, that cannot be clearly classified as MSI-H or MSS based on statistical cutoffs used to define those two categories.

As used herein, the term "gene product" refers to an RNA (e.g., mRNA or miRNA) or protein molecule transcribed or translated from a particular genomic locus, e.g., a particular gene. The genomic locus can be identified using a gene name, a chromosomal location, or any other genetic mapping metric.

As used herein, the term "ratio" refers to any comparison of a first metric X, or a first mathematical transformation thereof X' (e.g., measurement of a number of units of a genomic sequence in a first one or more biological samples or a first mathematical transformation thereof) to another metric Y or a second mathematical transformation thereof Y' (e.g., the number of units of a respective genomic sequence in a second one or more biological samples or a second mathematical transformation thereof) expressed as X/Y, Y/X, $\log_N(X/Y)$, $\log_N(Y/X)$, X'/Y, Y/X', $\log_N(X'/Y)$, or $\log_N(Y/X')$, X/Y', Y'/X, $\log_N(X/Y')$, $\log_N(Y'/X)$, X'/Y', Y'/X', $\log_N(X'/Y')$, or $\log_N(Y'/X')$, where N is any real number greater than 1 and where example mathematical transformations of X and Y include, but are not limited to raising X or Y to a power Z, multiplying X or Y by a constant Q, where Z and Q are any real numbers, and/or taking an M based logarithm of X and/or Y, where M is a real number greater than 1. In one non-limiting example, X is transformed to X' prior to ratio calculation by raising X by the power of two ($X^2$) and Y is transformed to Y' prior to ratio calculation by raising Y by the power of 3.2 ($Y^{3.2}$) and the ratio of X and Y is computed as $\log_2(X'/Y')$.

As used herein, the terms "expression level," "abundance level," or simply "abundance" refers to an amount of a gene product, (an RNA species, e.g., mRNA or miRNA, or protein molecule) transcribed or translated by a cell, or an average amount of a gene product transcribed or translated across multiple cells. When referring to mRNA or protein expression, the term generally refers to the amount of any RNA or protein species corresponding to a particular genomic locus, e.g., a particular gene. However, in some embodiments, an expression level can refer to the amount of a particular isoform of an mRNA or protein corresponding to a particular gene that gives rise to multiple mRNA or protein isoforms. The genomic locus can be identified using a gene name, a chromosomal location, or any other genetic mapping metric.

As used herein, the term "relative abundance" refers to a ratio of a first amount of a compound measured in a sample, e.g., a gene product (an RNA species, e.g., mRNA or miRNA, or protein molecule) or nucleic acid fragments having a particular characteristic (e.g., aligning to a particular locus or encompassing a particular allele), to a second amount of a compound measured in a second sample. In some embodiments, relative abundance refers to a ratio of an amount of species of a compound to a total amount of the compound in the same sample. For instance, a ratio of the amount of mRNA transcripts encoding a particular gene in a sample (e.g., aligning to a particular region of the exome) to the total amount of mRNA transcripts in the sample. In other embodiments, relative abundance refers to a ratio of an amount of a compound or species of a compound in a first sample to an amount of the compound of the species of the compound in a second sample. For instance, a ratio of a normalized amount of mRNA transcripts encoding a particular gene in a first sample to a normalized amount of mRNA transcripts encoding the particular gene in a second and/or reference sample.

As used herein, the terms "sequencing," "sequence determination," and the like refer to any biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "genetic sequence" refers to a recordation of a series of nucleotides present in a subject's RNA or DNA as determined by sequencing of nucleic acids from the subject.

As used herein, the term "sequence reads" or "reads" refers to nucleotide sequences produced by any nucleic acid sequencing process described herein or known in the art. Reads can be generated from one end of nucleic acid fragments ("single-end reads") or from both ends of nucleic acid fragments (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore® sequencing, for example, can provide sequence reads that can vary in size from tens to hundreds to thousands of base pairs. Illumina® parallel sequencing, for example, can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the term "read segment" refers to any form of nucleotide sequence read including the raw sequence reads obtained directly from a nucleic acid sequencing technique or from a sequence derived therefrom, e.g., an aligned sequence read, a collapsed sequence read, or a stitched sequence read.

As used herein, the term "read count" refers to the total number of nucleic acid reads generated, which may or may not be equivalent to the number of nucleic acid molecules generated, during a nucleic acid sequencing reaction.

As used herein, the term "read-depth," "sequencing depth," or "depth" can refer to a total number of unique nucleic acid fragments encompassing a particular locus or region of the genome of a subject that are sequenced in a particular sequencing reaction. Sequencing depth can be expressed as "Y×", e.g., 50×, 100×, etc., where "Y" refers to the number of unique nucleic acid fragments encompassing a particular locus that are sequenced in a sequencing reaction. In such a case, Y is necessarily an integer, because it represents the actual sequencing depth for a particular locus. Alternatively, read-depth, sequencing depth, or depth can refer to a measure of central tendency (e.g., a mean or mode) of the number of unique nucleic acid fragments that encompass one of a plurality of loci or regions of the genome of a subject that are sequenced in a particular sequencing reaction. For example, in some embodiments, sequencing depth refers to the average depth of every locus across an arm of a chromosome, a targeted sequencing panel, an exome, or an entire genome. In such case, Y may be expressed as a fraction or a decimal, because it refers to an average coverage across a plurality of loci. When a mean depth is recited, the actual depth for any particular locus may be different than the overall recited depth. Metrics can be determined that provide a range of sequencing depths in which a defined percentage of the total number of loci fall. For instance, a range of sequencing depths within which 90% or 95%, or 99% of the loci fall. As understood by the skilled artisan, different sequencing technologies provide different sequencing depths. For instance, low-pass whole genome sequencing can refer to technologies that provide a sequencing depth of less than 5×, less than 4×, less than 3×, or less than 2×, e.g., from about 0.5× to about 3×.

As used herein, the term "sequencing breadth" refers to what fraction of a particular reference exome (e.g., human reference exome), a particular reference genome (e.g., human reference genome), or part of the exome or genome has been analyzed. Sequencing breadth can be expressed as a fraction, a decimal, or a percentage, and is generally calculated as (the number of loci analyzed/the total number of loci in a reference exome or reference genome). The denominator of the fraction can be a repeat-masked genome, and thus 100% can correspond to all of the reference genome minus the masked parts. A repeat-masked exome or genome can refer to an exome or genome in which sequence repeats are masked (e.g., sequence reads align to unmasked portions of the exome or genome). In some embodiments, any part of an exome or genome can be masked and, thus, sequencing breadth can be evaluated for any desired portion of a reference exome or genome. In some embodiments, "broad sequencing" refers to sequencing/analysis of at least 0.1% of an exome or genome.

As used herein, the term "sequencing probe" refers to a molecule that binds to a nucleic acid with affinity that is based on the expected nucleotide sequence of the RNA or DNA present at that locus.

As used herein, the term "targeted panel" or "targeted gene panel" refers to a combination of probes for sequencing (e.g., by next-generation sequencing) nucleic acids present in a biological sample from a subject (e.g., a tumor sample, liquid biopsy sample, germline tissue sample, white blood cell sample, or tumor or tissue organoid sample), selected to map to one or more loci of interest on one or more chromosomes. An example set of loci/genes useful for precision oncology, e.g., via solid or liquid biopsy assay, that can be analyzed using a targeted panel is described in Table 1. In some embodiments, in addition to loci that are informative for precision oncology, a targeted panel includes one or more probes for sequencing one or more of a loci associated with a different medical condition, a loci used for internal control purposes, or a loci from a pathogenic organism (e.g., an oncogenic pathogen).

As used herein, the term, "reference exome" refers to any sequenced or otherwise characterized exome, whether partial or complete, of any tissue from any organism or pathogen that may be used to reference identified sequences from a subject. Typically, a reference exome will be derived from a subject of the same species as the subject whose sequences are being evaluated. Example reference exomes used for human subjects as well as many other organisms are provided in the on-line genome browser hosted by the National Center for Biotechnology Information ("NCBI"). An "exome" refers to the complete transcriptional profile of an organism or pathogen, expressed in nucleic acid sequences. As used herein, a reference sequence or reference exome often is an assembled or partially assembled exomic sequence from an individual or multiple individuals. In some embodiments, a reference exome is an assembled or partially assembled exomic sequence from one or more human individuals. The reference exome can be viewed as a representative example of a species' set of expressed genes. In some embodiments, a reference exome comprises sequences assigned to chromosomes.

As used herein, the term "reference genome" refers to any sequenced or otherwise characterized genome, whether partial or complete, of any organism or pathogen that may be used to reference identified sequences from a subject. Typically, a reference genome will be derived from a subject of the same species as the subject whose sequences are being evaluated. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38). For a haploid genome, there can be only one nucleotide at each locus. For a diploid genome, heterozygous loci can be identified; each heterozygous locus can have two alleles, where either allele can allow a match for alignment to the locus.

As used herein, the term "bioinformatics pipeline" refers to a series of processing stages used to determine characteristics of a subject's genome or exome based on sequencing data of the subject's genome or exome. A bioinformatics pipeline may be used to determine characteristics of a germline genome or exome of a subject and/or a cancer genome or exome of a subject. In some embodiments, the pipeline extracts information related to genomic alterations in the cancer genome of a subject, which is useful for guiding clinical decisions for precision oncology, from sequencing results of a biological sample, e.g., a tumor sample, liquid biopsy sample, reference normal sample, etc., from the subject. Certain processing stages in a bioinformatics may be 'connected,' meaning that the results of a first respective processing stage are informative and/or essential for execution of a second, downstream processing stage. For instance, in some embodiments, a bioinformatics pipeline includes a first respective processing stage for identifying genomic alterations that are unique to the cancer genome of a subject and a second respective processing stage that uses the quantity and/or identity of the identified genomic alterations to determine a metric that is informative for precision oncology, e.g., a tumor mutational burden. In some embodiments, the bioinformatics pipeline includes a reporting stage that generates a report of relevant and/or actionable information identified by upstream stages of the pipeline, which may or may not further include recommendations for aiding clinical therapy decisions.

As used herein, the term "limit of detection" or "LOD" refers to the minimal quantity of a feature that can be identified with a particular level of confidence. Accordingly, level of detection can be used to describe an amount of a substance that must be present in order for a particular assay to reliably detect the substance. A level of detection can also be used to describe a level of support needed for an algorithm to reliably identify a genomic alteration based on sequencing data. For example, a minimal number of unique sequence reads to support identification of a sequence variant such as a SNV.

As used herein, the term "BAM File" or "Binary file containing Alignment Maps" refers to a file storing sequencing data aligned to a reference sequence (e.g., a reference genome or exome). In some embodiments, a BAM file is a compressed binary version of a SAM (Sequence Alignment Map) file that includes, for each of a plurality of unique sequence reads, an identifier for the sequence read, information about the nucleotide sequence, information about the alignment of the sequence to a reference sequence, and optionally metrics relating to the quality of the sequence read and/or the quality of the sequence alignment. While BAM files generally relate to files having a particular format, for simplicity they are used herein to simply refer to a file, of any format, containing information about a sequence alignment, unless specifically stated otherwise.

As used herein, the term "measure of central tendency" refers to a central or representative value for a distribution of values. Non-limiting examples of measures of central tendency include an arithmetic mean, weighted mean, midrange, midhinge, trimean, geometric mean, geometric median, Winsorized mean, median, and mode of the distribution of values.

As used herein, the term "Positive Predictive Value" or "PPV" means the likelihood that a variant is properly called given that a variant has been called by an assay. PPV can be expressed as (number of true positives)/(number of false positives+number of true positives).

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

As used herein, the term "classification" can refer to any number(s) or other characters(s) that are associated with a particular property of a sample. For example, in some embodiments, the term "classification" can refer to a type of cancer in a subject, a stage of cancer in a subject, a prognosis for a cancer in a subject, a tumor load, a presence of tumor metastasis in a subject, and the like. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

As used herein, the term "sensitivity" or "true positive rate" (TPR) refers to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "specificity" or "true negative rate" (TNR) refers to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity characterizes the ability of a method to correctly identify one or more markers indicative of cancer.

As used herein, an "actionable genomic alteration" or "actionable variant" refers to a genomic alteration (e.g., a SNV, MNV, indel, rearrangement, copy number variation, or ploidy variation), or value of another cancer metric derived from nucleic acid sequencing data (e.g., a tumor mutational burden, MSI status, or tumor fraction), that is known or believed to be associated with a therapeutic course of action that is more likely to produce a positive effect in a cancer patient that has the actionable variant than in a similarly situated cancer patient that does not have the actionable variant. For instance, administration of EGFR inhibitors (e.g., afatinib, erlotinib, gefitinib) is more effective for treating non-small cell lung cancer in patients with an EGFR mutation in exons 19/21 than for treating non-small cell lung cancer in patients that do not have an EGFR mutations in exons 19/21. Accordingly, an EGFR mutation in exon 19/21 is an actionable variant. In some instances, an actionable variant is only associated with an improved treatment outcome in one or a group of specific cancer types. In other instances, an actionable variant is associated with an improved treatment outcome in substantially all cancer types.

As used herein, a "variant of uncertain significance" or "VUS" refers to a genomic alteration (e.g., a SNV, MNV, indel, rearrangement, copy number variation, or ploidy variation), or value of another cancer metric derived from nucleic acid sequencing data (e.g., a tumor mutational burden, MSI status, or tumor fraction), whose impact on disease development/progression is unknown.

As used herein, a "benign variant" or "likely benign variant" refers to a genomic alteration (e.g., a SNV, MNV, indel, rearrangement, copy number variation, or ploidy variation), or value of another cancer metric derived from nucleic acid sequencing data (e.g., a tumor mutational burden, MSI status, or tumor fraction), that is known or believed to not contribute to disease development/progression.

As used herein, a "pathogenic variant" or "likely pathogenic variant" refers to a genomic alteration (e.g., a SNV, MNV, indel, rearrangement, copy number variation, or ploidy variation), or value of another cancer metric derived from nucleic acid sequencing data (e.g., a tumor mutational burden, MSI status, or tumor fraction), that is known or believed to contribute to disease development/progression.

As used herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the therapeutic agent being administered.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

Reference will now be made in detail to embodiments, examples of which are illustrated in the accompanying drawings. In the following detailed description, numerous specific details are set forth in order to provide a thorough understanding of the present disclosure, including example systems, methods, techniques, instruction sequences, and computing machine program products that embody illustrative implementations. However, the illustrative discussions below are not intended to be exhaustive or to limit the implementations to the precise forms disclosed. Many modifications and variations are possible in view of the above teachings. The features described herein are not limited by the illustrated ordering of acts or events, as some acts can occur in different orders and/or concurrently with other acts or events.

The implementations provided herein are chosen and described in order to best explain the principles and their practical applications, to thereby enable others skilled in the art to best utilize the various embodiments with various modifications as are suited to the particular use contemplated. In some instances, well-known methods, procedures, components, circuits, and networks have not been described in detail so as not to unnecessarily obscure aspects of the embodiments. In other instances, it will be apparent to one of ordinary skill in the art that the present disclosure may be practiced without one or more of the specific details.

It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that though such a design effort might be complex and time-consuming, it will nevertheless be a routine undertaking of engineering for those of ordering skill in the art having the benefit of the present disclosure.

Example System Embodiments

Now that an overview of some aspects of the present disclosure and some definitions used in the present disclosure have been provided, details of an exemplary system for providing clinical support for personalized cancer therapy using a liquid biopsy assay are now described in conjunction with FIGS. 1A-1D. FIGS. 1A-1D collectively illustrate the topology of an example system for providing clinical support for personalized cancer therapy using a liquid biopsy assay, in accordance with some embodiments of the present disclosure. Advantageously, the example system illustrated in FIGS. 1A-1D improves upon conventional methods for providing clinical support for personalized cancer therapy by validating a somatic sequence variant in a test subject having a cancer condition.

FIG. 1A is a block diagram illustrating a system in accordance with some implementations. The device 100 in some implementations includes one or more processing units CPU(s) 102 (also referred to as processors), one or more network interfaces 104, a user interface 106, e.g., including a display 108 and/or an input 110 (e.g., a mouse, touchpad, keyboard, etc.), a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an operating system 116, which includes procedures for handling various basic system services and for performing hardware dependent tasks;
- a network communication module (or instructions) 118 for connecting the system 100 with other devices and/or a communication network 105;
- a test patient data store 120 for storing one or more collections of features from patients (e.g., subjects);
- a bioinformatics module 140 for processing sequencing data and extracting features from sequencing data, e.g., from liquid biopsy sequencing assays;
- a feature analysis module 160 for evaluating patient features, e.g., genomic alterations, compound genomic features, and clinical features; and
- a reporting module 180 for generating and transmitting reports that provide clinical support for personalized cancer therapy.

Although FIGS. 1A-1D depict a "system 100," the figures are intended more as a functional description of the various features that may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112. For example, in various implementations, one or more of the above identified elements are stored in one or more of the previously mentioned memory devices and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations.

In some implementations, the non-persistent memory 111 optionally stores a subset of the modules and data structures identified above. Furthermore, in some embodiments, the memory stores additional modules and data structures not described above. In some embodiments, one or more of the above-identified elements is stored in a computer system, other than that of system 100, that is addressable by system 100 so that system 100 may retrieve all or a portion of such data when needed.

For purposes of illustration in FIG. 1A, system 100 is represented as a single computer that includes all of the functionality for providing clinical support for personalized cancer therapy. However, while a single machine is illustrated, the term "system" shall also be taken to include any collection of machines that individually or jointly execute a set (or multiple sets) of instructions to perform any one or more of the methodologies discussed herein.

For example, in some embodiments, system 100 includes one or more computers. In some embodiments, the functionality for providing clinical support for personalized cancer therapy is spread across any number of networked computers and/or resides on each of several networked computers and/or is hosted on one or more virtual machines at a remote location accessible across the communications network 105. For example, different portions of the various modules and data stores illustrated in FIGS. 1A-1D can be stored and/or executed on the various instances of a processing device and/or processing server/database in the distributed diagnostic environment 210 illustrated in FIG. 2B (e.g., processing devices 224, 234, 244, and 254, processing server 262, and database 264).

The system may operate in the capacity of a server or a client machine in client-server network environment, as a peer machine in a peer-to-peer (or distributed) network environment, or as a server or a client machine in a cloud computing infrastructure or environment. The system may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine.

In another implementation, the system comprises a virtual machine that includes a module for executing instructions for performing any one or more of the methodologies disclosed herein. In computing, a virtual machine (VM) is an emulation of a computer system that is based on computer architectures and provides functionality of a physical computer. Some such implementations may involve specialized hardware, software, or a combination of hardware and software.

One of skill in the art will appreciate that any of a wide array of different computer topologies are used for the application and all such topologies are within the scope of the present disclosure.

Test Patient Data Store (120)

Referring to FIG. 1B, in some embodiments, the system (e.g., system 100) includes a patient data store 120 that stores data for patients 121-1 to 121-M (e.g., cancer patients or patients being tested for cancer) including one or more sequencing data 122, feature data 125, and clinical assessments 139. These data are used and/or generated by the various processes stored in the bioinformatics module 140 and feature analysis module 160 of system 100, to ultimately generate a report providing clinical support for personalized cancer therapy of a patient. While the feature scope of patient data 121 across all patients may be informationally dense, an individual patient's feature set may be sparsely populated across the entirety of the collective feature scope of all features across all patients. That is to say, the data stored for one patient may include a different set of features that the data stored for another patient. Further, while illustrated as a single data construct in FIG. 1B, different sets of patient data may be stored in different databases or modules spread across one or more system memories.

In some embodiments, sequencing data 122 from one or more sequencing reactions 122-i, including a plurality of sequence reads 123-i-1 to 123-i-K, is stored in the test patient data store 120. The data store may include different sets of sequencing data from a single subject, corresponding to different samples from the patient, e.g., a tumor sample, liquid biopsy sample, tumor organoid derived from a patient tumor, and/or a normal sample, and/or to samples acquired at different times, e.g., while monitoring the progression, regression, remission, and/or recurrence of a cancer in a subject. The sequence reads may be in any suitable file format, e.g., BCL, FASTA, FASTQ, etc. In some embodiments, sequencing data 122 is accessed by a sequencing data processing module 141, which performs various pre-processing, genome alignment, and demultiplexing operations, as described in detail below with reference to bioinformatics module 140. In some embodiments, sequence data that has been aligned to a reference construct, e.g., BAM file 124, is stored in test patient data store 120.

In some embodiments, the test patient data store 120 includes feature data 125, e.g., that is useful for identifying clinical support for personalized cancer therapy. In some embodiments, the feature data 125 includes personal characteristics 126 of the patient, such as patient name, date of birth, gender, ethnicity, physical address, smoking status, alcohol consumption characteristic, anthropomorphic data, etc.

In some embodiments, the feature data 125 includes medical history data 127 for the patient, such as cancer diagnosis information (e.g., date of initial diagnosis, date of metastatic diagnosis, cancer staging, tumor characterization, tissue of origin, previous treatments and outcomes, adverse effects of therapy, therapy group history, clinical trial history, previous and current medications, surgical history, etc.), previous or current symptoms, previous or current therapies, previous treatment outcomes, previous disease diagnoses, diabetes status, diagnoses of depression, diagnoses of other physical or mental maladies, and family medical history. In some embodiments, the feature data 125 includes clinical features 128, such as pathology data 128-1, medical imaging data 128-2, and tissue culture and/or tissue organoid culture data 128-3.

In some embodiments, yet other clinical features, such as previous laboratory testing results, are stored in the test patient data store 120. Medical history data 127 and clinical features may be collected from various sources, including at intake directly from the patient, from an electronic medical record (EMR) or electronic health record (EHR) for the patient, or curated from other sources, such as fields from various testing records (e.g., genetic sequencing reports).

In some embodiments, the feature data 125 includes genomic features 131 for the patient. Non-limiting examples of genomic features include allelic states 132 (e.g., the identity of alleles at one or more loci, support for wild type or variant alleles at one or more loci, support for SNVs/MNVs at one or more loci, support for indels at one or more loci, and/or support for gene rearrangements at one or more loci), allelic fractions 133 (e.g., ratios of variant to reference alleles (or vice versa), methylation states 132 (e.g., a distribution of methylation patterns at one or more loci and/or support for aberrant methylation patterns at one or more loci), genomic copy numbers 135 (e.g., a copy number value at one or more loci and/or support for an aberrant (increased or decreased) copy number at one or more loci), tumor mutational burden 136 (e.g., a measure of the number of mutations in the cancer genome of the subject), and microsatellite instability status 137 (e.g., a measure of the repeated unit length at one or more microsatellite loci and/or a classification of the MSI status for the patient's cancer). In some embodiments, one or more of the genomic features 131 are determined by a nucleic acid bioinformatics pipeline, e.g., as described in detail below with reference to FIGS. 4A-4F. In particular, in some embodiments, the feature data 125 include variant allele fractions 133, as determined using the improved methods for validating somatic sequence variants and described in further detail below with reference to FIGS. 1C, 1D, and 4F. In some embodiments, one or more of the genomic features 131 are obtained from an external testing source, e.g., not connected to the bioinformatics pipeline as described below.

In some embodiments, the feature data 125 further includes data 138 from other -omics fields of study. Non-limiting examples of -omics fields of study that may yield feature data useful for providing clinical support for personalized cancer therapy include transcriptomics, epigenomics, proteomics, metabolomics, metabonomics, microbiomics, lipidomics, glycomics, cellomics, and organoidomics.

In some embodiments, yet other features may include features derived from machine learning approaches, e.g., based at least in part on evaluation of any relevant molecular or clinical features, considered alone or in combination, not limited to those listed above. For instance, in some embodiments, one or more latent features learned from evaluation of cancer patient training datasets improve the diagnostic and prognostic power of the various analysis algorithms in the feature analysis module 160.

The skilled artisan will know of other types of features useful for providing clinical support for personalized cancer therapy. The listing of features above is merely representative and should not be construed to be limiting.

In some embodiments, a test patient data store 120 includes clinical assessment data 139 for patients, e.g., based on the feature data 125 collected for the subject. In some embodiments, the clinical assessment data 139 includes a catalogue of actionable variants and characteristics 139-1 (e.g., genomic alterations and compound metrics based on genomic features known or believed to be targetable by one or more specific cancer therapies), matched therapies 139-2 (e.g., the therapies known or believed to be particularly beneficial for treatment of subjects having actionable variants), and/or clinical reports 139-3 generated for the subject, e.g., based on identified actionable variants and characteristics 139-1 and/or matched therapies 139-2.

In some embodiments, clinical assessment data 139 is generated by analysis of feature data 125 using the various algorithms of feature analysis module 160, as described in further detail below. In some embodiments, clinical assessment data 139 is generated, modified, and/or validated by evaluation of feature data 125 by a clinician, e.g., an oncologist. For instance, in some embodiments, a clinician (e.g., at clinical environment 220) uses feature analysis module 160, or accesses test patient data store 120 directly, to evaluate feature data 125 to make recommendations for personalized cancer treatment of a patient. Similarly, in some embodiments, a clinician (e.g., at clinical environment 220) reviews recommendations determined using feature analysis module 160 and approves, rejects, or modifies the recommendations, e.g., prior to the recommendations being sent to a medical professional treating the cancer patient.

Bioinformatics Module (140)

Referring again to FIG. 1A, the system (e.g., system 100) includes a bioinformatics module 140 that includes a feature extraction module 145 and optional ancillary data processing constructs, such as a sequence data processing module 141 and/or one or more reference sequence constructs 158 (e.g., a reference genome, exome, or targeted-panel construct that includes reference sequences for a plurality of loci targeted by a sequencing panel).

In some embodiments, bioinformatics module 140 includes a sequence data processing module 141 that includes instructions for processing sequence reads, e.g., raw sequence reads 123 from one or more sequencing reactions 122, prior to analysis by the various feature extraction algorithms, as described in detail below. In some embodiments, sequence data processing module 141 includes one or more pre-processing algorithms 142 that prepare the data for analysis. In some embodiments, the pre-processing algorithms 142 include instructions for converting the file format of the sequence reads from the output of the sequencer (e.g., a BCL file format) into a file format compatible with downstream analysis of the sequences (e.g., a FASTQ or FASTA file format). In some embodiments, the pre-processing algorithms 142 include instructions for evaluating the quality of the sequence reads (e.g., by interrogating quality metrics like Phred score, base-calling error probabilities, Quality (Q) scores, and the like) and/or removing sequence reads that do not satisfy a threshold quality (e.g., an inferred base call accuracy of at least 80%, at least 90%, at least 95%, at least 99%, at least 99.5%, at least 99.9%, or higher). In some embodiments, the pre-processing algorithms 142 include instructions for filtering the sequence reads for one or more properties, e.g., removing sequences failing to satisfy a lower or upper size threshold or removing duplicate sequence reads.

In some embodiments, sequence data processing module 141 includes one or more alignment algorithms 143, for aligning pre-processed sequence reads 123 to a reference sequence construct 158, e.g., a reference genome, exome, or targeted-panel construct. Many algorithms for aligning sequencing data to a reference construct are known in the art, for example, BWA, Blat, SHRiMP, LastZ, and MAQ. One example of a sequence read alignment package is the Burrows-Wheeler Alignment tool (BWA), which uses a Burrows-Wheeler Transform (BWT) to align short sequence reads against a large reference construct, allowing for mismatches and gaps. Li and Durbin, Bioinformatics, 25(14): 1754-60 (2009), the content of which is incorporated herein by reference, in its entirety, for all purposes. Sequence read alignment packages import raw or pre-processed sequence reads 122, e.g., in BCL, FASTA, or FASTQ file formats, and output aligned sequence reads 124, e.g., in SAM or BAM file formats.

In some embodiments, sequence data processing module 141 includes one or more demultiplexing algorithms 144, for dividing sequence read or sequence alignment files generated from sequencing reactions of pooled nucleic acids into separate sequence read or sequence alignment files, each of which corresponds to a different source of nucleic acids in the nucleic acid sequencing pool. For instance, because of the cost of sequencing reactions, it is common practice to pool nucleic acids from a plurality of samples into a single sequencing reaction. The nucleic acids from each sample are tagged with a sample-specific and/or molecule-specific sequence tag (e.g., a UMI), which is sequenced along with the molecule. In some embodiments, demultiplexing algorithms 144 sort these sequence tags in the sequence read or sequence alignment files to demultiplex the sequencing data into separate files for each of the samples included in the sequencing reaction.

Bioinformatics module 140 includes a feature extraction module 145, which includes instructions for identifying diagnostic features, e.g., genomic features 131, from sequencing data 122 of biological samples from a subject, e.g., one or more of a solid tumor sample, a liquid biopsy sample, or a normal tissue (e.g., control) sample. For instance, in some embodiments, a feature extraction algorithm compares the identity of one or more nucleotides at a locus from the sequencing data 122 to the identity of the nucleotides at that locus in a reference sequence construct (e.g., a reference genome, exome, or targeted-panel construct) to determine whether the subject has a variant at that locus. In some embodiments, a feature extraction algorithm evaluates data other than the raw sequence, to identify a genomic alteration in the subject, e.g., an allelic ratio, a relative copy number, a repeat unit distribution, etc.

For instance, in some embodiments, feature extraction module 145 includes one or more variant identification modules that include instructions for various variant calling processes. In some embodiments, variants in the germline of the subject are identified, e.g., using a germline variant identification module 146. In some embodiments, variants in the cancer genome, e.g., somatic variants, are identified, e.g., using a somatic variant identification module 150. While separate germline and somatic variant identification modules are illustrated in FIG. 1A, in some embodiments they are integrated into a single module. In some embodiments, the variant identification module includes instructions for identifying one or more of nucleotide variants (e.g., single nucleotide variants (SNV) and multi-nucleotide variants (MNV)) using one or more SNV/MNV calling algorithms (e.g., algorithms 147 and/or 151), indels (e.g., insertions or deletions of nucleotides) using one or more indel calling algorithms (e.g., algorithms 148 and/or 152), and genomic rearrangements (e.g., inversions, translocation, and fusions of nucleotide sequences) using one or more genomic rearrangement calling algorithms (e.g., algorithms 149 and/or 153).

Figure 1D:
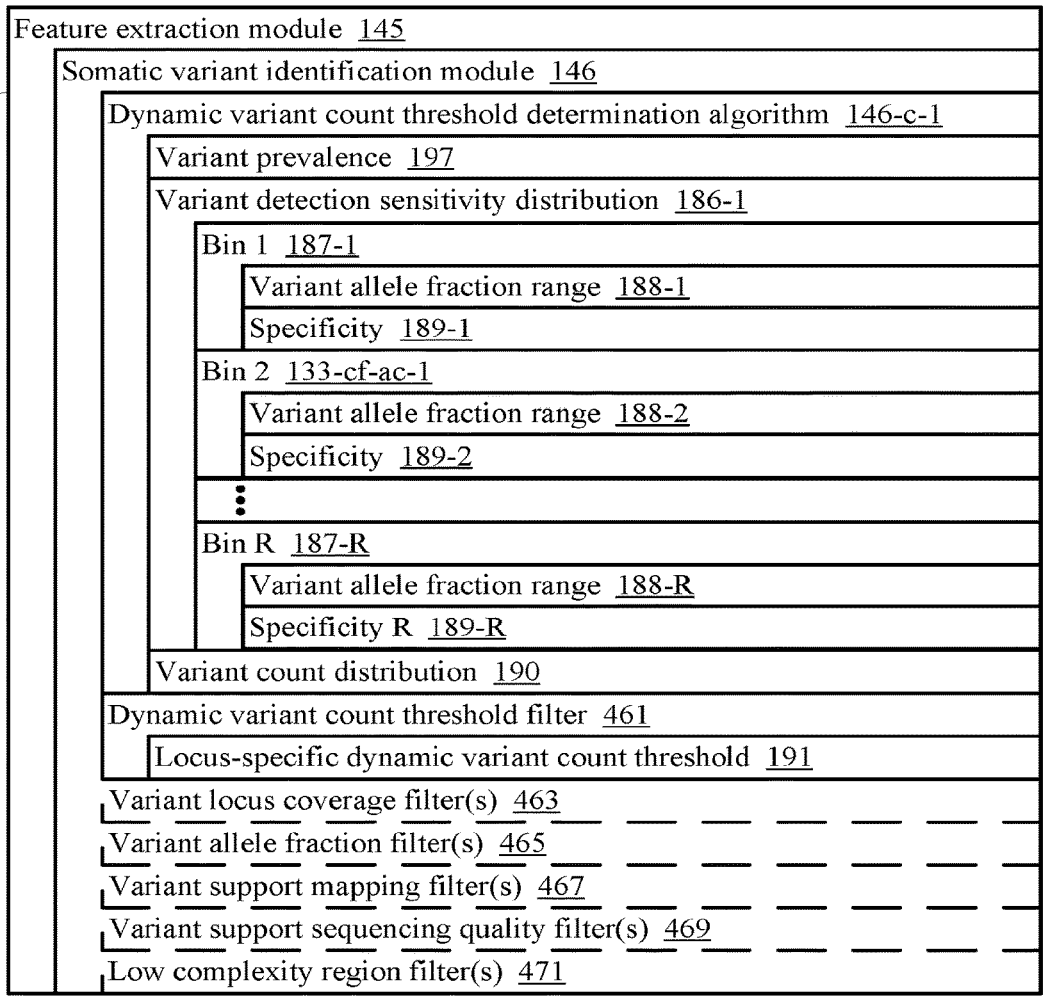

For example, referring to FIGS. 1C and 1D, in some embodiments, feature extraction module 145 comprises, in the variant identification module 146, a variant thresholding module 146-a, a sequence variant data store 146-r, and a variant validation module 146-o. In some such embodiments, the sequence variant data store 146-r comprises one or more candidate variants for a test subject identified by aligning to a reference sequence a plurality of sequence reads obtained from sequencing a liquid biopsy sample of the test subject, the one or more candidate variants corresponding to a respective one or more loci in the reference sequence. The plurality of sequence reads aligned to the reference sequence is used to identify a variant allele fragment count for each candidate variant. The sequence variant data store 146-r further comprises, in some embodiments, a plurality of variants from a first set of nucleic acids obtained from a cohort of subjects (e.g., from a tumor tissue biopsy for each subject in a baseline cohort of subjects). The variant thresholding module 146-*a* performs a function for each candidate variant in the one or more candidate variants where, for each corresponding locus 146-*b* (e.g., 146-*b*-1, . . . , 146-*b*-P), a dynamic variant count threshold 146-*d* (e.g., 146-*d*-1) is obtained based on a pre-test odds of a positive variant call for the locus, based on the prevalence of variants in the genomic region that includes the locus, using the plurality of variants for the baseline cohort. The variant thresholding module 146-*a* compares the variant allele fragment count 146-*c* (e.g., 146-*c*-1) for the candidate variant against the dynamic variant count threshold 146-*d* for the locus corresponding to the candidate variant. In some embodiments, the variant validation module 146-*o* determines whether the candidate variant is validated or rejected as a somatic sequence variant based on the comparison. For example, when the variant allele fragment count for the candidate variant satisfies the dynamic variant count threshold for the locus, the somatic sequence variant is validated, and when the variant allele fragment count for the candidate variant does not satisfy the dynamic variant count threshold for the locus, the somatic sequence variant is rejected.

In some embodiments, the dynamic variant count threshold is determined based on a distribution of variant detection sensitivities as a function of circulating variant allele fraction from the cohort of subjects (e.g., the baseline cohort). For example, referring to FIG. 1C, in some such embodiments, the variant thresholding module 146-*a* takes as input one or more variant allele fractions 133 from the genomic features module 131. In some such embodiments, the variant allele fractions 133 comprises a plurality of variant allele fractions obtained from tumor tissue biopsies 133-*t* (e.g., 133-*t*-1, 133-*t*-2 . . . , 1334-O) for the cohort of subjects. In some embodiments, the variant allele fractions comprise a plurality of variant allele fractions obtained from liquid biopsy samples 133-*cf* (e.g., 133-*cf*-1, 133-*cf*-2 . . . , 133-*cf*-N) for the cohort of subjects. In some embodiments, the circulating variant allele fraction is obtained by comparing the liquid biopsy variant allele fractions 133-*cf* to the tumor biopsy variant allele fraction 133-*t*.

Additional embodiments for using variant allele fractions (e.g., variant allele frequencies) to identify somatic variants are detailed below (see, Example Methods: Variant Identification).

A SNV/MNV algorithm 147 may identify a substitution of a single nucleotide that occurs at a specific position in the genome. For example, at a specific base position, or locus, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underlie differences in human susceptibility to a wide range of diseases (e.g.—sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome.

An indel calling algorithm 148 may identify an insertion or deletion of bases in the genome of an organism classified among small genetic variations. While indels usually measure from 1 to 10 000 base pairs in length, a microindel is defined as an indel that results in a net change of 1 to 50 nucleotides. Indels can be contrasted with a SNP or point mutation. An indel inserts and/or deletes nucleotides from a sequence, while a point mutation is a form of substitution that replaces one of the nucleotides without changing the overall number in the DNA. Indels, being insertions and/or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites.

A genomic rearrangement algorithm 149 may identify hybrid genes formed from two previously separate genes. It can occur as a result of translocation, interstitial deletion, or chromosomal inversion. Gene fusion can play an important role in tumorigenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

In some embodiments, feature extraction module 145 includes instructions for identifying one or more complex genomic alterations (e.g., features that incorporate more than a change in the primary sequence of the genome) in the cancer genome of the subject. For instance, in some embodiments, feature extraction module 145 includes modules for identifying one or more of copy number variation (e.g., copy number variation analysis module 153), microsatellite instability status (e.g., microsatellite instability analysis module 154), tumor mutational burden (e.g., tumor mutational burden analysis module 155), tumor ploidy (e.g., tumor ploidy analysis module 156), and homologous recombination pathway deficiencies (e.g., homologous recombination pathway analysis module 157).

Feature Analysis Module (160)

Referring again to FIG. 1A, the system (e.g., system 100) includes a feature analysis module 160 that includes one or more genomic alteration interpretation algorithms 161, one or more optional clinical data analysis algorithms 165, an optional therapeutic curation algorithm 165, and an optional recommendation validation module 167. In some embodiments, feature analysis module 160 identifies actionable variants and characteristics 139-1 and corresponding matched therapies 139-2 and/or clinical trials using one or more analysis algorithms (e.g., algorithms 162, 163, 164, and 165) to evaluate feature data 125. The identified actionable variants and characteristics 139-1 and corresponding matched therapies 139-2, which are optionally stored in test patient data store 120, are then curated by feature analysis module 160 to generate a clinical report 139-3, which is optionally validated by a user, e.g., a clinician, before being transmitted to a medical professional, e.g., an oncologist, treating the patient.

In some embodiments, the genomic alteration interpretation algorithms 161 include instructions for evaluating the effect that one or more genomic features 131 of the subject, e.g., as identified by feature extraction module 145, have on the characteristics of the patient's cancer and/or whether one or more targeted cancer therapies may improve the clinical outcome for the patient. For example, in some embodiments, one or more genomic variant analysis algorithms 163 evaluate various genomic features 131 by querying a database, e.g., a look-up-table ("LUT") of actionable genomic alterations, targeted therapies associated with the actionable genomic alterations, and any other conditions that should be met before administering the targeted therapy to a subject having the actionable genomic alteration. For instance, evidence suggests that depatuxizumab mafodotin (an anti-EGFR mAb conjugated to monomethyl auristatin F) has improved efficacy for the treatment of recurrent glioblastomas having EGFR focal amplifications. van den Bent M. et al., Cancer Chemother Pharmacol., 80(6):1209-17 (2017). Accordingly, the actionable genomic alteration LUT would have an entry for the focal amplification of the EGFR gene indicating that depatuxizumab mafodotin is a targeted therapy for glioblastomas (e.g., recurrent glioblastomas) having a focal gene amplification. In some instances, the LUT may also include counter indications for the associated targeted therapy, e.g., adverse drug interactions or personal characteristics that are counter-indicated for administration of the particular targeted therapy.

In some embodiments, a genomic alteration interpretation algorithm 161 determines whether a particular genomic feature 131 should be reported to a medical professional treating the cancer patient. In some embodiments, genomic features 131 (e.g., genomic alterations and compound features) are reported when there is clinical evidence that the feature significantly impacts the biology of the cancer, impacts the prognosis for the cancer, and/or impacts pharmacogenomics, e.g., by indicating or counter-indicating particular therapeutic approaches. For instance, a genomic alteration interpretation algorithm 161 may classify a particular CNV feature 135 as "Reportable," e.g., meaning that the CNV has been identified as influencing the character of the cancer, the overall disease state, and/or pharmacogenomics, as "Not Reportable," e.g., meaning that the CNV has not been identified as influencing the character of the cancer, the overall disease state, and/or pharmacogenomics, as "No Evidence," e.g., meaning that no evidence exists supporting that the CNV is "Reportable" or "Not Reportable," or as "Conflicting Evidence," e.g., meaning that evidence exists supporting both that the CNV is "Reportable" and that the CNV is "Not Reportable."

In some embodiments, the genomic alteration interpretation algorithms 161 include one or more pathogenic variant analysis algorithms 162, which evaluate various genomic features to identify the presence of an oncogenic pathogen associated with the patient's cancer and/or targeted therapies associated with an oncogenic pathogen infection in the cancer. For instance, RNA expression patterns of some cancers are associated with the presence of an oncogenic pathogen that is helping to drive the cancer. See, for example, U.S. patent application Ser. No. 16/802,126, filed Feb. 26, 2020, the content of which is hereby incorporated by reference, in its entirety, for all purposes. In some instances, the recommended therapy for the cancer is different when the cancer is associated with the oncogenic pathogen infection than when it is not. Accordingly, in some embodiments, e.g., where feature data 125 includes RNA abundance data for the cancer of the patient, one or more pathogenic variant analysis algorithms 162 evaluate the RNA abundance data for the patient's cancer to determine whether a signature exists in the data that indicates the presence of the oncogenic pathogen in the cancer. Similarly, in some embodiments, bioinformatics module 140 includes an algorithm that searches for the presence of pathogenic nucleic acid sequences in sequencing data 122. See, for example, U.S. Provisional Patent Application Ser. No. 62/978,067, filed Feb. 18, 2020, the content of which is hereby incorporated by reference, in its entirety, for all purposes. Accordingly, in some embodiments, one or more pathogenic variant analysis algorithms 162 evaluates whether the presence of an oncogenic pathogen in a subject is associated with an actionable therapy for the infection. In some embodiments, system 100 queries a database, e.g., a look-up-table ("LUT"), of actionable oncogenic pathogen infections, targeted therapies associated with the actionable infections, and any other conditions that should be met before administering the targeted therapy to a subject that is infected with the oncogenic pathogen. In some instances, the LUT may also include counter indications for the associated targeted therapy, e.g., adverse drug interactions or personal characteristics that are counter-indicated for administration of the particular targeted therapy.

In some embodiments, the genomic alteration interpretation algorithms 161 include one or more multi-feature analysis algorithms 164 that evaluate a plurality of features to classify a cancer with respect to the effects of one or more targeted therapies. For instance, in some embodiments, feature analysis module 160 includes one or more classifiers trained against feature data, one or more clinical therapies, and their associated clinical outcomes for a plurality of training subjects to classify cancers based on their predicted clinical outcomes following one or more therapies.

In some embodiments, the classifier is implemented as an artificial intelligence engine and may include gradient boosting models, random forest models, neural networks (NN), regression models, Naive Bayes models, and/or machine learning algorithms (MLA). An MLA or a NN may be trained from a training data set that includes one or more features 125, including personal characteristics 126, medical history 127, clinical features 128, genomic features 131, and/or other -omic features 138. MLAs include supervised algorithms (such as algorithms where the features/classifications in the data set are annotated) using linear regression, logistic regression, decision trees, classification and regression trees, naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines.

NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample.

While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators, that is, they can represent a wide variety of functions when given appropriate parameters.

In some embodiments, system 100 includes a classifier training module that includes instructions for training one or more untrained or partially trained classifiers based on feature data from a training dataset. In some embodiments, system 100 also includes a database of training data for use in training the one or more classifiers. In other embodiments, the classifier training module accesses a remote storage device hosting training data. In some embodiments, the training data includes a set of training features, including but not limited to, various types of the feature data 125 illustrated in FIG. 1B. In some embodiments, the classifier training module uses patient data 121, e.g., when test patient data store 120 also stores a record of treatments administered to the patient and patient outcomes following therapy.

In some embodiments, feature analysis module 160 includes one or more clinical data analysis algorithms 165, which evaluate clinical features 128 of a cancer to identify targeted therapies which may benefit the subject. For example, in some embodiments, e.g., where feature data 125 includes pathology data 128-1, one or more clinical data analysis algorithms 165 evaluate the data to determine whether an actionable therapy is indicated based on the histopathology of a tumor biopsy from the subject, e.g., which is indicative of a particular cancer type and/or stage of cancer. In some embodiments, system 100 queries a database, e.g., a look-up-table ("LUT"), of actionable clinical features (e.g., pathology features), targeted therapies associated with the actionable features, and any other conditions that should be met before administering the targeted therapy to a subject associated with the actionable clinical features 128 (e.g., pathology features 128-1). In some embodiments, system 100 evaluates the clinical features 128 (e.g., pathology features 128-1) directly to determine whether the patient's cancer is sensitive to a particular therapeutic agent. Further details on example methods, systems, and algorithms for classifying cancer and identifying targeted therapies based on clinical data, such as pathology data 128-1, imaging data 138-2, and/or tissue culture/organoid data 128-3 are discussed, for example, in U.S. patent application Ser. No. 16/830,186, filed on Mar. 25, 2020, U.S. patent application Ser. No. 16/789,363, filed on Feb. 12, 2020, and U.S. Provisional Application No. 63/007,874, filed on Apr. 9, 2020, the contents of which are hereby incorporated by reference, in their entireties, for all purposes.

In some embodiments, feature analysis module 160 includes a clinical trials module that evaluates test patient data 121 to determine whether the patient is eligible for inclusion in a clinical trial for a cancer therapy, e.g., a clinical trial that is currently recruiting patients, a clinical trial that has not yet begun recruiting patients, and/or an ongoing clinical trial that may recruit additional patients in the future. In some embodiments, a clinical trial module evaluates test patient data 121 to determine whether the results of a clinical trial are relevant for the patient, e.g., the results of an ongoing clinical trial and/or the results of a completed clinical trial. For instance, in some embodiments, system 100 queries a database, e.g., a look-up-table ("LUT") of clinical trials, e.g., active and/or completed clinical trials, and compares patient data 121 with inclusion criteria for the clinical trials, stored in the database, to identify clinical trials with inclusion criteria that closely match and/or exactly match the patient's data 121. In some embodiments, a record of matching clinical trials, e.g., those clinical trials that the patient may be eligible for and/or that may inform personalized treatment decisions for the patient, are stored in clinical assessment database 139.

In some embodiments, feature analysis module 160 includes a therapeutic curation algorithm 166 that assembles actionable variants and characteristics 139-1, matched therapies 139-2, and/or relevant clinical trials identified for the patient, as described above. In some embodiments, a therapeutic curation algorithm 166 evaluates certain criteria related to which actionable variants and characteristics 139-1, matched therapies 139-2, and/or relevant clinical trials should be reported and/or whether certain matched therapies, considered alone or in combination, may be counter-indicated for the patient, e.g., based on personal characteristics 126 of the patient and/or known drug-drug interactions. In some embodiments, the therapeutic curation algorithm then generates one or more clinical reports 139-3 for the patient. In some embodiments, the therapeutic curation algorithm generates a first clinical report 139-3-1 that is to be reported to a medical professional treating the patient and a second clinical report 139-3-2 that will not be communicated to the medical professional, but may be used to improve various algorithms within the system.

In some embodiments, feature analysis module 160 includes a recommendation validation module 167, that includes an interface allowing a clinician to review, modify, and approve a clinical report 139-3 prior to the report being sent to a medical professional, e.g., an oncologist, treating the patient.

In some embodiments, each of the one or more feature collections, sequencing modules, bioinformatics modules (including, e.g., alteration module(s), structural variant calling and data processing modules), classification modules and outcome modules are communicatively coupled to a data bus to transfer data between each module for processing and/or storage. In some alternative embodiments, each of the feature collection, alteration module(s), structural variant and feature store are communicatively coupled to each other for independent communication without sharing the data bus.

Further details on systems and exemplary embodiments of modules and feature collections are discussed in PCT Application PCT/US19/69149, titled "A METHOD AND PROCESS FOR PREDICTING AND ANALYZING PATIENT COHORT RESPONSE, PROGRESSION, AND SURVIVAL," filed Dec. 31, 2019, which is hereby incorporated herein by reference in its entirety.

Example Methods

Now that details of a system 100 for providing clinical support for personalized cancer therapy, e.g., with improved validation of somatic sequence variants, have been disclosed, details regarding processes and features of the system, in accordance with various embodiments of the present disclosure, are disclosed below. Specifically, example processes are described below with reference to FIGS. 2A, 3, 4A-4F, 5A-5B, 6, and 7. In some embodiments, such processes and features of the system are carried out by modules 118, 120, 140, 160, and/or 170, as illustrated in FIG. 1A. Referring to these methods, the systems described herein (e.g., system 100) include instructions for validating somatic variants that are improved compared to conventional methods for somatic variant detection.

Figure 2A:
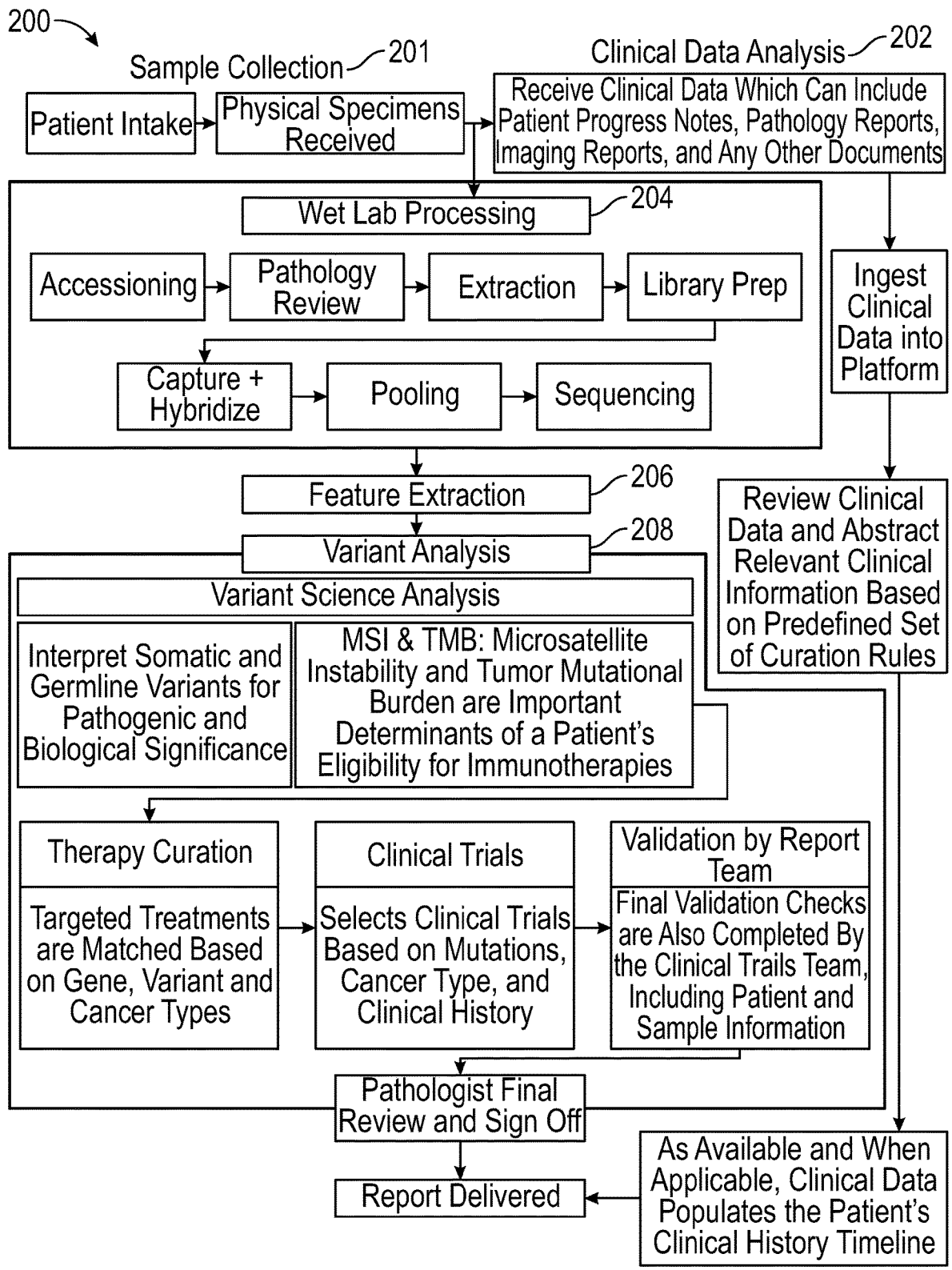
FIG. 2A illustrates an example workflow for generating a clinical report based on information generated from analysis of one or more patient specimens, in accordance with some embodiments of the present disclosure.
Figure 2B:
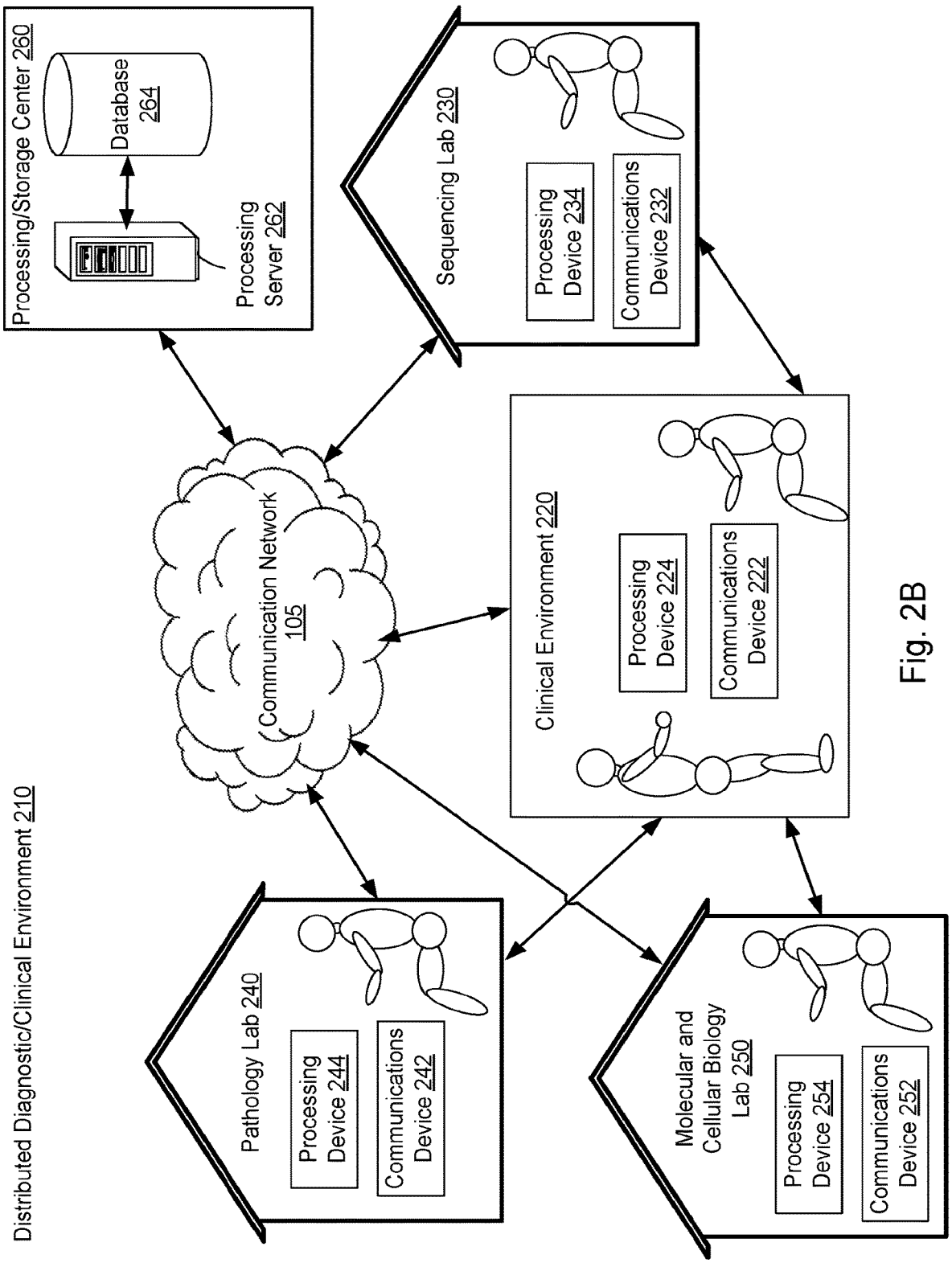
FIG. 2B illustrates an example of a distributed diagnostic environment for collecting and evaluating patient data for the purpose of precision oncology, in accordance with some embodiments of the present disclosure.

FIG. 2B: Distributed Diagnostic and Clinical Environment

In some aspects, the methods described herein for providing clinical support for personalized cancer therapy are performed across a distributed diagnostic/clinical environment, e.g., as illustrated in FIG. 2B. However, in some embodiments, the improved methods described herein for validating somatic sequence variants are performed at a single location, e.g., at a single computing system or environment, although ancillary procedures supporting the methods described herein, and/or procedures that make further use of the results of the methods described herein, may be performed across a distributed diagnostic/clinical environment.

FIG. 2B illustrates an example of a distributed diagnostic/clinical environment 210. In some embodiments, the distributed diagnostic/clinical environment is connected via communication network 105. In some embodiments, one or more biological samples, e.g., one or more liquid biopsy samples, solid tumor biopsy, normal tissue samples, and/or control samples, are collected from a subject in clinical environment 220, e.g., a doctor's office, hospital, or medical clinic, or at a home health care environment (not depicted). Advantageously, while solid tumor samples should be collected within a clinical setting, liquid biopsy samples can be acquired in a less invasive fashion and are more easily collected outside of a traditional clinical setting. In some embodiments, one or more biological samples, or portions thereof, are processed within the clinical environment 220 where collection occurred, using a processing device 224, e.g., a nucleic acid sequencer for obtaining sequencing data, a microscope for obtaining pathology data, a mass spectrometer for obtaining proteomic data, etc. In some embodiments, one or more biological samples, or portions thereof are sent to one or more external environments, e.g., sequencing lab 230, pathology lab 240, and/or molecular biology lab 250, each of which includes a processing device 234, 244, and 254, respectively, to generate biological data 121 for the subject. Each environment includes a communications device 222, 232, 242, and 252, respectively, for communicating biological data 121 about the subject to a processing server 262 and/or database 264, which may be located in yet another environment, e.g., processing/storage center 260. Thus, in some embodiments, different portions of the systems and methods described herein are fulfilled by different processing devices located in different physical environments.

Accordingly, in some embodiments, a method for providing clinical support for personalized cancer therapy, e.g., with improved validation of somatic sequence variants, is performed across one or more environments, as illustrated in FIG. 2B. For instance, in some such embodiments, a liquid biopsy sample is collected at clinical environment 220 or in a home healthcare environment. The sample, or a portion thereof, is sent to sequencing lab 230 where raw sequence reads 123 of nucleic acids in the sample are generated by sequencer 234. The raw sequencing data 123 is communicated, e.g., from communications device 232, to database 264 at processing/storage center 260, where processing server 262 extracts features from the sequence reads by executing one or more of the processes in bioinformatics module 140, thereby generating genomic features 131 for the sample. Processing server 262 may then analyze the identified features by executing one or more of the processes in feature analysis module 160, thereby generating clinical assessment 139, including a clinical report 139-3. A clinician may access clinical report 139-3, e.g., at processing/storage center 260 or through communications network 105, via recommendation validation module 167. After final approval, clinical report 139-3 is transmitted to a medical professional, e.g., an oncologist, at clinical environment 220, who uses the report to support clinical decision making for personalized treatment of the patient's cancer.

FIG. 2A: Example Workflow for Precision Oncology

FIG. 2A is a flowchart of an example workflow 200 for collecting and analyzing data in order to generate a clinical report 139 to support clinical decision making in precision oncology. Advantageously, the methods described herein improve this process, for example, by improving various stages within feature extraction 206, including validation of somatic sequence variants.

Briefly, the workflow begins with patient intake and sample collection 201, where one or more liquid biopsy samples, one or more tumor biopsy, and one or more normal and/or control tissue samples are collected from the patient (e.g., at a clinical environment 220 or home healthcare environment, as illustrated in FIG. 2B). In some embodiments, personal data 126 corresponding to the patient and a record of the one or more biological samples obtained (e.g., patient identifiers, patient clinical data, sample type, sample identifiers, cancer conditions, etc.) are entered into a data analysis platform, e.g., test patient data store 120. Accordingly, in some embodiments, the methods disclosed herein include obtaining one or more biological samples from one or more subjects, e.g., cancer patients. In some embodiments, the subject is a human, e.g., a human cancer patient.

In some embodiments, one or more of the biological samples obtained from the patient are a biological liquid sample, also referred to as a liquid biopsy sample. In some embodiments, one or more of the biological samples obtained from the patient are selected from blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. In some embodiments, the liquid biopsy sample includes blood and/or saliva. In some embodiments, the liquid biopsy sample is peripheral blood. In some embodiments, blood samples are collected from patients in commercial blood collection containers, e.g., using a PAXgene® Blood DNA Tubes. In some embodiments, saliva samples are collected from patients in commercial saliva collection containers, e.g., using an Oragene® DNA Saliva Kit.

In some embodiments, the liquid biopsy sample has a volume of from about 1 mL to about 50 mL. For example, in some embodiments, the liquid biopsy sample has a volume of about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, or greater.

Liquid biopsy samples include cell free nucleic acids, including cell-free DNA (cfDNA). As described above, cfDNA isolated from cancer patients includes DNA originating from cancerous cells, also referred to as circulating tumor DNA (ctDNA), cfDNA originating from germline (e.g., healthy or non-cancerous) cells, and cfDNA originating from hematopoietic cells (e.g., white blood cells). The relative proportions of cancerous and non-cancerous cfDNA present in a liquid biopsy sample varies depending on the characteristics (e.g., the type, stage, lineage, genomic profile, etc.) of the patient's cancer. As used herein, the 'tumor burden' of the subject refers to the percentage cfDNA that originated from cancerous cells.

As described herein, cfDNA is a particularly useful source of biological data for various implementations of the methods and systems described herein, because it is readily obtained from various body fluids. Advantageously, use of bodily fluids facilitates serial monitoring because of the ease of collection, as these fluids are collectable by non-invasive or minimally invasive methodologies. This is in contrast to methods that rely upon solid tissue samples, such as biopsies, which often times require invasive surgical procedures. Further, because bodily fluids, such as blood, circulate throughout the body, the cfDNA population represents a sampling of many different tissue types from many different locations.

In some embodiments, a liquid biopsy sample is separated into two different samples. For example, in some embodiments, a blood sample is separated into a blood plasma sample, containing cfDNA, and a buffy coat preparation, containing white blood cells.

In some embodiments, a plurality of liquid biopsy samples is obtained from a respective subject at intervals over a period of time (e.g., using serial testing). For example, in some such embodiments, the time between obtaining liquid biopsy samples from a respective subject is at least 1 day, at least 2 days, at least 1 week, at least 2 weeks, at least 1 month, at least 2 months, at least 3 months, at least 4 months, at least 6 months, or at least 1 year.

In some embodiments, one or more biological samples collected from the patient is a solid tissue sample, e.g., a solid tumor sample or a solid normal tissue sample. Methods for obtaining solid tissue samples, e.g., of cancerous and/or normal tissue are known in the art and are dependent upon the type of tissue being sampled. For example, bone marrow biopsies and isolation of circulating tumor cells can be used to obtain samples of blood cancers, endoscopic biopsies can be used to obtain samples of cancers of the digestive tract, bladder, and lungs, needle biopsies (e.g., fine-needle aspiration, core needle aspiration, vacuum-assisted biopsy, and image-guided biopsy, can be used to obtain samples of subdermal tumors, skin biopsies, e.g., shave biopsy, punch biopsy, incisional biopsy, and excisional biopsy, can be used to obtain samples of dermal cancers, and surgical biopsies can be used to obtain samples of cancers affecting internal organs of a patient. In some embodiments, a solid tissue sample is a formalin-fixed tissue (FFT). In some embodiments, a solid tissue sample is a macro-dissected formalin fixed paraffin embedded (FFPE) tissue. In some embodiments, a solid tissue sample is a fresh frozen tissue sample.

In some embodiments, a dedicated normal sample is collected from the patient, for co-processing with a liquid biopsy sample. Generally, the normal sample is of a non-cancerous tissue, and can be collected using any tissue collection means described above. In some embodiments, buccal cells collected from the inside of a patient's cheeks are used as a normal sample. Buccal cells can be collected by placing an absorbent material, e.g., a swab, in the subject's mouth and rubbing it against their cheek, e.g., for at least 15 second or for at least 30 seconds. The swab is then removed from the patient's mouth and inserted into a tube, such that the tip of the tube is submerged into a liquid that serves to extract the buccal cells off of the absorbent material. An example of buccal cell recovery and collection devices is provided in U.S. Pat. No. 9,138,205, the content of which is hereby incorporated by reference, in its entirety, for all purposes. In some embodiments, the buccal swab DNA is used as a source of normal DNA in circulating heme malignancies.

The biological samples collected from the patient are, optionally, sent to various analytical environments (e.g., sequencing lab 230, pathology lab 240, and/or molecular biology lab 250) for processing (e.g., data collection) and/or analysis (e.g., feature extraction). Wet lab processing 204 may include cataloguing samples (e.g., accessioning), examining clinical features of one or more samples (e.g., pathology review), and nucleic acid sequence analysis (e.g., extraction, library prep, capture+hybridize, pooling, and sequencing). In some embodiments, the workflow includes clinical analysis of one or more biological samples collected from the subject, e.g., at a pathology lab 240 and/or a molecular and cellular biology lab 250, to generate clinical features such as pathology features 128-3, imaging data 128-3, and/or tissue culture/organoid data 128-3.

In some embodiments, the pathology data 128-1 collected during clinical evaluation includes visual features identified by a pathologist's inspection of a specimen (e.g., a solid tumor biopsy), e.g., of stained H&E or IHC slides. In some embodiments, the sample is a solid tissue biopsy sample. In some embodiments, the tissue biopsy sample is a formalin-fixed tissue (FFT), e.g., a formalin-fixed paraffin-embedded (FFPE) tissue. In some embodiments, the tissue biopsy sample is an FFPE or FFT block. In some embodiments, the tissue biopsy sample is a fresh-frozen tissue biopsy. The tissue biopsy sample can be prepared in thin sections (e.g., by cutting and/or affixing to a slide), to facilitate pathology review (e.g., by staining with immunohistochemistry stain for IHC review and/or with hematoxylin and eosin stain for H&E pathology review). For instance, analysis of slides for H&E staining or IHC staining may reveal features such as tumor infiltration, programmed death-ligand 1 (PD-L1) status, human leukocyte antigen (HLA) status, or other immunological features.

In some embodiments, a liquid sample (e.g., blood) collected from the patient (e.g., in EDTA-containing collection tubes) is prepared on a slide (e.g., by smearing) for pathology review. In some embodiments, macrodissected FFPE tissue sections, which may be mounted on a histopathology slide, from solid tissue samples (e.g., tumor or normal tissue) are analyzed by pathologists. In some embodiments, tumor samples are evaluated to determine, e.g., the tumor purity of the sample, the percent tumor cellularity as a ratio of tumor to normal nuclei, etc. For each section, background tissue may be excluded or removed such that the section meets a tumor purity threshold, e.g., where at least 20% of the nuclei in the section are tumor nuclei, or where at least 25%, 30%, 40%, 50%, 60%, 70%, 80%, 90%, or more of the nuclei in the section are tumor nuclei.

In some embodiments, pathology data 128-1 is extracted, in addition to or instead of visual inspection, using computational approaches to digital pathology, e.g., providing morphometric features extracted from digital images of stained tissue samples. A review of digital pathology methods is provided in Bera, K. et al., Nat. Rev. Clin. Oncol., 16:703-15 (2019), the content of which is hereby incorporated by reference, in its entirety, for all purposes. In some embodiments, pathology data 128-1 includes features determined using machine learning algorithms to evaluate pathology data collected as described above.

Further details on methods, systems, and algorithms for using pathology data to classify cancer and identify targeted therapies are discussed, for example, in are discussed, for example, in U.S. patent application Ser. No. 16/830,186, filed on Mar. 25, 2020, and U.S. Provisional Application No. 63/007,874, filed on Apr. 9, 2020, the contents of which are hereby incorporated by reference, in their entireties, for all purposes.

In some embodiments, imaging data 128-2 collected during clinical evaluation includes features identified by review of in-vitro and/or in-vivo imaging results (e.g., of a tumor site), for example a size of a tumor, tumor size differentials over time (such as during treatment or during other periods of change). In some embodiments, imaging data 128-2 includes features determined using machine learning algorithms to evaluate imaging data collected as described above.

Further details on methods, systems, and algorithms for using medical imaging to classify cancer and identify targeted therapies are discussed, for example, in are discussed, for example, in U.S. patent application Ser. No. 16/830,186, filed on Mar. 25, 2020, and U.S. Provisional Application No. 63/007,874, filed on Apr. 9, 2020, the contents of which are hereby incorporated by reference, in their entireties, for all purposes.

In some embodiments, tissue culture/organoid data 128-3 collected during clinical evaluation includes features identified by evaluation of cultured tissue from the subject. For instance, in some embodiments, tissue samples obtained from the patients (e.g., tumor tissue, normal tissue, or both) are cultured (e.g., in liquid culture, solid-phase culture, and/or organoid culture) and various features, such as cell morphology, growth characteristics, genomic alterations, and/or drug sensitivity, are evaluated. In some embodiments, tissue culture/organoid data 128-3 includes features determined using machine learning algorithms to evaluate tissue culture/organoid data collected as described above. Examples of tissue organoid (e.g., personal tumor organoid) culturing and feature extractions thereof are described in U.S. Provisional Application Ser. No. 62/924,621, filed on Oct. 22, 2019, and U.S. patent application Ser. No. 16/693,117, filed on Nov. 22, 2019, the contents of which are hereby incorporated by reference, in their entireties, for all purposes.

Figure 3:
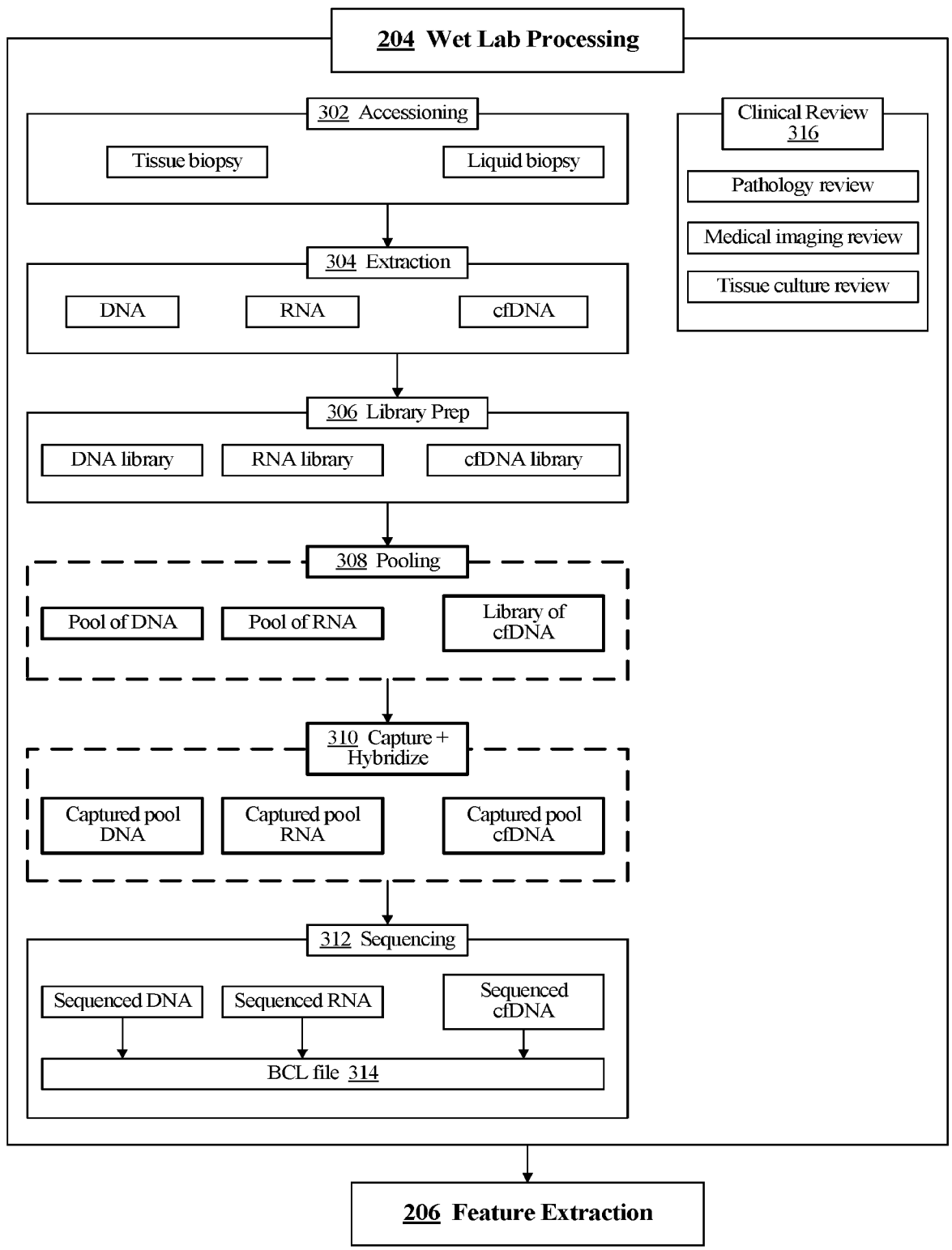
FIG. 3 provides an example flow chart of processes and features for liquid biopsy sample collection and analysis for use in precision oncology, in accordance with some embodiments of the present disclosure.

Nucleic acid sequencing of one or more samples collected from the subject is performed, e.g., at sequencing lab 230, during wet lab processing 204. An example workflow for nucleic acid sequencing is illustrated in FIG. 3. In some embodiments, the one or more biological samples obtained at the sequencing lab 230 are accessioned (302), to track the sample and data through the sequencing process.

Next, nucleic acids, e.g., RNA and/or DNA are extracted (304) from the one or more biological samples. Methods for isolating nucleic acids from biological samples are known in the art, and are dependent upon the type of nucleic acid being isolated (e.g., cfDNA, DNA, and/or RNA) and the type of sample from which the nucleic acids are being isolated (e.g., liquid biopsy samples, white blood cell buffy coat preparations, formalin-fixed paraffin-embedded (FFPE) solid tissue samples, and fresh frozen solid tissue samples). The selection of any particular nucleic acid isolation technique for use in conjunction with the embodiments described herein is well within the skill of the person having ordinary skill in the art, who will consider the sample type, the state of the sample, the type of nucleic acid being sequenced and the sequencing technology being used.

For instance, many techniques for DNA isolation, e.g., genomic DNA isolation, from a tissue sample are known in the art, such as organic extraction, silica adsorption, and anion exchange chromatography. Likewise, many techniques for RNA isolation, e.g., mRNA isolation, from a tissue sample are known in the art. For example, acid guanidinium thiocyanate-phenol-chloroform extraction (see, for example, Chomczynski and Sacchi, 2006, Nat Protoc, 1(2):581-85, which is hereby incorporated by reference herein), and silica bead/glass fiber adsorption (see, for example, Poeckh, T. et al., 2008, Anal Biochem., 373(2): 253-62, which is hereby incorporated by reference herein). The selection of any particular DNA or RNA isolation technique for use in conjunction with the embodiments described herein is well within the skill of the person having ordinary skill in the art, who will consider the tissue type, the state of the tissue, e.g., fresh, frozen, formalin-fixed, paraffin-embedded (FFPE), and the type of nucleic acid analysis that is to be performed.

In some embodiments where the biological sample is a liquid biopsy sample, e.g., a blood or blood plasma sample, cfDNA is isolated from blood samples using commercially available reagents, including proteinase K, to generate a liquid solution of cfDNA.

In some embodiments, isolated DNA molecules are mechanically sheared to an average length using an ultrasonicator (for example, a Covaris ultrasonicator). In some embodiments, isolated nucleic acid molecules are analyzed to determine their fragment size, e.g., through gel electrophoresis techniques and/or the use of a device such as a LabChip GX Touch. The skilled artisan will know of an appropriate range of fragment sizes, based on the sequencing technique being employed, as different sequencing techniques have differing fragment size requirements for robust sequencing. In some embodiments, quality control testing is performed on the extracted nucleic acids (e.g., DNA and/or RNA), e.g., to assess the nucleic acid concentration and/or fragment size. For example, sizing of DNA fragments provides valuable information used for downstream processing, such as determining whether DNA fragments require additional shearing prior to sequencing.

Wet lab processing 204 then includes preparing a nucleic acid library from the isolated nucleic acids (e.g., cfDNA, DNA, and/or RNA). For example, in some embodiments, DNA libraries (e.g., gDNA and/or cfDNA libraries) are prepared from isolated DNA from the one or more biological samples. In some embodiments, the DNA libraries are prepared using a commercial library preparation kit, e.g., the KAPA Hyper Prep Kit, a New England Biolabs (NEB) kit, or a similar kit.

In some embodiments, during library preparation, adapters (e.g., UDI adapters, such as Roche SeqCap dual end adapters, or UMI adapters such as full length or stubby Y adapters) are ligated onto the nucleic acid molecules. In some embodiments, the adapters include unique molecular identifiers (UMIs), which are short nucleic acid sequences (e.g., 3-10 base pairs) that are added to ends of DNA fragments during adapter ligation. In some embodiments, UMIs are degenerate base pairs that serve as a unique tag that can be used to identify sequence reads originating from a specific DNA fragment. In some embodiments, e.g., when multiplex sequencing will be used to sequence DNA from a plurality of samples (e.g., from the same or different subjects) in a single sequencing reaction, a patient-specific index is also added to the nucleic acid molecules. In some embodiments, the patient specific index is a short nucleic acid sequence (e.g., 3-20 nucleotides) that are added to ends of DNA fragments during library construction, that serve as a unique tag that can be used to identify sequence reads originating from a specific patient sample. Examples of identifier sequences are described, for example, in Kivioja et al., Nat. Methods 9(1):72-74 (2011) and Islam et al., Nat. Methods 11(2):163-66 (2014), the contents of which are hereby incorporated by reference, in their entireties, for all purposes.

In some embodiments, an adapter includes a PCR primer landing site, designed for efficient binding of a PCR or second-strand synthesis primer used during the sequencing reaction. In some embodiments, an adapter includes an anchor binding site, to facilitate binding of the DNA molecule to anchor oligonucleotide molecules on a sequencer flow cell, serving as a seed for the sequencing process by providing a starting point for the sequencing reaction. During PCR amplification following adapter ligation, the UMIs, patient indexes, and binding sites are replicated along with the attached DNA fragment. This provides a way to identify sequence reads that came from the same original fragment in downstream analysis.

In some embodiments, DNA libraries are amplified and purified using commercial reagents, (e.g., Axygen MAG PCR clean up beads). In some such embodiments, the concentration and/or quantity of the DNA molecules are then quantified using a fluorescent dye and a fluorescence microplate reader, standard spectrofluorometer, or filter fluorometer. In some embodiments, library amplification is performed on a device (e.g., an Illumina C-Bot2) and the resulting flow cell containing amplified target-captured DNA libraries is sequenced on a next generation sequencer (e.g., an Illumina HiSeq 4000 or an Illumina NovaSeq 6000) to a unique on-target depth selected by the user. In some embodiments, DNA library preparation is performed with an automated system, using a liquid handling robot (e.g., a SciClone NGSx).

In some embodiments, where feature data 125 includes methylation states 132 for one or more genomic locations, nucleic acids isolated from the biological sample (e.g., cfDNA) are treated to convert unmethylated cytosines to uracils, e.g., prior to generating the sequencing library. Accordingly, when the nucleic acids are sequenced, all cytosines called in the sequencing reaction were necessarily methylated, since the unmethylated cytosines were converted to uracils and accordingly would have been called as thymidines, rather than cytosines, in the sequencing reaction. Commercial kits are available for bisulfate-mediated conversion of methylated cytosines to uracils, for instance, the EZ DNA Methylation™-Gold, EZ DNA Methylation™-Direct, and EZ DNA Methylation™-Lightning kit (available from Zymo Research Corp (Irvine, Calif.)). Commercial kits are also available for enzymatic conversion of methylated cytosines to uracils, for example, the APOBEC-Seq kit (available from NEBiolabs, Ipswich, Mass.).

In some embodiments, wet lab processing 204 includes pooling (308) DNA molecules from a plurality of libraries, corresponding to different samples from the same and/or different patients, to forming a sequencing pool of DNA libraries. When the pool of DNA libraries is sequenced, the resulting sequence reads correspond to nucleic acids isolated from multiple samples. The sequence reads can be separated into different sequence read files, corresponding to the various samples represented in the sequencing read based on the unique identifiers present in the added nucleic acid fragments. In this fashion, a single sequencing reaction can generate sequence reads from multiple samples. Advantageously, this allows for the processing of more samples per sequencing reaction.

In some embodiments, wet lab processing 204 includes enriching (310) a sequencing library, or pool of sequencing libraries, for target nucleic acids, e.g., nucleic acids encompassing loci that are informative for precision oncology and/or used as internal controls for the sequencing or bioinformatics processes. In some embodiments, enrichment is achieved by hybridizing target nucleic acids in the sequencing library to probes that hybridize to the target sequences, and then isolating the captured nucleic acids away from off-target nucleic acids that are not bound by the capture probes.

Advantageously, enriching for target sequences prior to sequencing nucleic acids significantly reduces the costs and time associated with sequencing, facilitates multiplex sequencing by allowing multiple samples to be mixed together for a single sequencing reaction, and significantly reduces the computation burden of aligning the resulting sequence reads, as a result of significantly reducing the total amount of nucleic acids analyzed from each sample.

In some embodiments, the enrichment is performed prior to pooling multiple nucleic acid sequencing libraries. However, in other embodiments, the enrichment is performed after pooling nucleic acid sequencing libraries, which has the advantage of reducing the number of enrichment assays that have to be performed.

In some embodiments, the enrichment is performed prior to generating a nucleic acid sequencing library. This has the advantage that fewer reagents are needed to perform both the enrichment (because there are fewer target sequences at this point, prior to library amplification) and the library production (because there are fewer nucleic acid molecules to tag and amplify after the enrichment). However, this raises the possibility of pull-down bias and/or that small variations in the enrichment protocol will result in less consistent results.

In some embodiments, nucleic acid libraries are pooled (two or more DNA libraries may be mixed to create a pool) and treated with reagents to reduce off-target capture, for example Human COT-1 and/or IDT xGen Universal Blockers. Pools may be dried in a vacufuge and resuspended. DNA libraries or pools may be hybridized to a probe set (for example, a probe set specific to a panel that includes loci from at least 100, 600, 1,000, 10,000, etc. of the 19,000 known human genes) and amplified with commercially available reagents (for example, the KAPA HiFi HotStart ReadyMix). For example, in some embodiments, a pool is incubated in an incubator, PCR machine, water bath, or other temperature-modulating device to allow probes to hybridize. Pools may then be mixed with Streptavidin-coated beads or another means for capturing hybridized DNA-probe molecules, such as DNA molecules representing exons of the human genome and/or genes selected for a genetic panel.

Pools may be amplified and purified more than once using commercially available reagents, for example, the KAPA HiFi Library Amplification kit and Axygen MAG PCR clean up beads, respectively. The pools or DNA libraries may be analyzed to determine the concentration or quantity of DNA molecules, for example by using a fluorescent dye (for example, PicoGreen pool quantification) and a fluorescence microplate reader, standard spectrofluorometer, or filter fluorometer. In one example, the DNA library preparation and/or capture is performed with an automated system, using a liquid handling robot (for example, a SciClone NGSx).

In some embodiments, e.g., where a whole genome sequencing method will be used, nucleic acid sequencing libraries are not target-enriched prior to sequencing, in order to obtain sequencing data on substantially all of the competent nucleic acids in the sequencing library. Similarly, in some embodiments, e.g., where a whole genome sequencing method will be used, nucleic acid sequencing libraries are not mixed, because of bandwidth limitations related to obtaining significant sequencing depth across an entire genome. However, in other embodiments, e.g., where a low pass whole genome sequencing (LPWGS) methodology will be used, nucleic acid sequencing libraries can still be pooled, because very low average sequencing coverage is achieved across a respective genome, e.g., between about 0.5× and about 5×.

In some embodiments, a plurality of nucleic acid probes (e.g., a probe set) is used to enrich one or more target sequences in a nucleic acid sample (e.g., an isolated nucleic acid sample or a nucleic acid sequencing library), e.g., where one or more target sequences is informative for precision oncology. For instance, in some embodiments, one or more of the target sequences encompasses a locus that is associated with an actionable allele. That is, variations of the target sequence are associated with targeted therapeutic approaches. In some embodiments, one or more of the target sequences and/or a property of one or more of the target sequences is used in a classifier trained to distinguish two or more cancer states.

In some embodiments, the probe set includes probes targeting one or more gene loci, e.g., exon or intron loci. In some embodiments, the probe set includes probes targeting one or more loci not encoding a protein, e.g., regulatory loci, miRNA loci, and other non-coding loci, e.g., that have been found to be associated with cancer. In some embodiments, the plurality of loci includes at least 25, 50, 100, 150, 200, 250, 300, 350, 400, 500, 750, 1000, 2500, 5000, or more human genomic loci.

In some embodiments, the probe set includes probes targeting one or more of the genes listed in Table 1. In some embodiments, the probe set includes probes targeting at least 5 of the genes listed in Table 1. In some embodiments, the probe set includes probes targeting at least 10 of the genes listed in Table 1. In some embodiments, the probe set includes probes targeting at least 25 of the genes listed in Table 1. In some embodiments, the probe set includes probes targeting at least 50 of the genes listed in Table 1. In some embodiments, the probe set includes probes targeting at least 75 of the genes listed in Table 1. In some embodiments, the probe set includes probes targeting at least 100 of the genes listed in Table 1. In some embodiments, the probe set includes probes targeting all of the genes listed in Table 1.

Table 1. An example panel of 105 genes that are informative for precision oncology.

TABLE 1

Example Gene Panel for Precision Oncology

| | | | | | | |
|---|---|---|---|---|---|---|
| ALK | B2M | ERRFI1 | IDH2 | MSH6 | PIK3R1 | SPOP |
| FGFR2 | BAP1 | ESR1 | JAK1 | MTOR | PMS2 | STK11 |
| FGFR3 | BRCA1 | EZH2 | JAK2 | MYCN | PTCH1 | TERT |
| NTRK1 | BRCA2 | FBXW7 | JAK3 | NF1 | PTEN | TP53 |
| RET | BTK | FGFR1 | KDR | NF2 | PTPN11 | TSC1 |
| ROS1 | CCND1 | FGFR4 | KEAP1 | NFE2L2 | RAD51C | TSC2 |
| BRAF | CCND2 | FLT3 | KIT | NOTCH1 | RAF1 | UGT1A1 |
| AKT1 | CCND3 | FOXL2 | KRAS | NPM1 | RB1 | VHL |
| AKT2 | CDH1 | GATA3 | MAP2K1 | NRAS | RHEB | CCNE1 |
| APC | CDK4 | GNA11 | MAP2K2 | PALB2 | RHOA | CD274 |
| AR | CDK6 | GNAQ | MAPK1 | PBRM1 | RIT1 | EGFR |
| ARAF | CDKN2A | GNAS | MLH1 | PDCD1LG2 | RNF43 | ERBB2 |
| ARID1A | CTNNB1 | HNF1A | MPL | PDGFRA | SDHA | MET |
| ATM | DDR2 | HRAS | MSH2 | PDGFRB | SMAD4 | MYC |
| ATR | DPYD | IDH1 | MSH3 | PIK3CA | SMO | KMT2A |

In some embodiments, the probe set includes probes targeting one or more of the genes listed in List 1, provided below. In some embodiments, the probe set includes probes targeting at least 5 of the genes listed in List 1. In some embodiments, the probe set includes probes targeting at least 10 of the genes listed in List 1. In some embodiments, the probe set includes probes targeting at least 25 of the genes listed in List 1. In some embodiments, the probe set includes probes targeting at least 50 of the genes listed in List 1. In some embodiments, the probe set includes probes targeting at least 70 of the genes listed in List 1. In some embodiments, the probe set includes probes targeting all of the genes listed in List 1.

In some embodiments, the probe set includes probes targeting one or more of the genes listed in List 2, provided below. In some embodiments, the probe set includes probes targeting at least 5 of the genes listed in List 2. In some embodiments, the probe set includes probes targeting at least 10 of the genes listed in List 2. In some embodiments, the probe set includes probes targeting at least 25 of the genes listed in List 2. In some embodiments, the probe set includes probes targeting at least 50 of the genes listed in List 2. In some embodiments, the probe set includes probes targeting at least 75 of the genes listed in List 2. In some embodiments, the probe set includes probes targeting at least 100 of the genes listed in List 2. In some embodiments, the probe set includes probes targeting all of the genes listed in List 2.

In some embodiments, panels of genes including one or more genes from the following lists are used for analyzing specimens, sequencing, and/or identification. In some embodiments, panels of genes for analyzing specimens, sequencing, and/or identification include one or more genes from List 1 or List 2. In some embodiments, panels of genes for analyzing specimens, sequencing, and/or identification include one or more genes from:

List 1: AKT1 (14q32.33), ALK (2p23.2-23.1), APC (5q22.2), AR (Xq12), ARAF (Xp11.3), ARID1A (1p36.11), ATM (11q22.3), BRAF (7q34), BRCA1 (17q21.31), BRCA2 (13q13.1), CCND1 (11q13.3), CCND2 (12p13.32), CCNE1 (19q12), CDH1 (16q22.1), CDK4 (12q14.1), CDK6 (7q21.2), CDKN2A (9p21.3), CTNNB1 (3p22.1), DDR2 (1q23.3), EGFR (7p11.2), ERBB2 (17q12), ESR1 (6q25.1-25.2), EZH2 (7q36.1), FBXW7 (4q31.3), FGFR1 (8p11.23), FGFR2 (10q26.13), FGFR3 (4p16.3), GATA3 (10p14), GNA11 (19p13.3), GNAQ (9q21.2), GNAS (20q13.32), HNF1A (12q24.31), HRAS (11p15.5), IDH1 (2q34), IDH2 (15q26.1), JAK2 (9p24.1), JAK3 (19p13.11), KIT (4q12), KRAS (12p12.1), MAP2K1 (15q22.31), MAP2K2 (19p13.3), MAPK1 (22q11.22), MAPK3 (16p11.2), MET (7q31.2), MLH1 (3p22.2), MPL (1p34.2), MTOR (1p36.22), MYC (8q24.21), NF1 (17q11.2), NFE2L2 (2q31.2), NOTCH1 (9q34.3), NPM1 (5q35.1), NRAS (1p13.2), NTRK1 (1q23.1), NTRK3 (15q25.3), PDGFRA (4q12), PIK3CA (3q26.32), PTEN (10q23.31), PTPN11 (12q24.13), RAF1 (3p25.2), RB1 (13q14.2), RET (10q11.21), RHEB (7q36.1), RHOA (3p21.31), RIT1 (1q22), ROS1 (6q22.1), SMAD4 (18q21.2), SMO (7q32.1), STK11 (19p13.3), TERT (5p15.33), TP53 (17p13.1), TSC1 (9q34.13), and VHL (3p25.3).

List 2: ABL1, ACVR1B, AKT1, AKT2, AKT3, ALK, ALOX12B, AMER1 (FAM123B), APC, AR, ARAF, ARFRP1, ARID1A, ASXL1, ATM, ATR, ATRX, AURKA, AURKB, AXIN1, AXL, BAP1, BARD1, BCL2, BCL2L1, BCL2L2, BCL6, BCOR, BCORL1, BRAF, BRCA1, BRCA2, BRD4, BRIP1, BTG1, BTG2, BTK, C11orf30 (EMSY), C17orf39 (GID4), CALR, CARD11, CASP8, CBFB, CBL, CCND1, CCND2, CCND3, CCNE1, CD22, CD274 (PD-L1), CD70, CD79A, CD79B, CDC73, CDH1, CDK12, CDK4, CDK6, CDK8, CDKN1A, CDKN1B, CDKN2A, CDKN2B, CDKN2C, CEBPA, CHEK1, CHEK2, CIC, CREBBP, CRKL, CSF1R, CSF3R, CTCF, CTNNA1, CTNNB1, CUL3, CUL4A, CXCR4, CYP17A1, DAXX, DDR1, DDR2, DIS3, DNMT3A, DOT1L, EED, EGFR, EP300, EPHA3, EPHB1, EPHB4, ERBB2, ERBB3, ERBB4, ERCC4, ERG, ERRFI1 ESR1, EZH2, FAM46C, FANCA, FANCC, FANCG, FANCL, FAS, FBXW7, FGF10, FGF12, FGF14, FGF19, FGF23, FGF3, FGF4, FGF6, FGFR1, FGFR2, FGFR3, FGFR4, FH, FLCN, FLT1, FLT3, FOXL2, FUBP1, GABRA6, GATA3, GATA4, GATA6, GNA11, GNA13, GNAQ, GNAS, GRM3, GSK3B, H3F3A, HDAC1, HGF, HNF1A, HRAS, HSD3B1, ID3, IDH1, IDH2, IGF1R, IKBKE, IKZF1, INPP4B, IRF2, IRF4, IRS2, JAK1, JAK2, JAK3, JUN, KDM5A, KDM5C, KDM6A, KDR, KEAP1, KEL, KIT, KLHL6, KMT2A, KMT2D (MLL2), KRAS, LTK, LYN, MAF, MAP2K1 (MEK1), MAP2K2 (MEK2), MAP2K4, MAP3K1, MAP3K13, MAPK1, MCL1, MDM2, MDM4, MED12, MEF2B, MEN1, MERTK, MET, MITF, MKNK1, MLH1, MPL, MRE11A, MSH2, MSH3, MSH6, MST1R, MTAP, MTOR, MUTYH, MYC, MYCL (MYCL1), MYCN, MYD88, NBN, NF1, NF2, NFE2L2, NFKBIA, NKX2-1, NOTCH1, NOTCH2, NOTCH3, NPM1, NRAS, NSD3 (WHSC1L1), NT5C2, NTRK1, NTRK2, NTRK3, P2RY8, PALB2, PARK2, PARP1, PARP2, PARP3, PAXS, PBRM1, PDCD1 (PD-1), PDCD1LG2 (PD-L2), PDGFRA, PDGFRB, PDK1, PIK3C2B, PIK3C2G, PIK3CA, PIK3CB, PIK3R1, PIM1, PMS2, POLD1, POLE, PPARG, PPP2R1A, PPP2R2A, PRDM1, PRKAR1A, PRKCI, PTCH1, PTEN, PTPN11, PTPRO, QKI, RAC1, RAD21, RAD51, RAD51B, RAD51C, RAD51D, RAD52, RAD54L, RAF1, RARA, RB1, RBM10, REL, RET, RICTOR, RNF43, ROS1, RPTOR, SDHA, SDHB, SDHC, SDHD, SETD2, SF3B1, SGK1, SMAD2, SMAD4, SMARCA4, SMARCB1, SMO, SNCAIP, SOCS1, SOX2, SOX9, SPEN, SPOP, SRC, STAG2, STAT3, STK11, SUFU, SYK, TBX3, TEK, TERC, TERT, TET2, ncRNA, Promoter, TGFBR2, TIPARP, TNFAIP3, TNFRSF14, TP53, TSC1, TSC2, TYRO3, U2AF1, VEGFA, VHL, WHSC1, WT1, XPO1, XRCC2, ZNF217, and ZNF703.

Generally, probes for enrichment of nucleic acids (e.g., cfDNA obtained from a liquid biopsy sample) include DNA, RNA, or a modified nucleic acid structure with a base sequence that is complementary to a locus of interest. For instance, a probe designed to hybridize to a locus in a cfDNA molecule can contain a sequence that is complementary to either strand, because the cfDNA molecules are double stranded. In some embodiments, each probe in the plurality of probes includes a nucleic acid sequence that is identical or complementary to at least 10, at least 11, at least 12, at least 13, at least 14, or at least 15 consecutive bases of a loci of interest. In some embodiments, each probe in the plurality of probes includes a nucleic acid sequence that is identical or complementary to at least 20, 25, 30, 40, 50, 75, 100, 150, 200, or more consecutive bases of a locus of interest.

Targeted panels provide several benefits for nucleic acid sequencing. For example, in some embodiments, algorithms for discriminating between, e.g., a first and second cancer condition can be trained on smaller, more informative data sets (e.g., fewer genes), which leads to more computationally efficient training of classifiers that discriminate between the first and second cancer states. Such improvements in computational efficiency, owing to the reduced size of the discriminating gene set, can advantageously either be used to speed up classifier training or be used to improve the performance of such classifiers (e.g., through more extensive training of the classifier).

In some embodiments, the gene panel is a whole-exome panel that analyzes the exomes of a biological sample. In some embodiments, the gene panel is a whole-genome panel that analyzes the genome of a specimen. In some embodiments, the gene panel is optimized for use with liquid biopsy samples (e.g., to provide clinical decision support for solid tumors). See, for example, Table 1 above.

In some embodiments, the probes include additional nucleic acid sequences that do not share any homology to the loci of interest. For example, in some embodiments, the probes also include nucleic acid sequences containing an identifier sequence, e.g., a unique molecular identifier (UMI), e.g., that is unique to a particular sample or subject. Examples of identifier sequences are described, for example, in Kivioja et al., 2011, Nat. Methods 9(1), pp. 72-74 and Islam et al., 2014, Nat. Methods 11(2), pp. 163-66, which are incorporated by reference herein. Similarly, in some embodiments, the probes also include primer nucleic acid sequences useful for amplifying the nucleic acid molecule of interest, e.g., using PCR. In some embodiments, the probes also include a capture sequence designed to hybridize to an anti-capture sequence for recovering the nucleic acid molecule of interest from the sample.

Likewise, in some embodiments, the probes each include a non-nucleic acid affinity moiety covalently attached to nucleic acid molecule that is complementary to the loci of interest, for recovering the nucleic acid molecule of interest.

Non-limited examples of non-nucleic acid affinity moieties include biotin, digoxigenin, and dinitrophenol. In some embodiments, the probe is attached to a solid-state surface or particle, e.g., a dipstick or magnetic bead, for recovering the nucleic acid of interest. In some embodiments, the methods described herein include amplifying the nucleic acids that bound to the probe set prior to further analysis, e.g., sequencing. Methods for amplifying nucleic acids, e.g., by PCR, are well known in the art.

Sequence reads are then generated (312) from the sequencing library or pool of sequencing libraries. Sequencing data may be acquired by any methodology known in the art. For example, next generation sequencing (NGS) techniques such as sequencing-by-synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators. In some embodiments, sequencing is performed using next generation sequencing technologies, such as short-read technologies. In other embodiments, long-read sequencing or another sequencing method known in the art is used.

Next-generation sequencing produces millions of short reads (e.g., sequence reads) for each biological sample. Accordingly, in some embodiments, the plurality of sequence reads obtained by next-generation sequencing of cfDNA molecules are DNA sequence reads. In some embodiments, the sequence reads have an average length of at least fifty nucleotides. In other embodiments, the sequence reads have an average length of at least 50, 60, 70, 80, 90, 100, 150, 200, 250, 300, or more nucleotides.

In some embodiments, sequencing is performed after enriching for nucleic acids (e.g., cfDNA, gDNA, and/or RNA) encompassing a plurality of predetermined target sequences, e.g., human genes and/or non-coding sequences associated with cancer. Advantageously, sequencing a nucleic acid sample that has been enriched for target nucleic acids, rather than all nucleic acids isolated from a biological sample, significantly reduces the average time and cost of the sequencing reaction. Accordingly, in some embodiments, the methods described herein include obtaining a plurality of sequence reads of nucleic acids that have been hybridized to a probe set for hybrid-capture enrichment (e.g., of one or more genes listed in Table 1).

In some embodiments, panel-targeting sequencing is performed to an average on-target depth of at least 500×, at least 750×, at least 1000×, at least 2500×, at least 500×, at least 10,000×, or greater depth. In some embodiments, samples are further assessed for uniformity above a sequencing depth threshold (e.g., 95% of all targeted base pairs at 300× sequencing depth). In some embodiments, the sequencing depth threshold is a minimum depth selected by a user or practitioner.

In some embodiments, the sequence reads are obtained by a whole genome or whole exome sequencing methodology. In some such embodiments, whole exome capture is performed with an automated system, using a liquid handling robot (for example, a SciClone NGSx). Whole genome sequencing, and to some extent whole exome sequencing, is typically performed at lower sequencing depth than smaller target-panel sequencing reactions, because many more loci are being sequenced. For example, in some embodiments, whole genome or whole exome sequencing is performed to an average sequencing depth of at least 3×, at least 5×, at least 10×, at least 15×, at least 20×, or greater. In some embodiments, low-pass whole genome sequencing (LPWGS) techniques are used for whole genome or whole exome sequencing. LPWGS is typically performed to an average sequencing depth of about 0.25× to about 5×, more typically to an average sequencing depth of about 0.5× to about 3×.

Because of the differences in the sequencing methodologies, data obtained from targeted-panel sequencing is better suited for certain analyses than data obtained from whole genome/whole exome sequencing, and vice versa. For instance, because of the higher sequencing depth achieved by targeted-panel sequencing, the resulting sequence data is better suited for the identification of variant alleles present at low allelic fractions in the sample, e.g., less than 20%. By contrast, data generated from whole genome/whole exome sequencing is better suited for the estimation of genome-wide metrics, such as tumor mutational burden, because the entire genome is better represented in the sequencing data. Accordingly, in some embodiments, a nucleic acid sample, e.g., a cfDNA, gDNA, or mRNA sample, is evaluated using both targeted-panel sequencing and whole genome/whole exome sequencing (e.g., LPWGS).

In some embodiments, the raw sequence reads resulting from the sequencing reaction are output from the sequencer in a native file format, e.g., a BCL file. In some embodiments, the native file is passed directly to a bioinformatics pipeline (e.g., variant analysis 206), components of which are described in detail below. In other embodiments, pre-processing is performed prior to passing the sequences to the bioinformatics platform. For instance, in some embodiments, the format of the sequence read file is converted from the native file format (e.g., BCL) to a file format compatible with one or more algorithms used in the bioinformatics pipeline (e.g., FASTQ or FASTA). In some embodiments, the raw sequence reads are filtered to remove sequences that do not meet one or more quality thresholds. In some embodiments, raw sequence reads generated from the same unique nucleic acid molecule in the sequencing read are collapsed into a single sequence read representing the molecule, e.g., using UMIs as described above. In some embodiments, one or more of these pre-processing activities is performed within the bioinformatics pipeline itself.

In one example, a sequencer may generate a BCL file. A BCL file may include raw image data of a plurality of patient specimens which are sequenced. BCL image data is an image of the flow cell across each cycle during sequencing. A cycle may be implemented by illuminating a patient specimen with a specific wavelength of electromagnetic radiation, generating a plurality of images which may be processed into base calls via BCL to FASTQ processing algorithms which identify which base pairs are present at each cycle. The resulting FASTQ file includes the entirety of reads for each patient specimen paired with a quality metric, e.g., in a range from 0 to 64 where a 64 is the best quality and a 0 is the worst quality. In embodiments where both a liquid biopsy sample and a normal tissue sample are sequenced, sequence reads in the corresponding FASTQ files may be matched, such that a liquid biopsy-normal analysis may be performed.

FASTQ format is a text-based format for storing both a biological sequence, such as a nucleotide sequence, and its corresponding quality scores. These FASTQ files are analyzed to determine what genetic variants or copy number changes are present in the sample. Each FASTQ file contains reads that may be paired-end or single reads, and may be short-reads or long-reads, where each read represents one detected sequence of nucleotides in a nucleic acid molecule that was isolated from the patient sample or a copy of the nucleic acid molecule, detected by the sequencer. Each read in the FASTQ file is also associated with a quality rating. The quality rating may reflect the likelihood that an error occurred during the sequencing procedure that affected the associated read. In some embodiments, the results of paired-end sequencing of each isolated nucleic acid sample are contained in a split pair of FASTQ files, for efficiency. Thus, in some embodiments, forward (Read 1) and reverse (Read 2) sequences of each isolated nucleic acid sample are stored separately but in the same order and under the same identifier.

In various embodiments, the bioinformatics pipeline may filter FASTQ data from the corresponding sequence data file for each respective biological sample. Such filtering may include correcting or masking sequencer errors and removing (trimming) low quality sequences or bases, adapter sequences, contaminations, chimeric reads, overrepresented sequences, biases caused by library preparation, amplification, or capture, and other errors.

While workflow 200 illustrates obtaining a biological sample, extracting nucleic acids from the biological sample, and sequencing the isolated nucleic acids, in some embodiments, sequencing data used in the improved systems and methods described herein (e.g., which include improved methods for validating a somatic sequence variant in a test subject having a cancer condition) is obtained by receiving previously generated sequence reads, in electronic form.

Referring again to FIG. 2A, nucleic acid sequencing data 122 generated from the one or more patient samples is then evaluated (e.g., via variant analysis 206) in a bioinformatics pipeline, e.g., using bioinformatics module 140 of system 100, to identify genomic alterations and other metrics in the cancer genome of the patient. An example overview for a bioinformatics pipeline is described below with respect to FIGS. 4A-4F. Advantageously, in some embodiments, the present disclosure improves bioinformatics pipelines, like pipeline 206, by improving methods and systems of validating somatic sequence variants.

Figure 4A:
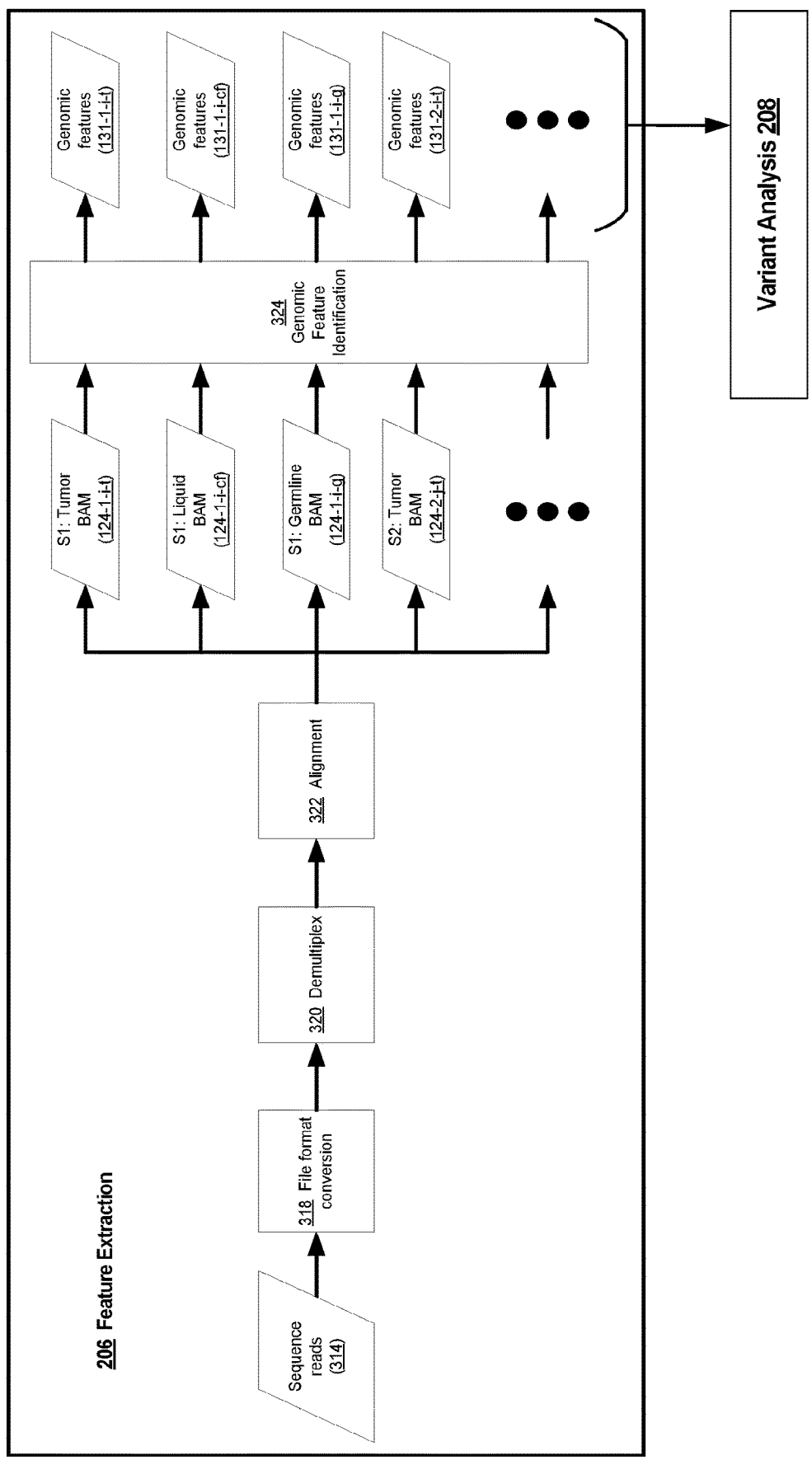
FIGS. 4A, 4B, 4C, 4D, 4E, and 4F collectively illustrate an example bioinformatics pipeline for precision oncology, in accordance with various embodiments of the present disclosure.
Figure 4B:
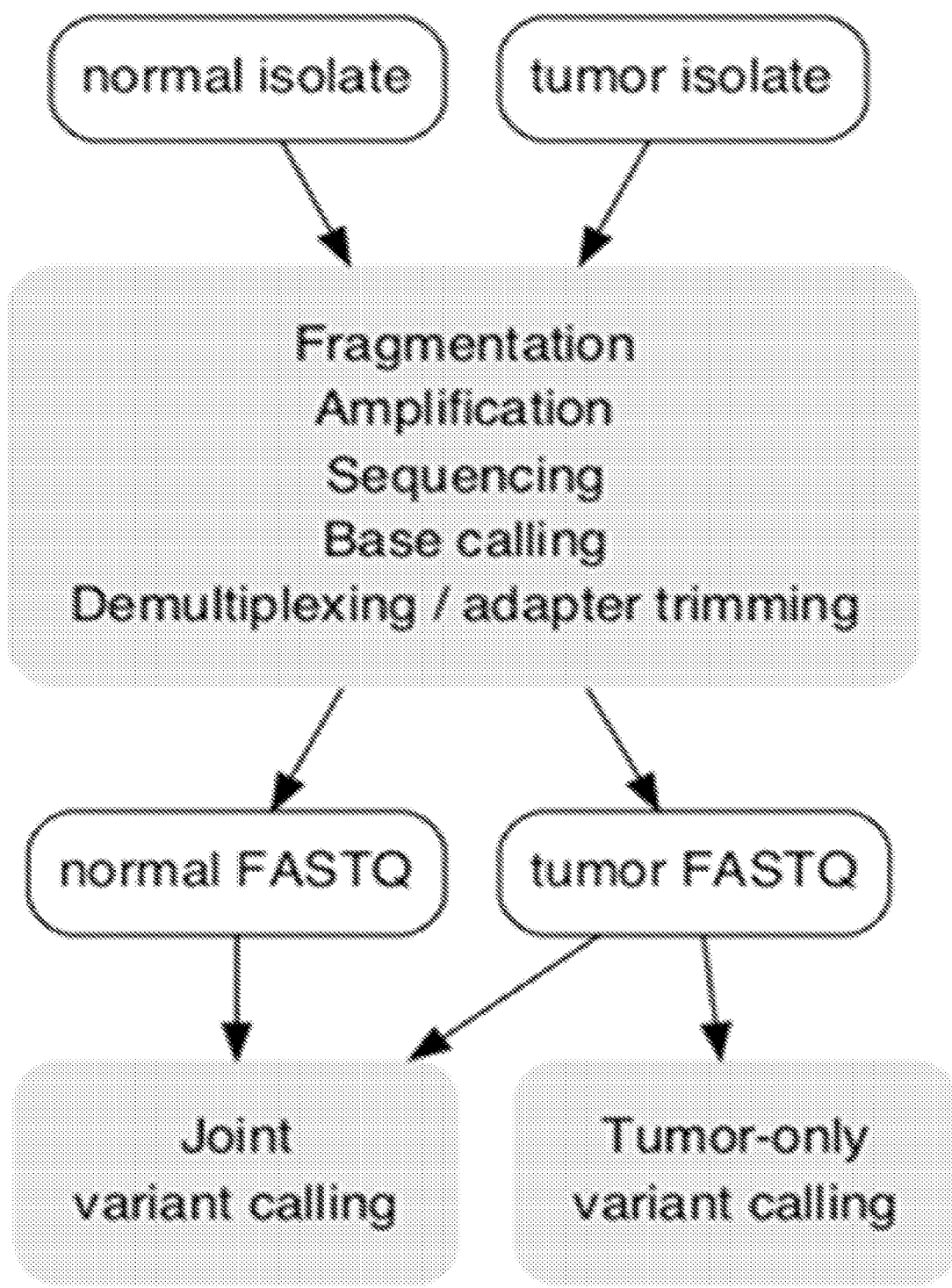
Figure 4C:
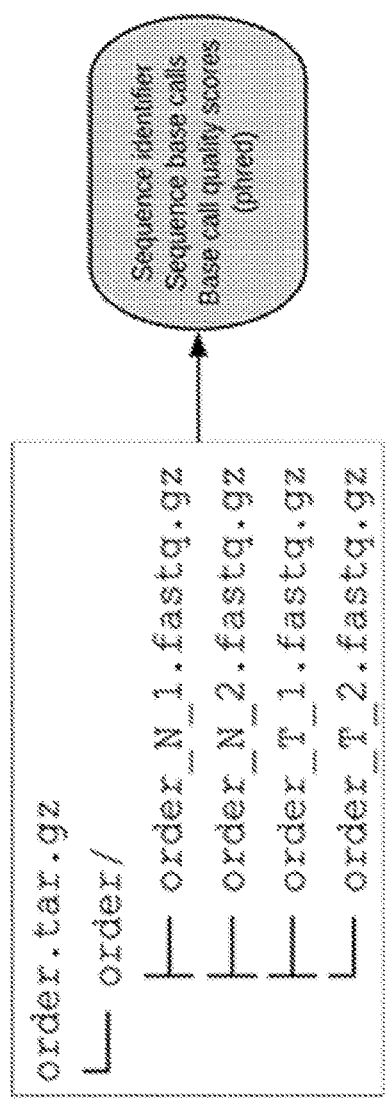
Figure 4D:
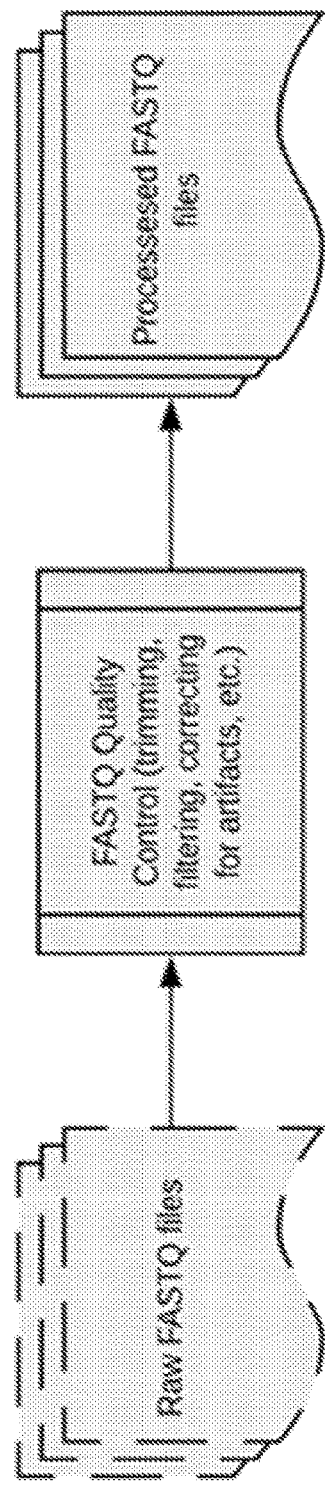

FIG. 4A illustrates an example bioinformatics pipeline 206 (e.g., as used for feature extraction in the workflows illustrated in FIGS. 2A and 3) for providing clinical support for precision oncology. As shown in FIG. 4A, sequencing data 122 obtained from the wet lab processing 204 (e.g., sequence reads 314) is input into the pipeline.

In various embodiments, the bioinformatics pipeline includes a circulating tumor DNA (ctDNA) pipeline for analyzing liquid biopsy samples. The pipeline may detect SNVs, INDELs, copy number amplifications/deletions and genomic rearrangements (for example, fusions). The pipeline may employ unique molecular index (UMI)-based consensus base calling as a method of error suppression as well as a Bayesian tri-nucleotide context-based position level error suppression. In various embodiments, it is able to detect variants having a 0.1%, 0.15%, 0.2%, 0.25%, 0.3%, 0.4%, or 0.5% variant allele fraction.

In some embodiments, the sequencing data is processed (e.g., using sequence data processing module 141) to prepare it for genomic feature identification 385. For instance, in some embodiments as described above, the sequencing data is present in a native file format provided by the sequencer. Accordingly, in some embodiments, the system (e.g., system 100) applies a pre-processing algorithm 142 to convert the file format (318) to one that is recognized by one or more upstream processing algorithms. For example, BCL file outputs from a sequencer can be converted to a FASTQ file format using the bcl2fastq or bcl2fastq2 conversion software (Illumina®). FASTQ format is a text-based format for storing both a biological sequence, such as nucleotide sequence, and its corresponding quality scores. These FASTQ files are analyzed to determine what genetic variants, copy number changes, etc., are present in the sample.

In some embodiments, other preprocessing functions are performed, e.g., filtering sequence reads 122 based on a desired quality, e.g., size and/or quality of the base calling. In some embodiments, quality control checks are performed to ensure the data is sufficient for variant calling. For instance, entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools, for example, a software tool such as Skewer. See, Jiang, H. et al., BMC Bioinformatics 15(182):1-12 (2014). FASTQ files may be analyzed for rapid assessment of quality control and reads, for example, by a sequencing data QC software such as AfterQC, Kraken, RNA-SeQC, FastQC, or another similar software program. For paired end reads, reads may be merged.

In some embodiments, when both a liquid biopsy sample and a normal tissue sample from the patient are sequenced, two FASTQ output files are generated, one for the liquid biopsy sample and one for the normal tissue sample. A 'matched' (e.g., panel-specific) workflow is run to jointly analyze the liquid biopsy-normal matched FASTQ files. When a matched normal sample is not available from the patient, FASTQ files from the liquid biopsy sample are analyzed in the 'tumor-only' mode. See, for example, FIG. 4B. If two or more patient samples are processed simultaneously on the same sequencer flow cell, e.g., a liquid biopsy sample and a normal tissue sample, a difference in the sequence of the adapters used for each patient sample barcodes nucleic acids extracted from both samples, to associate each read with the correct patient sample and facilitate assignment to the correct FASTQ file.

For efficiency, in some embodiments, the results of paired-end sequencing of each isolate are contained in a split pair of FASTQ files. Forward (Read 1) and reverse (Read 2) sequences of each tumor and normal isolate are stored separately but in the same order and under the same identifier. See, for example, FIG. 4C. In various embodiments, the bioinformatics pipeline may filter FASTQ data from each isolate. Such filtering may include correcting or masking sequencer errors and removing (trimming) low quality sequences or bases, adapter sequences, contaminations, chimeric reads, overrepresented sequences, biases caused by library preparation, amplification, or capture, and other errors. See, for example, FIG. 4D.

Similarly, in some embodiments, sequencing (312) is performed on a pool of nucleic acid sequencing libraries prepared from different biological samples, e.g., from the same or different patients. Accordingly, in some embodiments, the system demultiplexes (320) the data (e.g., using demultiplexing algorithm 144) to separate sequence reads into separate files for each sequencing library included in the sequencing pool, e.g., based on UMI or patient identifier sequences added to the nucleic acid fragments during sequencing library preparation, as described above. In some embodiments, the demultiplexing algorithm is part of the same software package as one or more pre-processing algorithms 142. For instance, the bcl2fastq or bcl2fastq2 conversion software (Illumina®) include instructions for both converting the native file format output from the sequencer and demultiplexing sequence reads 122 output from the reaction.

The sequence reads are then aligned (322), e.g., using an alignment algorithm 143, to a reference sequence construct 158, e.g., a reference genome, reference exome, or other reference construct prepared for a particular targeted-panel sequencing reaction. For example, in some embodiments, individual sequence reads 123, in electronic form (e.g., in FASTQ files), are aligned against a reference sequence construct for the species of the subject (e.g., a reference human genome) by identifying a sequence in a region of the reference sequence construct that best matches the sequence of nucleotides in the sequence read. In some embodiments, the sequence reads are aligned to a reference exome or reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. Any of a variety of alignment tools can be used for this task.

For instance, local sequence alignment algorithms compare subsequences of different lengths in the query sequence (e.g., sequence read) to subsequences in the subject sequence (e.g., reference construct) to create the best alignment for each portion of the query sequence. In contrast, global sequence alignment algorithms align the entirety of the sequences, e.g., end to end. Examples of local sequence alignment algorithms include the Smith-Waterman algorithm (see, for example, Smith and Waterman, J Mol. Biol., 147(1):195-97 (1981), which is incorporated herein by reference), Lalign (see, for example, Huang and Miller, Adv. Appl. Math, 12:337-57 (1991), which is incorporated by reference herein), and PatternHunter (see, for example, Ma B. et al., Bioinformatics, 18(3):440-45 (2002), which is incorporated by reference herein).

In some embodiments, the read mapping process starts by building an index of either the reference genome or the reads, which is then used to retrieve the set of positions in the reference sequence where the reads are more likely to align. Once this subset of possible mapping locations has been identified, alignment is performed in these candidate regions with slower and more sensitive algorithms. See, for example, Hatem et al., 2013, "Benchmarking short sequence mapping tools," BMC Bioinformatics 14: p. 184; and Flicek and Birney, 2009, "Sense from sequence reads: methods for alignment and assembly," Nat Methods 6(Suppl. 11), S6-S12, each of which is hereby incorporated by reference. In some embodiments, the mapping tools methodology makes use of a hash table or a Burrows—Wheeler transform (BWT). See, for example, Li and Homer, 2010, "A survey of sequence alignment algorithms for next-generation sequencing," Brief Bioinformatics 11, pp. 473-483, which is hereby incorporated by reference.

Other software programs designed to align reads include, for example, Novoalign (Novocraft, Inc.), Bowtie, Burrows Wheeler Aligner (BWA), and/or programs that use a Smith-Waterman algorithm. Candidate reference genomes include, for example, hg19, GRCh38, hg38, GRCh37, and/or other reference genomes developed by the Genome Reference Consortium. In some embodiments, the alignment generates a SAM file, which stores the locations of the start and end of each read according to coordinates in the reference genome and the coverage (number of reads) for each nucleotide in the reference genome.

For example, in some embodiments, each read of a FASTQ file is aligned to a location in the human genome having a sequence that best matches the sequence of nucleotides in the read. There are many software programs designed to align reads, for example, Novoalign (Novocraft, Inc.), Bowtie, Burrows Wheeler Aligner (BWA), programs that use a Smith-Waterman algorithm, etc. Alignment may be directed using a reference genome (for example, hg19, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. In some embodiments, one or more SAM files are generated for the alignment, which store the locations of the start and end of each read according to coordinates in the reference genome and the coverage (number of reads) for each nucleotide in the reference genome. The SAM files may be converted to BAM files. In some embodiments, the BAM files are sorted, and duplicate reads are marked for deletion, resulting in de-duplicated BAM files.

In some embodiments, adapter-trimmed FASTQ files are aligned to the 19th edition of the human reference genome build (HG19) using Burrows-Wheeler Aligner (BWA, Li and Durbin, Bioinformatics, 25(14):1754-60 (2009)). Following alignment, reads are grouped by alignment position and UMI family and collapsed into consensus sequences, for example, using fgbio tools (fulcrumgenomics.github.io/fgbio/). Bases with insufficient quality or significant disagreement among family members (for example, when it is uncertain whether the base is an adenine, cytosine, guanine, etc.) may be replaced by N's to represent a wildcard nucleotide type. PHRED scores are then scaled based on initial base calling estimates combined across all family members. Following single-strand consensus generation, duplex consensus sequences are generated by comparing the forward and reverse oriented PCR products with mirrored UMI sequences. In various embodiments, a consensus can be generated across read pairs. Otherwise, single-strand consensus calls will be used. Following consensus calling, filtering is performed to remove low-quality consensus fragments. The consensus fragments are then re-aligned to the human reference genome using BWA. A BAM output file is generated after the re-alignment, then sorted by alignment position, and indexed.

In some embodiments, where both a liquid biopsy sample and a normal tissue sample are analyzed, this process produces a liquid biopsy BAM file (e.g., Liquid BAM 124-1-$i$-$cf$) and a normal BAM file (e.g., Germline BAM 124-1-$i$-$g$), as illustrated in FIG. 4A. In various embodiments, BAM files may be analyzed to detect genetic variants and other genetic features, including single nucleotide variants (SNVs), copy number variants (CNVs), gene rearrangements, etc.

In some embodiments, the sequencing data is normalized, e.g., to account for pull-down, amplification, and/or sequencing bias (e.g., mappability, GC bias etc.). See, for example, Schwartz et al., PLoS ONE 6(1):e16685 (2011) and Benjamini and Speed, Nucleic Acids Research 40(10):

e72 (2012), the contents of which are hereby incorporated by reference, in their entireties, for all purposes.

In some embodiments, SAM files generated after alignment are converted to BAM files 124. Thus, after preprocessing sequencing data generated for a pooled sequencing reaction, BAM files are generated for each of the sequencing libraries present in the master sequencing pools. For example, as illustrated in FIG. 4A, separate BAM files are generated for each of three samples acquired from subject 1 at time i (e.g., tumor BAM 124-1-$i$-$t$ corresponding to alignments of sequence reads of nucleic acids isolated from a solid tumor sample from subject 1, Liquid BAM 124-1-$i$-$cf$ corresponding to alignments of sequence reads of nucleic acids isolated from a liquid biopsy sample from subject 1, and Germline BAM 124-1-$i$-$g$ corresponding to alignments of sequence reads of nucleic acids isolated from a normal tissue sample from subject 1), and one or more samples acquired from one or more additional subjects at time j (e.g., Tumor BAM 124-2-$j$-$t$ corresponding to alignments of sequence reads of nucleic acids isolated from a solid tumor sample from subject 2). In some embodiments, BAM files are sorted, and duplicate reads are marked for deletion, resulting in de-duplicated BAM files. For example, tools like SamBAMBA mark and filter duplicate alignments in the sorted BAM files.

Many of the embodiments described below, in conjunction with FIGS. 4A-4F, relate to analyses performed using sequencing data from cfDNA of a cancer patient, e.g., obtained from a liquid biopsy sample of the patient. Generally, these embodiments are independent and, thus, not reliant upon any particular sequencing data generation methods, e.g., sample preparation, sequencing, and/or data preprocessing methodologies. However, in some embodiments, the methods described below include one or more features 204 of generating sequencing data, as illustrated in FIGS. 2A and 3.

Alignment files prepared as described above (e.g., BAM files 124) are then passed to a feature extraction module 145, where the sequences are analyzed (324) to identify genomic alterations (e.g., SNVs/MNVs, indels, genomic rearrangements, copy number variations, etc.) and/or determine various characteristics of the patient's cancer (e.g., MSI status, TMB, tumor ploidy, HRD status, tumor fraction, tumor purity, methylation patterns, etc.). Many software packages for identifying genomic alterations are known in the art, for example, freebayes, PolyBayse, samtools, GATK, pindel, SAMtools, Breakdancer, Cortex, Crest, Delly, Gridss, Hydra, Lumpy, Manta, and Socrates. For a review of many of these variant calling packages see, for example, Cameron, D. L. et al., Nat. Commun., 10(3240):1-11 (2019), the content of which is hereby incorporated by reference, in its entirety, for all purposes. Generally, these software packages identify variants in sorted SAM or BAM files 124, relative to one or more reference sequence constructs 158. The software packages then output a file e.g., a raw VCF (variant call format), listing the variants (e.g., genomic features 131) called and identifying their location relevant to the reference sequence construct (e.g., where the sequence of the sample nucleic acids differ from the corresponding sequence in the reference construct). In some embodiments, system 100 digests the contents of the native output file to populate feature data 125 in test patient data store 120. In other embodiments, the native output file serves as the record of these genomic features 131 in test patient data store 120.

Generally, the systems described herein can employ any combination of available variant calling software packages and internally developed variant identification algorithms. In some embodiments, the output of a particular algorithm of a variant calling software is further evaluated, e.g., to improve variant identification. Accordingly, in some embodiments, system 100 employs an available variant calling software package to perform some of all of the functionality of one or more of the algorithms shown in feature extraction module 145.

In some embodiments, as illustrated in FIG. 1A, separate algorithms (or the same algorithm implemented using different parameters) are applied to identify variants unique to the cancer genome of the patient and variants existing in the germline of the subject. In other embodiments, variants are identified indiscriminately and later classified as either germline or somatic, e.g., based on sequencing data, population data, or a combination thereof. In some embodiments, variants are classified as germline variants, and/or non-actionable variants, when they are represented in the population above a threshold level, e.g., as determined using a population database such as ExAC or gnomAD. For instance, in some embodiments, variants that are represented in at least 1% of the alleles in a population are annotated as germline and/or non-actionable. In other embodiments, variants that are represented in at least 2%, at least 3%, at least 4%, at least 5%, at least 7.5%, at least 10%, or more of the alleles in a population are annotated as germline and/or non-actionable. In some embodiments, sequencing data from a matched sample from the patient, e.g., a normal tissue sample, is used to annotate variants identified in a cancerous sample from the subject. That is, variants that are present in both the cancerous sample and the normal sample represent those variants that were in the germline prior to the patient developing cancer and can be annotated as germline variants.

In various aspects, the detected genetic variants and genetic features are analyzed as a form of quality control. For example, a pattern of detected genetic variants or features may indicate an issue related to the sample, sequencing procedure, and/or bioinformatics pipeline (e.g., example, contamination of the sample, mislabeling of the sample, a change in reagents, a change in the sequencing procedure and/or bioinformatics pipeline, etc.).

Figure 4E:
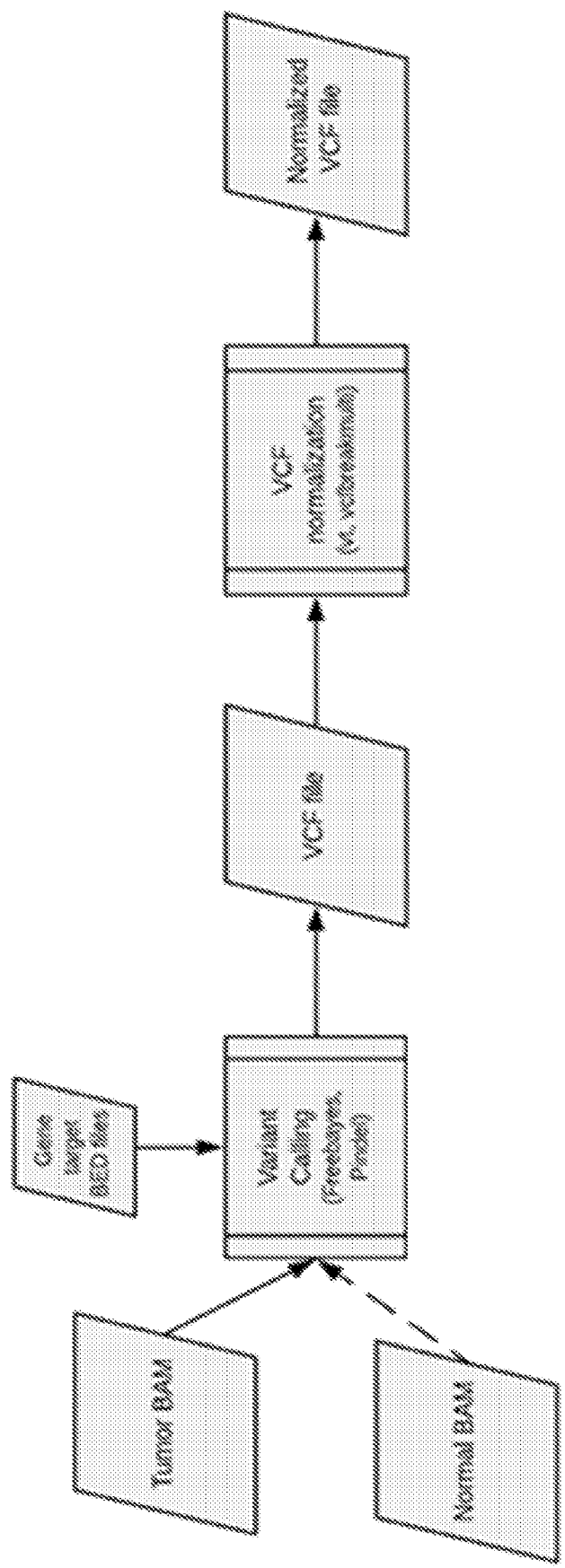

FIG. 4E illustrates an example workflow for genomic feature identification (324). This particular workflow is only an example of one possible collection and arrangement of algorithms for feature extraction from sequencing data 124. Generally, any combination of the modules and algorithms of feature extraction module 145, e.g., illustrated in FIG. 1A, can be used for a bioinformatics pipeline, and particularly for a bioinformatics pipeline for analyzing liquid biopsy samples. For instance, in some embodimentsan architecture useful for the methods and systems described herein includes at least one of the modules or variant calling algorithms shown in feature extraction module 145. In some embodiments, an architecture includes at least 2, 3, 4, 5, 6, 7, 8, 9, 10, or more of the modules or variant calling algorithms shown in feature extraon module 145. Further, in some embodiments, feature extraction modules and/or algorithms not illustrated in FIG. 1A find use in the methods and systems described herein.

Variant Identification

In some embodiments, variant analysis of aligned sequence reads, e.g., in SAM or BAM format, includes identification of single nucleotide variants (SNVs), multiple nucleotide variants (MNVs), indels (e.g., nucleotide additions and deletions), and/or genomic rearrangements (e.g., inversions, translocations, and gene fusions) using variant identification module 146, e.g., which includes a SNV/MNV calling algorithm (e.g., SNV/MNV calling algorithm 147), an indel calling algorithm (e.g., indel calling algorithm 148), and/or one or more genomic rearrangement calling algorithms (e.g., genomic rearrangement calling algorithm 149). An overview of an example method for variant identification is shown in FIG. 4E. Essentially, the module first identifies a difference between the sequence of an aligned sequence read 124 and the reference sequence to which the sequence read is aligned (e.g., an SNV/MNV, an indel, or a genomic rearrangement) and makes a record of the variant, e.g., in a variant call format (VCF) file. For instance, software packages such as freebayes and pindel are used to call variants using sorted BAM files and reference BED files as the input. For a review of variant calling packages see, for example, Cameron, D. L. et al., Nat. Commun., 10(3240):1-11 (2019). A raw VCF file (variant call format) file is output, showing the locations where the nucleotide base in the sample is not the same as the nucleotide base in that position in the reference sequence construct.

In some embodiments, as illustrated in FIG. 4E, raw VCF data is then normalized, e.g., by parsimony and left alignment. For example, software packages such as vcfbreakmulti and vt are used to normalize multi-nucleotide polymorphic variants in the raw VCF file and a variant normalized VCF file is output. See, for example, E. Garrison, "Vcflib: A C++ library for parsing and manipulating VCF files, GitHub, available on the internet at github.com/ekg/ycflib (2012), the content of which is hereby incorporated by reference, in its entirety, for all purposes. In some embodiments, a normalization algorithm is included within the architecture of a broader variant identification software package.

An algorithm is then used to annotate the variants in the (e.g., normalized) VCF file, e.g., determines the source of the variation, e.g., whether the variant is from the germline of the subject (e.g., a germline variant), a cancerous tissue (e.g., a somatic variant), a sequencing error, or of an undeterminable source. In some embodiments, an annotation algorithm is included within the architecture of a broader variant identification software package. However, in some embodiments, an external annotation algorithm is applied to (e.g., normalized) VCF data obtained from a conventional variant identification software package. The choice to use a particular annotation algorithm is well within the purview of the skilled artisan, and in some embodiments is based upon the data being annotated.

For example, in some embodiments, where both a liquid biopsy sample and a normal tissue sample of the patient are analyzed, variants identified in the normal tissue sample inform annotation of the variants in the liquid biopsy sample. In some embodiments, where a particular variant is identified in the normal tissue sample, that variant is annotated as a germline variant in the liquid biopsy sample. Similarly, in some embodiments, where a particular variant identified in the liquid biopsy sample is not identified in the normal tissue sample, the variant is annotated as a somatic variant when the variant otherwise satisfies any additional criteria placed on somatic variant calling, e.g., a threshold variant allele fraction (VAF) in the sample.

By contrast, in some embodiments, where only a liquid biopsy sample is being analyzed, the annotation algorithm relies on other characteristics of the variant in order to annotate the origin of the variant. For instance, in some embodiments, the annotation algorithm evaluates the VAF of the variant in the sample, e.g., alone or in combination with additional characteristics of the sample, e.g., tumor fraction. Accordingly, in some embodiments, where the VAF is within a first range encompassing a value that corresponds to a 1:1 distribution of variant and reference alleles in the sample, the algorithm annotates the variant as a germline variant, because it is presumably represented in cfDNA originating from both normal and cancer tissues. Similarly, in some embodiments, where the VAF is below a baseline variant threshold, the algorithm annotates the variant as undeterminable, because there is not sufficient evidence to distinguish between the possibility that the variant arose as a result of an amplification or sequencing error and the possibility that the variant originated from a cancerous tissue. Similarly, in some embodiments, where the VAF falls between the first range and the baseline variant threshold, the algorithm annotates the variant as a somatic variant.

In some embodiments, the baseline variant threshold is a value from 0.01% VAF to 0.5% VAF. In some embodiments, the baseline variant threshold is a value from 0.05% VAF to 0.35% VAF. In some embodiments, the baseline variant threshold is a value from 0.1% VAF to 0.25% VAF. In some embodiments, the baseline variant threshold is about 0.01% VAF, 0.015% VAF, 0.02% VAF, 0.025% VAF, 0.03% VAF, 0.035% VAF, 0.04% VAF, 0.045% VAF, 0.05% VAF, 0.06% VAF, 0.07% VAF, 0.075% VAF, 0.08% VAF, 0.09% VAF, 0.1% VAF, 0.15% VAF, 0.2% VAF, 0.25% VAF, 0.3% VAF, 0.35% VAF, 0.4% VAF, 0.45% VAF, 0.5% VAF, or greater. In some embodiments, the baseline variant threshold is different for variants located in a first region, e.g., a region identified as a mutational hotspot and/or having high genomic complexity, than for variants located in a second region, e.g., a region that is not identified as a mutational hotspot and/or having average genomic complexity. For example, in some embodiments, the baseline variant threshold is a value from 0.01% to 0.25% for variants located in the first region and is a value from 0.1% to 0.5% for variants located in the second region.

In some embodiments, the first region is a region of interest in the genome that may have been manually selected based on criteria (for example, selection may be based on a known likelihood that a region is associated with variants) and the second region is a region that did not meet the selection criteria. In some embodiments, the baseline variant threshold is a value from 0.01% to 0.5% for variants located in the first region and is a value from 1% to 5% for variants located in the second region. In some embodiments, the first region is a region of interest in the genome that may have been manually selected based on criteria (for example, selection may be based on a known likelihood that a region is associated with variants) and the second region is a region selected based on a second set of criteria.

In some embodiments, a baseline variant threshold is influenced by the sequencing depth of the reaction, e.g., a locus-specific sequencing depth and/or an average sequencing depth (e.g., across a targeted panel and/or complete reference sequence construct). In some embodiments, the baseline variant threshold is dependent upon the type of variant being detected. For example, in some embodiments, different baseline variant thresholds are set for SNPs/MNVs than for indels and/or genomic rearrangements. For instance, while an apparent SNP may be introduced by amplification and/or sequencing errors, it is much less likely that a genomic rearrangement is introduced this way and, thus, a lower baseline variant threshold may be appropriate for genomic rearrangements than for SNPs/MNVs.

In some embodiments, one or more additional criteria are required to be satisfied before a variant can be annotated as a somatic variant. For instance, in some embodiments, a threshold number of unique sequence reads encompassing the variant must be present to annotate the variant as somatic. In some embodiments, the threshold number of unique sequence reads is 2, 3, 4, 5, 7, 10, 12, 15, or greater. In some embodiments, the threshold number of unique sequence reads is only applied when certain conditions are met, e.g., when the variant allele is located in a region of a certain genomic complexity. In some embodiments, the certain genomic complexity is a low genomic complexity. In some embodiments, the certain genomic complexity is an average genomic complexity. In some embodiments, the certain genomic complexity is a high genomic complexity.

In some embodiments, a threshold sequencing coverage, e.g., a locus-specific and/or an average sequencing depth (e.g., across a targeted panel and/or complete reference sequence construct) must be satisfied to annotate the variant as somatic. In some embodiments, the threshold sequencing coverage is 50×, 100×, 150×, 200×, 250×, 300×, 350×, 400× or greater. In some embodiments, the variant is located in a microsatellite instable (MSI) region. In some embodiments, the variant is not located in a microsatellite instable (MSI) region. In some embodiments, the variant has sufficient signal-to-noise ratio.

In some embodiments, bases contributing to the variant satisfy a threshold mapping quality to annotate the variant as somatic. In some embodiments, alignments contributing to the variant must satisfy a threshold alignment quality to annotate the variant as somatic. In some embodiments, a threshold value is determined for a variant detected in a somatic (cancer) sample by analyzing the threshold metric (for example, the baseline variant threshold is determined by analyzing VAF, or the threshold sequencing coverage is determined by analyzing coverage) associated with that variant in a group of germline (normal) samples that were each processed by the same sample processing and sequencing protocol as the somatic sample (process-matched). This may be used to ensure the variants are not caused by observed artifact generating processes.

In some embodiments, the threshold value is set above the median base fraction of the threshold metric value associated with the variant in more than a specified percentage of process-matched germline samples, e.g., 1, 2, 3, 4, 5, 6, 7, 8, 9, 10, or more standard deviations above the median base fraction of the threshold metric value associated with 25%, 30, 40, 50, 60, 70, 75, or more of the processed-matched germline samples. For example, in one embodiment, the threshold value is set to a value 5 standard deviations above the median base fraction of the threshold metric value associated with the variant in more than 50% of the process matched germline samples.

In some embodiments, variants around homopolymer and multimer regions known to generate artifacts may be specifically filtered to avoid such artifacts. For example, in some embodiments, strand specific filtering is performed in the direction of the read in order to minimize stranded artifacts. Similarly, in some embodiments, variants that do not exceed the stranded minimum deviation for their specific locus within a known artifact-generating region may be filtered to avoid artifacts.

Variants may be filtered using dynamic methods, such as through the application of Bayes' Theorem through a likelihood ratio test. In some such embodiments, the threshold is dynamically calibrated to account for variants with low support (e.g., due to low tumor fraction, low circulating tumor fraction, and/or low sequencing depths). The dynamic threshold may be based on, for example, factors such as sample specific error rate, the error rate from a healthy reference pool (e.g., a pool of process matched healthy control samples for validation of variants detected in tumor samples), and information from internal human solid tumors (e.g., for validation of variants detected in liquid biopsy samples). Accordingly, in some embodiments, the dynamic filtering method employs a tri-nucleotide context-based Bayesian model. That is, in some embodiments, the threshold for filtering any particular putative variant is dynamically calibrated using a context-based Bayesian model that considers one or more of a sample-specific sequencing error rate, a process-matched control sequencing error rate, and/or a variant-specific frequency (e.g., determined from similar cancers). In this fashion, a minimum number of alternative alleles required to positively identify a true variant is determined for individual alleles and/or loci.

In some embodiments, the dynamic threshold is selected from a Bayesian probability model, where the selection is based on one or more error rates and/or information from one or more baseline variant distributions. For example, in some embodiments, the dynamic threshold is selected based on a variant detection specificity that is calculated using a distribution of variant detection sensitivities, where the distribution of variant detection sensitivities is a function of circulating variant allele fraction from a plurality of baseline and/or reference alleles (e.g., from a cohort of subjects). Filtration of variants using a dynamic threshold (e.g., to validate the presence of a somatic variant) is performed by comparing the number of unique sequence reads encompassing the variant (e.g., a variant allele fragment count for the variant) against the dynamic threshold.

As described herein, in some embodiments, the methods described herein (e.g., methods 400, 450, and 500 as illustrated in FIGS. 4 and 5) include one or more data collection steps, in addition to data analysis and downstream steps. For example, as described herein, e.g., with reference to FIGS. 2 and 3, in some embodiments, the methods include collection of a liquid biopsy sample and, optionally, one or more matching biological samples from the subject (e.g., a matched cancerous and/or matched non-cancerous sample from the subject). Likewise, as described herein, e.g., with reference to FIGS. 2 and 3, in some embodiments, the methods include extraction of DNA from the liquid biopsy sample and, optionally, one or more matching biological samples from the subject (e.g., a matched cancerous and/or matched non-cancerous sample from the subject). Similarly, as herein, e.g., with reference to FIGS. 2 and 3, in some embodiments, the methods include nucleic acid sequencing of DNA from the liquid biopsy sample and, optionally, one or more matching biological samples from the subject (e.g., a matched cancerous and/or matched non-cancerous sample from the subject).

However, in other embodiments, the methods described herein begin with obtaining nucleic acid sequencing results, e.g., raw or collapsed sequence reads of DNA from a liquid biopsy sample and, optionally, one or more matching biological samples from the subject (e.g., a matched cancerous and/or matched non-cancerous sample from the subject), from which the statistics needed for somatic variant identification (e.g., variant allele count 133-*ac* and/or variant allele fraction 133-*af*) can be determined. For example, in some embodiments, sequencing data 122 for a patient 121 is accessed and/or downloaded over network 105 by system 100.

Similarly, in some embodiments, the methods described herein begin with obtaining the genomic features needed for somatic variant identification (e.g., variant allele count 133-*ac* and/or variant allele fraction 133-*af*) for a sequencing of a liquid biopsy sample and, optionally, one or more matching biological samples from the subject (e.g., a matched cancerous and/or matched non-cancerous sample from the subject). For example, in some embodiments, variant allele counts 133-*cf-ac* and/or variant allele fractions 133-*cf-af* for sequencing data 122 of patient 121 is accessed and/or downloaded over network 105 by system 100.

One goal of the liquid biopsy assays described herein is to detect variant alterations at low circulating fractions, which requires that low levels of support be sufficient to call a variant. Therefore, consistent thresholds to filter variants that do not take into account variant context and local sequence specific error cannot be used.

In some embodiments, a dynamic variant filtering method is applied which uses an application of Bayes' Theorem through the likelihood ratio test. The dynamic threshold is based on sample specific error rate, the error rate from a healthy reference pool, and from internal human solid tumors. The basic application of the likelihood ratio test is as follows:

$$\text{post-test-odds} = \text{pre-test-odds} * \text{sensitivity}/(1-\text{specificity})$$

Given a fixed value for post-test-adds, the specificity can be solved for. The specificity represents the minimum acceptable quantile of an error distribution (e.g., a BetaBinomial, Beta, and Poisson error distribution). The above equation can be refactored to the one below:

$$\text{specificity} = 1 - \text{pre-test-odds} * \text{sensitivity}/\text{post-test-odds}$$

Specificity can then be plugged into the quantile error (e.g., BetaBinomial, Beta, or Poisson) function to derive the minimum number of alternative alleles that can be observed at a given depth to validate a candidate somatic variant.

In some embodiments, the post-test odds are post-test probability/(1−post-test probability). The post-test probability is the probability of having a positive variant given Bayes Theorem. The post-test-odds is pre-defined.

In some embodiments, the pre-test odds are pre-test probability/(1−pre-test probability). The pre-test probability is the probability of having a positive variant given the patient's cancer-type and the prevalence of variant alterations within a genomic region encompassing a candidate somatic sequence variant in a reference population having the same cancer type.

In some embodiments, a pre-test-odds multiplier is applied to the pre-test odds for a resistance mutation that would develop and/or become more prominent within a heterogenous population of cancer cells in response to therapeutic treatment. The multiplier is applied to specific genomic regions (e.g., exon windows) containing the resistance mutation position. In some embodiments, the multiplier is only applied in specified cancer contexts. For example, in some embodiments, a multiplier is applied to a pre-test odds for a genomic region containing a mutation that is resistant to at least one cancer therapy used to treat the type of cancer the subject has. For example, if a given mutation is known to have resistance to a therapy used to treat breast cancer, but not to any of the therapies used to treat brain cancer, a multiplier will be applied to the pre-test odds for the genomic region encompassing the mutation if the subject has breast cancer, but not if the subject has brain cancer.

In some embodiments, sensitivity is the fraction of variants detected by the liquid biopsy assay at a given variant allele fraction (e.g., 0.1%, 0.25%, 0.5%, etc.).

Calculating the pre-test probability. In some embodiments, the pre-test probability is calculated using historical data for a set of reference subjects having the same type of cancer, e.g., from sequencing of solid tumor samples. In this fashion, it is possible to accurately assess the prevalence of specific variants within the population of advanced human tumors. In some embodiments, the set of reference subjects is at least 10 reference subjects. In some embodiments, the set of reference subjects is at least 50 reference subjects. In some embodiments, the set of reference subjects is at least 100 reference subjects. In some embodiments, the set of reference subjects is at least 500 reference subjects. In some embodiments, the set of reference subjects is at least 1000 reference subjects. In some embodiments, the set of reference subjects is at least 5000 reference subjects. In some embodiments, the set of reference subjects is at least 10000 reference subjects.

In some embodiments, variant prevalence is calculated by indexing genomic regions (e.g., exons) in the reference sample and counting the number of variants in each genomic region (e.g., exon) for each cancer-type. The number of patients who have at least one variant in the genomic region (e.g., the exon)/the number of patients equals the variant prevalence. The pre-test-odds are calculated from the prevalence by pre-test-odds=prevalence/(1−prevalence).

In some embodiments, for a cancer where the number of patients in the reference is too low to calculate prevalence, a default pan cancer cancer-type is used. Where no prevalence can be calculated, the mean variant prevalence across cancer-types is used.

In some embodiments, pre-test-odds are not calculated each time an input sample is run. Rather, in some embodiments, it is read from a pre-existing file, which will be evaluated and regenerated if deemed necessary.

Calculating the pre-test-odds multiplier. Resistance mutations have historically low prevalence and variant allele fraction and may incorrectly be filtered by the dynamic variant filtering method due to low pre-test-odds caused by their inherent low prevalence in the population. The resistance mutations develop in response to therapeutic treatment, and detecting resistance mutations early provides insights into the current treatment strategy. Low variant allele frequency, low prevalence resistance mutations in historic solid tumor samples have been identified. The high sensitivity of the liquid biopsy assay described herein permits the early detection of these resistance mutations in circulating DNA. Examples of such resistance mutations include PIK3CA p.E545K in breast cancer, EGFR p.T790M in non-small cell lung cancer, and AR p.H875Y for prostate cancer.

In some embodiments, to estimate the pre-test-odds-multiplier required to pass resistance mutations down to low variant allele fractions (e.g., 0.01% VAF, 0.05% VAF, 0.1% VAF, 0.15% VAF, 0.2% VAF, 0.25% VAF, 0.3% VAF, 0.4% VAF, 0.5% VAF, and the like), the average depth for each variant position is utilized from the reference pool (e.g., the reference pool used to determine the pre-test odds) depth, at a high minimum average depth (e.g., 500×, 1000×, 1500×, 2000×, 2500×, 3000×, 4000×, 5000×, or more). For each resistance mutation, the number of alternate alleles required to achieve the low VAF (e.g., 0.01% VAF, 0.05% VAF, 0.1% VAF, 0.15% VAF, 0.2% VAF, 0.25% VAF, 0.3% VAF, 0.4% VAF, 0.5% VAF, and the like) were calculated. The total alternate alleles and depth for each resistance mutation was input to the Dynamic Variant Filtering method, and multipliers were applied until those resistance mutations passed the filtering strategy.

In some embodiments, the minimum multiplier required to pass resistance mutations is determined when the input sample alternate allele count is greater than the background alternate allele count (as outlined in Calculating Testing Sample Alt Allele Count and Calculating Background Alt Allele Count below). In some embodiments, the multiplier is selected based on the multiplier required to pass the variant at a low variant allele fraction (e.g., 0.1% VAF or 0.25% VAF). In some embodiments, a maximum value for the multiplier is applied, in order to prevent excessive artifacts from passing the filter. Large multipliers may permit false positive variants to pass the Dynamic Variant Filtering method, however, large multipliers are necessary to pass resistance mutations that have historically low prevalence. In some embodiments, the maximum multiplier is between 750 and 1500. In some embodiments, the maximum multiplier is between 900 and 1100. In some embodiments, the maximum multiplier is between 1000 and 1050.

In some embodiments, the usage of the pre-test-odds-multiplier is limited by cancer-type context and genomic region (e.g., exon-window). In some embodiments, therefore, the multipliers will not be applied to all genomic regions (e.g., exon-windows) given a specified cancer-type, nor all cancer-types given a specific genomic region (e.g., exon-window).

Calculating testing sample variant allele count. In some embodiments, the filtering method (the statistical method used for the Dynamic Variant Filtering method) is selected from a beta-binomial distribution model, a beta distribution model, and a Poisson distribution model. In some embodiments, the model is a beta-binomial model. In some embodiments, when applying a quantile beta-binomial distribution, the sum of the input sample alternate reads is divided by the input sample sequencing depth at each variant position, and then multiplied by the reference pool depth (the sequencing depth at genomic positions for a pool of reference, e.g., healthy normal, controls). For additional information on Beta-binomial models see, for example, Tripathi R. et al., "Estimation of Parameters in the Beta Binomial Model," Ann. Inst. Statist. Math, 46(2):317-31 (1994), the disclosure of which is incorporated herein by reference in its entirety.

Calculating background variant allele count. In some embodiments, the background variant allele count calculation takes into account the background error from a pool of reference (e.g., healthy normal subjects), the input sample error, and the prevalence of historical variants in the reference cancer subjects. The quantile beta-binomial model considers (i) reference pool depth (the sequencing depth at genomic positions for a pool of reference, e.g., healthy normal, controls), background posterior error average from the input sample, and alpha calculated from the pre-test-odds, sensitivity, and the post-test-odds (e.g., where alpha is equal to 1−specificity=pre-test-odds*sensitivity/post-test-odds). For example, in some embodiments, the pre-test-odds calculated for a specific genomic region (e.g., exon window) and cancer-type will yield a unique alpha for each variant, given that the variants do not fall in the same genomic region (e.g., exon window)).

In some embodiments, the background posterior error incorporates a reaction-specific sequencing error rate (e.g., a trinucleotide error average), a locus-specific, process-matched sequencing error rate (e.g., the reference pool error, which is a sum of alternate reads for each position/depth from a pool of healthy normal controls), and a shrinkage weight parameter. In some embodiments, the reaction-specific sequencing error rate (e.g., trinucleotide error average) is an aggregate of the input sample background average, where the input sample background average equals the error counts for each position divided by the position-specific sequencing depth. In some embodiments, the sample background average is then aggregated for each trinucleotide context. In some embodiments, the trinucleotide average is used to calculate the shrinkage weight parameter. In some embodiments, the shrinkage weight parameter equals the trinucleotide error average divided by the sum of the trinucleotide error average and the reference pool error. In instances when the shrinkage weight parameter is undefined, it is changed to 1. In some embodiments, the final calculation of the background posterior error is calculated as:

background posterior error=shrinkage weight parameter*reaction-specific sequencing error rate (e.g., a trinucleotide error average)+(1−shrinkage weight parameter)*healthy subject error.

In some embodiments, a reference pool error can be used in place of an input sample background average, for calculating the background posterior average error rate.

In some embodiments, the alpha for the beta-binomial distribution is calculated using the pre-test-odds, sensitivity, and post-test-odds, where:

alpha=1−specificity=pre-test-odds*sensitivity/post-test-odds

Accordingly, in some embodiments, the background posterior average, the reference pool depth, and the alpha are used in calculating the input to the quantile beta-binomial function. The alpha is used in calculating the mean value of the beta-binomial distribution, which equals 1−alpha/2. The size of the quantile beta-binomial is the matrix of the reference pool depth. The shape 1 parameter for the quantile beta-binomial function is the reference pool depth multiplied by the background posterior average error rate, and the shape 2 parameter of the quantile beta-binomial function is the shape 1 parameter subtracted from reference pool depth.

The output from the quantile BetaBinomial function is the minimum value a variant needs to be called. Any variant that has a normalized allele count below the quantile(BetaBinomial) output will be filtered due to the high background error observed at that position.

Figure 4F:
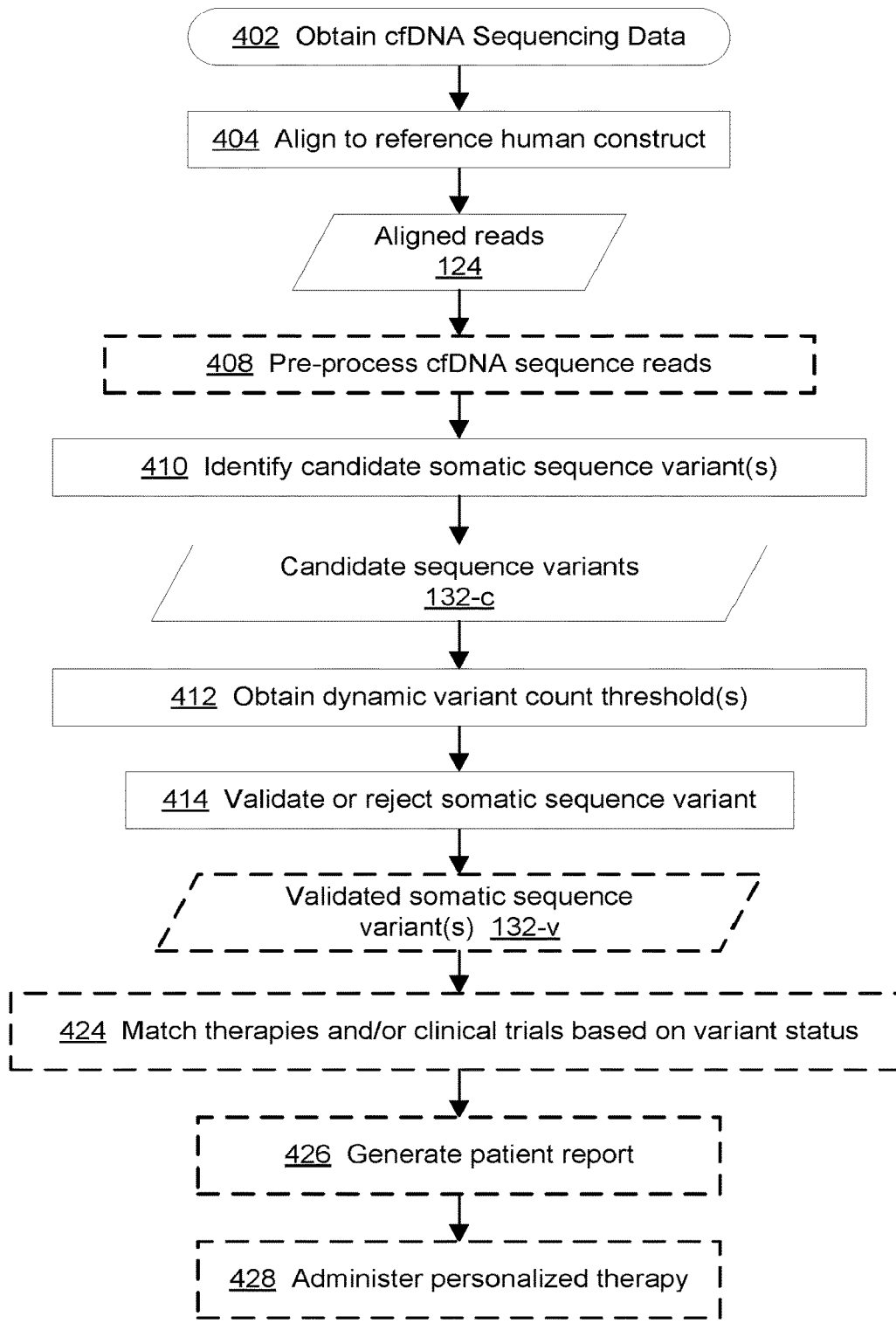

For example, FIG. 4F illustrates a flow chart of a method 400 for validating a somatic sequence variant in a test subject having a cancer condition, in accordance with some embodiments of the present disclosure.

In some embodiments, the method includes obtaining (402) cell-free DNA sequencing data 122 from a sequencing reaction of a liquid biopsy sample of a test subject 121 (e.g., sequence reads 123-1-1-1, . . . , 123-1-1-K for sequence run 122-1-1 for a liquid biopsy sample from patient 121-1, as illustrated in FIG. 1B) As described herein, in some embodiments, the obtaining includes a step of sequencing cell-free nucleic acids from a liquid biopsy sample. Example methods for sequencing cell-free nucleic acids are described herein. Sequence reads 123 from the sequencing data 122 are then aligned (404) to a human reference sequence (e.g., a human genome or a portion of a human genome, e.g., 1%, 5%, 10%, 15%, 20%, 25%, 30%, 40%, 50%, 60%, 75%, 90%, 95%, 99%, or more of the human genome, or to a map of a human reference genome or a set of human reference genomes, or a portion thereof), thereby generating a plurality of aligned reads 124. Optionally, the pre-aligned sequence reads 123 and/or aligned sequence reads 124 are pre-processed (408) using any of the methods disclosed above (e.g., normalization, bias correction, etc.). In some embodiments, as described herein, device 100 obtains previously aligned sequence reads.

The aligned sequences reads 124 are then evaluated to identify mismatches with the reference construct (e.g., reference genome or set of reference genomes), thereby identifying one or more candidate somatic sequence variants 132-*c* at respective genomic loci. The number of aligned sequence reads containing the sequence variant at the locus are determined, thereby defining a variant allele fragment count 132-*c*-*ac* (e.g., variant allele fragment count 132-*c*-1-*ac* as illustrated in FIG. 1C). In some embodiments, the number of aligned sequence reads containing the locus of the candidate variant allele (regardless of the identity of the allele represented in the sequence read) are also determined, thereby defining a variant allele locus count 132-*c*-*lc* (e.g., variant allele locus count 132-*c*-1-*lc* as illustrated in FIG. 1C). Accordingly, in some embodiments, the variant allele fragment count 132-*c*-*ac* can be compared to the variant allele locus count 132-*c*-*lc* to determine a variant allele fraction 132-*c*-*vf* (e.g., variant allele fraction 132-*c*-1-*vf* as illustrated in FIG. 1C) for the candidate variant allele. This represents a measure of the portion of sequence reads encompassing the nucleotide(s) that is altered in the candidate variant allele that include the candidate variant. In some embodiments, as described below, this measure can be used to define a sensitivity for the detection of the candidate variant based on a distribution of detection sensitivities corresponding to detection of a variant within a genomic region encompassing the locus in reference samples with defined variant allele fractions.

Method 400 then includes obtaining (412) a dynamic variant count threshold 191 for the candidate variant allele. As described herein, in some embodiments, the dynamic variant count threshold is based upon a prevalence of sequence variations in a genomic region encompassing the locus of the candidate variant allele in cancer patients sharing one or more similarities with the test subject. For example, in some embodiments, this prevalence defines a pre-test odds that the test subject has a sequence variant within the genomic region encompassing the locus at which the candidate sequence variant is located. In some embodiments, this pre-test odds is used in an application of Bayes theorem to derive a minimal amount of support required of the sequencing reaction to validate the presence of the candidate sequence variant in a cancerous tissue of the subject at a desired confidence level. Information about Bayes theorem and Bayesian inference can be found, for instance, in Section 8.7 of Stuart, A. and Ord, K. (1994), Kendall's Advanced Theory of Statistics: Volume I—Distribution Theory, Edward Arnold; and Gelman, A. et al., (2013), Bayesian Data Analysis, Third Edition, Chapman and Hall/CRC, ISBN 978-1-4398-4095-5, the disclosure of both of which are incorporated herein by reference for their teachings of how to implement Bayes theorem and Bayesian inference.

In some embodiments, the prevalence of sequence variants in the genomic region encompassing the locus of the candidate variant allele is determined from a population of reference cancer subjects having the same type of cancer. In some embodiments, the population of reference cancer subjects is further defined by a matching personal characteristic, e.g., an age, gender, race, smoking status, or any other personal characteristic. In some embodiments, the population of reference subjects is further defined by a plurality of matching personal characteristics, e.g., at least 2, 3, 4, 5, 6, 7, 8, 9, 10, or more person characteristics, in addition to cancer type.

For instance, in some embodiments, the prevalence of sequence variants is determined from variant prevalence training data 192, as illustrated in FIG. 1F. The variant prevalence training data 192 includes data on the variants found in a cancerous tissue from a plurality of reference subjects 193. For example, training data 192 for reference subject 1 193-1 includes a cancer type 194-1 and a list of somatic sequence variants 195-1, including individual variants 196-1-1 . . . 196-1-S. To determine a prevalence for a particular candidate sequence variant detected for a test subject, a genomic region encompassing the locus of the candidate sequence variant is defined (e.g., the exon of a gene in which a candidate sequence variant is detected). Then, it is determined what portion of reference subjects 193, that have the same cancer as the test subject, have a sequence variant located within the defined genomic region (e.g., the exon of the gene).

In some embodiments, e.g., when only a limited set of defined candidate variants will be validated, sequence variant prevalence is predetermined and stored in a database, e.g., in non-persistent memory 111, or in an addressable remote server, as a look-up table. In other embodiments, system 100 determines a sequence variant prevalence for a genomic region and matching patient profile upon identification of a candidate sequence variant, e.g., by filtering variant prevalence training data 192 for the relevant genomic region and matching reference subjects.

Generally, the genomic region encompassing the candidate sequence variant is larger than a single nucleotide. For example, in some embodiments, the genomic region includes at least 10 nucleotides, at least 50 nucleotides, at least 100 nucleotides, at least 250 nucleotides, at least 500 nucleotides, at least 1000 nucleotides, at least 2500 nucleotides, or more nucleotides. In some embodiments, the genomic region is no larger than 10,000 nucleotides, not larger than 7500 nucleotides, no larger than 5000 nucleotides, no larger than 2500 nucleotides, or fewer nucleotides. In some embodiments, the genomic region is from 10 nucleotides to 10,000 nucleotides. In some embodiments, the genomic region is from 25 nucleotides to 5000 nucleotides. In some embodiments, the genomic region is from 50 nucleotides to 2500 nucleotides.

In some embodiments, when the candidate sequence variant falls within a protein coding sequence, the genomic region is defined as the exon in which the candidate sequence variant is located. In some embodiments, the genomic region is defined as several adjacent exons, including the exon in which the candidate sequence variant is located. In some embodiments, when the candidate sequence variant falls within a protein coding sequence, the genomic region is defined as all exons of the gene in which the candidate sequence variant is located. In some embodiments, when the candidate sequence variant falls within a protein coding sequence, the genomic region is defined as the entire gene in which the candidate sequence variant is located. Similarly, in some embodiments, when the candidate sequence variant falls within an intronic sequence of a gene, the genomic region is defined as the entire intron in which the candidate sequence variant is located, or several adjacent introns including the intron in which the candidate sequence variant is located.

In some embodiments, the genomic region encompassing the candidate sequence variant is a fixed window encompassing, e.g., surrounding, the candidate sequence variant. For example, in some embodiments, when the candidate sequence variant falls within a non-coding portion of the genome, the genomic region is defined as a fixed window surrounding the candidate sequence variant. However, in some embodiments, when the sequence variant falls within a non-coding genetic element, e.g., a promoter, enhancer, etc., the genomic region is defined as the entirety of the genetic element.

In some implementations, the genomic region encompassing the candidate sequence variant is dependent upon the sequence context of the locus. For example, when the candidate sequence variant falls within a coding sequence, the exon or several adjacent exons defines the genomic region, but when the candidate sequence variant falls within a non-coding sequence, the genomic region is defined by a fixed window encompassing the candidate sequence variant.

In some embodiments, the genomic region encompassing the candidate sequence variant is dependent upon a known or inferred effect of the sequence variant. For instance, as described in more detail below, in some embodiments, when the candidate sequence variant causes, or is inferred to cause, a partial or complete loss of function mutation in a gene, the genomic region is defined by all exons of the gene in which the candidate sequence variant is located. Similarly, as described in more detail below, in some embodiments, when the candidate sequence variant causes, or is inferred to cause, a gain of function mutation in a gene having one or more hotspots for gain of function mutations, the genomic region is defined as those exons of the gene encompassing the one or more hotspots.

In some embodiments, when the candidate sequence variant falls within a genomic region associated with a known therapeutic resistance gene for the cancer of the subject, the pre-test odds determined based on the historical prevalence data is multiplied by a pre-test-odds multiplier (e.g., as described above).

In some embodiments, the Bayesian analysis is further informed by defining the specificity of variant detection based on an apparent variant allele fraction in the sample. For example, in some embodiments, the variant allele fraction for the candidate sequence variant is determined by a comparison of the variant allele fragment count 132-*c-ac* to the variant allele locus count 132-*c-lc* (e.g., a ratio of the variant allele fragment count to the variant allele locus count), thereby determining a variant allele fraction 132-*c-vf*. In some embodiments, the variant allele fraction is then compared to a distribution of variant detection specificities established based on a set of training samples (e.g., sensitivity distribution training data) with known variant allele fractions. For example, in some embodiments, nucleic acids from each of a plurality of training samples 181 having a known variant allele fraction 184 for one or more variant alleles 183 is sequenced according to a processed-matched sequencing reaction (e.g., using a substantially identical or identical sequencing reaction), and it is determined whether each sequence variant can be detected, e.g., defining a detection status 185 for each locus/variant 183. Over a large number of training samples, a specificity of detection of variants having different variant allele fractions can be determined. In some embodiments, the specificity is determined on a locus-by-locus basis, such that the specificity of detection is specific for the genomic region or locus encompassing the candidate sequence variant. In some embodiments, the specificity is determined globally, e.g., not on a locus-by-locus basis.

A correlation can then be established between the measured detection specificity and the variant allele fraction (e.g., variant detection sensitivity distribution 186). In some embodiments, the correlation is a linear or non-linear fit between measured detection specificities and variant allele fractions. In other embodiments, the correlation is determined by binning specificities (e.g., in bins 187) as a function of ranges of variant allele fractions 188, and determining a measure of central tendency (e.g., a mean) for the specificities 189 in the bin. The variant allele fraction 132-*c-ac* determined for the candidate sequence variant is then compared to the established correlation (e.g., variant detection sensitivity distribution 186) to define the specificity of detection for the candidate sequence variant.

In some embodiments, the Bayesian analysis is further informed by accounting for the sequencing error rate for the variant allele and, accordingly, the probability that the candidate sequence variant is a product of a sequencing error, rather than a genomic variant. In some embodiments, a reaction-specific error rate (e.g., a trinucleotide sequencing error rate) is determined for the sequencing reaction (e.g., using an internal control spiked into the reaction). In some embodiments, a locus-specific error rate is determined from historical sequencing errors at the genomic region, or specific locus, encompassing the candidate sequence variant. In some embodiments, both a reaction-specific sequencing error rate and a locus-specific error rate are used to define a variant count distribution (e.g., variant count distribution 190), representing the number of variant allele counts (e.g., variant allele fragment count 132-*c-ac*) necessary to validate the presence of the candidate variant sequence in the cancer of the subject at a defined detection sensitivity. In some embodiments, a distribution, such as a beta binomial distribution, is established based on the reaction-specific sequencing error rate and the locus-specific error rate.

Method 400 then includes applying (414) the dynamic variant count threshold (e.g., locus-specific dynamic variant count threshold 191) to the sequencing data, e.g., by determining whether the variant allele fragment count 132-*c-ac* for the candidate sequence variant satisfies the threshold, and validating the candidate sequence variant (e.g., creating a record 132-*v* of the validation) when the threshold is satisfied or rejecting the candidate sequence variant when the threshold is not satisfied. In some embodiments, one or more additional filters, relating to global sequencing metrics and/or locus-specific sequencing metrics (e.g., one or more of variant locus coverage filter(s) 463, variant allele fraction filter(s) 465, variant support mapping filter(s) 467, variant support sequencing quality filter(s) 469, and low complexity region filter(s) 471, as illustrated in FIG. 1D) must be satisfied before validating a candidate sequence variant.

As described in further detail herein, in some embodiments, one or more validated variant statuses 132-*v* are used to match (424) the subject with a targeted therapy and/or a clinical trial. In some embodiments, as described in further detail herein, one or more validated variant statuses 132-*v* for one or more actionable variants 139-1-1, one or more matched therapies 139-1-2, and/or one or more matched clinical trials are used to generate (426) a patient report 139-1-3. In some embodiments, the patient report is transmitted to a medical professional treating the subject. In some embodiments, the patient is then administered (428) a personalized course of therapy, e.g., based on a matched therapy and/or clinical trial.

In some embodiments, the methods of validating a candidate somatic sequence variant using a dynamic threshold described herein fall within the context of a larger variant detection method, e.g., as illustrated by method 450 illustrated in FIGS. 4G1-4G3. For example, in some embodiments, the method includes obtaining (452) cfDNA sequence reads, as described herein, and aligning (454) those reads to a reference construct (e.g., a reference genome or mapped representation of several reference genomes), to generate aligned sequences 124 (e.g., a plurality of unique sequence reads). In some embodiments, putative somatic sequence variants are identified (456), e.g., those sequence variants having a variant allele fraction that is lower than expected for a germline sequence variant (which should be around 50% after accounting for an estimated circulating tumor fraction for the liquid biopsy sample), e.g., less than 30%, less than 20%, less than 10% etc. One or more candidate somatic sequence variants are then validated by applying one or more filters. For instance, as described herein, a dynamic variant count threshold is determined (459) and then used to apply (460) a dynamic probabilistic variant count filter to sequencing data for the candidate somatic sequence variant. In some embodiments, the method also includes applying (462) a variant loci coverage filter. In some embodiments, the method also includes applying (464) a variant allele fraction filter. In some embodiments, the method also includes applying (466) a variant support mapping filter. In some embodiments, the method also includes applying (468) a variant support sequencing quality filter. In some embodiments, the method also includes applying (470) a low complexity region filter. When all selected candidate somatic sequence variants have been validated or rejected according to these filters (472), the process proceeds with a reporting function.

In some embodiments, method 450 also includes validating (474) the sequencing data globally, using any of the metrics described herein. In some embodiments, the validation includes applying (476) a loci minimal coverage filter. In some embodiments, the validation includes applying (478) a loci central tendency coverage filter. In some embodiments, the validation includes applying (480) a total sequence read filter. In some embodiments, the validation includes applying (481) a sequence read quality filter. In some embodiments, the validation includes applying a sequencing control filter (482). The entire sequencing reaction is then validated or rejected (483) based on whether the sequencing data passes these global filters.

In some embodiments, method 450 also includes validating (485) one or more germline mutations. In some embodiments, candidate germline sequence variants are identified (484), e.g., those sequence variants having a variant allele fraction that is higher than expected for a somatic sequence variant. In some embodiments, the validation includes applying (486) a germline-specific variant allele fraction filter. In some embodiments, the validation includes applying (487) a variant support mapping filter. In some embodiments, the validation includes applying (488) a variant support sequencing quality filter. When all selected candidate germline sequence variants have been validated or rejected according to these filters (489), the process proceeds with a reporting function.

As described in further detail herein, in some embodiments, one or more validated variant statuses 132-v are used to match (490) the subject with a targeted therapy and/or a clinical trial. In some embodiments, as described in further detail herein, one or more validated variant statuses 132-v for one or more actionable variants 139-1-1, one or more matched therapies 139-1-2, and/or one or more matched clinical trials are used to generate (492) a patient report 139-1-3. In some embodiments, the patient report is transmitted to a medical professional treating the subject. In some embodiments, the patient is then administered (494) a personalized course of therapy, e.g., based on a matched therapy and/or clinical trial.

In some embodiments, all, or nearly all, of the aligned sequence reads are evaluated to identify candidate sequence variants (e.g., candidate somatic sequence variants and/or candidate germline sequence variants). In other embodiments, a subset of the aligned sequence reads is evaluated to identify candidate sequence variants. For example, in one embodiment, targeted-panel sequencing reaction is used to generate sequencing data 122 and only sequence reads corresponding to the target panel (on-target reads) are evaluated to identify candidate sequence variants. In some embodiments, targeted-panel sequencing reaction is used to generate sequencing data 122 and a subset of sequence reads corresponding to a subset of the target panel are evaluated to identify candidate sequence variants. In some embodiments, a subset of the sequence reads corresponding to a subset of genes, regardless of whether the sequencing reaction is a targeted-panel sequencing reaction, a whole exome sequencing reaction, or a whole genome sequencing reaction, are evaluated to identify candidate sequence variants. In some embodiments, a subset of sequence reads corresponding to a defined set of regions within the genome, e.g., one or more genes, one or more introns, one or more exons, one or more subregion of an intron and/or exon associated with cancer etiology, etc., are evaluated to identify candidate sequence variants.

Alternatively, in some embodiments, regardless of what subset of aligned sequence reads are evaluated to identify candidate sequence variants, only a subset of candidate sequence variants is further validated. For example, in some embodiments, only candidate sequence variants corresponding to the target panel (on-target reads) are validated. Similarly, in some embodiments, only candidate sequence variants corresponding to a subset of the target panel are validated. Likewise, in some embodiments, only candidate sequence variants corresponding to a subset of genes, regardless of whether the sequencing reaction is a targeted-panel sequencing reaction, a whole exome sequencing reaction, or a whole genome sequencing reaction, are validated. Similarly, in some embodiments, only candidate variants corresponding to a defined set of regions within the genome, e.g., one or more genes, one or more introns, one or more exons, one or more subregion of an intron and/or exon associated with cancer etiology, etc., are validated.

In some embodiments, different sets of sequence variants are evaluated depending on the type of cancer being evaluated. That is, when the subject has a first type of cancer, candidate sequence variants in a first set of genomic loci are evaluated, typically associated with the etiology of the first type cancer and/or a particular course of actionable therapy for the first type cancer, and when the subject has a second type of cancer, candidate sequence variants in a second set of genomic loci are evaluated, typically associated with the etiology of the second type cancer and/or a particular course of actionable therapy for the second type of cancer. These selections may be applied at the level of initial sequence read evaluation (e.g., only sequence reads corresponding to a defined set of loci are evaluated to identify a candidate sequence variant) or the validation level (e.g., sequence reads corresponding to a larger set of loci are evaluated to identify candidate sequence variants, but only those candidates corresponding to a defined set are further validated).

Similarly, in some embodiments, for one or more target loci falling within a gene exon, only candidate sequence variants that would result in an amino acid change in the amino acid sequence encoded by the gene are evaluated. In some embodiments, any candidate sequence variant resulting in an amino acid change are evaluated. In some embodiments, candidate sequence variants resulting in a defined amino acid change, e.g., an amino acid change associated with cancer etiology and/or a particular actionable cancer therapy, are evaluated. In some embodiments, only a subset of validated sequence variants is included on a clinical report for the sample. That is, in some embodiments, aligned sequence reads corresponding to all or a subset of genomic loci are evaluated to identify candidate sequence variants, all or a subset of identified candidate sequence variants are evaluated for validation, and only a subset of all possibly validated sequence variants are included on a clinical report generated for the sample.

For example, lists of example candidate sequence variants for evaluation in breast cancer, non-small cell lung cancer, prostate cancer, pan cancer, and cancer of unknown origin are provided below. Standard nomenclature is used to describe chromosomal location and specific amino acid variants, as described further by the Human Genome Variation Society, e.g., at the URL varnomen.hgvs.org/recommendations/protein/variant/substitution/.

For example, in some embodiments, the subject has breast cancer and candidate variants associated with at least one of the following genes and/or genetic loci are evaluated: ERBB2 (or a genetic locus including a chromosomal position of 17:37880220 and/or 17:37881064), EGFR (or a genetic locus including a chromosomal position of 7:55227926, 7:55242511, and/or 7:55249022), ESR1 (or a genetic locus including a chromosomal position of 6:152419922, 6:152419923 and/or 6:152419926), KRAS (or a genetic locus including a chromosomal position of 12:25380275, 12:25380276, 12:25380277, and/or 12:25380279), MAP2K1 (or a genetic locus including a chromosomal position of 15:66729162 and/or 15:66729163), MET (or a genetic locus including a chromosomal position of 7:116422117 and/or 7:116423413); MTOR (or a genetic locus including a chromosomal position of 1:11187094, 1:11187096, and/or 1:11187796), NTRK1 (or a genetic locus including a chromosomal position of 1:156846342, 1:156849044 and/or 1:156849144), and PIK3CA (or a genetic locus including a chromosomal position of 3:178936082, 3:178936091, 3:178936092, 3:178936093, 3:178952084, and/or 3:178952085). In some embodiments, the subject has breast cancer and candidate variants associated with at least 2, at least 3, at least 4, at least 5, at least 6, at least 7, or at least 8 of the genes listed above (or loci including the enumerated corresponding chromosomal positions) are evaluated. In some embodiments, the subject has breast cancer and candidate variants associated with any of the genes listed above (or loci including the enumerated corresponding chromosomal positions) are evaluated.

In some of the embodiments described above where the subject has breast cancer, only a subset of possible candidate sequence variants in the ERBB2 gene are evaluated and/or reported. In some embodiments, the subset of possible candidate sequence variants in the ERBB2 gene includes variants resulting in an amino acid change selected from L755*, L755S, L755W, T7981, T798K, and T798R.

In some of the embodiments described above where the subject has breast cancer, only a subset of possible candidate sequence variants in the EGFR gene are evaluated and/or reported. In some embodiments, the subset of possible candidate sequence variants in the EGFR gene includes variants resulting in an amino acid change selected from G465*, G465R, D761H, D761N, D761Y, V774L, and V774M.

In some of the embodiments described above where the subject has breast cancer, only a subset of possible candidate sequence variants in the ESR1 gene are evaluated and/or reported. In some embodiments, the subset of possible candidate sequence variants in the ESR1 gene includes variants resulting in an amino acid change selected from Y537D, Y537H, Y537N, Y537C, Y537S, Y537F, D538A, D538G, and D538V.

In some of the embodiments described above where the subject has breast cancer, only a subset of possible candidate sequence variants in the KRAS gene are evaluated and/or reported. In some embodiments, the subset of possible candidate sequence variants in the KRAS gene includes variants resulting in an amino acid change selected from G60D, Q61H, Q61Q, Q61L, Q61P, Q61R, Q61*, Q61E, and Q61K.

In some of the embodiments described above where the subject has breast cancer, only a subset of possible candidate sequence variants in the MAP2K1 gene are evaluated and/or reported. In some embodiments, the subset of possible candidate sequence variants in the MAP2K1 gene includes variants resulting in an amino acid change selected from P124A, P124S, P124T, P124R, P124L, P124Q.

In some of the embodiments described above where the subject has breast cancer, only a subset of possible candidate sequence variants in the MET gene are evaluated and/or reported. In some embodiments, the subset of possible candidate sequence variants in the MET gene includes variants resulting in an amino acid change selected from F1200I, F1200L, F1200V, Y1230D, Y1230H, and Y1230N.

In some of the embodiments described above where the subject has breast cancer, only a subset of possible candidate sequence variants in the MTOR gene are evaluated and/or reported. In some embodiments, the subset of possible candidate sequence variants in the MTOR gene includes variants resulting in an amino acid change selected from A2034E, A2034G, A2034V, F2108F, F21081, F2108L, and F2108V.

In some of the embodiments described above where the subject has breast cancer, only a subset of possible candidate sequence variants in the NTRK1 gene are evaluated and/or reported. In some embodiments, the subset of possible candidate sequence variants in the NTRK1 gene includes variants resulting in an amino acid change selected from G595R, G595W, F646I, F646L, F646V, D679A, D679G, and D679V.

In some of the embodiments described above where the subject has breast cancer, only a subset of possible candidate sequence variants in the PIK3CA gene are evaluated and/or reported. In some embodiments, the subset of possible candidate sequence variants in the PIK3CA gene includes variants resulting in an amino acid change selected from E542K, E545*, E545K, E545Q, E545A, E545G, E545V, E545D, E545E, H1047D, H1047Y, H1047N, H1047L, H1047P, H1047R.

Similarly, in some embodiments, the subject has non-small cell lung cancer and candidate variants associated with at least one of the following genes and/or genetic loci are evaluated: ALK (or a genetic locus including a chromosomal position of 2:29443613, 2:29443631, 2:29443695, 2:29443697, 2:29445213, and/or 2:29445258), B2M (or a genetic locus including a chromosomal position of 15:45003745), BRAF (or a genetic locus including a chromosomal position of 7:140453135, 7:140453136, and/or 7:140453137), EGFR (or a genetic locus including a chromosomal position of 7:55227926, 7:55241704, 7:55241705, 7:55241706, 7:55242469, 7:55242511, 7:55249022, 7:55249071, 7:55249091, 7:55249092, 7:55249093, 7:55249094, and/or 7:55259515), ERBB2 (or a genetic locus including a chromosomal position of 17:37880220), KRAS (or a genetic locus including a chromosomal position of 12:25378562, 12:25378643, 12:25380275, 12:25380276, 12:25380277, 12:25380279, 12:25398255, 12:25398280, 12:25398281, 12:25398282, 12:25398283, 12:25398284, and/or 12:25398285), MAP2K1 (or a genetic locus including a chromosomal position of 15:66729162 and/or 15:66729163), MET (or a genetic locus including a chromosomal position of 7:116422117 and/or 7:116423413), NTRK1 (or a genetic locus including a chromosomal position of 1:156846342, 1:156849044, and/or 1:156849144), PIK3CA (or a genetic locus including a chromosomal position of 3:178936091, 3:178936092, 3:178936093, 3:178952072, 3:178952084, and/or 3:178952085), and STK11 (or a genetic locus including a chromosomal position of 19:1218483, 19:1220370, 19:1220487, 19:1220629, and/or 19:1220649). In some embodiments, the subject has non-small cell lung cancer and candidate variants associated with at least 2, at least 3, at least 4, at least 5, at least 6, at least 7, at least 8, at least 9, or at least 10 of the genes listed above (or loci including the enumerated corresponding chromosomal positions) are evaluated. In some embodiments, the subject has non-small cell lung cancer and candidate variants associated with any of the genes listed above (or loci including the enumerated corresponding chromosomal positions) are evaluated.

In some of the embodiments described above where the subject has non-small cell lung cancer, only a subset of possible candidate sequence variants in the ALK gene are evaluated and/or reported. In some embodiments, the subset of possible candidate sequence variants in the ALK gene includes variants resulting in an amino acid change selected from G1202*, G1202R, L1196L, L1196M, L1196V, F1174F, F1174L, F1174I, F1174V, I1171N, I1171S, I1171T, C1156F, C1156S, and C1156Y.

In some of the embodiments described above where the subject has non-small cell lung cancer, only a subset of possible candidate sequence variants in the BRAF gene are evaluated and/or reported. In some embodiments, the subset of possible candidate sequence variants in the BRAF gene includes variants resulting in an amino acid change selected from V600*, V600A, V600E, V600G, V600L, and V600M.

In some of the embodiments described above where the subject has non-small cell lung cancer, only a subset of possible candidate sequence variants in the EGFR gene are evaluated and/or reported. In some embodiments, the subset of possible candidate sequence variants in the EGFR gene includes variants resulting in an amino acid change selected from G465*, G465R, L718L, L718M, L718V, L718P, L718Q, L718R, L747I, L747L, L747V, D761H, D761N, D761Y, V774L, V774M, T790K, T790M, T790R, C797G, C797R, C797S, C797F, C797Y, C797*, C797C, C797W, L798F, L798I, L798V, L858P, L858Q, and L858R.

In some of the embodiments described above where the subject has non-small cell lung cancer, only a subset of possible candidate sequence variants in the ERBB2 gene are evaluated and/or reported. In some embodiments, the subset of possible candidate sequence variants in the ERBB2 gene includes variants resulting in an amino acid change selected from L755*, L755S, and L755W.

In some of the embodiments described above where the subject has non-small cell lung cancer, only a subset of possible candidate sequence variants in the KRAS gene are evaluated and/or reported. In some embodiments, the subset of possible candidate sequence variants in the KRAS gene includes variants resulting in an amino acid change selected from A146T, D119N, Q61H, Q61Q, Q61L, Q61P, Q61R, Q61*, Q61E, Q61K, G60V, Q22K, G13G, G13A, G13V, G13D, G13C, G13R, G13S, G12G, G12A, G12V, G12D, G12C, G12R, and G12S.

In some of the embodiments described above where the subject has non-small cell lung cancer, only a subset of possible candidate sequence variants in the MAP2K1 gene are evaluated and/or reported. In some embodiments, the subset of possible candidate sequence variants in the MAP2K1 gene includes variants resulting in an amino acid change selected from P124A, P124S, P124T, P124R, P124L, and P124Q.

In some of the embodiments described above where the subject has non-small cell lung cancer, only a subset of possible candidate sequence variants in the MET gene are evaluated and/or reported. In some embodiments, the subset of possible candidate sequence variants in the MET gene includes variants resulting in an amino acid change selected from F1200I, F1200L, F1200V, Y1230D, Y1230H, and Y1230N.

In some of the embodiments described above where the subject has non-small cell lung cancer, only a subset of possible candidate sequence variants in the NTRK1 gene are evaluated and/or reported. In some embodiments, the subset of possible candidate sequence variants in the NTRK1 gene includes variants resulting in an amino acid change selected from G595R, G595W, F646I, F646L, F646V, D679A, D679G, and D679V.

In some of the embodiments described above where the subject has non-small cell lung cancer, only a subset of possible candidate sequence variants in the PIK3CA gene are evaluated and/or reported. In some embodiments, the subset of possible candidate sequence variants in the PIK3CA gene includes variants resulting in an amino acid change selected from E545*, E545K, E545Q, E545A, E545G, E545V, E545D, E545E, M1043V, H1047D, H1047Y, H1047N, H1047L, H1047P, and H1047R.

In some of the embodiments described above where the subject has non-small cell lung cancer, only a subset of possible candidate sequence variants in the STK11 gene are evaluated and/or reported. In some embodiments, the subset of possible candidate sequence variants in the STK11 gene includes variants resulting in an amino acid change selected from E120*, D194Y, S216F, and E223*, as well as nucleotide substitution c.465-2A>T.

Similarly, in some embodiments, the subject has prostate cancer and candidate variants associated with at least one of the following genes and/or genetic loci are evaluated: AR (or a genetic locus including a chromosomal position of X:66766292, X:66931463, X:66931504, X:66937370, X:66937371, X:66937372, X:66943543, X:66943549, and/or X:66943552), EGFR (or a genetic locus including a chromosomal position of 7:55227926, 7:55242511, and/or 7:55249022), ERBB2 (or a genetic locus including a chromosomal position of 17:37880220), KRAS (or a genetic locus including a chromosomal position of 12:25380275, 12:25380276, and/or 12:25380277), MAP2K1 (or a genetic locus including a chromosomal position of 15:66729162 and/or 15:66729163), MET (or a genetic locus including a chromosomal position of 7:116422117 and/or 7:116423413), NTRK1 (or a genetic locus including a chromosomal position of 1:156846342, 1:156849044, and/or 1:156849144), and PIK3CA (or a genetic locus including a chromosomal position of 3:178952084 and/or 3:178952085). In some embodiments, the subject has prostate cancer and candidate variants associated with at least 2, at least 3, at least 4, at least 5, at least 6, or at least 7 of the genes listed above (or loci including the enumerated corresponding chromosomal positions) are evaluated. In some embodiments, the subject has prostate cancer and candidate variants associated with any of the genes listed above (or loci including the enumerated corresponding chromosomal positions) are evaluated.

In some of the embodiments described above where the subject has prostate cancer, only a subset of possible candidate sequence variants in the AR gene are evaluated and/or reported. In some embodiments, the subset of possible candidate sequence variants in the AR gene includes variants resulting in an amino acid change selected from W435L, L702H, L702P, L702R, V716M, W742G, W742R, W742*, W742L, W742S, W742C, H875Y, F877L, T878A, T878P, and T878S.

In some of the embodiments described above where the subject has prostate cancer, only a subset of possible candidate sequence variants in the EGFR gene are evaluated and/or reported. In some embodiments, the subset of possible candidate sequence variants in the EGFR gene includes variants resulting in an amino acid change selected from G465*, G465R, D761H, D761N, D761Y, V774L, and V774M.

In some of the embodiments described above where the subject has prostate cancer, only a subset of possible candidate sequence variants in the ERBB2 gene are evaluated and/or reported. In some embodiments, the subset of possible candidate sequence variants in the ERBB2 gene includes variants resulting in an amino acid change selected from L755*, L755S, and L755W.

In some of the embodiments described above where the subject has prostate cancer, only a subset of possible candidate sequence variants in the KRAS gene are evaluated and/or reported. In some embodiments, the subset of possible candidate sequence variants in the KRAS gene includes variants resulting in an amino acid change selected from Q61H, Q61Q, Q61L, Q61P, Q61R, Q61*, Q61E, and Q61K.

In some of the embodiments described above where the subject has prostate cancer, only a subset of possible candidate sequence variants in the MAP2K1 gene are evaluated and/or reported. In some embodiments, the subset of possible candidate sequence variants in the MAP2K1 gene includes variants resulting in an amino acid change selected from P124A, P124S, P124T, P124R, P124L, and P124Q.

In some of the embodiments described above where the subject has prostate cancer, only a subset of possible candidate sequence variants in the MET gene are evaluated and/or reported. In some embodiments, the subset of possible candidate sequence variants in the MET gene includes variants resulting in an amino acid change selected from F1200I, F1200L, F1200V, Y1230D, Y1230H, and Y1230N.

In some of the embodiments described above where the subject has prostate cancer, only a subset of possible candidate sequence variants in the NTRK1 gene are evaluated and/or reported. In some embodiments, the subset of possible candidate sequence variants in the NTRK1 gene includes variants resulting in an amino acid change selected from G595R, G595W, F646I, F646L, F646V, D679A, D679G, and D679V.

In some of the embodiments described above where the subject has prostate cancer, only a subset of possible candidate sequence variants in the PIK3CA gene are evaluated and/or reported. In some embodiments, the subset of possible candidate sequence variants in the PIK3CA gene includes variants resulting in an amino acid change selected from H1047D, H1047Y, H1047N, H1047L, H1047P, and H1047R.

In one example, the cancer condition is any type of cancer (for example, pan-cancer) and the somatic variants validated by this method include variants associated with any of the following genes: EGFR (or a genetic locus including a chromosomal position of 7:55227926, 7:55242511, and/or 7:55249022), ERBB2 (or a genetic locus including a chromosomal position of 17:37880220), KRAS (or a genetic locus including a chromosomal position of 12:25380275, 12:25380276, and/or 12:25380277), MAP2K1 (or a genetic locus including a chromosomal position of 15:66729162 and/or 15:66729163), MET (or a genetic locus including a chromosomal position of 7:116422117 and/or 7:116423413), NTRK1 (or a genetic locus including a chromosomal position of 1:156846342, 1:156849044, and/or 1:156849144), PIK3CA (or a genetic locus including a chromosomal position of 3:178952084 and/or 3:178952085), and TP53. In some embodiments, the subject has any cancer (e.g., pan cancer) and candidate variants associated with at least 2, at least 3, at least 4, at least 5, at least 6, or at least 7 of the genes listed above (or loci including the enumerated corresponding chromosomal positions) are evaluated. In some embodiments, the subject has any cancer (e.g., pan cancer) and candidate variants associated with any of the genes listed above (or loci including the enumerated corresponding chromosomal positions) are evaluated.

In some of the embodiments described above where the subject has any type of cancer (e.g., pan-cancer), only a subset of possible candidate sequence variants in the EGFR gene are evaluated and/or reported. In some embodiments, the subset of possible candidate sequence variants in the EGFR gene includes variants resulting in an amino acid change selected from G465*, G465R, D761H, D761N, D761Y, V774L, and V774M.

In some of the embodiments described above where the subject has any type of cancer (e.g., pan-cancer), only a subset of possible candidate sequence variants in the ERBB2 gene are evaluated and/or reported. In some embodiments, the subset of possible candidate sequence variants in the ERBB2 gene includes variants resulting in an amino acid change selected from L755*, L755S, and L755W.

In some of the embodiments described above where the subject has any type of cancer (e.g., pan-cancer), only a subset of possible candidate sequence variants in the KRAS gene are evaluated and/or reported. In some embodiments, the subset of possible candidate sequence variants in the KRAS gene includes variants resulting in an amino acid change selected from Q61H, Q61Q, Q61L, Q61P, Q61R, Q61*, Q61E, and Q61K.

In some of the embodiments described above where the subject has any type of cancer (e.g., pan-cancer), only a subset of possible candidate sequence variants in the MAP2K1 gene are evaluated and/or reported. In some embodiments, the subset of possible candidate sequence variants in the MAP2K1 gene includes variants resulting in an amino acid change selected from P124A, P124S, P124T, P124R, P124L, and P124Q.

In some of the embodiments described above where the subject has any type of cancer (e.g., pan-cancer), only a subset of possible candidate sequence variants in the MET gene are evaluated and/or reported. In some embodiments, the subset of possible candidate sequence variants in the MET gene includes variants resulting in an amino acid change selected from F1200I, F1200L, F1200V, Y1230D, Y1230H, and Y1230N.

In some of the embodiments described above where the subject has any type of cancer (e.g., pan-cancer), only a subset of possible candidate sequence variants in the NTRK1 gene are evaluated and/or reported. In some embodiments, the subset of possible candidate sequence variants in the NTRK1 gene includes variants resulting in an amino acid change selected from G595R, G595W, F646I, F646L, F646V, D679A, D679G, and D679V.

In some of the embodiments described above where the subject has any type of cancer (e.g., pan-cancer), only a subset of possible candidate sequence variants in the PIK3CA gene are evaluated and/or reported. In some embodiments, the subset of possible candidate sequence variants in the PIK3CA gene includes variants resulting in an amino acid change selected from H1047D, H1047Y, H1047N, H1047L, H1047P, and H1047R.

Similarly, in some embodiments, the subject has a tumor of unknown origin or a cancer of unknown primary and candidate variants associated with at least one of the following genes and/or genetic loci are evaluated: EGFR (or a genetic locus including a chromosomal position of 7:55227926, 7:55242511, and/or 7:55249022), ERBB2 (or a genetic locus including a chromosomal position of 17:37880220), KRAS (or a genetic locus including a chromosomal position of 12:25380275, 12:25380276, 12:25380277, and/or 12:25398255), MAP2K1 (or a genetic locus including a chromosomal position of 15:66729162 and/or 15:66729163), MET (or a genetic locus including a chromosomal position of 7:116422117 and/or 7:116423413), NRAS (or a genetic locus including a chromosomal position of 1:115258748), NTRK1 (or a genetic locus including a chromosomal position of 1:156846342, 1:156849044, and/or 1:156849144), PIK3CA (or a genetic locus including a chromosomal position of 3:178927980, 3:178952084 and/or 3:178952085), and TP53. In some embodiments, the subject has any cancer (e.g., pan cancer) and candidate variants associated with at least 2, at least 3, at least 4, at least 5, at least 6, at least 7, or at least 8 of the genes listed above (or loci including the enumerated corresponding chromosomal positions) are evaluated. In some embodiments, the subject has any cancer (e.g., pan cancer) and candidate variants associated with any of the genes listed above (or loci including the enumerated corresponding chromosomal positions) are evaluated.

In some of the embodiments described above where the subject has a tumor of unknown origin or a cancer of unknown primary, only a subset of possible candidate sequence variants in the EGFR gene are evaluated and/or reported. In some embodiments, the subset of possible candidate sequence variants in the EGFR gene includes variants resulting in an amino acid change selected from G465*, G465R, D761H, D761N, D761Y, V774L, and V774M.

In some of the embodiments described above where the subject has a tumor of unknown origin or a cancer of unknown primary, only a subset of possible candidate sequence variants in the ERBB2 gene are evaluated and/or reported. In some embodiments, the subset of possible candidate sequence variants in the ERBB2 gene includes variants resulting in an amino acid change selected from L755*, L755S, and L755W.

In some of the embodiments described above where the subject has a tumor of unknown origin or a cancer of unknown primary, only a subset of possible candidate sequence variants in the KRAS gene are evaluated and/or reported. In some embodiments, the subset of possible candidate sequence variants in the KRAS gene includes variants resulting in an amino acid change selected from Q61H, Q61Q, Q61L, Q61P, Q61R, Q61*, Q61E, Q61K, and Q22K.

In some of the embodiments described above where the subject has a tumor of unknown origin or a cancer of unknown primary, only a subset of possible candidate sequence variants in the MAP2K1 gene are evaluated and/or reported. In some embodiments, the subset of possible candidate sequence variants in the MAP2K1 gene includes variants resulting in an amino acid change selected from P124A, P124S, P124T, P124R, P124L, and P124Q.

In some of the embodiments described above where the subject has a tumor of unknown origin or a cancer of unknown primary, only a subset of possible candidate sequence variants in the MET gene are evaluated and/or reported. In some embodiments, the subset of possible candidate sequence variants in the MET gene includes variants resulting in an amino acid change selected from F1200I, F1200L, F1200V, Y1230D, Y1230H, and Y1230N.

In some of the embodiments described above where the subject has a tumor of unknown origin or a cancer of unknown primary, only a subset of possible candidate sequence variants in the NRAS gene are evaluated and/or reported. In some embodiments, the subset of possible candidate sequence variants in the NRAS gene includes variants resulting in an amino acid change of G12S.

In some of the embodiments described above where the subject has a tumor of unknown origin or a cancer of unknown primary, only a subset of possible candidate sequence variants in the NTRK1 gene are evaluated and/or reported. In some embodiments, the subset of possible candidate sequence variants in the NTRK1 gene includes variants resulting in an amino acid change selected from G595R, G595W, F646I, F646L, F646V, D679A, D679G, and D679V.

In some of the embodiments described above where the subject has a tumor of unknown origin or a cancer of unknown primary, only a subset of possible candidate sequence variants in the PIK3CA gene are evaluated and/or reported. In some embodiments, the subset of possible candidate sequence variants in the PIK3CA gene includes variants resulting in an amino acid change selected from C420R, H1047D, H1047Y, H1047N, H1047L, H1047P, and H1047R.

In other embodiments, the cancer condition is acute myeloid leukemia, adrenal cancer, b cell lymphoma, basal cell carcinoma, biliary cancer, bladder cancer, brain cancer, breast cancer, cervical cancer, chromophobe renal cell carcinoma, clear cell renal cell carcinoma, colorectal cancer, confirm at path review (cancer type unconfirmed), endocrine tumor, endometrial cancer, esophageal cancer, gastric cancer, gastrointestinal stromal tumor, glioblastoma, head and neck cancer, head and neck squamous cell carcinoma, heme other, high-grade glioma, kidney cancer, liver cancer, low grade glioma, medulloblastoma, melanoma, meningioma, mesothelioma, multiple myeloma, neuroblastoma, non-clear cell renal cell carcinoma, non-small cell lung cancer, oropharyngeal cancer, ovarian cancer, pan-cancer, pancreatic cancer, peritoneal cancer, prostate cancer, sarcoma, skin cancer, small cell lung cancer, t cell lymphoma, testicular cancer, thymoma, thyroid cancer, tumor of unknown origin, or uveal melanoma.

In some embodiments, certain variants pre-identified on a whitelist may be rescued, e.g., not filtered out, when they fail to pass selective filters, e.g., MSI/SN, a Bayesian filtering method, and/or a coverage, VAF or region-based filter. The rationale for whitelisting a variant is to apply less stringent filtering criteria to such a variant so that it can be reviewed and/or reported. In some embodiments, one or more variant on the whitelist is a common pathogenic variant, e.g., with high clinical relevance. In this fashion, when a variant on the whitelist fails to pass certain filters, it will be rescued and not filtered out. As used herein, MSI/SN refers to a variant filter for filtering out potential artifactual variants based on the MSI (microsatellite instable) and SN (signal-to-noise ratio) values calculated by the variant caller VarDict. See, for example, VarDict documentation, available on the internet at github.com/AstraZeneca-NGSNarDictJava.

In some embodiments, one or more locus and/or genomic region is blacklisted, preventing somatic variant annotation for variants identified at the locus or region. In some embodiments, the variant has a length of 120, 100, 80, 60, 40, 20, 10, 5 or less base pairs. In various embodiments, any combination of the additional criteria, as well as additional criteria not listed above, may be applied to the variant calling process. Again, in some embodiments, different criteria are applied to the annotation of different types of variants.

In some embodiments, liquid biopsy assays are used to detect variant alterations present at low circulating fractions in the patient's blood. In such circumstances, it may be warranted to lower the requirements for positively identifying a variant. That is, in some embodiments, low levels of support may be sufficient to call a variant, dependent upon the reason for using the liquid biopsy assay.

In some embodiments, SNV/INDEL detection is accomplished using VarDict (github.com/AstraZeneca-NGS/VarDictJava). Both SNVs and INDELs are called and then sorted, deduplicated, normalized and annotated. The annotation uses SnpEff to add transcript information, 1000 genomes minor allele frequencies, COSMIC reference names and counts, ExAC allele frequencies, and Kaviar population allele frequencies. The annotated variants are then classified as germline, somatic, or uncertain using a Bayesian model based on prior expectations informed by databases of germline and cancer variants. In some embodiments, uncertain variants are treated as somatic for filtering and reporting purposes.

In some embodiments, genomic rearrangements (e.g., inversions, translocations, and gene fusions) are detected following de-multiplexing by aligning tumor FASTQ files against a human reference genome using a local alignment algorithm, such as BWA. In some embodiments, DNA reads are sorted, and duplicates may be marked with a software, for example, SAMBlaster. Discordant and split reads may be further identified and separated. These data may be read into a software, for example, LUMPY, for structural variant detection. In some embodiments, structural alterations are grouped by type, recurrence, and presence and stored within a database and displayed through a fusion viewer software tool. The fusion viewer software tool may reference a database, for example, Ensembl, to determine the gene and proximal exons surrounding the breakpoint for any possible transcript generated across the breakpoint. The fusion viewer tool may then place the breakpoint 5' or 3' to the subsequent exon in the direction of transcription. For inversions, this orientation may be reversed for the inverted gene. After positioning of the breakpoint, the translated amino acid sequences may be generated for both genes in the chimeric protein, and a plot may be generated containing the remaining functional domains for each protein, as returned from a database, for example, Uniprot.

For instance, in an example implementation, gene rearrangements are detected using the SpeedSeq analysis pipeline. Chiang et al., 2015, "SpeedSeq: ultra-fast personal genome analysis and interpretation," Nat Methods, (12), pg. 966. Briefly, FASTQ files are aligned to hg19 using BWA. Split reads mapped to multiple positions and read pairs mapped to discordant positions are identified and separated, then utilized to detect gene rearrangements by LUMPY. Layer et al., 2014, "LUMPY: a probabilistic framework for structural variant discovery," Genome Biol, (15), pg. 84. Fusions can then be filtered according to the number of supporting reads.

In some embodiments, putative fusion variants supported by fewer than a minimum number of unique sequence reads are filtered. In some embodiments, the minimum number of unique sequence reads is 2, 3, 4, 5, 6, 7, 8, 9, 10, 12, 15, or 20 unique sequence reads.

Allelic Fraction Determination

In some embodiments, the analysis of aligned sequence reads, e.g., in SAM or BAM format, includes determination of variant allele fractions (133) for one or more of the variant alleles 132 identified as described above. In some embodiments, a variant allele fraction module 151 tallies the instances that each allele is represented by a unique sequence read encompassing the variant locus of interest, generating a count for each allele represented at that locus. In some embodiments, these tallies are used to determine the ratio of the variant allele, e.g., an allele other than the most prevalent allele in the subject's population for a respective locus, to a reference allele. This variant allele fraction 133 can be used in several places in the feature extraction 206 workflow. For instance, in some embodiments, a variant allele fraction is used during annotations of identified variants, e.g., when determining whether the allele originated from a germline cell or a somatic cell. In other instances, a variant allele fraction is used in a process for estimating a tumor fraction for a liquid biopsy sample or a tumor purity for a solid tumor fraction. For instance, variant allele fractions for a plurality of somatic alleles can be used to estimate the percentage of sequence reads originating from one copy of a cancerous chromosome. Assuming a 100% tumor purity and that each cancer cell caries one copy of the variant allele, the overall purity of the tumor can be estimated. This estimate, of course, can be further corrected based on other information extracted from the sequencing data, such as copy number alterations, tumor ploidy aberrations, tumor heterozygosity, etc.

Methylation Determination

In some embodiments, where nucleic acid sequencing library was processed by bi-sulfite treatment or enzymatic methyl-cytosine conversion, as described above, the analysis of aligned sequence reads, e.g., in SAM or BAM format, includes determination of methylation states 132 for one or more loci in the genome of the patient. In some embodiments, methylation sequencing data is aligned to a reference sequence construct 158 in a different fashion than non-methylation sequencing, because non-methylated cytosines are converted to uracils, and the resulting uracils are ultimately sequenced as thymines, whereas methylated cytosine are not converted and sequenced as cytosine. Different approaches, therefore, have to be used to align these modified sequences to a reference sequence construct, such as seeding alignments with shorter regions of identity or converting all cytosines to thymidines in the sequencing data and then aligning the data to reference sequence constructs for both the plus and minus strand of the sequence construct. For review of these approaches, see Zhou Q. et al., BMC Bioinformatics, 20(47):1-11 (2019), the content of which is hereby incorporated by reference, in its entirety, for all purposes. Algorithms for calling methylated bases are known in the art. For example, Bismark is able to distinguish between cytosines in CpG, CHG, and CHH contexts. Krueger F. and Andrews S R, Bioinformatics, 27(11):1571-71 (2011), the content of which is hereby incorporated by reference, in its entirety, for all purposes.

Copy Number Variation Analysis:

In some embodiments, the analysis of aligned sequence reads, e.g., in SAM or BAM format, includes determination of the copy number 135 for one or more locus, using a copy number variation analysis module 153. In some embodiments, where both a liquid biopsy sample and a normal tissue sample of the patient are analyzed, de-duplicated BAM files and a VCF generated from the variant calling pipeline are used to compute read depth and variation in heterozygous germline SNVs between sequencing reads for each sample. By contrast, in some embodiments, where only a liquid biopsy sample is being analyzed, comparison between a tumor sample and a pool of process-matched normal controls is used. In some embodiments, copy number analysis includes application of a circular binary segmentation algorithm and selection of segments with highly differential $\log_2$ ratios between the cancer sample and its comparator (e.g., a matched normal or normal pool). In some embodiments, approximate integer copy number is assessed from a combination of differential coverage in segmented regions and an estimate of stromal admixture (for example, tumor purity, or the portion of a sample that is cancerous vs. non-cancerous, such as a tumor fraction for a liquid biopsy sample) is generated by analysis of heterozygous germline SNVs.

For instance, in an example implementation, copy number variants (CNVs) are analyzed using the CNVkit package. Talevich et al., PLoS Comput Biol, 12:1004873 (2016), the content of which is hereby incorporated by reference, in its entirety, for all purposes. CNVkit is used for genomic region binning, coverage calculation, bias correction, normalization to a reference pool, segmentation and visualization. The $\log_2$ ratios between the tumor sample and a pool of process matched healthy samples from the CNVkit output are then annotated and filtered using statistical models whereby the amplification status (amplified or not amplified) of each gene is predicted and non-focal amplifications are removed.

In some embodiments, copy number variations (CNVs) are analyzed using a combination of an open-source tool, such as CNVkit, and an annotation/filtering algorithm, e.g., implemented via a python script. CNVkit is used initially to perform genomic region binning, coverage calculation, bias correction, normalization to a reference pool, segmentation and, optionally, visualization. The bin-level copy ratios and segment-level copy ratios, in addition to their corresponding confidence intervals, from the CNVkit output are then used in the annotation and filtering where the copy number state (amplified, neutral, deleted) of each segment and bin are determined and non-focal amplifications/deletions are filtered out based on a set of acceptance criteria. In some embodiments, one or more copy number variations selected from amplifications in the MET, EGFR, ERBB2, CD274, CCNE1, and MYC genes, and deletions in the BRCA1 and BRCA2 genes are analyzed. However, the methods described herein is not limited to only these reportable genes.

In some embodiments, CNV analysis is performed using a tumor BAM file, a target region BED file, a pool of process matched normal samples, and inputs for initial reference pool construction. Inputs for initial reference pool construction include one or more of normal BAM files, a human reference genome file, mappable regions of the genome, and a blacklist that contains recurrent problematic areas of the genome.

CNVkit utilizes both targeted captured sequencing reads and non-specifically captured off-target reads to infer copy number information. The targeted genomic regions specified in the probe target BED file are divided to target bins with an average size of, e.g., 100 base pairs, which can be specified by the user. The genomic regions between the target regions, e.g., excluding regions that cannot be mapped reliably, are automatically divided into off-target (also referred to as anti-target) bins with an average size of, e.g., 150 kbp, which again can be specified by the user. Raw $\log_2$-transformed depths are then calculated from the alignments in the input BAM file and written to two tab-delimited .cnn files, one for each of the target and off-target bins.

A pooled reference is constructed from a panel of process matched normal samples. The raw $\log_2$ depths of target and off-target bins in each normal sample are computed as described above, and then each are median-centered and corrected for bias including GC content, genome sequence repetitiveness, target size, and/or spacing. The corrected target and off-target $\log_2$ depths are combined, and a weighted average and spread are calculated as Tukey's biweight location and midvariance in each bin. These values are written to a tab delimited reference .cnn file, which is used to normalize an input tumor sample as follows.

The raw $\log_2$ depths of an input sample are median-centered and bias-corrected as described in the reference construction. The corrected $\log_2$ depth of each bin is then subtracted by the corresponding $\log_2$ depth in the reference file, resulting in the $\log_2$ copy ratios (also referred to as copy ratios or $\log_2$ ratios) between the input tumor sample and the reference pool. These values are written to a tab-delimited .cnr file.

The copy ratios are then segmented, e.g., via a circular binary segmentation (CBS) algorithm or another suitable segmentation algorithm, whereby adjacent bins are grouped to larger genomic regions (segments) of equal copy number. The segment's copy ratio is calculated as the weighted mean of all bins within the segment. The confidence interval of the segment mean is estimated by bootstrapping the bin-level copy ratios within the segment. The segments' genomic ranges, copy ratios and confidence intervals are written to a tab-delimited .cns file.

$\log_2$ transformed copy ratios, $\log_2$ copy ratios, $\log_2$-transformed depths, $\log_2$-transformed read depths, $\log_2$ depths, corrected $\log_2$ depths, $\log_2$ ratios, $\log_2$ read depths, and $\log_2$ depth correction values have been discussed herein by way of example. In each instance where such a term is used, it will be appreciated that log base 2 is presented by way of example only and that the present disclosure is not so limited. Indeed, logarithms to any base N may be used, (e.g., where N is a positive number greater than 1 for instance), and thus the present disclosure fully supports $\log_N$ transformed copy ratios, $\log_N$ copy ratios, $\log_N$-transformed depths, $\log_N$-transformed read depths, $\log_N$ depths, corrected $\log_N$ depths, $\log_N$ ratios, $\log_N$ read depths, and $\log_N$ depth correction values as respective substitutes for $\log_2$ transformed copy ratios, $\log_2$ copy ratios, $\log_2$-transformed depths, $\log_2$-transformed read depths, $\log_2$ depths, corrected $\log_2$ depths, $\log_2$ ratios, $\log_2$ read depths, and $\log_2$ depth correction values.

Microsatellite Instability (MSI):

In some embodiments, analysis of aligned sequence reads, e.g., in SAM or BAM format, includes analysis of the microsatellite instability status 137 of a cancer, using a microsatellite instability analysis module 154. In some embodiments, an MSI classification algorithm classifies a cancer into three categories: microsatellite instability-high (MSI-H), microsatellite stable (MSS), or microsatellite equivocal (MSE). Microsatellite instability is a clinically actionable genomic indication for cancer immunotherapy. In microsatellite instability-high (MSI-H) tumors, defects in DNA mismatch repair (MMR) can cause a hypermutated phenotype where alterations accumulate in the repetitive microsatellite regions of DNA. MSI detection is conventionally performed by subjecting tumor tissue ("solid biopsy") to clinical next-generation sequencing or specific assays, such as MMR IHC or MSI PCR.

For example, microsatellite instability status can be assessed by determining the number of repeating units present at a plurality of microsatellite loci, e.g., 5, 10, 15, 20, 25, 30, 40, 50, 75, 100, 250, 500, 750, 1000, 2500, 5000, or more loci. In some embodiments, only reads encompassing a microsatellite locus that include a significant number of flanking nucleotides on both ends, e.g., at least 5, 10, 15, or more nucleotides flanking each end, are used for the analysis in order to avoid using reads that do not completely cover the locus. In some embodiments, a minimal number of reads, e.g., at least 5, 10, 20, 30, 40, 50, or more reads have to meet this criteria in order to use a particular microsatellite locus, in order to ensure the accuracy of the determination given the high incidence of polymerase slipping during replication of these repeated sequences.

In some embodiments, each locus is tested individually for instability, e.g., as measured by a change or variance in the number of nucleotide base repeats, e.g., in cancer-derived nucleotide sequences relative to a normal sample or standard, for example, using the Kolmogorov-Smirnov test. For example, if $p \leq 0.05$, the locus is considered unstable. The proportion of unstable microsatellite loci may be fed into a logistic regression classifier trained on samples from various cancer types, especially cancer types which have clinically determined MSI statuses, for example, colorectal and endometrial cohorts. For MSI testing where only a liquid biopsy sample is analyzed, the mean and variance for the number of repeats may be calculated for each microsatellite locus. A vector containing the mean and variance data may be put into a classifier (e.g., a support vector machine classification algorithm) trained to provide a probability that the patient is MSI-H, which may be compared to a threshold value. In some embodiments, the threshold value for calling the patient as MSI-H is at least 60% probability, or at least 65% probability, 70% probability, 75% probability, 80% probability, or greater. In some embodiments, a baseline threshold may be established to call the patient as MSS. In some embodiments, the baseline threshold is no more than 40%, or no more than 35% probability, 30% probability, 25% probability, 20% probability, or less. In some embodiments, when the output of the classifier falls within the range between the MSI-H and MSS thresholds, the patient is identified as MSE.

Other methods for determining the MSI status of a subject are known in the art. For example, in some embodiments, microsatellite instability analysis module 154 employs an MSI evaluation methods described in U.S. Provisional Patent Application Ser. No. 62/881,845, filed Aug. 1, 2019, or U.S. Provisional Application Ser. No. 62/931,600, filed Nov. 6, 2019, the contents of which are hereby incorporated by reference, in their entireties, for all purposes.

Tumor Mutational Burden (TMB):

In some embodiments, the analysis of aligned sequence reads, e.g., in SAM or BAM format, includes determination of a mutation burden for the cancer (e.g., a tumor mutational burden 136), using a tumor mutational burden analysis module 155. Generally, a tumor mutational burden is a measure of the mutations in a cancer per unit of the patient's genome. For example, a tumor mutational burden may be expressed as a measure of central tendency (e.g., an average) of the number of somatic variants per million base pairs in the genome. In some embodiments, a tumor mutational burden refers to only a set of possible mutations, e.g., one or more of SNVs, MNVs, indels, or genomic rearrangements. In some embodiments, a tumor mutational burden refers to only a subset of one or more types of possible mutations, e.g., non-synonymous mutations, meaning those mutations that alter the amino acid sequence of an encoded protein. In other embodiments, for example, a tumor mutational burden refers to the number of one or more types of mutations that occur in protein coding sequences, e.g., regardless of whether they change the amino acid sequence of the encoded protein.

As an example, in some embodiments, a tumor mutational burden (TMB) is calculated by dividing the number of mutations (e.g., all variants or non-synonymous variants) identified in the sequencing data (e.g., as represented in a VCF file) by the size (e.g., in megabases) of a capture probe panel used for targeted sequencing. In some embodiments, a variant is included in tumor mutation burden calculation only when certain criteria are met. For instance, in some embodiments, a threshold sequence coverage for the locus associated with the variant must be met before the variant is included in the calculation, e.g., at least 25×, 50×, 75×, 100×, 250×, 500×, or greater. Similarly, in some embodiments, a minimum number of unique sequence reads encompassing the variant allele must be identified in the sequencing data, e.g., at least 4, 5, 6, 7, 8, 9, 10, or more unique sequence reads. In some embodiments, a threshold variant allelic fraction threshold must be satisfied before the variant is included in the calculation, e.g., at least 0.01%, 0.1%, 0.25%, 0.5%, 0.75%, 1%, 1.5%, 2%, 2.5%, 3%, 4%, 5%, or greater. In some embodiments, an inclusion criteria may be different for different types of variants and/or different variants of the same type. For instance, a variant detected in a mutation hotspot within the genome may face less rigorous criteria than a variant detected in a more stable locus within the genome.

Other methods for calculating tumor mutation burden in liquid biopsy samples and/or solid tissue samples are known in the art. See, for example, Fenizia F. et al., Transl Lung Cancer Res., 7(6):668-77 (2018) and Georgiadis A et al., Clin. Cancer Res., 25(23):7024-34 (2019), the disclosures of which are hereby incorporated by reference, in their entireties, for all purposes.

Homologous Recombination Status (HRD):

In some embodiments, analysis of aligned sequence reads, e.g., in SAM or BAM format, includes analysis of whether the cancer is homologous recombination deficient (HRD status 137-3), using a homologous recombination pathway analysis module 157.

Homologous recombination (HR) is a normal, highly conserved DNA repair process that enables the exchange of genetic information between identical or closely related DNA molecules. It is most widely used by cells to accurately repair harmful breaks (e.g., damage) that occur on both strands of DNA. DNA damage may occur from exogenous (external) sources like UV light, radiation, or chemical damage; or from endogenous (internal) sources like errors in DNA replication or other cellular processes that create DNA damage. Double strand breaks are a type of DNA damage.

Using poly (ADP-ribose) polymerase (PARP) inhibitors in patients with HRD compromises two pathways of DNA repair, resulting in cell death (apoptosis). The efficacy of PARP inhibitors is improved not only in ovarian cancers displaying germline or somatic BRCA mutations, but also in cancers in which HRD is caused by other underlying etiologies.

In some embodiments, HRD status can be determined by inputting features correlated with HRD status into a classifier trained to distinguish between cancers with homologous recombination pathway deficiencies and cancers without homologous recombination pathway deficiencies. For example, in some embodiments, the features include one or more of (i) a heterozygosity status for a first plurality of DNA damage repair genes in the genome of the cancerous tissue of the subject, (ii) a measure of the loss of heterozygosity across the genome of the cancerous tissue of the subject, (iii) a measure of variant alleles detected in a second plurality of DNA damage repair genes in the genome of the cancerous tissue of the subject, and (iv) a measure of variant alleles detected in the second plurality of DNA damage repair genes in the genome of the non-cancerous tissue of the subject. In some embodiments, all four of the features described above are used as features in an HRD classifier. More details about HRD classifiers using these and other features are described in U.S. patent application Ser. No. 16/789,363, filed Feb. 12, 2020, the content of which is hereby incorporated by reference, in its entirety, for all purposes.

Circulating Tumor Fraction:

In some embodiments, the analysis of aligned sequence reads, e.g., in SAM or BAM format, includes estimation of a circulating tumor fraction for the liquid biopsy sample. Tumor fraction or circulating tumor fraction is the fraction of cell free nucleic acid molecules in the sample that originates from a cancerous tissue of the subject, rather than from a non-cancerous tissue (e.g., a germline or hematopoietic tissue). Several open source analysis packages have modules for calculating tumor fraction from solid tumor samples. For instance, PureCN (Riester, M., et al., Source Code Biol Med, 11:13 (2016)) is designed to estimate tumor purity from targeted short-read sequencing data of solid tumor samples. Similarly, FACETS (Shen R, Seshan V E, Nucleic Acids Res., 44(16):e131 (2016)) is designed to estimate tumor fraction from sequencing data of solid tumor samples. However, estimating tumor fraction from a liquid biopsy sample is more difficult because of the, generally, lower tumor fraction relative to a solid tumor sample and typic small size of a targeted panel used for liquid biopsy sequencing. Indeed, packages such as PureCN and FACETS perform poorly at low tumor fractions and with sequencing data generated using small targeted-panels.

In some embodiments, circulating tumor fraction is estimated from a targeted-panel sequencing reaction of a liquid biopsy sample using an off-target read methodology, e.g., as described herein with reference to FIG. 4F. Briefly, a circulating tumor fraction estimate is determined from reads in the target captured regions, as well as off-target reads uniformly distributed across the human reference genome. Segments having similar copy ratios, e.g., as assigned via circular binary segmentation (CBS) during CNV analysis, are fit to integer copy states, e.g., via an expectation-maximization algorithm using the sum of squared error of the segment log 2 ratios (normalized to genomic interval size) to expected ratios given a putative copy state and tumor fraction. For more information on expectation maximization algorithms see, for example, Sundberg, Rolf (1974). "Maximum likelihood theory for incomplete data from an exponential family". Scandinavian Journal of Statistics. 1 (2): 49-58, the content of which is hereby incorporated by reference in its entirety. A measure of fit between corresponding segment-level coverage ratios and assigned integer copy states across the plurality of simulated circulating tumor fractions is then used to select the simulated circulating tumor fraction to be used as the circulating tumor fraction for the liquid biopsy sample. In some embodiments, error minimization is used to identify the simulated tumor fraction providing the best fit to the data.

In some embodiments, a measure of fit between corresponding segment-level coverage ratios and assigned integer copy states across the plurality of simulated circulating tumor fractions (e.g., using an error minimization algorithm) provides a number of local optima (e.g., local minima for an error minimization model or local maxima for a fix maximization model) for the best fit between the segment-level coverage ratios and assigned integer copy states. In some such embodiments, a second estimate of circulating tumor fraction is used to select the local optima (e.g., the local minima in best agreement with the second estimate of circulating tumor fraction) to be used as the circulating tumor fraction for the liquid biopsy sample.

For example, in some embodiments, multiple local optima (e.g., minima) can be disambiguated based on a difference between somatic and germline variant allele fractions. The assumption is that the variant allele fraction (VAF) of germline variants that exhibit loss of heterozygosity (LOH) will increase or decrease by the amount approximately equal to half of the tumor purity (e.g., the circulating tumor fraction for a liquid biopsy sample). With a matched normal sample (e.g., where sequencing data for both a liquid biopsy sample and a non-cancerous sample from the subject is available, or where sequencing data for both a solid tumor sample and a non-cancerous sample from the subject is available), for a given heterozygous germline variant, the VAF delta can be calculated as delta=abs($VAF_{tumor}$–$VAF_{normal}$). However, for tumor only sequencing (e.g., where sequencing data is only available for a liquid biopsy sample or a solid tumor sample), the $VAF_{normal}$ is unknown. In some embodiments, the $VAF_{normal}$ is assumed to be 50%. To increase statistical power and account for the imprecision in the VAF by sequencing, the delta for all such variants are calculated and the circulating tumor fraction estimate (ctFE) for this method is calculated as ctFE=max(2×delta) for all variant delta values. While this can be used as a method for ctFE alone, its precision is limited by the number of detected LOH variants. For a small panel, there are few expected LOH variants and thus the ctFE may not be precise on its own. However, it can be used to disambiguate multiple local optima (e.g., minima), especially for high tumor fraction values estimated by the off-target read methodology described herein. For that, the off-target read methodology ctFE peaks corresponding to all the local optima (e.g., minima) are identified and the one closest to the ctFE estimated by LOH delta is chosen as the most likely global optima (e.g., minima).

Several other methods may also be used to estimate circulating tumor fractions. In some embodiments, these methods are used in combination with the off-target tumor estimate method described herein. For example, in some embodiments, one or more of these methodologies is used to generate an estimate of tumor fraction, which is then used to identify the nearest local optima (e.g., minima) obtained from the tumor fraction estimation methods described above, and further herein.

For example, the ichorCNA package applies a probabilistic model to normalized read coverages from ultra-low pass whole genome sequencing data of cell-free DNA to estimate tumor fraction in the liquid biopsy sample. For more information, see, Adalsteinsson, V. A. et al., Nat Commun 8:1324 (2017), the content of which is disclosed herein for its description of a probabilistic tumor fraction estimation model in the "methods" section. Similarly, Tiancheng H. et al., describe a Maximum Likelihood model based on the copy number of an allele in the sample and variant allele frequency in paired-control samples. For more information, see, Tiancheng H. et al., Journal of Clinical Oncology 37:15 suppl, e13053-e13053 (2019), the content of which is disclosed herein for its description of a Maximum Likelihood tumor fraction estimation model.

In some embodiments, a statistic for somatic variant allele fractions determined for the liquid biopsy sample is used as an estimate for the circulating tumor fraction of the liquid biopsy sample. For example, in some embodiments, a measure of central tendency (e.g., a mean or median) for a plurality of variant allele fractions determined for the liquid biopsy sample is used as an estimate of circulating tumor fraction. In some embodiments, a lowest (minimum) variant allele fraction determined for the liquid biopsy sample is used as an estimate of circulating tumor fraction. In some embodiments, a highest (maximum) variant allele fraction determined for the liquid biopsy sample is used as an estimate of circulating tumor fraction. In some embodiments, a range defined by two or more of these statistics is used to limit the range of simulated tumor fraction analysis via the off-target read methodology described herein. For instance, in some embodiments, lower and upper bounds of the simulated tumor fraction analysis are defined by the minimum variant allele fraction and the maximum variant allele fraction determined for a liquid biopsy sample, respectively. In some embodiments, the range is further expanded, e.g., on either or both the lower and upper bounds. For example, in some embodiments, the lower bound of a simulated tumor fraction analysis is defined as 0.5-times the minimum variant allele fraction, 0.75-times the minimum variant allele fraction, 0.9-times the minimum variant allele fraction, 1.1-times the minimum variant allele fraction, 1.25-times the minimum variant allele fraction, 1.5-times the minimum variant allele fraction, or a similar multiple of the minimum variant allele fraction determined for the liquid biopsy sample. Similarly, in some embodiments, the upper bound of a simulated tumor fraction analysis is defined as 2.5-times the maximum variant allele fraction, 2-times the maximum variant allele fraction, 1.75-times the maximum variant allele fraction, 1.5-times the maximum variant allele fraction, 1.25-times the maximum variant allele fraction, 1.1-times the maximum variant allele fraction, 0.9-times the maximum variant allele fraction, or a similar multiple of the maximum variant allele fraction determined for the liquid biopsy sample.

In some embodiments, circulating tumor fraction is estimated based on a distribution of the lengths of cfDNA in the liquid biopsy sample. In some embodiments, sequence reads are binned according to their position within the genome, e.g., as described elsewhere herein. For each bin, the length of each fragment is determined. Each fragment is then classified as belonging to one of a plurality of classes, e.g., one of two classes corresponding to a population of short fragments and a population of long fragments. In some embodiments, the classification is performed using a static length threshold, e.g., that is the same across all the bins. In some embodiments, the classification is performed using a dynamic length threshold. In some embodiments, a dynamic length threshold is determined by comparing the distribution of fragment lengths in liquid biopsy samples from reference subjects that do not have cancer to the distribution of fragment lengths in liquid biopsy samples from reference subjects that have cancer, in a positional fashion.

For example, in some embodiments, the comparison is done over windows spanning entire chromosomes, e.g., each chromosome defines a comparison window over which a dynamic length threshold is determined. In some embodiments, the comparison is done over a window spanning a single bin, e.g., each bin defines a comparison window over which a dynamic length threshold is determined. In certain embodiments, the bin determination may be made according to various genomic features. For example, the comparison window may be based on a chromosome by chromosome basis, or a chromosomal arm by chromosomal arm basis. In some embodiments, the comparison window is based on a gene level basis. In some embodiments, the comparison window is a fixed size, such as 1 KB, 5 KB, 10 KB, 25 kB, 50 kB, 100 kB, 25 KB, 500 KB, 1 MB, 2 MB, 3 MB, or more. In some embodiments, the reference subjects having cancer used to determine the dynamic fragment length is matched to the cancer type of the subject whose liquid biopsy sample is being evaluated.

Once each fragment is classified as belonging to either the population of short fragments or the population of long fragments, a model trained to estimate circulating tumor fraction based on fragment length distribution data across the genome is applied to the binned data to generate an estimate of the circulating tumor fraction for the liquid biopsy sample. In some embodiments, a comparison of (i) the population of short fractions and (ii) the population of long fragments is made for each bin, e.g., a fraction of the number of short fragments to the number of long fragments in each bin is determined and used as an input for the model. In some embodiments, the model is a probabilistic model (e.g., an application of Bayes theorem), a deep learning model (e.g., a neural network, such as a convolutional neural network), or an admixture model.

In some embodiments, two or more of the circulating tumor estimation models described herein are used to generate respective tumor fraction estimates, which are combined to form a final tumor fraction estimate. For example, in some embodiments, a measure of central tendency (e.g., a mean) for several tumor fraction estimates is determined and used as the final tumor fraction estimate. In some embodiments, a tumor fraction estimate derived from a plurality of estimation models, e.g., a measure of central tendency for several tumor fraction estimates is used to identify the nearest local optima (e.g., minima) obtained from the tumor fraction estimation methods described above, and further herein.

Concurrent Testing

Unless stated otherwise, as used herein, the term "concurrent" as it relates to assays refers to a period of time between zero and ninety days. In some embodiments, concurrent tests using different biological samples from the same subject (e.g., two or more of a liquid biopsy sample, cancerous tissue—such as a solid tumor sample or blood sample for a blood-based cancer—and a non-cancerous sample) are performed within a period of time (e.g., the biological samples are collected within the period of time) of from 0 days to 90 days. In some embodiments, concurrent tests using different biological samples from the same subject (e.g., two or more of a liquid biopsy sample, cancerous tissue—such as a solid tumor sample or blood sample for a blood-based cancer—and a non-cancerous sample) are performed within a period of time (e.g., the biological samples are collected within the period of time) of from 0 days to 60 days. In some embodiments, concurrent tests using different biological samples from the same subject (e.g., two or more of a liquid biopsy sample, cancerous tissue—such as a solid tumor sample or blood sample for a blood-based cancer—and a non-cancerous sample) are performed within a period of time (e.g., the biological samples are collected within the period of time) of from 0 days to 30 days. In some embodiments, concurrent tests using different biological samples from the same subject (e.g., two or more of a liquid biopsy sample, cancerous tissue—such as a solid tumor sample or blood sample for a blood-based cancer—and a non-cancerous sample) are performed within a period of time (e.g., the biological samples are collected within the period of time) of from 0 days to 21 days. In some embodiments, concurrent tests using different biological samples from the same subject (e.g., two or more of a liquid biopsy sample, cancerous tissue—such as a solid tumor sample or blood sample for a blood-based cancer—and a non-cancerous sample) are performed within a period of time (e.g., the biological samples are collected within the period of time) of from 0 days to 14 days. In some embodiments, concurrent tests using different biological samples from the same subject (e.g., two or more of a liquid biopsy sample, cancerous tissue—such as a solid tumor sample or blood sample for a blood-based cancer—and a non-cancerous sample) are performed within a period of time (e.g., the biological samples are collected within the period of time) of from 0 days to 7 days. In some embodiments, concurrent tests using different biological samples from the same subject (e.g., two or more of a liquid biopsy sample, cancerous tissue—such as a solid tumor sample or blood sample for a blood-based cancer—and a non-cancerous sample) are performed within a period of time (e.g., the biological samples are collected within the period of time) of from 0 days to 3 days.

In some embodiments, a liquid biopsy assay may be used concurrently with a solid tumor assay to return more comprehensive information about a patient's variants. For example, a blood specimen and a solid tumor specimen may be sent to a laboratory for evaluation. The solid tumor specimen may be analyzed using a bioinformatics pipeline to produce a solid tumor result. A solid tumor assay is described, for instance, in U.S. patent application Ser. No. 16/657,804, the content of which is hereby incorporated by reference, in its entirety, for all purposes. The cancer type of the solid tumor may include, for example, non small cell lung cancer, colorectal cancer, or breast cancer. Alterations identified in the tumor/matched normal result may include, for example, EGFR+ for non small cell lung cancer; HER2+ for breast cancer; or KRAS G12C for several cancers.

In some embodiments, a blood specimen may be divided into a first portion and a second portion. The first portion of the blood specimen and the solid tumor specimen may be analyzed using a bioinformatics pipeline to produce a tumor/matched normal result. The second portion of the blood specimen may be analyzed using a bioinformatics pipeline to produce a liquid biopsy result. For example, the blood specimen may be analyzed using at least an improvement in somatic variant identification, e.g., as described herein in the section entitled "Systems and Methods for Improved Validation of Somatic Sequence Variants" and/or "Variant Identification." For example, the blood specimen may be analyzed using an improvement in focal copy number identification, e.g., as described herein in the section entitled "Copy Number Variation." For example, the blood specimen may be analyzed using an improvement in circulating tumor fraction determination, e.g., as described above in the section entitled "Circulating Tumor Fraction."

Therapies may be identified for further consideration in response to receiving the tumor or tumor/matched normal result along with the liquid biopsy result. For example, if the results overall indicate that the patient has HER2+ breast cancer, neratinib may be identified along with the test results for further consideration by the ordering clinician. The solid tumor or tumor/matched normal assay may be ordered concurrently; their results may be delivered concurrently; and they may be analyzed concurrently.

Quality Control

In some embodiments, a positive sensitivity control sample is processed and sequenced along with one or more clinical samples. In some embodiments, the control sample is included in at least one flow cell of a multi-flow cell reaction and is processed and sequenced each time a set of samples is sequenced or periodically throughout the course of a plurality of sets of samples. In some embodiments, the control includes a pool of controls. In some embodiments, a quality control analysis requires that read metrics of variants present in the control sample fall within acceptable criteria. In some embodiments, a quality control requires approval by a pathologist before the results are reported.

In some embodiments, the quality control system includes methods that pass samples for reporting if various criteria are met. Similarly, in some embodiments, the system includes methods that allow for more manual review if a sample does not meet the criteria established for automatic pass. In some embodiments, the criteria for pass of panel sequencing results include one or more of the following:

A criterion for the on-target rate of the sequencing reaction, defined as a comparison (e.g., a ratio) of (i) the number of sequenced nucleotides or reads falling within the targeted panel region of a genome and (ii) the number of sequenced nucleotides or reads falling outside of the targeted panel region of the genome. Generally, an on-target rate threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a minimum on-target rate threshold of at least 30%, at least 40%, at least 50%, at least 60%, at least 70%, or greater. In some embodiments, the on-target rate criteria is implemented as a range of acceptable on-target rates, e.g., requiring that the on-target rate for a reaction is from 30% to 70%, from 30% to 80%, from 40% to 70%, from 40% to 80%, and the like.

A criterion for the number of total reads generated by the sequencing reaction, including both unique sequence reads and non-unique sequence reads. Generally, a total read number threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a minimum number of total reads threshold of at least 100 million, 110 million, 120 million, 130 million, 140 million, 150 million, 160 million, 170 million, 180 million, 190 million, 200 million, or more total sequence reads. In some embodiments, the criterion is implemented as a range of acceptable number of total reads, e.g., requiring that the sequencing reaction generate from 50 million to 300 million total sequence reads, from 100 million to 300 million sequence reads, from 100 million to 200 million sequence reads, and the like.

A criterion for the number of unique reads generated by the sequencing reaction. Generally, a unique read number threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a minimum number of total reads threshold of at least 3 million, 4 million, 5 million, 6 million, 7 million, 8 million, 9 million, or more unique sequence reads. In some embodiments, the criterion is implemented as a range of acceptable number of unique reads, e.g., requiring that the sequencing reaction generate from 2 million to 10 million total sequence reads, from 3 million to 9 million sequence reads, from 3 million to 9 million sequence reads, and the like.

A criterion for unique read depth across the panel, defined as a measure of central tendency (e.g., a mean or median) for a distribution of the number of unique reads in the sequencing reaction encompassing the genomic regions targeted by each probe. For instance, in some embodiments, an average unique read depth is calculated for each targeted region defined in a target region BED file, using a first calculation of the number of reads mapped to the region multiplied by the read length, divided by the length of the region, if the length of the region is longer than the read length, or otherwise using a second calculation of the number of reads falling within the region multiplied by the read length. The median of unique read depth across the panel is then calculated as the median of those average unique read depths of all targeted regions. In some embodiments, the resolution as to how depth is calculated is increased or decreased, e.g., in cases where it is necessary or desirable to calculate depth for each base, or for a single gene. Generally, a unique read depth threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a minimum unique read depth threshold of at least 1500, 1750, 2000, 2250, 2500, 2750, 3000, 3250, 3500, or higher unique read depth. In some embodiments, the criterion is implemented as a range of acceptable unique read depth, e.g., requiring that the sequencing reaction generate a unique read depth of from 1000 to 4000, from 1500 to 4000, from 1500 to 4000, and the like.

A criterion for the unique read depth of a lowest percentile across the panel, defined as a measure of central tendency (e.g., a mean or median) for a distribution of the number of unique reads in the sequencing reaction encompassing the genomic regions targeted by each probe that fall within the lowest percentile of genomic regions by read depth (e.g., the first, second, third, fourth, fifth, tenth, fifteenth, twentieth, twenty-fifth, or similar percentile). Generally, a unique read depth at a lowest percentile threshold will be selected based on the sequencing technology used, the size of the targeted panel, the lowest percentile selected, and the expected number of sequence reads generated by the combination of the technology and targeted panel used. For example, in some embodiments where next generation sequencing-by-synthesis technology is used, the criterion is implemented as a minimum unique read depth threshold at the fifth percentile of at least 500, 750, 1000, 1250, 1500, 1750, 2000, 2250, 2500, or higher unique read depth. In some embodiments, the criterion is implemented as a range of acceptable unique read depth at the fifth percentile, e.g., requiring that the sequencing reaction generate a unique read depth at the fifth percentile of from 250 to 3000, from 500 to 3000, from 500 to 2500, and the like.

A criterion for the deamination or OxoG Q-score of a sequencing reaction, defined as a Q-score for the occurrence of artifacts arising from template oxidation/deamination. Generally, a deamination or OxoG Q-score threshold will be selected based on the sequencing technology used. For example, in some embodiments where next generation sequencing-by-synthesis technology is used, the criterion is implemented as a minimum deamination or OxoG Q-score threshold of at least 10, 20, 30, 40, 5,0 6,0 70, 80, 90, or higher. In some embodiments, the criterion is implemented as a range of acceptable deamination or OxoG Q-scores, e.g., from 10 to 100, from 10 to 90, and the like.

A criterion for the estimated contamination fraction is of a sequencing reaction, defined as an estimate of the fraction of template fragments in the sample being sequenced arising from contamination of the sample, commonly expressed as a decimal, e.g., where 1% contamination is expressed as 0.01. An example method for estimating contamination in a sequencing method is described in Jun G. et al., Am. J. Hum. Genet., 91:839-48 (2012). For example, in some embodiments, the criterion is implemented as a maximum contamination fraction threshold of no more than 0.001, 0.0015, 0.002, 0.0025, 0.003, 0.0035, 0.004. In some embodiments, the criterion is implemented as a range of acceptable contamination fractions, e.g., from 0.0005 to 0.005, from 0.0005 to 0.004, from 0.001 to 0.004, and the like.

A criterion for the fingerprint correlation score of a sequencing reaction, defined as a Pearson correlation coefficient calculated between the variant allele fractions of a set of pre-defined single nucleotide polymorphisms (SNPs) in two samples. An example method for determining a fingerprint correlation score is described in Sejoon L. et al., Nucleic Acids Research, Volume 45, Issue 11, 20 Jun. 2017, Page e103, the content of which is incorporated herein by reference, in its entirety, for all purposes. For example, in some embodiments, the criterion is implemented as a minimum fingerprint correlation score threshold of at least 0.1, 0.2, 0.3, 0.4, 0.5, 0.6, 0.7, 0.8, 0.9, or higher. In some embodiments, the criterion is implemented as a range of acceptable fingerprint correlation scores, e.g., from 0.1 to 0.9, from 0.2 to 0.9, from 0.3 to 0.9, and the like.

A criterion for the raw coverage of a minimum percentage of the genomic regions targeted by a probe, defined as a minimum number of unique reads in the sequencing reaction encompassing each of a minimum percentage (e.g., at least 80%, 85%, 90%, 95%, 98%, 99%, 99.5%, 99.9%, and the like) of the genomic regions targeted by the probe panel. In some embodiments, the term "unique read depth" is used to distinguish deduplicated reads from raw reads that may contain multiple reads sequenced from the same original DNA molecule via PCR. Generally, a raw coverage of a minimum percentage of the genomic regions targeted by a probe threshold will be selected based on the sequencing technology used, the size of the targeted panel, the minimum percentage selected, and the expected number of sequence reads generated by the combination of the technology and targeted panel used. For example, in some embodiments where next generation sequencing-by-synthesis technology is used, the criterion is implemented as a raw coverage of 95% of the genomic regions targeted by a probe threshold of at least 500, 750, 1000, 1250, 1500, 1750, 2000, 2250, 2500, or higher unique read depth. In some embodiments, the criterion is implemented as a range of acceptable unique read depth for 95% of the genomic regions targeted by a probe, e.g., requiring that the sequencing reaction generate a unique read depth for 95% of the targeted regions of from 250 to 3000, from 500 to 3000, from 500 to 2500, and the like.

A criterion for the PCR duplication rate of a sequencing reaction, defined as the percentage of sequence reads that arise from the same template molecule as at least one other sequence read generated by the reaction. Generally, a PCR duplication rate threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a minimum PCR duplication rate threshold of at least 91%, 92%, 93%, 94%, 95%, 96%, 97%, 98%, 99%, or higher. In some embodiments, the criterion is implemented as a range of acceptable PCR duplication rates, e.g., of from 90% to 100%, from 90% to 99%, from 91% to 99%, and the like.

Similarly, in some embodiments, the quality control system includes methods that fail samples for reporting if various criteria are met. In some embodiments, the system includes methods that allow for more manual review if a sample does meet the criteria established for automatic fail. In some embodiments, the criteria for failing panel sequencing results include one or more of the following:

A criterion for the on-target rate of the sequencing reaction, defined as a comparison (e.g., a ratio) of (i) the number of sequenced nucleotides or reads falling within the targeted panel region of a genome and (ii) the number of sequenced nucleotides or reads falling outside of the targeted panel region of the genome. Generally, an on-target rate threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a maximum on-target rate threshold of no more than 30%, 40%, 50%, 60%, 70%, or greater. That is, the criterion for failing the sample is satisfied when the on-target rate for the sequencing reaction is below the maximum on-target rate threshold. In some embodiments, the on-target rate criteria is implemented as not falling within a range of acceptable on-target rates, e.g., falling outside of an on-target rate for a reaction of from 30% to 70%, from 30% to 80%, from 40% to 70%, from 40% to 80%, and the like.

A criterion for the number of total reads generated by the sequencing reaction, including both unique sequence reads and non-unique sequence reads. Generally, a total read number threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a maximum number of total reads threshold of no more than 100 million, 110 million, 120 million, 130 million, 140 million, 150 million, 160 million, 170 million, 180 million, 190 million, 200 million, or more total sequence reads. That is, the criterion for failing the sample is satisfied when the number of total reads for the sequencing reaction is below the maximum total read threshold. In some embodiments, the criterion is implemented as not falling within a range of acceptable number of total reads, e.g., falling outside of a range of from 50 million to 300 million total sequence reads, from 100 million to 300 million sequence reads, from 100 million to 200 million sequence reads, and the like.

A criterion for the number of unique reads generated by the sequencing reaction. Generally, a unique read number threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a maximum number of total reads threshold of no more than 3 million, 4 million, 5 million, 6 million, 7 million, 8 million, 9 million, or more unique sequence reads. That is, the criterion for failing the sample is satisfied when the number of unique reads for the sequencing reaction is below the maximum total read threshold. In some embodiments, the criterion is implemented as not falling within a range of acceptable number of unique reads, e.g., falling outside of a range of from 2 million to 10 million total sequence reads, from 3 million to 9 million sequence reads, from 3 million to 9 million sequence reads, and the like.

A criterion for unique read depth across the panel, defined as a measure of central tendency (e.g., a mean or median) for a distribution of the number of unique reads in the sequencing reaction encompassing the genomic regions targeted by each probe. Generally, a unique read depth threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a maximum unique read depth threshold of no more than 1500, 1750, 2000, 2250, 2500, 2750, 3000, 3250, 3500, or higher unique read depth. That is, the criterion for failing the sample is satisfied when the unique read depth across the panel for the sequencing reaction is below the maximum total read threshold. In some embodiments, the criterion is implemented as falling outside of a range of acceptable unique read depth, e.g., falling outside of a unique read depth range of from 1000 to 4000, from 1500 to 4000, from 1500 to 4000, and the like.

A criterion for the unique read depth of a lowest percentile across the panel, defined as a measure of central tendency (e.g., a mean or median) for a distribution of the number of unique reads in the sequencing reaction encompassing the genomic regions targeted by each probe that fall within the lowest percentile of genomic regions by read depth (e.g., the first, second, third, fourth, fifth, tenth, fifteenth, twentieth, twenty-fifth, or similar percentile).

Generally, a unique read depth at a lowest percentile threshold will be selected based on the sequencing technology used, the size of the targeted panel, the lowest percentile selected, and the expected number of sequence reads generated by the combination of the technology and targeted panel used. For example, in some embodiments where next generation sequencing-by-synthesis technology is used, the criterion is implemented as a maximum unique read depth threshold at the fifth percentile of no more than 500, 750, 1000, 1250, 1500, 1750, 2000, 2250, 2500, or higher unique read depth. That is, the criterion for failing the sample is satisfied when the unique read depth at a lowest percentile threshold for the sequencing reaction is below the maximum unique read depth at a lowest percentile threshold. In some embodiments, the criterion is implemented as falling outside of a range of acceptable unique read depth at the fifth percentile, e.g., falling outside of a unique read depth at the fifth percentile range of from 250 to 3000, from 500 to 3000, from 500 to 2500, and the like.

A criterion for the deamination or OxoG Q-score of a sequencing reaction, defined as a Q-score for the occurrence of artifacts arising from template oxidation/deamination. Generally, a deamination or OxoG Q-score threshold will be selected based on the sequencing technology used. For example, in some embodiments where next generation sequencing-by-synthesis technology is used, the criterion is implemented as a maximum deamination or OxoG Q-score threshold of no more than 10, 20, 30, 40, 5,0 6,0 70, 80, 90, or higher. That is, the criterion for failing the sample is satisfied when the deamination or OxoG Q-score for the sequencing reaction is below the maximum deamination or OxoG Q-score threshold. In some embodiments, the criterion is implemented as falling outside of a range of acceptable deamination or OxoG Q-scores, e.g., falling outside of a deamination or OxoG Q-score range of from 10 to 100, from 10 to 90, and the like.

A criterion for the estimated contamination fraction is of a sequencing reaction, defined as an estimate of the fraction of template fragments in the sample being sequenced arising from contamination of the sample, commonly expressed as a decimal, e.g., where 1% contamination is expressed as 0.01. An example method for estimating contamination in a sequencing method is described in Jun G. et al., Am. J. Hum. Genet., 91:839-48 (2012). For example, in some embodiments, the criterion is implemented as a minimum contamination fraction threshold of at least 0.001, 0.0015, 0.002, 0.0025, 0.003, 0.0035, 0.004. That is, the criterion for failing the sample is satisfied when the contamination fraction for the sequencing reaction is above the minimum contamination fraction threshold. In some embodiments, the criterion is implemented as falling outside of a range of acceptable contamination fractions, e.g., falling outside of a contamination fraction range of from 0.0005 to 0.005, from 0.0005 to 0.004, from 0.001 to 0.004, and the like.

A criterion for the fingerprint correlation score of a sequencing reaction, defined as a Pearson correlation coefficient calculated between the variant allele fractions of a set of pre-defined single nucleotide polymorphisms (SNPs) in two samples. An example method for determining a fingerprint correlation score is described in Sejoon L. et al., Nucleic Acids Research, Volume 45, Issue 11, 20 Jun. 2017, Page e103. For example, in some embodiments, the criterion is implemented as a maximum fingerprint correlation score threshold of no more than 0.1, 0.2, 0.3, 0.4, 0.5, 0.6, 0.7, 0.8, 0.9, or higher. That is, the criterion for failing the sample is satisfied when the fingerprint correlation score for the sequencing reaction is below the maximum fingerprint correlation score threshold. In some embodiments, the criterion is implemented as falling outside of a range of acceptable fingerprint correlation scores, e.g., falling outside of a fingerprint correlation range of from 0.1 to 0.9, from 0.2 to 0.9, from 0.3 to 0.9, and the like.

A criterion for the raw coverage of a minimum percentage of the genomic regions targeted by a probe, defined as a minimum number of unique reads in the sequencing reaction encompassing each of a minimum percentage (e.g., at least 80%, 85%, 90%, 95%, 98%, 99%, 99.5%, 99.9%, and the like) of the genomic regions targeted by the probe panel. Generally, a raw coverage of a minimum percentage of the genomic regions targeted by a probe threshold will be selected based on the sequencing technology used, the size of the targeted panel, the minimum percentage selected, and the expected number of sequence reads generated by the combination of the technology and targeted panel used. For example, in some embodiments where next generation sequencing-by-synthesis technology is used, the criterion is implemented as a raw coverage of 95% of the genomic regions targeted by a probe threshold of no more than 500, 750, 1000, 1250, 1500, 1750, 2000, 2250, 2500, or higher unique read depth. That is, the criterion for failing the sample is satisfied when the raw coverage of a minimum percentage of the genomic regions targeted by a probe for the sequencing reaction is below the maximum raw coverage of a minimum percentage of the genomic regions targeted by a probe threshold. In some embodiments, the criterion is implemented as falling outside of a range of acceptable unique read depth for 95% of the genomic regions targeted by a probe, e.g., requiring that the sequencing reaction generate a unique read depth for 95% of the targeted regions falling outside of a range of from 250 to 3000, from 500 to 3000, from 500 to 2500, and the like.

A criterion for the PCR duplication rate of a sequencing reaction, defined as the percentage of sequence reads that arise from the same template molecule as at least one other sequence read generated by the reaction. Generally, a PCR duplication rate threshold will be selected based on the sequencing technology used, the size of the targeted panel, and the expected number of sequence reads generated by the combination of the technology and targeted panel used. For example, in some embodiments where next generation sequencing-by-synthesis technology is used, the criterion is implemented as a maximum PCR duplication rate threshold of at least 91%, 92%, 93%, 94%, 95%, 96%, 97%, 98%, 99%, or higher. That is, the criterion for failing the sample is satisfied when the PCR duplication rate for the sequencing reaction is below the maximum PCR duplication rate threshold. In some embodiments, the criterion is implemented as falling outside of a range of acceptable PCR duplication rates, e.g., of from 90% to 100%, from 90% to 99%, from 91% to 99%, and the like.

Thresholds for the auto-pass and auto-fail criteria may be established with reference to one another but are not necessarily set at the same level. For instance, in some embodiments, samples with a metric that falls between auto-pass and auto-fail criteria may be routed for manual review by a qualified bioinformatics scientist. Samples that are failed either automatically or by manual review may be routed to medical and laboratory teams for final review and can be released for downstream processing at the discretion of the laboratory medical director or designee.

Systems and Methods for Improved Validation of Somatic Sequence Variants

An overview of methods for providing clinical support for personalized cancer therapy is described above with reference to FIGS. 2-4 above. Below, systems and methods for improving validation of somatic sequence variants, e.g., within the context of the methods and systems described above, are described with reference to FIGS. 5A and 5B.

Many of the embodiments described below, in conjunction with FIGS. 5A and 5B, relate to analyses performed using sequencing data for cfDNA obtained from a liquid biopsy sample of a cancer patient. Generally, these embodiments are independent and, thus, not reliant upon any particular DNA sequencing methods. However, in some embodiments, the methods described below include generating the sequencing data.

For example, provided herein is a generalized application of Bayes' Theorem through the likelihood ratio test for diagnostic assays that allows dynamic calibration of filtering thresholds for somatic sequence variant detection in a patient, in accordance with some embodiments of the present disclosure. These thresholds are based on sample specific error rate, error rate from a pool of process matched healthy control samples, and/or a cohort of human solid tumors to inform our probability models. The method takes the form of the following formula:

$$\text{odds(post-test)} = (\text{odds(pre-test)}) \times \left(\frac{\text{sensitivity}}{1 - \text{specificity}}\right)$$

where:

odds(post-test) is the post-test odds of a variant being positive given the application of Bayes Theorem, odds(pre-test) is the pre-test odds of a positive given the cancer type of the patient and the prevalence (measured as a fraction) of alterations detected in that gene or within a specific genomic window within a reference population with the cancer type, sensitivity is the sensitivity bin nearest that measured for the assay at a proposed circulating variant fraction, specificity is a term to be solved for, denoting the level of uncertainty that is acceptable given some fixed value of odds(post-test). Specificity can be replaced as the quantile of a distribution, such as a beta binomial distribution, (see below) defined by the within sample trinucleotide error rate and the background base position specific error rate, d(beta-binomial) is a beta binomial distribution defined by specified parameters (alpha, beta, Pr), and Min(AO) is the minimum number of alternate alleles observed for a given sample.

Given a fixed value for odds(post-test), it is possible to solve instead for specificity or, rather, the minimum acceptable quantile of the beta binomial error distribution. Therefore, the equation can be reframed as:

$$\text{specificity} = 1 - \left((\text{sensitivity}) \times \left(\frac{\text{odds(pre-test)}}{\text{odds(post-test)}}\right)\right).$$

Solving for specificity gives the quantile of the beta binomial function which can then be plugged into quantile(beta-binomial) to derive a minimum number of alternative alleles observed at a given depth, or:

$$\text{Min}(A0) = \text{quantile}\left(1 - \left((\text{sensitivity}) \times \left(\frac{\text{odds(pre-test)}}{\text{odds(post-test)}}\right)\right), d(\text{distribution})\right),$$

e.g., where d(distribution is d(beta-binomial).

Determining Pre-Test Probability:

In some embodiments, pre-test probability, which is related to odds(pre-test), is defined as:

$$\text{odds(pre-test)} = \left(\frac{\text{probability(pre-test)}}{1 - \text{probability(pre-test)}}\right),$$

and is determined through historical data derived from matched solid tumor test data. By analyzing an extensive set of cancers and using process matched liquid biopsy and tissue biopsy samples to identify somatic variants with high confidence, it is possible to accurately assess the prevalence of specific variants within a population of advanced human cancers. For a population of patients most likely to require liquid biopsy type tests, the sampling distribution most closely models the distribution into which any given patient receiving the test will fall. To model this prevalence, there are two factors at play: gene level prevalence, and genomic window level prevalence.

Assessing Prevalence by Sliding Window Segmentation:

In some embodiments, in order to get an accurate estimate of prevalence, it is critical to divide the estimated rate of mutation by the mechanism of disease. Gain of function (GOF) mutations tend to cluster in "hotspots," whereas loss of function (LOF) mutations tend to be scattered throughout a gene and suppress or eliminate a protein's wild type behaviors. Due to this evolutionary constraint on mutation position, prevalence calculation must take into account whether a gene has a GOF or LOF mechanism of disease. While this cannot be directly analyzed given available data, it is possible to bootstrap this calculation by segmentation of mutational prevalence across exons.

Based on historical sequencing data, it is possible to bin mutations by exon. In order to assess whether a single exon is enriched for mutations over the rest of the gene (a hotspot or GOF gene), a rolling Poisson test of difference is applied jumping from exon to exon. If there is a single (or multiple) exons that show statistically significant deviation from other exons within the gene, that region is annotated as the window of interest. Prevalence is subsequently calculated as prevalence within the exon(s) encompassing the window of interest.

If no exons can be shown to be over-represented for mutations, the gene is assumed to have an LOF mechanism of action and the prevalence for the whole gene having an alteration within the specified cancer type is used. When a variant is being assessed for filtering, the prevalence within the pre-specified window or the prevalence within the gene itself is used as the pre-test probability (Pr(pre-test)) for the likelihood ratio test.

Referring to Block 500, the present disclosure provides a method for validating a somatic sequence variant in a test subject having a cancer condition, at a computer system having one or more processors, and memory storing one or more programs for execution by the one or more processors.

Referring to Block 502, the method comprises obtaining, from a first sequencing reaction, a corresponding sequence of each cell-free DNA fragment in a first plurality of cell-free DNA fragments in a liquid biopsy sample of the test subject, thus obtaining a first plurality of sequence reads, e.g., a plurality of de-duplicated sequence reads, where each sequence read correspond to a unique cell-free DNA fragment from the sample. In some embodiments, the first plurality of sequence reads includes at least 1000 sequence reads. In some embodiments, the first plurality of sequence reads includes at least 10,000 sequence reads. In some embodiments, the first plurality of sequence reads includes at least 100,000 sequence reads. In some embodiments, the first plurality of sequence reads includes at least 200,000, 300,000, 400,000, 500,000, 750,000, 1,000,000, 2,500,000, 5,000,000 sequence reads, or more.

In some embodiments, the liquid biopsy sample is blood. In some embodiments, the liquid biopsy sample comprises blood, whole blood, peripheral blood, plasma, serum, or lymph of the test subject.

In some embodiments, the cancer condition is a particular type and stage of cancer (e.g., stage 2 lung cancer). Advantageously, the variant filtering methods described herein are superior to filtering methods that simply account for the tumor fraction of a sample. This is achieved, in part, by accounting for the types of mutations found in a particular type of cancer, which improves the quality of the pre-odds probability of finding a particular type of variant (e.g., a variant within a particular genomic region) in a sample from a subject with a known type of cancer. Accordingly, in some embodiments, the pre-odds probabilities are based on as specific of a cancer type as possible, e.g., accounting for one or more of a type of cancer, an origin of the cancer, the stage of the cancer, any previously known genomic variants in the cancer (e.g., whether a breast cancer subject is BRCA1 or BRCA2 positive), a personal characteristic of the subject, e.g., age, gender, race, smoking status, alcohol consumption status, etc.), any pathology classification of the cancer, etc. However, there are practical considerations when determining the level of specificity for which a subject's cancer should be specified when matching the cancer to a training cohort. For instance, when an insufficient number of training samples from matching samples are available for calculation of pre-test odds, the specificity of the cancer classification should be reduced in order to provide a large enough sample of training data to provide meaningful prior information. In some embodiments, the test subject, the liquid biopsy sample, the cancer condition, and/or methods and systems for obtaining, accessioning, storing, processing, preparing and/or analyzing thereof, comprise any of the embodiments as described above in the present disclosure with reference to FIGS. 2-4.

In some embodiments, the first sequencing reaction is a panel-enriched sequencing reaction. For example, in some embodiments, the first sequencing reaction is a panel-enriched sequencing reaction of a first plurality of enriched loci, and each respective locus in the plurality of enriched loci are sequenced at an average unique sequence depth of at least 250×. In some such embodiments, each respective locus in the plurality of enriched loci are sequenced at an average unique sequence depth of at least 1000×. In some embodiments, the first plurality of sequence reads is obtained from ultra-high depth sequencing (e.g., where each locus in a plurality of loci are sequenced at an average coverage of at least 1000×, at least 2500×, or at least 5000×). Example genes that are informative for precision oncology, e.g., when implemented in a liquid biopsy-based assay, are shown in Table 1. In some embodiments, a panel-enriched sequencing reaction described herein uses a probe set that includes at least 5, 10, 15, 20, 25, 30, 40, 50, 60, 70, 75, 80, 90, 100, or all 105 of the genes listed in Table 1.

In some embodiments, the first sequencing reaction is a whole genome sequencing reaction, and the average sequencing depth of the reaction across the genome is at least 5×, 10×, 15×, 20×, 25×, 30×, 40×, 50×, or higher.

In some embodiments, the first plurality of sequence reads includes at least 50,000 sequence reads, at least 100,000 sequence reads, at least 250,000 sequence reads, at least 500,000 sequence reads, at least 1,000,000 sequence reads, at least 5,000,000 sequence reads, or more.

In some embodiments, the first sequencing reaction and/or the first plurality of sequence reads includes any of the embodiments as described above in the present disclosure. For example, in some embodiments, methods and systems for nucleic acid extraction, library preparation, capture and hybridization, pooling, sequencing, aligning, normalization and/or other sequence read processing comprise any of the embodiments as described above in the present disclosure with reference to FIGS. 2-4.

Referring to Block 504, the method further comprises aligning each respective sequence read in the first plurality of sequence reads to a reference sequence for the species of the subject thus identifying (i) a variant allele fragment count for a candidate variant, where the candidate variant maps to a locus in the reference sequence, and (ii) a locus fragment count for the locus encompassing the candidate variant. In some embodiments, the variant allele fragment count refers to a unique number of sequence reads in the test subject that encompass the candidate variant. In some embodiments, the locus fragment count refers to the number of sequence reads in the test subject that map to the respective locus encompassing the candidate variant.

As described above, in some embodiments, the reference sequence is a reference genome, e.g., a reference human genome. In some embodiments, a reference genome has several blacklisted regions, such that the reference genome covers only about 75%, 80%, 85%, 90%, 95%, 98%, 99%, 99.5%, or 99.9% of the entire genome for the species of the subject. In some embodiments, the reference sequence for the subject covers at least 10% of the entire genome for the species of the subject, or at least 15%, 20%, 25%, 30%, 35%, 40%, 45%, 50%, 55%, 60%, 65%, 70%, 75%, or more of the entire genome for the species of the subject. In some embodiments, the reference sequence for the subject represents a partial or whole exome for the species of the subject. For instance, in some embodiments, the reference sequence for the subject covers at least 10% of the exome for the species of the subject, or at least 15%, 20%, 25%, 30%, 35%, 40%, 45%, 50%, 55%, 60%, 65%, 70%, 75%, 80%, 85%, 90%, 95%, 98%, 99%, 99.9%, or 100% of the exome for the species of the subject. In some embodiments, the reference sequence covers a plurality of loci that constitute a panel of genomic loci, e.g., a panel of genes used in a panel-enriched sequencing reaction. An example of genes useful for precision oncology, e.g., which may be targeted with such a panel, are shown in Table 1. Accordingly, in some embodiments, the reference sequence for the subject covers at least 100 kb of the genome for the species of the subject. In other embodiments, the reference sequence for the subject covers at least 250 kb, 500 kb, 750 kb, 1 Mb, 2 Mb, 5 Mb, 10 Mb, 25 Mb, 50 Mb, 100 Mb, 250 Mb, or more of the genome for the species of the subject. However, in some embodiments, there is no size limitation of the reference sequence. For example, in some embodiments, the reference sequence can be a sequence for a single locus, e.g., a single exon, gene, etc.) within the genome for the species of the subject.

Referring to Block 506, the method further comprises comparing the variant allele fragment count for the candidate variant against a dynamic variant count threshold for the locus in the reference sequence that the candidate variant maps to. The dynamic variant count threshold is based upon a pre-test odds of a positive variant call for the locus based upon the prevalence of variants in a genomic region that includes the locus from a first set of nucleic acids obtained from a cohort of subjects having the cancer condition.

For example, in some embodiments, the dynamic variant count threshold is determined based on the number of sequence variants that map to the respective locus, obtained from a sequencing of nucleic acids from a cohort of subjects having the cancer condition (e.g., a baseline variant threshold). In some embodiments, the cohort of subjects having the cancer condition are matched to at least one personal characteristic of the test subject (e.g., age, gender, race, smoking status, average alcohol consumption, other underlying medical conditions, etc.).

In some embodiments, the dynamic variant count threshold is also based upon a sequencing error rate for the sequencing reaction. For example, in some such embodiments, the sequencing error rate for the sequencing reaction is a trinucleotide sequencing error rate. In some embodiments, the dynamic variant count threshold is also based upon a background sequencing error rate determined for the locus.

Referring to Block 508, in some embodiments, the method further comprises obtaining a distribution of variant detection sensitivities as a function of circulating variant allele fraction from the cohort of subjects. The distribution of variant detection sensitivities is based on the circulating variant allele fraction of a second set of nucleic acids collected from the cohort of subjects relative to variant alleles detected in the first set of nucleic acids collected from the cohort of subjects. The first set of nucleic acids are from solid tumor biopsies of the cohort of subjects, and the second set of nucleic acids are cell-free nucleic acids from liquid biopsies of the cohort of subjects.

FIG. 6 illustrates a flow chart of a method 600 for obtaining a distribution of variant detection sensitivities as a function of circulating variant allele fraction from a cohort of subjects, in accordance with some embodiments of the present disclosure. For example, referring to Block 602, matched liquid biopsy and solid tumor samples are obtained from a set of training subjects. In some embodiments, the training subjects comprise any of the cancer conditions, personal characteristics, and/or feature data described above in the present disclosure. Furthermore, in some embodiments, obtaining the matched liquid biopsy and solid tumor samples comprise any of the methods and embodiments described above in the present disclosure.

Referring to Block 604, the solid tumor sample is sequenced (e.g., by extracting nucleic acids from the solid tumor sample and performing a sequencing reaction for the sample). The plurality of sequence reads obtained from sequencing the solid tumor sample are aligned to a reference genome (e.g., a human reference genome), thus determining any sequence variants included in the solid tumor sample. Referring to Block 606, the liquid biopsy sample is sequenced as described above for the solid tumor sample, thus determining any sequence variants included in the liquid biopsy sample.

Referring to Block 608, the results of the sequencing reactions are compared by comparing the sequence variants detected in the liquid biopsy sample against the sequence variants detected in the solid tumor sample (e.g., a measure of how many of the variants detected in the solid tumor sample were also detected in the liquid biopsy sample, or a circulating variant allele fraction). The comparison determines a variant detection sensitivity for each variant (e.g., corresponding to a respective locus) in the liquid biopsy sample. Referring to Block 610, each variant detection sensitivity is binned, in a plurality of bins, with respect to an estimated tumor fraction for the liquid biopsy sample, thus obtaining a distribution of variant detection sensitivities.

In some embodiments, a distribution of variant detection sensitivities is established based on a set of training samples (e.g., sensitivity distribution training data) with known variant allele fractions, e.g., samples derived from a solid tumor sample for which one or more variant allele fraction has been determined (e.g., by deep sequencing of the sample). For example, in some embodiments, nucleic acids from each of a plurality of training samples 181 having a known variant allele fraction 184 for one or more variant alleles 183 is sequenced according to a processed-matched sequencing reaction (e.g., using a substantially identical or identical sequencing reaction), and it is determined whether each sequence variant can be detected, e.g., defining a detection status 185 for each locus/variant 183. Over a large number of training samples, a specificity of detection of variants having different variant allele fractions can be determined. In some embodiments, the specificity is determined on a locus-by-locus basis, such that the specificity of detection is specific for the genomic region or locus encompassing the candidate sequence variant. In some embodiments, the specificity is determined globally, e.g., not on a locus-by-locus basis. Referring again to Block 508, in some embodiments, the method comprises estimating a circulating variant fraction for the candidate variant. In some embodiments, the circulating variant fraction for the candidate variant is the ratio of the variant allele fragment count to the locus fragment count (e.g., the proportion of sequence reads that include the candidate variant in the plurality of sequence reads that map to the respective locus encompassing the variant). In some embodiments, the circulating variant fraction is based only upon the variant allele frequency for that locus. In some alternative embodiments, the circulating variant fraction is a circulating tumor fraction determined for the sample.

For example, in some embodiments, the circulating variant fraction is specific to the variant being validated. In some such embodiments, the estimated variant fraction is determined by calculating the percentage of sequence reads encompassing the locus that include the variant (e.g., a variant allele fraction).

In some embodiments, the estimated circulating variant fraction for the candidate variant is an estimated tumor fraction for the sample, where the estimated tumor fraction for the sample is estimated based on a second sequencing reaction comprising low-pass whole-genome methylation sequencing of a second plurality of cell-free DNA fragments in the liquid biopsy sample of the test subject.

In some such embodiments, the dynamic threshold for the locus is set based upon a desired variant detection specificity determined by the relationship:

$$\text{specificity} = 1 - \left( (\text{sensitivity}) \times \left( \frac{\text{odds(pre-test)}}{\text{odds(post-test)}} \right) \right)$$

where sensitivity is the variant detection sensitivity in the distribution of variant detection sensitivities that corresponds to the circulating variant fraction for the candidate variant, odds(post-test) is the post-test odds of a positive variant call for the locus, and odds(pre-test) is the pre-test odds of the positive variant call for the locus.

In some embodiments, the specificity is used to select a quantile of a beta-binomial distribution of the minimal variant allele fragment count required to support a positive variant call for the locus, thus defining the dynamic threshold for the locus. The beta-binomial distribution is defined by the sequencing error rate for the sequencing reaction and the background sequencing error rate determined for the locus. For example, in some embodiments, the minimum number of alternative alleles required to validate a positive variant call is represented by $$\mathrm{Min}(A0) = \mathrm{quantile}\left(1 - \left((\text{sensitivity}) \times \left(\frac{\text{odds(pre-test)}}{\text{odds(post-test)}}\right)\right), d(\text{beta-binomial})\right)$$

In some embodiments, as described in FIG. 6, obtaining the distribution of variant detection sensitivities comprises binning variant detection sensitivities in a plurality of bins as a function of circulating variant allele fraction. Each bin in the plurality of bins is associated with a corresponding variant detection sensitivity and sensitivity is the variant detection sensitivity corresponding to the respective bin, in the plurality of bins that encompasses the circulating variant fraction for the candidate variant. In some alternative embodiments, the distribution of variant detection sensitivities is a continuous function.

Additional details and embodiments for obtaining thresholds for filtering variants (e.g., dynamic thresholds) are described above in the present disclosure (see, Example Methods: Variant Identification).

In some embodiments, the pre-test odds of a positive variant call for the locus is based on (i) the prevalence of variants in the genomic region that includes the locus from the first set of nucleic acids obtained from the cohort of subjects having the cancer condition (e.g., the percentage of patients with the particular cancer type that have a variant in the region of interest), and (ii) a known or inferred effect of the variants. When the known or inferred effect of a variant is loss-of-function (LOF) of a gene that includes the locus, the genomic region used to compute the pre-test probability is the entire gene, and when the known or inferred effect of a variant is gain-of-function (GOF) of the gene that includes the locus, the genomic region used to compute the pre-test probability is the exon, of the gene, that includes the locus.

In some such embodiments, the effect of the variants is inferred by binning each respective variant of the variants in the genomic region that includes the locus from the first set of nucleic acids obtained from the cohort of subjects having the cancer condition into a respective bin, in a plurality of bins for the gene that include the locus, corresponding to the exon encompassing the respective variant in the gene. Each bin in the plurality of bins corresponds to a different exon of the respective gene. After determining whether any bin in the plurality of bins contains significantly more variants than the other bins in the plurality of bins, the effect of the sequence variant is inferred to be a gain-of-function of the gene when a bin contains significantly more variants than the other bins in the plurality of bins. Alternatively, the effect of the sequence variant is inferred to be a loss-of-function of the gene when no bin in the plurality of bins contains significantly more sequence variants than the other bins in the plurality of bins.

For example, FIG. 7 illustrates a method of inferring an effect of a sequence variant as a gain-of-function or a loss-of-function of a gene, in accordance with some embodiments of the present disclosure.

Figure 7A:
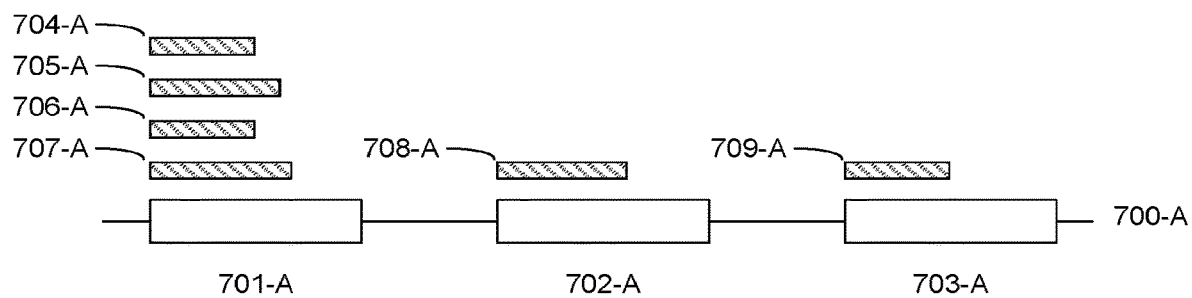
FIGS. 7A and 7B collectively illustrate a method of inferring an effect of a sequence variant as a gain-of-function or a loss-of-function of a gene, in accordance with some embodiments of the present disclosure.

FIG. 7A illustrates a gene 700-A with a plurality of exons 701-A, 702-A, 703-A. Each exon corresponds to a bin in a plurality of bins. A first exon 701-A comprises a region of interest (e.g., a locus) that encompasses a candidate variant. A plurality of sequence variants (e.g., 704-A, 705-A, 706-A, 707-A, 708-A, 709-A) is obtained from a sequencing of nucleic acids from a cohort of subjects, where each sequence variant maps to a respective locus in the gene. The effect of the variants is inferred by binning each sequence variant into the respective bin corresponding to the exon to which the respective variant maps. Thus, sequence variants 704-A, 705-A, 706-A, and 707-A are binned into the bin corresponding to exon 701-A, sequence variant 708-A is binned into the bin corresponding to exon 702-A, and sequence variant 709-A is binned into the bin corresponding to exon 703-A. In FIG. 7A, it can be determined that the bin corresponding to exon 701-A contains significantly more variants than the other bins in the plurality of bins, and thus the effect of the sequence variant is inferred to be a gain-of-function of the gene. In such case, the genomic region used to compute the pre-test probability is the exon 701-A of the gene, that includes the locus encompassing the candidate variant.

Figure 7B:
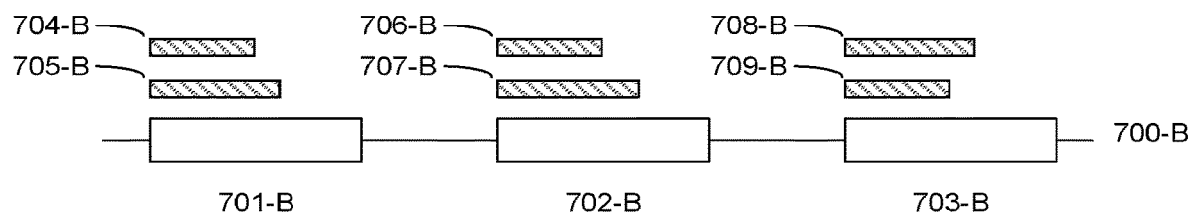

Alternatively, FIG. 7B illustrates a gene 700-B with a plurality of exons 701-B, 702-B, 703-B. Each exon corresponds to a bin in a plurality of bins. A first exon 701-B comprises a region of interest (e.g., a locus) that encompasses a candidate variant. A plurality of sequence variants (e.g., 704-B, 705-B, 706-B, 707-B, 708-B, 709-B) is obtained from a sequencing of nucleic acids from a cohort of subjects, where each sequence variant maps to a respective locus in the gene. The effect of the variants is inferred by binning each sequence variant into the respective bin corresponding to the exon to which the respective variant maps. Thus, sequence variants 704-B and 705-B are binned into the bin corresponding to exon 701-B, sequence variant 706-B and 707-B are binned into the bin corresponding to exon 702-B, and sequence variant 708-B and 709-B are binned into the bin corresponding to exon 703-B. In FIG. 7B, it can be determined that no bin in the plurality of bins contains significantly more sequence variants than the other bins in the plurality of bins, and thus the effect of the sequence variant is inferred to be a loss-of-function of the gene. In such case, the genomic region used to compute the pre-test probability is the entire gene.

In some such embodiments, determining whether any bin in the plurality of bins contains significantly more variants than the other bins in the plurality of bins comprises applying a rolling Poisson test of difference between bin counts corresponding to adjacent exons in the gene.

Referring to Block 510, the method further comprises validating the presence of the somatic sequence variant in the test subject when the variant allele fragment count for the candidate variant satisfies the dynamic variant count threshold for the locus, or rejecting the presence of the somatic sequence variant in the test subject when the variant allele fragment count for the candidate variant does not satisfy the dynamic variant count threshold for the locus. In some embodiments, the validating includes other variant filtering criteria, as described above in the present disclosure (see, Example Methods: Variant Identification).

In some embodiments, the methods and systems disclosed herein are used for precision oncology applications. For example, in some embodiments, the method further comprises generating a report for the test subject comprising the identity of variant alleles having variant allele counts, in the first sequencing reaction, that satisfy the dynamic variant count threshold. In some embodiments, the generated report further comprises therapeutic recommendations for the test subject based on the identity of one or more of the reported variant alleles. Additional embodiments for precision oncology applications, including matched clinical trials, matched therapies, report generation, and/or other aspects of the digital and laboratory health care platform are described in detail below.

Another aspect of the present disclosure provides a computer system comprising one or more processors and a non-transitory computer-readable medium including computer-executable instructions that, when executed by the one or more processors, cause the processors to perform a method according to any one of the embodiments disclosed herein.

Another aspect of the present disclosure provides a non-transitory computer-readable storage medium having stored thereon program code instructions that, when executed by a processor, cause the processor to perform the method according to any one of the embodiments disclosed herein.

In some embodiments, the methods described herein include generating a clinical report 139-3 (e.g., a patient report), providing clinical support for personalized cancer therapy, and/or using the information curated from sequencing of a liquid biopsy sample, as described above. In some embodiments, the report is provided to a patient, physician, medical personnel, or researcher in a digital copy (for example, a JSON object, a pdf file, or an image on a website or portal), a hard copy (for example, printed on paper or another tangible medium). A report object, such as a JSON object, can be used for further processing and/or display. For example, information from the report object can be used to prepare a clinical laboratory report for return to an ordering physician. In some embodiments, the report is presented as text, as audio (for example, recorded or streaming), as images, or in another format and/or any combination thereof.

The report includes information related to the specific characteristics of the patient's cancer, e.g., detected genetic variants, epigenetic abnormalities, associated oncogenic pathogenic infections, and/or pathology abnormalities. In some embodiments, other characteristics of a patient's sample and/or clinical records are also included in the report. For example, in some embodiments, the clinical report includes information on clinical variants, e.g., one or more of copy number variants (e.g., for actionable genes CCNE1, CD274(PD-L1), EGFR, ERBB2(HER2), MET, MYC, BRCA1, and/or BRCA2), fusions, translocations, and/or rearrangements (e.g., in actionable genes ALK, ROS1, RET, NTRK1, FGFR2, FGFR3, NTRK2 and/or NTRK3), pathogenic single nucleotide polymorphisms, insertion-deletions (e.g., somatic/tumor and/or germline/normal), therapy biomarkers, microsatellite instability status, and/or tumor mutational burden.

Variant Characterization

In some embodiments, a predicted functional effect and/or clinical interpretation for one or more identified variants is curated by using information from variant databases. In some embodiments, a weighted-heuristic model is used to characterize each variant.

In some embodiments, identified clinical variants are labeled as "potentially actionable", "biologically relevant", "variants of unknown significance (VUSs)", or "benign". Potentially actionable alterations are protein-altering variants with an associated therapy based on evidence from the medical literature. Biologically relevant alterations are protein-altering variants that may have functional significance or have been observed in the medical literature but are not associated with a specific therapy. Variants of unknown significance (VUSs) are protein-altering variants exhibiting an unclear effect on function and/or without sufficient evidence to determine their pathogenicity. In some embodiments, benign variants are not reported. In some embodiments, variants are identified through aligning the patient's DNA sequence to the human genome reference sequence version hg19 (GRCh37). In some embodiments, actionable and biologically relevant somatic variants are provided in a clinical summary during report generation.

For instance, in some embodiments, variant classification and reporting is performed, where detected variants are investigated following criteria from known evolutionary models, functional data, clinical data, literature, and other research endeavors, including tumor organoid experiments. In some embodiments, variants are prioritized and classified based on known gene-disease relationships, hotspot regions within genes, internal and external somatic databases, primary literature, and other features of somatic drivers. Variants can be added to a patient (or sample, for example, organoid sample) report based on recommendations from the AMP/ASCO/CAP guidelines. Additional guidelines may be followed. Briefly, pathogenic variants with therapeutic, diagnostic, or prognostic significance may be prioritized in the report. Non-actionable pathogenic variants may be included as biologically relevant, followed by variants of uncertain significance. Translocations may be reported based on features of known gene fusions, relevant breakpoints, and biological relevance. Evidence may be curated from public and private databases or research and presented as 1) consensus guidelines 2) clinical research, or 3) case studies, with a link to the supporting literature. Germline alterations may be reported as secondary findings in a subset of genes for consenting patients. These may include genes recommended by the American College of Medical Genetics and Genomics (ACMG) and additional genes associated with cancer predisposition or drug resistance.

In some embodiments, a clinical report 139-3 includes information about clinical trials for which the patient is eligible, therapies that are specific to the patient's cancer, and/or possible therapeutic adverse effects associated with the specific characteristics of the patient's cancer, e.g., the patient's genetic variations, epigenetic abnormalities, associated oncogenic pathogenic infections, and/or pathology abnormalities, or other characteristics of the patient's sample and/or clinical records. For example, in some embodiments, the clinical report includes such patient information and analysis metrics, including cancer type and/or diagnosis, variant allele fraction, patient demographic and/or institution, matched therapies (e.g., FDA approved and/or investigational), matched clinical trials, variants of unknown significance (VUS), genes with low coverage, panel information, specimen information, details on reported variants, patient clinical history, status and/or availability of previous test results, and/or version of bioinformatics pipeline.

In some embodiments, the results included in the report, and/or any additional results (for example, from the bioinformatics pipeline), are used to query a database of clinical data, for example, to determine whether there is a trend showing that a particular therapy was effective or ineffective in treating (e.g., slowing or halting cancer progression), and/or adverse effects of such treatments in other patients having the same or similar characteristics.

In some embodiments, the results are used to design cell-based studies of the patient's biology, e.g., tumor organoid experiments. For example, an organoid may be genetically engineered to have the same characteristics as the specimen and may be observed after exposure to a therapy to determine whether the therapy can reduce the growth rate of the organoid, and thus may be likely to reduce the growth rate of cancer in the patient associated with the specimen. Similarly, in some embodiments, the results are used to direct studies on tumor organoids derived directly from the patient. An example of such experimentation is described in U.S. Provisional Patent Application No. 62/944,292, filed Dec. 5, 2019, the content of which is hereby incorporated by reference, in its entirety, for all purposes.

As illustrated in FIG. 2A, in some embodiments, a clinical report is checked for final validation, review, and sign-off by a medical practitioner (e.g., a pathologist). The clinical report is then sent for action (e.g., for precision oncology applications).

Digital and Laboratory Health Care Platform:

In some embodiments, the methods and systems described herein are utilized in combination with, or as part of, a digital and laboratory health care platform that is generally targeted to medical care and research. It should be understood that many uses of the methods and systems described above, in combination with such a platform, are possible. One example of such a platform is described in U.S. patent application Ser. No. 16/657,804, filed Oct. 18, 2019, which is hereby incorporated herein by reference in its entirety for all purposes.

For example, an implementation of one or more embodiments of the methods and systems as described above may include microservices constituting a digital and laboratory health care platform supporting analysis of liquid biopsy samples to provide clinical support for personalized cancer therapy. Embodiments may include a single microservice for executing and delivering analysis of liquid biopsy samples to clinical support for personalized cancer therapy or may include a plurality of microservices each having a particular role, which together implement one or more of the embodiments above. In one example, a first microservice may execute sequence analysis in order to deliver genomic features to a second microservice for curating clinical support for personalized cancer therapy based on the identified features. Similarly, the second microservice may execute therapeutic analysis of the curated clinical support to deliver recommended therapeutic modalities, according to various embodiments described herein.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A microservices-based order management system is disclosed, for example, in U.S. Prov. Patent Application No. 62/873,693, filed Jul. 12, 2019, which is hereby incorporated herein by reference in its entirety for all purposes.

For example, continuing with the above first and second microservices, an order management system may notify the first microservice that an order for curating clinical support for personalized cancer therapy has been received and is ready for processing. The first microservice may execute and notify the order management system once the delivery of genomic features for the patient is ready for the second microservice. Furthermore, the order management system may identify that execution parameters (prerequisites) for the second microservice are satisfied, including that the first microservice has completed, and notify the second microservice that it may continue processing the order to curate clinical support for personalized cancer therapy, according to various embodiments described herein.

Where the digital and laboratory health care platform further includes a genetic analyzer system, the genetic analyzer system may include targeted panels and/or sequencing probes. An example of a targeted panel is disclosed, for example, in U.S. Prov. Patent Application No. 62/902,950, filed Sep. 19, 2019, which is incorporated herein by reference and in its entirety for all purposes. In one example, targeted panels may enable the delivery of next generation sequencing results for providing clinical support for personalized cancer therapy according to various embodiments described herein. An example of the design of next-generation sequencing probes is disclosed, for example, in U.S. Prov. Patent Application No. 62/924,073, filed Oct. 21, 2019, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting nucleic acid (e.g., cfDNA, DNA and/or RNA) read counts aligned to a reference genome. The methods and systems described above may be utilized, for example, to ingest the cfDNA, DNA and/or RNA read counts and produce genomic features as a result.

When the digital and laboratory health care platform further includes an RNA data normalizer, any RNA read counts may be normalized before processing embodiments as described above. An example of an RNA data normalizer is disclosed, for example, in U.S. patent application Ser. No. 16/581,706, filed Sep. 24, 2019, which is incorporated herein by reference and in its entirety for all purposes.

When the digital and laboratory health care platform further includes a genetic data deconvoluter, any system and method for deconvoluting may be utilized for analyzing genetic data associated with a specimen having two or more biological components to determine the contribution of each component to the genetic data and/or determine what genetic data would be associated with any component of the specimen if it were purified. An example of a genetic data deconvoluter is disclosed, for example, in U.S. patent application Ser. No. 16/732,229 and PCT/US19/69161, filed Dec. 31, 2019, U.S. Prov. Patent Application No. 62/924,054, filed Oct. 21, 2019, and U.S. Prov. Patent Application No. 62/944,995, filed Dec. 6, 2019, each of which is hereby incorporated herein by reference and in its entirety for all purposes.

When the digital and laboratory health care platform further includes an automated RNA expression caller, RNA expression levels may be adjusted to be expressed as a value relative to a reference expression level, which is often done in order to prepare multiple RNA expression data sets for analysis to avoid artifacts caused when the data sets have differences because they have not been generated by using the same methods, equipment, and/or reagents. An example of an automated RNA expression caller is disclosed, for example, in U.S. Prov. Patent Application No. 62/943,712, filed Dec. 4, 2019, which is incorporated herein by reference and in its entirety for all purposes. The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, and so forth. An example tumor of unknown origin engine is disclosed, for example, in U.S. Prov. Patent Application No. 62/855,750, filed May 31, 2019, which is incorporated herein by reference and in its entirety for all purposes. An example of an HLA LOH engine is disclosed, for example, in U.S. Prov. Patent Application No. 62/889,510, filed Aug. 20, 2019, which is incorporated herein by reference and in its entirety for all purposes. An example of a tumor mutational burden (TMB) engine is disclosed, for example, in U.S. Prov. Patent Application No. 62/804,458, filed Feb. 12, 2019, which is incorporated herein by reference and in its entirety for all purposes. An example of a PD-L1 status engine is disclosed, for example, in U.S. Prov. Patent Application No. 62/854,400, filed May 30, 2019, which is incorporated herein by reference and in its entirety for all purposes. An additional example of a PD-L1 status engine is disclosed, for example, in U.S. Prov. Patent Application No. 62/824,039, filed Mar. 26, 2019, which is incorporated herein by reference and in its entirety for all purposes. An example of a homologous recombination deficiency engine is disclosed, for example, in U.S. Prov. Patent Application No. 62/804,730, filed Feb. 12, 2019, which is incorporated herein by reference and in its entirety for all purposes. An example of a cellular pathway activation report engine is disclosed, for example, in U.S. Prov. Patent Application No. 62/888,163, filed Aug. 16, 2019, which is incorporated herein by reference and in its entirety for all purposes. An example of an immune infiltration engine is disclosed, for example, in U.S. patent application Ser. No. 16/533,676, filed Aug. 6, 2019, which is incorporated herein by reference and in its entirety for all purposes. An additional example of an immune infiltration engine is disclosed, for example, in U.S. Patent Application No. 62/804,509, filed Feb. 12, 2019, which is incorporated herein by reference and in its entirety for all purposes. An example of an MSI engine is disclosed, for example, in U.S. patent application Ser. No. 16/653,868, filed Oct. 15, 2019, which is incorporated herein by reference and in its entirety for all purposes. An additional example of an MSI engine is disclosed, for example, in U.S. Prov. Patent Application No. 62/931,600, filed Nov. 6, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the therapies may be matched according to the systems and methods disclosed in U.S. Prov. Patent Application No. 62/804,724, filed Feb. 12, 2019, which is incorporated herein by reference and in its entirety for all purposes. For example, the clinical trials may be matched according to the systems and methods disclosed in U.S. Prov. Patent Application No. 62/855,913, filed May 31, 2019, which is incorporated herein by reference and in its entirety for all purposes.

The report may include a comparison of the results to a database of results from many specimens. An example of methods and systems for comparing results to a database of results are disclosed in U.S. Prov. Patent Application No. 62/786,739, filed Dec. 31, 2018, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, filed Nov. 22, 2019; U.S. Prov. Patent Application No. 62/924,621, filed Oct. 22, 2019; and U.S. Prov. Patent Application No. 62/944,292, filed Dec. 5, 2019, each of which is incorporated herein by reference and in its entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, filed Oct. 22, 2019, which is incorporated herein by reference and in its entirety for all purposes.

It should be understood that the examples given above are illustrative and do not limit the uses of the systems and methods described herein in combination with a digital and laboratory health care platform.

The results of the bioinformatics pipeline may be provided for report generation 208. Report generation may comprise variant science analysis, including the interpretation of variants (including somatic and germline variants as applicable) for pathogenic and biological significance. The variant science analysis may also estimate microsatellite instability (MSI) or tumor mutational burden. Targeted treatments may be identified based on gene, variant, and cancer type, for further consideration and review by the ordering physician. In some aspects, clinical trials may be identified for which the patient may be eligible, based on mutations, cancer type, and/or clinical history. Subsequent validation may occur, after which the report may be finalized for sign-out and delivery. In some embodiments, a first or second report may include additional data provided through a clinical dataflow 202, such as patient progress notes, pathology reports, imaging reports, and other relevant documents. Such clinical data is ingested, reviewed, and abstracted based on a predefined set of curation rules. The clinical data is then populated into the patient's clinical history timeline for report generation.

Further details on clinical report generation are disclosed in U.S. patent application Ser. No. 16/789,363 (PCT/US20/180002), filed Feb. 12, 2020, which is hereby incorporated herein by reference in its entirety.

Specific Embodiments of the Disclosure

In some aspects, the systems and methods disclosed herein may be used to support clinical decisions for personalized treatment of cancer. For example, in some embodiments, the methods described herein identify actionable genomic variants and/or genomic states with associated recommended cancer therapies. In some embodiments, the recommended treatment is dependent upon whether or not the subject has a particular actionable variant and/or genomic status. Recommended treatment modalities can be therapeutic drugs and/or assignment to one or more clinical trials. Generally, current treatment guidelines for various cancers are maintained by various organizations, including the National Cancer Institute and Merck & Co., in the Merck Manual.

In some embodiments, the methods described herein further includes assigning therapy and/or administering therapy to the subject based on the identification of an actionable genomic variant and/or genomic state, e.g., based on whether or not the subject's cancer will be responsive to a particular personalized cancer therapy regimen. For example, in some embodiments, when the subject's cancer is classified as having a first actionable variant and/or genomic state, the subject is assigned or administered a first personalized cancer therapy that is associated with the first actionable variant and/or genomic state, and when the subject's cancer is classified as having a second actionable variant and/or genomic state, the subject is assigned or administered a second personalized cancer therapy that is associated with the second actionable variant. Assignment or administration of a therapy or a clinical trial to a subject is thus tailored for treatment of the actionable variants and/or genomic states of the cancer patient.

EXAMPLES

Example 1

The Cancer Genome Atlas (TCGA)

The Cancer Genome Atlas (TCGA) is a publicly available dataset comprising more than two petabytes of genomic data for over 11,000 cancer patients, including clinical information about the cancer patients, metadata about the samples (e.g., the weight of a sample portion, etc.) collected from such patients, histopathology slide images from sample portions, and molecular information derived from the samples (e.g., mRNA/miRNA expression, protein expression, copy number, etc.). The TCGA dataset includes data on 33 different cancers: breast (breast ductal carcinoma, bread lobular carcinoma) central nervous system (glioblastoma multiforme, lower grade glioma), endocrine (adrenocortical carcinoma, papillary thyroid carcinoma, paraganglioma & pheochromocytoma), gastrointestinal (cholangiocarcinoma, colorectal adenocarcinoma, esophageal cancer, liver hepatocellular carcinoma, pancreatic ductal adenocarcinoma, and stomach cancer), gynecologic (cervical cancer, ovarian serous cystadenocarcinoma, uterine carcinosarcoma, and uterine corpus endometrial carcinoma), head and neck (head and neck squamous cell carcinoma, uveal melanoma), hematologic (acute myeloid leukemia, Thymoma), skin (cutaneous melanoma), soft tissue (sarcoma), thoracic (lung adenocarcinoma, lung squamous cell carcinoma, and mesothelioma), and urologic (chromophobe renal cell carcinoma, clear cell kidney carcinoma, papillary kidney carcinoma, prostate adenocarcinoma, testicular germ cell cancer, and urothelial bladder carcinoma).

Example 2

Method of Validating a Liquid Biopsy Assay

Conducting Sample Collection, Storage, Nucleic Acid Isolation, and Library Preparation.

To validate a liquid biopsy assay in accordance with some embodiments of the present disclosure, 188 unique specimens were sequenced. These unique specimens included 10 blood specimens purchased from BioIVT, 56 residual plasma samples, 39 whole-blood samples, 4 cfDNA reference standards set in synthetic plasma (Horizon Discovery's Multiplex I cfDNA Reference Standards HD812, HD813, HD814, HD815), and 2 cfDNA reference standard isolates (Horizon Discovery's Structural Multiplex cfDNA reference standard HD786, and 100% Multiplex I Wild Type Reference Standard HD776). Furthermore, an additional 55 blood samples with matched tumor samples were utilized to compare the liquid biopsy and solid tumor tests, and 375 blood samples were sequenced for low-pass whole-genome sequencing (LPWGS) analysis. Sequence data from an additional 1,000 patient samples that were previously sequenced were utilized for retrospective and clinical analyses. All blood was received in Cell-free DNA BCT® blood collection tubes (Streck). Plasma was prepared immediately after accessioning and stored at −80° C. until later nucleic acid extraction and library preparation. At this time, cfDNA was isolated from plasma using the Qiagen QlAamp MinElute ccfDNA Midi Kit (QIAGEN), conducted according to instructions provided by the manufacturer. Automated library preparation was performed on a SciClone NGSx (Perkin Elmer). All cfDNA samples were normalized with molecular grade water to a maximum of 50 microliters (μL).

Conducting the Liquid Biopsy Sequencing Assay.

The liquid biopsy assay utilized New England BioLab's NEBNext® Ultra™ II DNA Library Prep Kit for Illumina®, IDT's xGen CS Adapters, unique molecular indices (UMI), and 96 pairs of barcodes to prepare cfDNA sequencing libraries with unique sample identifiers (IDs). Each sample was ligated to a dual unique index. The dual unique index enables multiplexed sequencing of up to 7 patients and 1 positive control per SP NovaSeq flow cell, 16 patients and 1 positive control per S1 NovaSeq flow cell, 34 patients and 1 positive control per S2 NovaSeq flow cell, and 84 patients and 1 positive control per S4 NovaSeq flow cell. The library preparation protocol is optimized for greater than or equal to 20 nanograms (ng) cfDNA input to maximize mutation detection sensitivity. The final library was sequenced on an Illumina NovaSeq sequencer. Furthermore, analysis was performed using a bioinformatics pipeline and analysis server.

The Bioinformatics Pipeline.

Adapter-trimmed FASTQ files are aligned to the nineteenth edition of the human reference genome build (hg19) using Burrows-Wheeler Aligner (BWA). Li et al., 2009, "Fast and accurate short read alignment with Burrows-Wheeler transform," Bioinformatics, (25), pg. 1754. Following alignment, reads were grouped by alignment position and UMI family, and collapsed into consensus sequences using fgbio tools (available online at fulcrumgenomics.github.io/fgbio/). Bases with insufficient quality or significant disagreement among family members were reverted to N's. Phred scores were scaled based on initial base calling estimates combined across all family members. Following single-strand consensus sequence generation, duplex consensus sequences were generated by comparing the forward and reverse oriented PCR products with mirrored UMI sequences. Consensus sequences were re-aligned to the human reference genome using BWA. BAM files are generated and indexed after the re-alignment.

SNV and indel variants were detected using VarDict. Lai et al., 2016, "VarDict: a novel and versatile variant caller for next-generation sequencing in cancer research," Nucleic Acids Res, (44), pg. 108. SNVs were called down to 0.1% VAF for specified hotspot target regions and 0.25% VAF at all other base positions across the panel. Indels were called down to 0.5% VAF for variants within specific regions of interest. Any indels outside of these regions were called down to 5% VAF. All SNVs and indels were then sorted, deduplicated, normalized, and annotated accordingly. Following annotation, variants were classified as germline, somatic, or uncertain using a Bayesian model based on prior expectations informed by various internal and external databases of germline and cancer variants. Uncertain variants are treated as somatic for filtering and reporting purposes. Following classification, variants were filtered based on a plurality of quality metrics including coverage, VAF, strand bias, and genomic complexity. Additionally, variants were filtered with a Bayesian tri-nucleotide context-based model with position level background error rates estimated from a pool of process matched healthy controls. Furthermore, known artifactual variants were removed.

Copy number variants (CNVs) were analyzed utilizing CNVkit and a CNV annotation and filtering algorithm provided by the present disclosure. Talevich et al., 2016, "CNVkit: Genome-Wide Copy Number Detection and Visualization from Targeted DNA Sequencing," PLoS Comput Biol, (12), pg. 1004873. This CNVkit provides genomic region binning, coverage calculation, bias correction, normalization to a reference pool, segmentation, and visualization. The $\log_2$ ratios between the tumor sample and a pool of process matched healthy samples from the CNVkit output were annotated and filtered using statistical models, such that the amplification status (e.g., amplified or not-amplified) of each gene is predicted and non-focal amplifications are removed.

Rearrangements were detected using the SpeedSeq analysis pipeline. Chiang et al., 2015, "SpeedSeq: ultra-fast personal genome analysis and interpretation," Nat Methods, (12), pg. 966. Briefly, FASTQ files were aligned to hg19 using BWA. Split reads mapped to multiple positions and read pairs mapped to discordant positions were identified and separated, then utilized to detect gene rearrangements by LUMPY. Layer et al., 2014, "I.M. LUMPY: a probabilistic framework for structural variant discovery," Genome Biol, (15), pg. 84. Fusions were then filtered according to the number of supporting reads.

Predicted functional effect and clinical interpretation for each variant was curated by automated software using information from both internal and external databases. A weighted-heuristic model was used, which has logic-based recommendations from the AMP/ASCO/CAP/ClinGen Somatic working group and ACMG guidelines. Li et al., 2017, "Standards and Guidelines for the Interpretation and Reporting of Sequence Variants in Cancer: A Joint Consensus Recommendation of the Association for Molecular Pathology, American Society of Clinical Oncology, and College of American Pathologists," The Journal of molecular diagnostics, (19), pg. 4; Kalia et al., 2017, "Recommendations for reporting of secondary findings in clinical exome and genome sequencing, 2016 update (ACMG SF v2.0): a policy statement of the American College of Medical Genetics and Genomics," Genetics in Medicine, (19), pg. 249.

The relative frequency and distribution are determined for any read containing repetitive sequences to detect microsatellite instability. To predict the probability of an unstable locus, a k-nearest neighbors model (with k=100) was utilized along with normalized percent lower, mean lower, and mean log-likelihood metrics. The percentage of unstable loci was calculated from the probabilities of each sample, with greater than 50% unstable loci considered microsatellite instability-high (MSI-H).

The Validation Approach.

The present disclosure conducted extensive validation studies to establish robust technical perform of the liquid biopsy assay. Limit of detection (LOD) was determined by assessing analytical sensitivity in reference standards with 5%, 1%, 0.5%, 0.25%, and 0.1% VAF generated from the Horizon Discovery reference set. The Horizon Discovery set includes 160 bp cfDNA fragments from human cell lines in an artificial plasma matrix to closely resemble cfDNA extracted from human plasma. VAFs of SNVs and indels, including EGFR (ΔE746-A750), EGFR (V769-D770insASV), EGFR A767_V769dup, EGFR (L858R), EGFR (T790M), KRAS (G12D), NRAS (A59T), NRAS (Q61K), AKT1 E17K, PIK3CA (E545K), and GNA11 Q209L, and CNVs and rearrangements, including CCDC6/RET, SLC34A2/ROS1, MET, MYC, and MYCN, were measured in reference samples by the liquid biopsy assay of the present disclosure. Each measurement was conducted with a minimum of three replicates at 10 ng, 30 ng, and 50 ng of DNA. Sensitivity was determined by the number of detected variants divided by the total number of variants present in the reference samples. Samples with an on-target rate of less than 30% were excluded from the instant analysis, and MET (4.5 copies) was included in CNV sensitivity determinations. Sensitivity of greater than 90% was considered reliable detection.

Analytical specificity was determined using 44 normal samples titrated at 1%, 2.5%, or 5% from a wild-type cfDNA reference standard with a list of confirmed true-negative SNVs, indels, CNVs and rearrangements. Specificity was determined by the number of known true-negative variants divided by the number of true-negative variants plus false-positive variants identified by the liquid biopsy assay.

To assess inter-instrument concordance between the sequencing instruments, 10 patient libraries were sequenced on each instrument (3 NovaSeqs). Variants seen below the lower limit of detection (LLOD) (0.25% for SNVs and 0.50% for indels) were excluded from concordance analysis.

To establish analytical accuracy, the results of 40 validation samples were compared to the results of an orthogonal reference method (Roche's AVENIO ctDNA assay). Analytical accuracy was determined by the number of detected variants divided by the total number of variants present in the sample. Variants that were off-target or below LLOD (0.25% for SNVs and 0.5% for indels) were excluded from the instant analysis.

Conducting Digital Droplet Polymerase Chain Reaction (ddPCR).

Five variants were validated on the ddPCR platform: KRAS G12D (Integrated DNA Technologies, IDT, published sequences); TERT promoter mutations c.-124C>T (C228T) & c.-146C>T (C250T) (Thermo Fisher Scientific); and TP53 p.R273H and TP53 p.R175H (Thermo Fisher Scientific). Each amplification reaction was performed in 25 µL and contained 1× Genotyping Master Mix (Thermo Fisher Scientific), 1× droplet stabilizer (RainDance), 1× of primer/probe mixture for TERT and TP53 (for KRAS: 800 nM of each primer and 500 nM of each probe) plus template. To improve the lower limit of detection, 4-cycle amplification was conducted prior to droplet generation. Amplification for KRAS was conducted using the cycling conditions of: 1 cycle of 95° C. (0.6° C./s ramp) for 10 minutes, 4 cycles of 95° C. (0.6° C./s ramp) for 15 seconds and 60° C. for 2 minutes, followed by 1 cycle of 98° C. (0.6° C./s ramp) for 10 minutes. Cycling conditions for the TP53 variants were the same as those for KRAS with the exception of the annealing and extension temperature, which was set at 55° C. for 2 minutes. Amplification for TERT followed Thermo Fisher's recommendation as follows: 1 cycle of 96° C. (1.6° C./s ramp) for 10 minutes, 4 cycles of 98° C. (1.6° C./s ramp) for 30 seconds and 55° C. for 2 minutes, followed by 1 cycle of 55° C. (1.6° C./s ramp) for 2 minutes. Accordingly, droplets generated on the RainDance Source, and amplification performed following the above cycling conditions with cycle numbers of 45 for both KRAS and TP53, and 54 for TERT. Furthermore, droplets were analyzed on a RainDance Sense droplet reader. Additionally, RainDrop Analyst II v1.1.0 analysis software was utilized to acquire and analyze data.

The Concordance Between Liquid Biopsy and Solid Tumor Assays.

Matched liquid biopsy and solid tumor sample pairs (n=55) were used to determine analytical sensitivity and specificity. Solid tumor and matched normal samples obtained from peripheral blood buffy coat were analyzed with the solid tumor assay, and corresponding blood plasma samples were analyzed with the liquid biopsy assay of the present disclosure. Only variants in the reportable range of both the solid tumor and liquid biopsy panels were included in these analyses (e.g., genes in the liquid biopsy gene panel is a subset of genes in the solid tumor gene panel). Germline, intronic, and synonymous variants identified in the solid tumor assay and the liquid biopsy assay were excluded from analysis with the exception of intronic splice variants. To determine analytical sensitivity, the number of variants called in both the liquid biopsy assay and the solid tumor assay (e.g., true positives) was divided by the sum of true positives and those called only in the solid tumor assay. To determine analytical specificity the number of positions reported in neither the liquid biopsy assay nor the solid tumor assay (e.g., true negatives) was divided by the sum of true negatives and variants only called in the liquid biopsy assay.

To improve variant calling in the liquid biopsy assay, a strategy that dynamically determines local sequence errors using Bayes Theorem and the likelihood ratio test was developed. The dynamic threshold was determined using a sample-specific error rate, the error rate from healthy control samples, and from a reference cohort of solid tumor samples. Accordingly, the method of the present disclosure was conducted on 55 matched liquid biopsy/solid tumor tissue samples, with variants detected in the solid tumor assay as the source of truth. Using sensitivity thresholds defined by the LOD analysis, fixed post-test-odds (e.g., equal to the P(post-test)/[1−P(post-test)]), as well as pre-test-odds. The Pre-test-odds were determined using historical data from the solid tumor assay with an equation identical to the post-test-odds calculation). Accordingly, the following formula was determined based on the above: specificity=1−pre-test-odds*sensitivity/post-test-odds The specificity was input to a beta-binomial function and yielded the minimum number of alternate alleles to call a variant at a particular depth. The pre-test-odds metric was specific to individual cancer cohorts and individual genes, allowing for cancer-specific pre-test-odds to be applied to individual exons.

Conducting Low-Pass Whole Genome Sequencing and Analysis.

Blood samples from 375 patients were sequenced using low-pass whole-genome sequencing (LPWGS) across four flow cells. Sequencing coverage metrics for these samples were determined using Picard CollectWgsMetrics. The tumor fraction and ploidy values for each sample were estimated using ichorCNA with a specific reference panel of 47 normal samples. Adalsteinsson et al., (2017), "Scalable whole-exome sequencing of cell-free DNA reveals high concordance with metastatic tumors" Nat Commun, (8), pg. 1324. Reported variants from the corresponding liquid biopsy analysis of each sample were utilized to assess the accuracy of the tumor fraction estimates.

Determining Estimation of Circulating Tumor Fraction.

Circulating tumor fraction estimate (ctFE) was determined using a novel method, Off-Target Tumor Estimation Routine (OTTER), from off-target reads uniformly distributed across the human reference genome. As described above, the CNVkit was conducted on each sample, and segments were assigned via circular binary segmentation (CBS). Olshen et al., 2004, "Circular binary segmentation for the analysis of array-based DNA copy number data," Biostatistics, (5), pg. 557. Segments were then fit to integer copy states via an expectation-maximization algorithm using the sum of squared error of the segment $\log_2$ ratios (e.g., normalized to genomic interval size) to expected ratios given a putative copy state and tumor purity. Estimates were confirmed by comparing results against LPWGS of the original patient isolate. As such, results are shown using randomly selected, de-identified samples.

Clinical Profiling of Liquid Biopsy Patients.

De-identified molecular and abstracted clinical data were evaluated in a cohort of 1,000 patients randomly selected from a specific reference clinicogenomic database. All data were de-identified in accordance with the Health Insurance Portability and Accountability Act (HIPAA). Dates used for analyses were relative to the first liquid biopsy sequencing date of each patient, and year of the first sequencing date was randomly off-set. Variants included in the analyses were those classified as pathogenic or likely pathogenic, and further divided into actionable if matched to diagnostic, prognostic or therapeutic evidence or biologically relevant. Outcomes were determined according to the most recent clinical response noted in patient records. The study protocol was submitted to the Advarra Institutional Review Board (IRB), which determined the research was exempt from IRB oversight and approved a waiver of HIPAA authorization for this study.

Example 3

Results of Validating Liquid Biopsy Assay

Liquid Biopsy Validation Summary.

The liquid biopsy oncology assay is a 105-gene hybrid capture NGS panel designed to detect actionable somatic variant targets in plasma. Referring to FIGS. 16A through 16C, the liquid biopsy assay detects mutations in four variant classes, including: single nucleotide variants (SNVs) and insertion-deletions (indels) in all 105 genes, copy number variants (CNVs) in 6 genes, and chromosomal rearrangements in 7 genes. To validate the liquid biopsy assay, a total of 188 samples were sequenced. The runs generated an average of 261.7 M±40.7 M total reads with 130.7 M±20.3 M read pairs and a unique median read depth of 4999.128±1288.843. The average percent of mapped reads across all runs was 99.876%±0.0078.

Referring to FIG. 13, determined analytical sensitivity for all SNVs, indels, CNVs, and rearrangements targeted in the reference samples is provided. Accordingly, SNVs were reliably detected at greater than or equal to 0.25% VAF with 30 ng of input DNA (93.75% [45/48] sensitivity), indels at greater than or equal to 0.5% VAF with 30 ng (95.83% [23/24] sensitivity), CNVs at greater than or equal to 0.5% VAF with 10 ng (100.00% [8/8] sensitivity), and rearrangements at greater than or equal to 1% VAF with 30 ng (90% [9/10] sensitivity). Referring to FIG. 14, analytical specificity is provided in which 100% for SNVs, indels, and rearrangements; and 96.2% for CNVs on samples with greater than or equal to 0.25% VAF with 30 ng of input DNA.

Accordingly, intra-assay and inter-assay concordance between the replicates in the present disclosure was 100% for SNVs, indicating a high degree of repeatability and reproducibility. Moreover, the inter-instrument concordance was 96.70% for SNVs and 100% for indels, with a combined concordance of 96.83% across instruments. Additionally, interfering substances including genomic DNA, ethanol, and isopropanol did not cause a change in the detection of variants. Concordance between controls and samples with interfering substances was high (e.g., 100%) among samples that passed filtering, and were above the LOD.

The Accuracy of the Liquid Biopsy Assay Compared to Orthogonal Assays.

Referring to FIG. 15, to evaluate analytical accuracy, the present disclosure compared the liquid biopsy assay to the Roche AVENIO ctDNA assay. In 30 ng cfDNA samples analyzed by liquid biopsy assay and AVENIO cfDNA assay (n=40), sensitivity for SNVs, indels, CNVs and rearrangements was 94.8%, 100%, 100%, and 100%, respectively. In the 6 SNVs that were not detected, 5 were called but filtered out due to insufficient evidence. In 10 ng samples, sensitivity for SNV, indel, CNV, and rearrangements was 91.9%, 100%, 80%, and 100%, respectively. Of the 7 SNVs that were not detected, 6 were present in sequencing data but filtered out due to insufficient evidence.

Figure 8A:
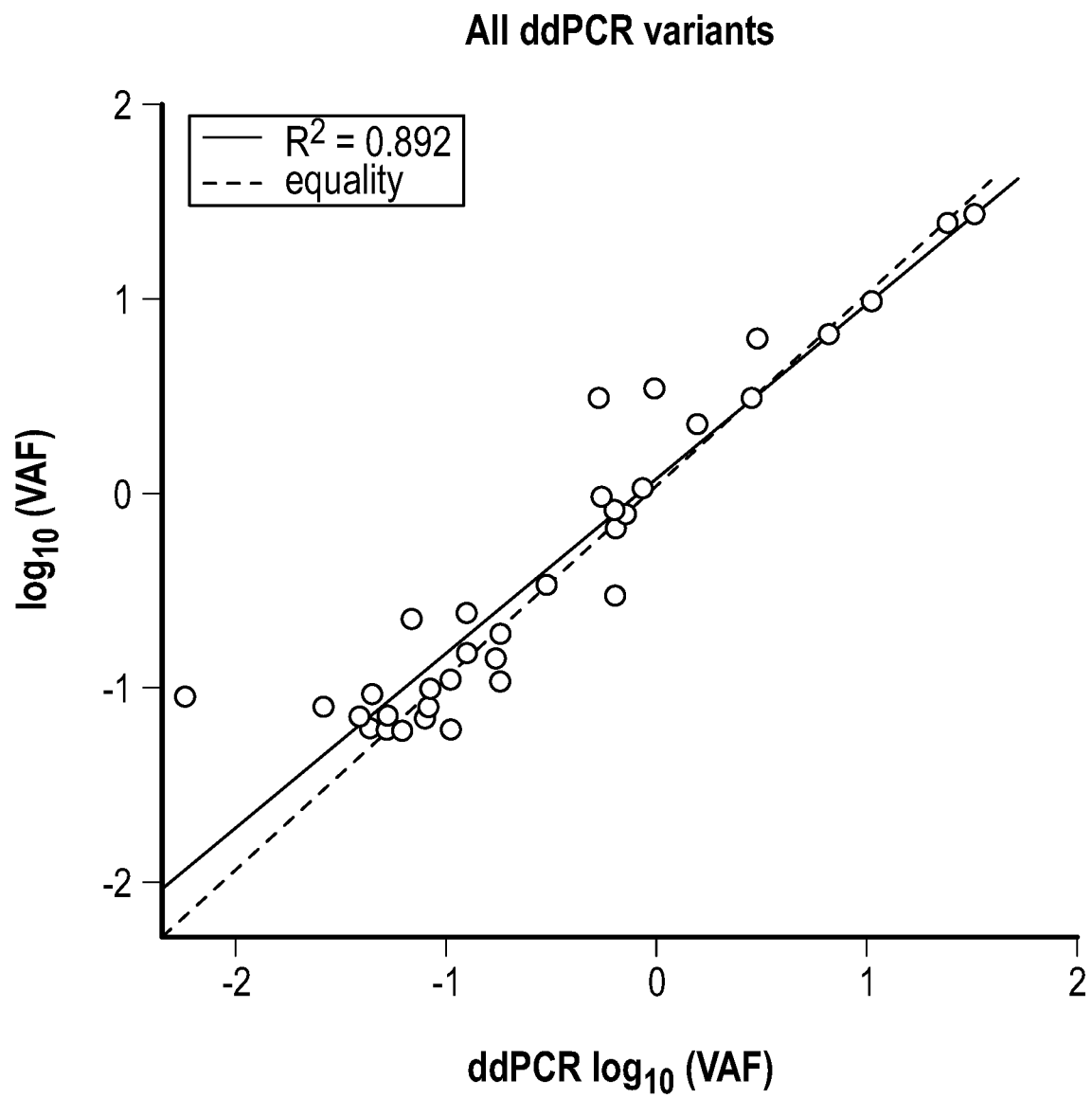
FIGS. 8A, 8B, 8C, and 8D collectively illustrate results of an inter-assay comparison between a liquid biopsy assay, a digital droplet polymerase chain reaction (ddPCR), and a solid-tumor biopsy assay, in accordance with various embodiments of the present disclosure.
Figure 8B:
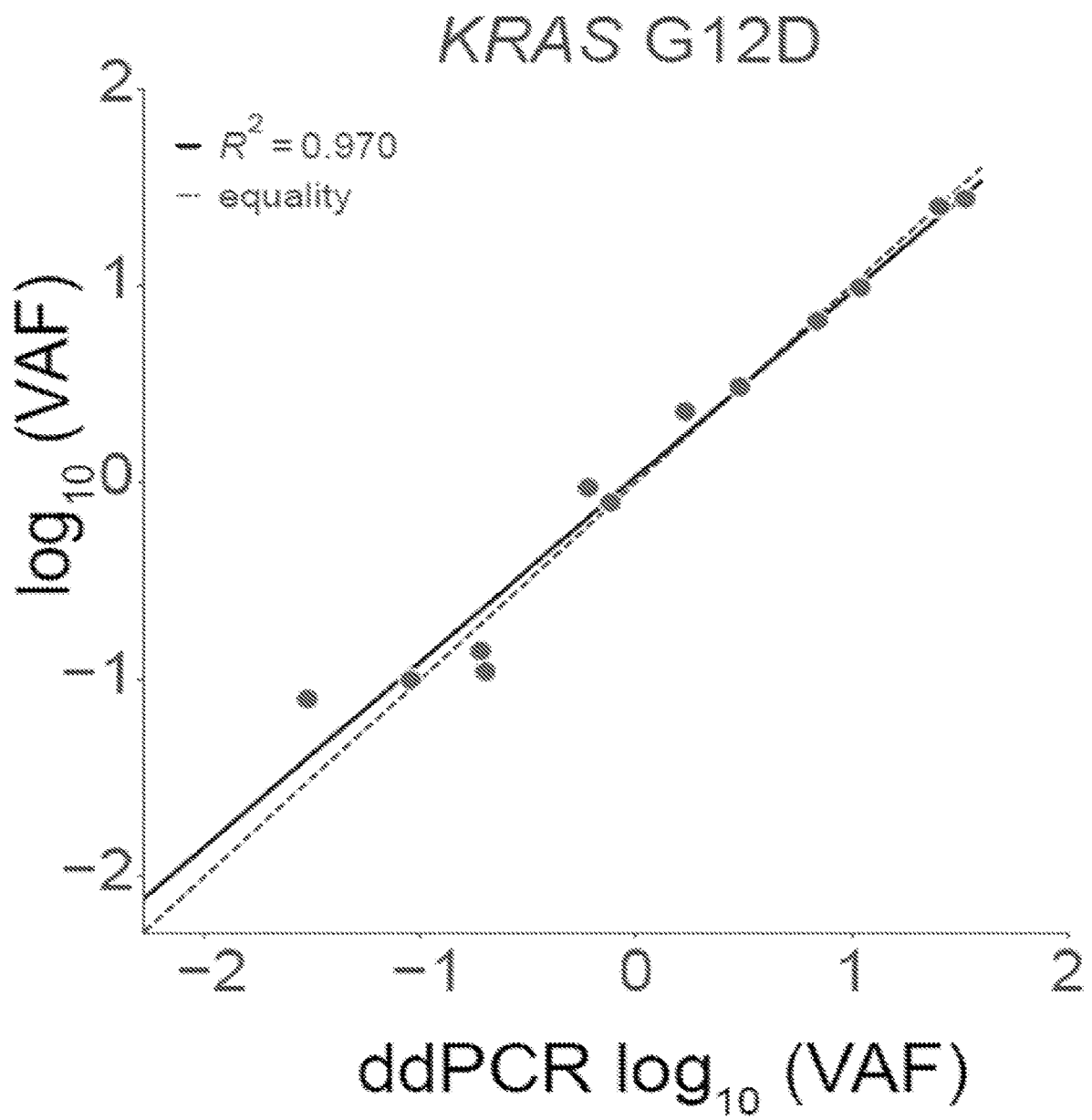

Referring to FIGS. 8A and 8B, to further validate the liquid biopsy assay results, patients with reported variants KRAS G12D (n=12), TERT c.-124 (n=7), TERT c.-146 (n=5), TP53 R273H (n=7), and TP53 R175H (n=7) were selected for analysis by ddPCR. Liquid biopsy NGS VAF was compared with ddPCR VAF to determine concordance. Accordingly, 100% PPV and a high correlation between ddPCR results and liquid biopsy VAF ($R^2$=0.892), as well as individual variants such as KRAS G12D ($R^2$=0.970), as shown in FIGS. 8A and 8B. These results indicate the liquid biopsy assay of the present disclosure can be used to accurately identify hotspot mutations. Specifically, FIG. 8A illustrates results of an inter-assay comparison between liquid biopsy, ddPCR, and solid tumor results for patients samples with selected variants (n=38) analyzed by ddPCR and compared with liquid biopsy variant allele fraction (VAF), resulting in high correlation overall ($R^2$=0.892). FIG. 8B illustrates results of an inter-assay comparison between liquid biopsy, ddPCR, and solid tumor results for patient samples with individual variants such as KRAS G12D (n=12, $R^2$=0.970).

The Concordance Between Liquid Biopsy and Solid Tumor Tissue Assay.

Comparisons between analytical sensitivity and specificity in matched solid tumor and liquid biopsy tests from 55 patients were determined. Since solid tumor matched samples include both tumor tissue and buffy coat (e.g., normal comparator), a specific classification strategy was utilized to determine and exclude germline variants from the analysis. Beaubier et al., 2019, "Clinical validation of the xT next-generation targeted oncology sequencing assay," Onctotarget, 10(24), pg. 2384. Removing intronic and synonymous variants, benign and likely benign variants, as well as variants below the LOD for solid tumor and liquid biopsy assays resulted in 145 concordant SNVs, 20 concordant indels, and 11 concordant CNVs. 66 SNVs, 11 indels, and 8 CNVs were identified that were reported in the solid tumor assay but not the liquid biopsy assay, as well as 209 SNVs, 14 indels, and 7 CNVs that were reported in the liquid biopsy assay but not the solid tumor assay. Accordingly, the specificity of the liquid biopsy assay was 100.00% for SNVs and indels and 96.67% for CNVs. Referring to FIG. 17, a Bayesian dynamic filtering methodology was utilized to further reduce discordance by 11.45%, improving the specificity of variant calling in the liquid biopsy assay. The overall sensitivity of the liquid biopsy assay compared to the solid tumor assay was 68.18% for SNVs and indels and 57.89% for CNVs. When limiting analysis to clinically actionable targets, 107 concordant variants and 37 discordant, for a sensitivity of 74.31%, were reported.

Figure 8C:
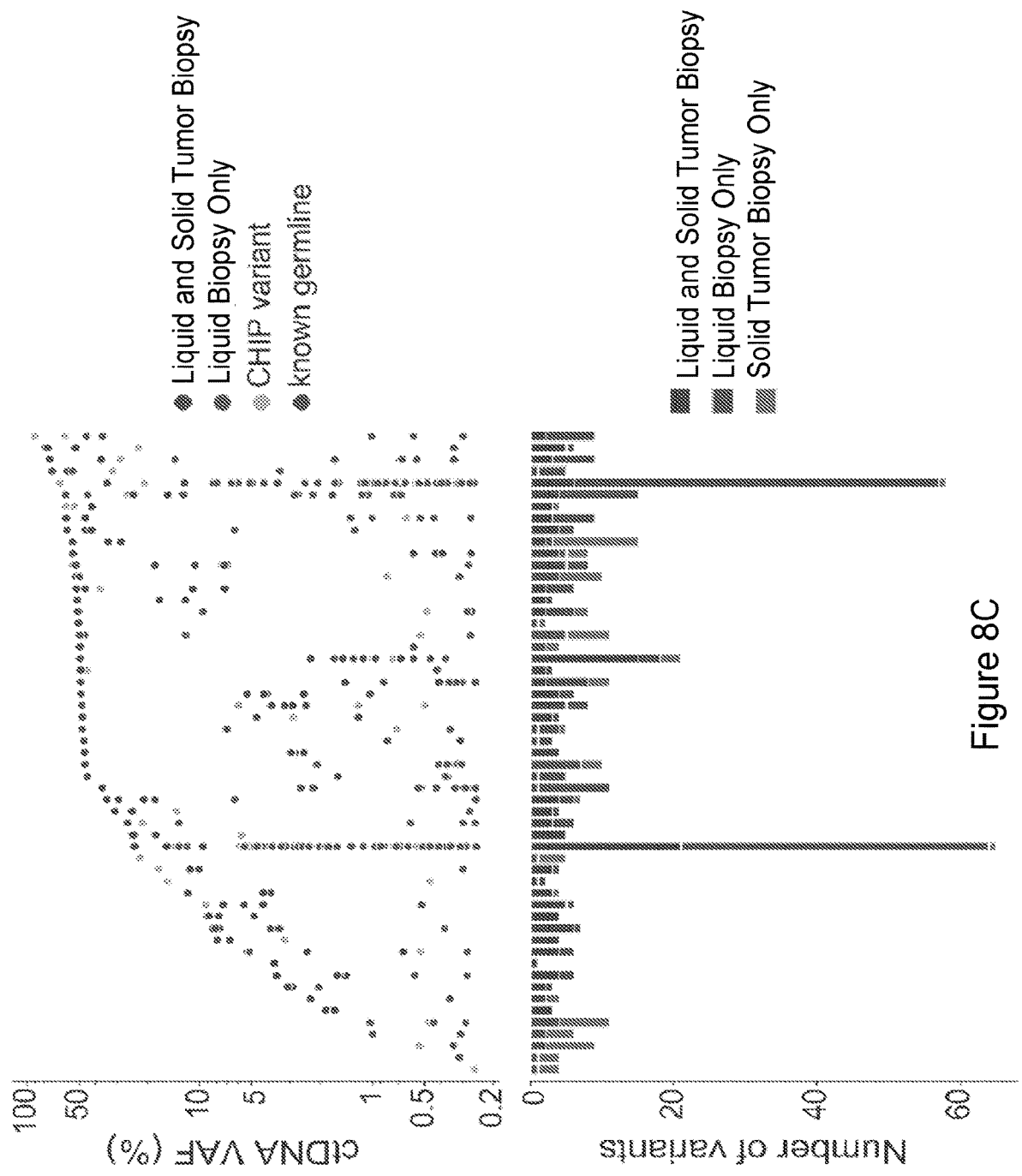

Furthermore, comparisons between the sample classification of reportable variants between matched samples with liquid biopsy and solid tumor testing were determined. Referring to FIG. 8C, variants were considered CH variants if found in the plasma as well as in the solid tumor normal sample but were not present at levels consistent with germline variation. Accordingly, this classification of germline and CH variants in liquid biopsy is possible with a corresponding solid tumor assay or a germline sequencing analysis from the buffy coat. Notably, two samples have a large number of variants only detected in liquid biopsy, many of which are at low VAFs. These samples were subsequently determined to have very high tumor mutational burdens (TMBs) in their corresponding solid tumor analyses. Accordingly, the large number of liquid biopsy variants at low VAFs and high TMBs suggest that these tumors may be more heterogeneous and that some variants are more easily detected in blood. Specifically, FIG. 8C illustrates results of an inter-assay comparison between liquid biopsy, ddPCR, and solid tumor results for sample classification of reportable variants, in which microsatellite instability (MSI) was detected by the liquid biopsy assay in six out of sixteen MSI-high patents, with 100% as indicated by the one or more blue dots depicted above the dotted line.

Figure 8D:
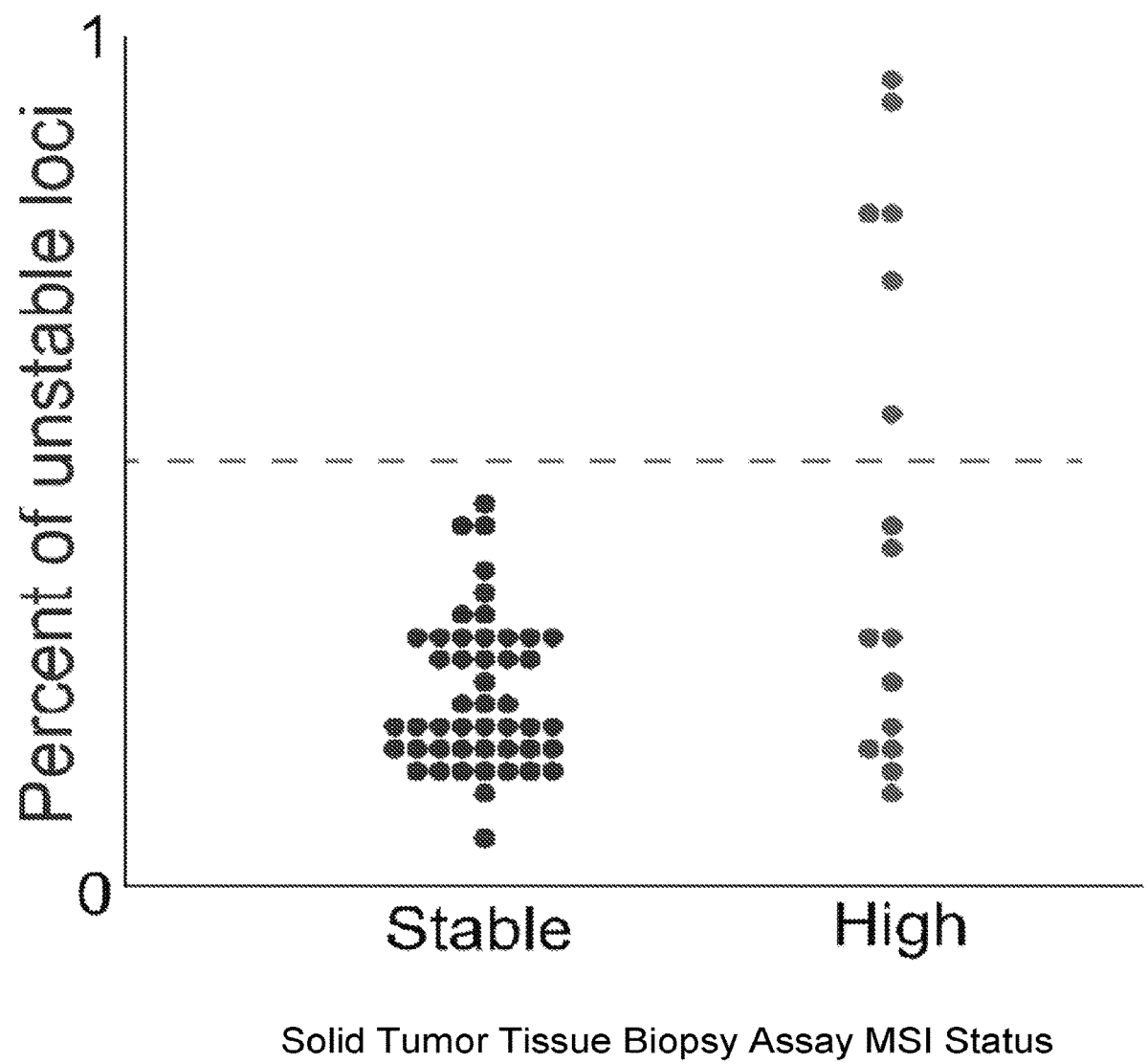

Finally, liquid biopsy validation samples were utilized to assess microsatellite instability in patients whose MSI status was previously confirmed by a specific reference clinically validated solid tumor MSI test or immunohistochemistry. Referring to FIG. 8D, the liquid biopsy assay reported MSI-H status in 37.5% (6/16) of orthogonally confirmed MSI-H patients at 100% (6/6) positive predictive value. Accordingly, comparisons between the solid tumor and liquid biopsy assays demonstrate the strengths of the liquid biopsy assay and the added value of using multiple assays to detect genomic drivers of cancer. Specifically, FIG. 8D illustrates results from liquid biopsy and solid tumor assays compared in patients who received both tests (n=55) of FIG. 8A and FIG. 8B, in which the percent circulating tumor DNA VAF, depicted above the dashed line, and number of reportable variants detected, depicted below the dashed line, for each individual patient were categorized by assay type and CHIP or germline status.

OTTER, a Novel Method for Estimating Tumor Fraction.

Figure 9A:
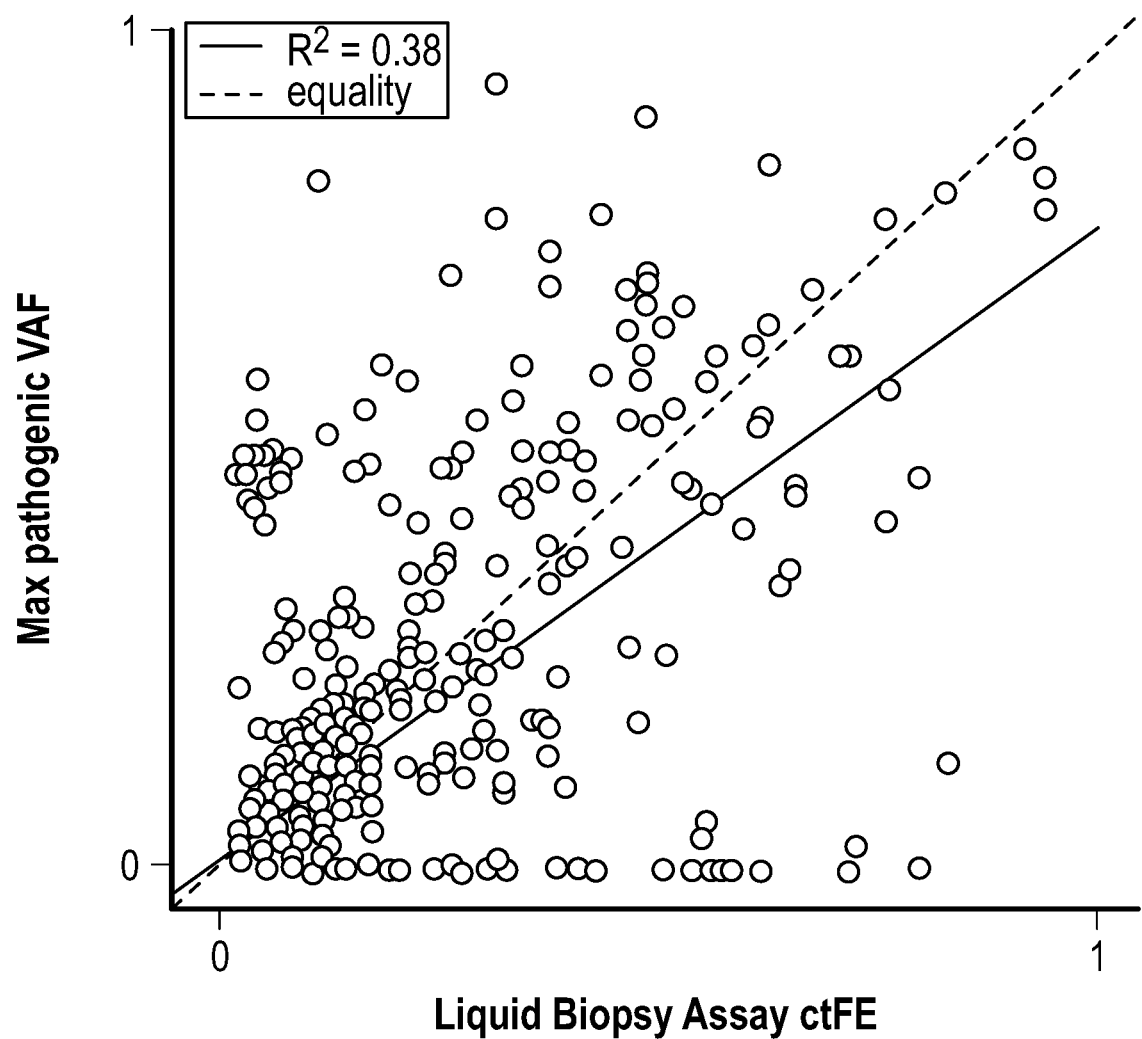
FIGS. 9A, 9B, 9C, 9D, 9E, 9F, 9G, and 9H collectively illustrate results of a comparison between circulating tumor fraction estimate (ctFE) and variant allele fraction (VAF) using an Off-Target Tumor Estimation Routine (OTTER) method, in accordance with various embodiments of the present disclosure.
Figure 9B:
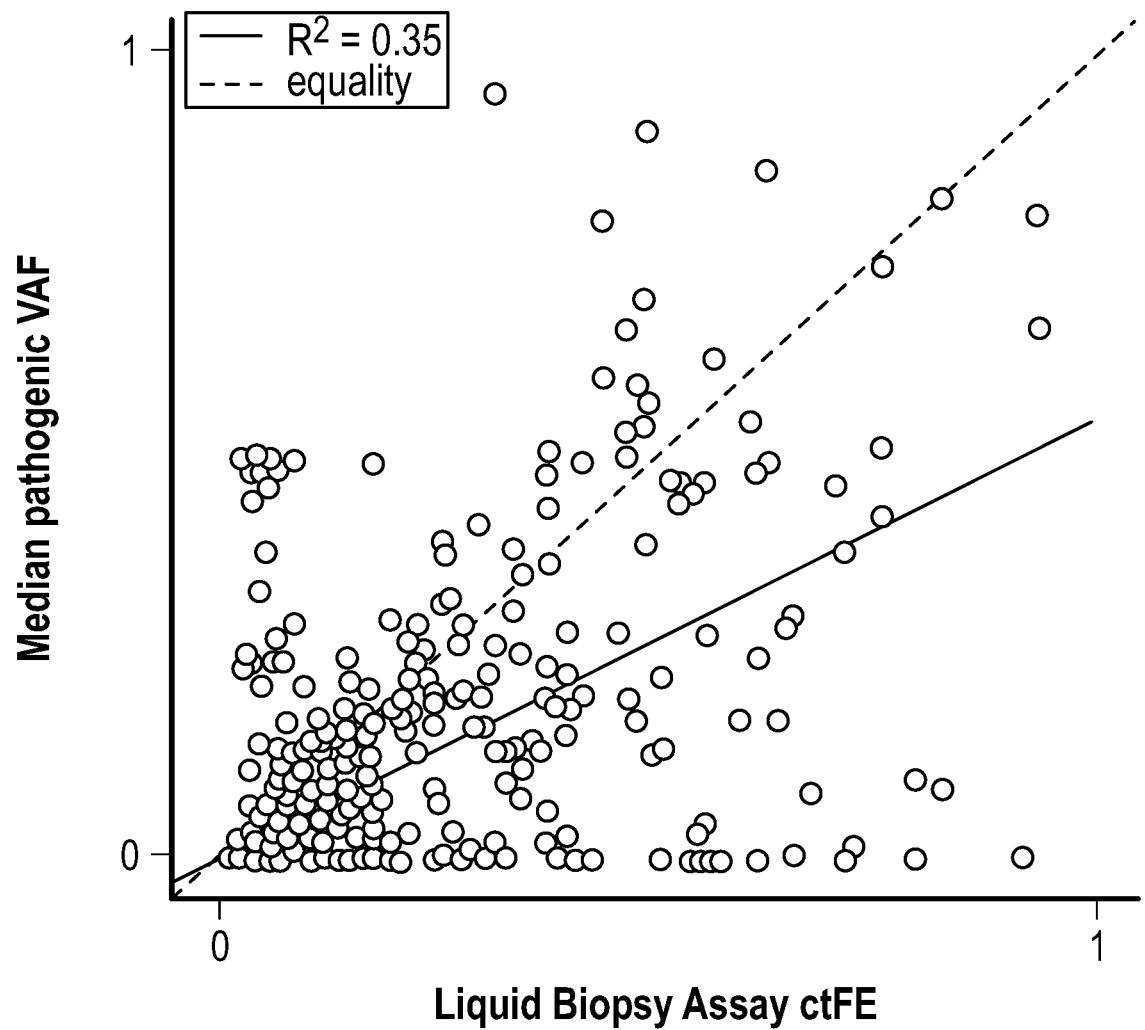
Figure 9C:
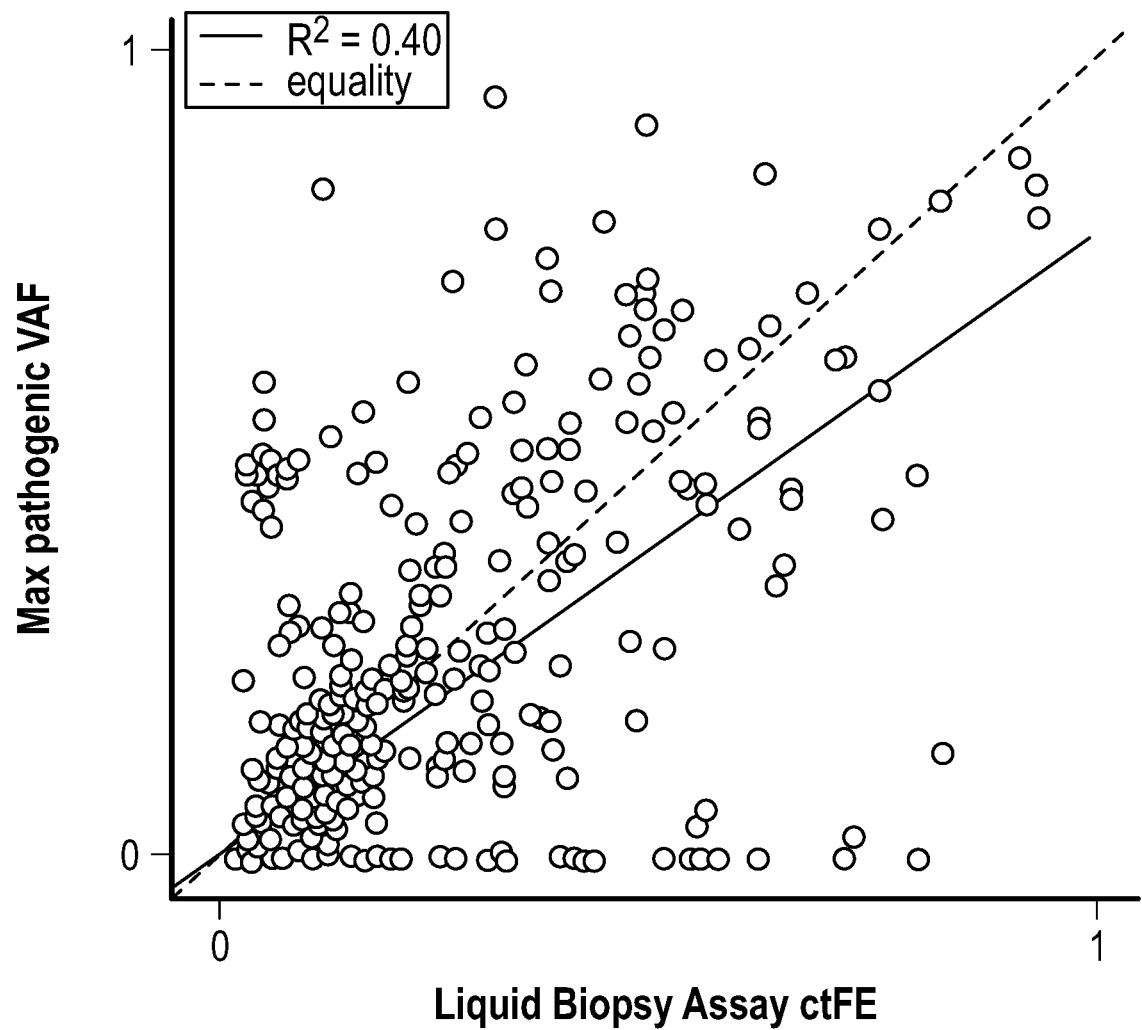
Figure 9D:
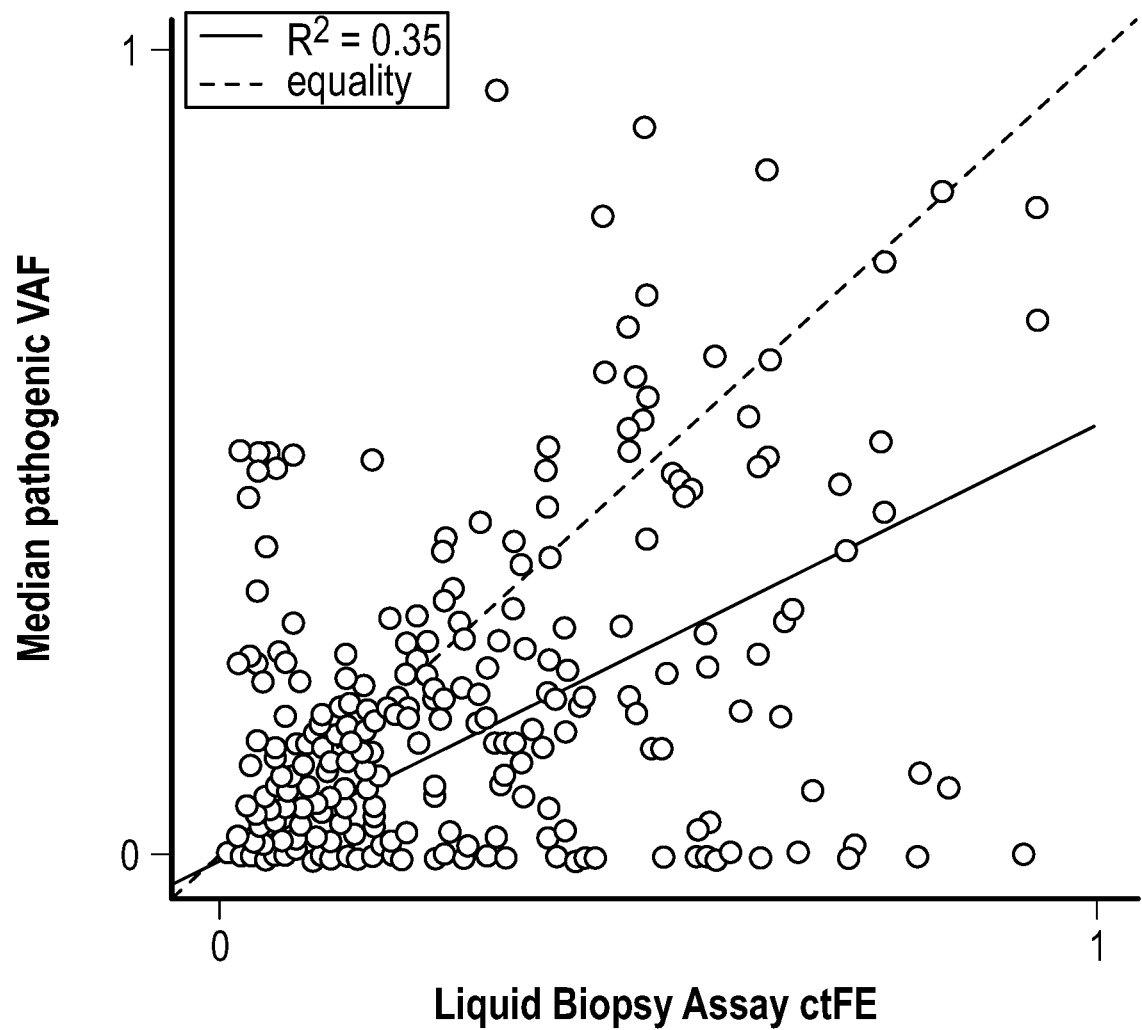
Figure 9E:
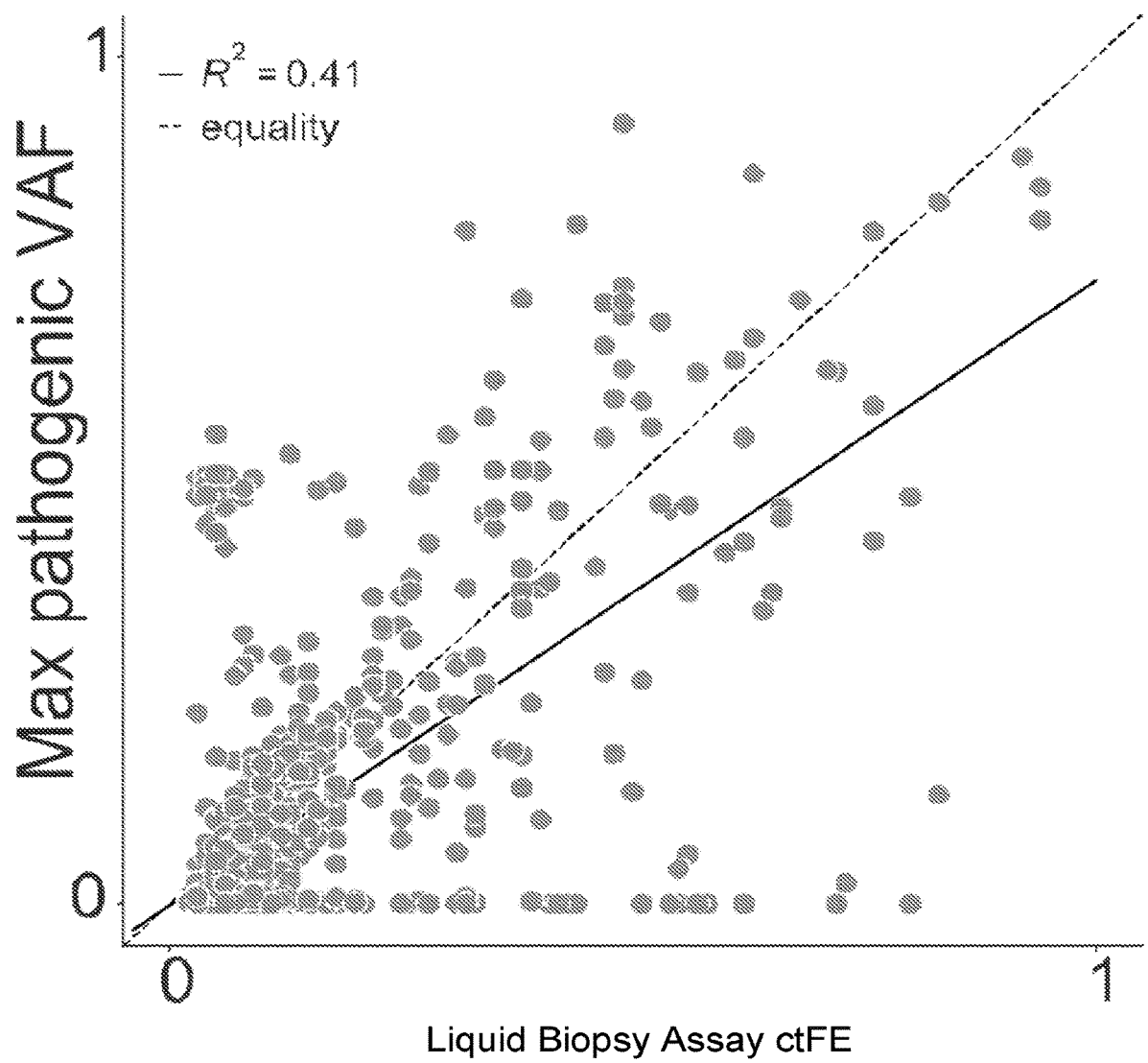
Figure 9F:
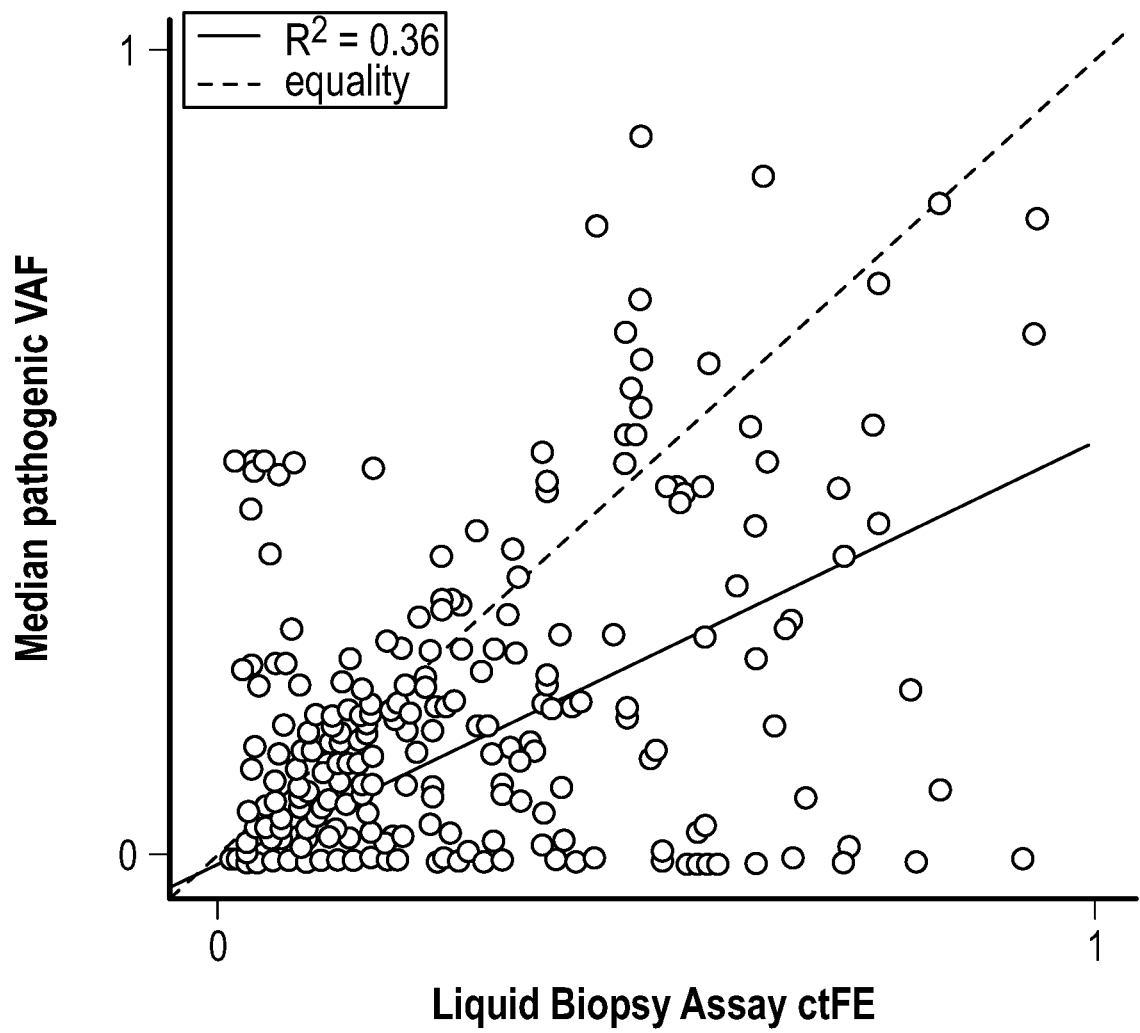
Figure 9G:
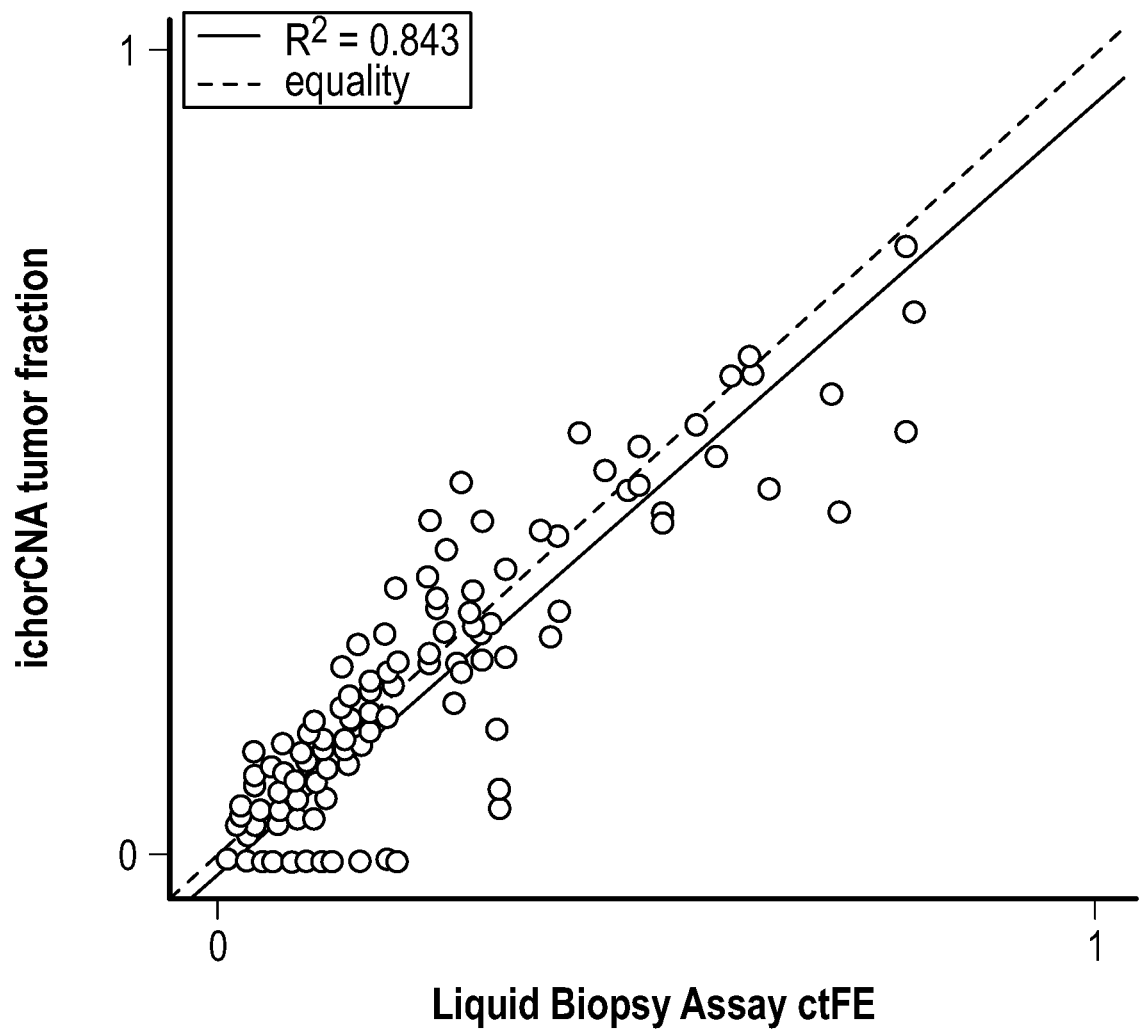
Figure 9H:
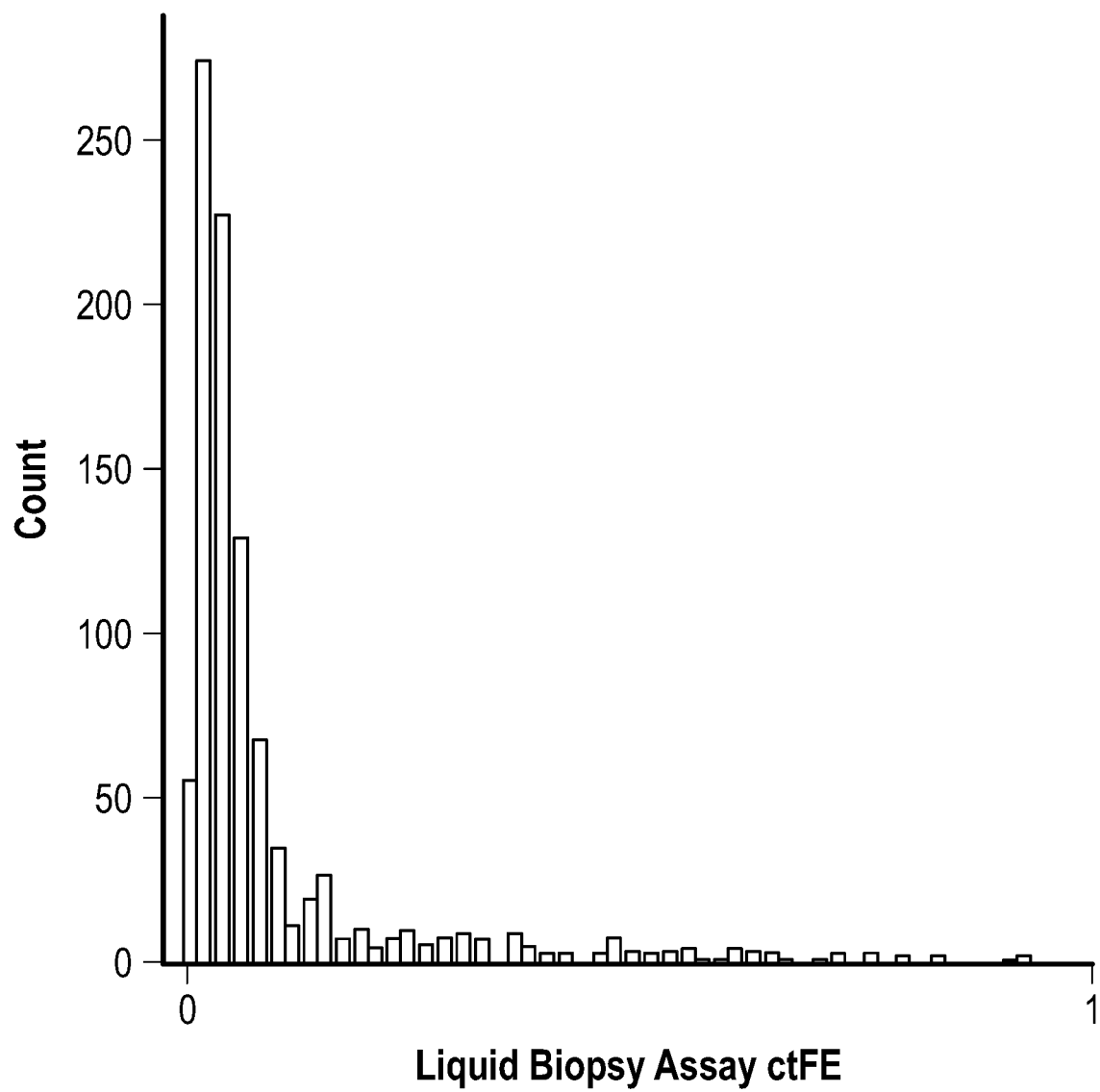

An accurate measure of tumor fraction can provide an improved understanding of variants identified through liquid biopsy testing. In the present disclosure, a novel method, Off-Target Tumor Estimation Routine (OTTER), for determining a more accurate circulating tumor fraction estimate (ctFE) was developed. Referring to FIGS. 9A and 9B, comparisons between OTTER ctFE with VAFs from 1,000 random patient samples across cancer types were determined, such that liquid biopsy ctFE correlates with max pathogenic VAF and median VAF. Referring to FIGS. 9C through 9F, removing germline variants and amplified regions from these analyses further increased the correlation. Plausible liquid biopsy ctFE estimates are expected to be greater than or equal to the maximal somatic VAF in a sample that is not on an amplified region. Referring to FIG. 9H, overall, after removing germline variants and variants on amplified regions, 90.8% of median VAFs are less than or equal to the corresponding liquid biopsy ctFEs. Referring to FIG. 9H, the distribution of liquid biopsy ctFE for the liquid biopsy 1,000 cohort is provided. Accordingly, the median ctFE was 0.07 with a mean ctFE of 0.12.

In addition to VAF, LPWGS is increasingly utilized to estimate tumor fractions and thought to be a more accurate measure than VAF. Adalsteinsson et al., 2017; Chen et al., 2019, "Next-generation sequencing in liquid biopsy: cancer screening and early detection," Hum Genomics, (13), pg. 34. Referring to FIG. 9G, comparisons between LPWGS ichorCNA-predicted circulating tumor fraction to the OTTER ctFE in matched patient samples (n=375) determined a strong correlation between methods ($R^2=0.843$, P=4.71e-152). Accordingly, this correlation indicates that OTTER ctFEs are highly concordant with estimates using LPWGS but can be determined directly from the targeted-panel sequencing without requiring additional sequencing.

Specifically, FIG. 9A illustrates results from circulating tumor fraction estimate (ctFE) and variant allele fraction (VAF) in which ctFE of liquid biopsy-sequenced patients (n=1,000) was correlated with max pathogenic VAF ($R^2=0.38$). FIG. 9B illustrates results from ctFE and VAF in which ctFE of liquid biopsy-sequenced patients (n=1,000) was correlated with medium VAF ($R^2=0.35$). FIG. 9C illustrates results from ctFE and VAF in which ctFE of liquid biopsy-sequenced patients (n=1,000) in which germline variants were removed, increasing the correlation with max pathogenic VAF ($R^2=0.40$). FIG. 9D illustrates results from ctFE and VAF in which ctFE of liquid biopsy-sequenced patients (n=1,000) in which germline variants were removed, without increasing the correlation with medium VAF ($R^2=0.35$). FIG. 9E illustrates results from ctFE and VAF in which ctFE of liquid biopsy-sequenced patients (n=1,000) in which amplified regions from these analyses were removed, increasing the correlation with max pathogenic VAF ($R^2=0.41$). FIG. 9F illustrates results from ctFE and VAF in which ctFE of liquid biopsy-sequenced patients (n=1,000) in which amplified regions from these analyses were removed, increasing the correlation with medium VAF ($R^2=0.36$). FIG. 9G illustrates results from ctFE and VAF in which ctFE of liquid biopsy-sequenced patients (n=1,000) in which samples that also underwent low-pass whole genome sequencing (LPWGS, n=375), a strong correlation between LPWGS-predicted tumor fraction and ctFE ($R^2=0.843$) is found. Furthermore, FIG. 9G illustrates results from ctFE and VAF in which ctFE of liquid biopsy-sequenced patients (n=1,000) and the overall distribution of ctFE across the cohort (median ctFE=0.07, mean ctFE=0.12, and standard deviation=0.15).

Retrospective Clinical Profiling of the Liquid Biopsy Assay Against a 1,000-Subject Cohort.

Figure 10A:
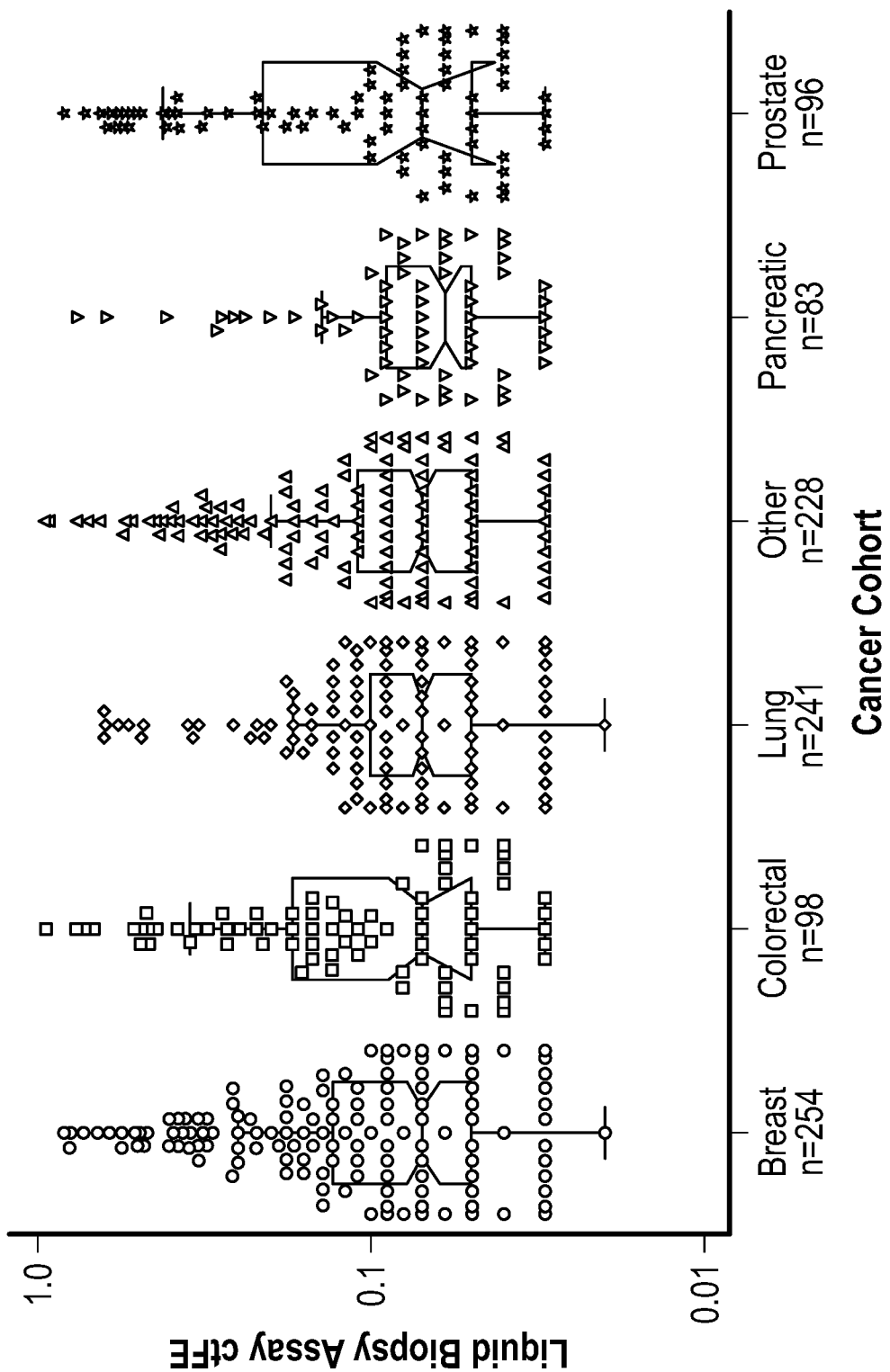
FIGS. 10A and 10B collectively illustrate results of evaluating ctFE and mutational landscape according to cancer type, in accordance with various embodiments of the present disclosure.
Figure 10B:
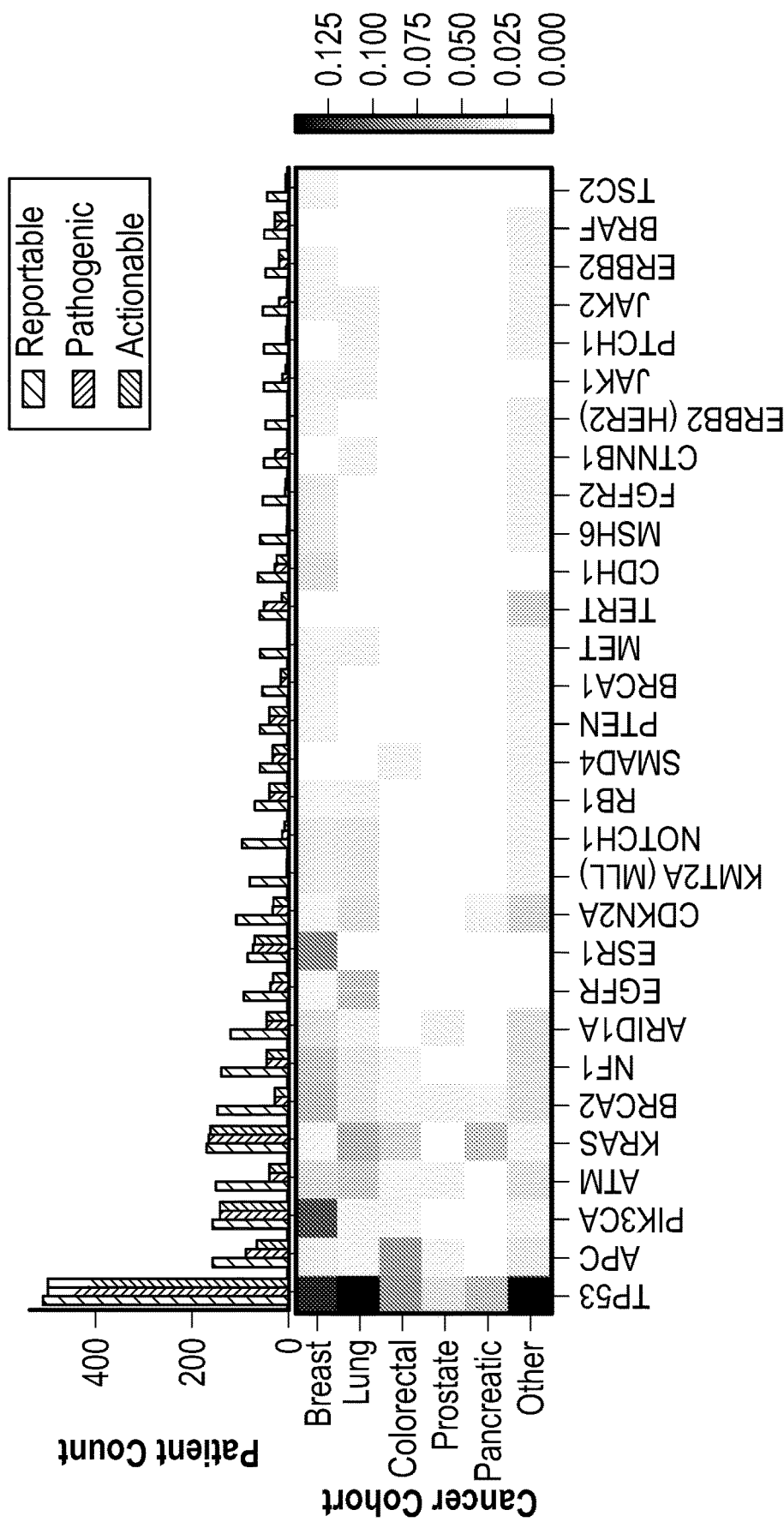

To evaluate the clinical utility of the liquid biopsy, de-identified molecular and clinical data from 1,000 samples across cancer types were selected for clinical profiling. This included 55.7% female and 44.3% male patients, with a median age of 66 years, and interquartile range of 15. Referring to FIG. 18, this cohort included patients from 24 cancer categories, with breast (n=254), colorectal (n=98), lung (n=241), pancreatic (n=83), and prostate (n=96) being the most common. Referring to FIG. 10A, the median ctFE predicted by OTTER was 0.07 for all cancer types, with the exception of prostate, which was 0.06. Referring to FIG. 10B, in this cohort, 8,099 mutations were reported, of which 2,732 were pathogenic, and 2,238 were clinically actionable. Specifically, FIG. 10A illustrates circulating tumor fraction estimate (ctFE) and mutational landscape by cancer type, in which median ctFE among the most common cancer types was 0.07, with the exception of prostate (ctFE=0.06). FIG. 10B illustrates circulating tumor fraction estimate (ctFE) and mutational landscape by cancer type, in which variants are categorized as reportable, pathogenic, or actionable. Across all patients, the most commonly mutated gene was TP53. The heatmap was normalized within rows to depict the most prevalent variants detected for each common cancer type in the cohort (breast n=254, colorectal n=98, lung n=241, pancreatic n=83, and prostate n=96).

Accordingly, the most frequently mutated gene in the liquid biopsy 1,000 cohort was TP53 (51.1% of patients). The most commonly mutated genes were TP53, PIK3CA, ESR1, BRCA2, NF1, ATM and APC in breast cancer, TP53, EGFR, ATM and KRAS in lung cancer, and TP53, APC, and KRAS in colorectal cancer. These findings are consistent with existing literature on commonly mutated genes in each cancer type and suggest the liquid biopsy test accurately detects variants of interest to the broader cancer community. van Heiden et al, 2019; Dal Maso et al., 2019; Savli et al., 2019, "TP53, EGFR and PIK3CA gene variations observed as prominent biomarkers in breast and lung cancer by plasma cell-free DNA genomic testing," J Biotechnol, (300), pg. 87; Cheng et al., 2019, "Liquid Biopsy Detects Relapse Five Months Earlier than Regular Clinical Follow-Up and Guides Targeted Treatment in Breast Cancer," Case Rep Oncol Med, pg. 6545298; Keup et al., 2019, "Targeted deep sequencing revealed variants in cell-free DNA of hormone receptor-positive metastatic breast cancer patients," Cell Mol Life Sci, print.; Li et al., 2019, "Genomic profiling of cell-free circulating tumor DNA in patients with colorectal cancer and its fidelity to the genomics of the tumor biopsy," J Gastrointest Oncol, (10), pg. 831.

Advanced Disease is Associated with Higher Estimated Tumor Fraction.

Figure 11A:
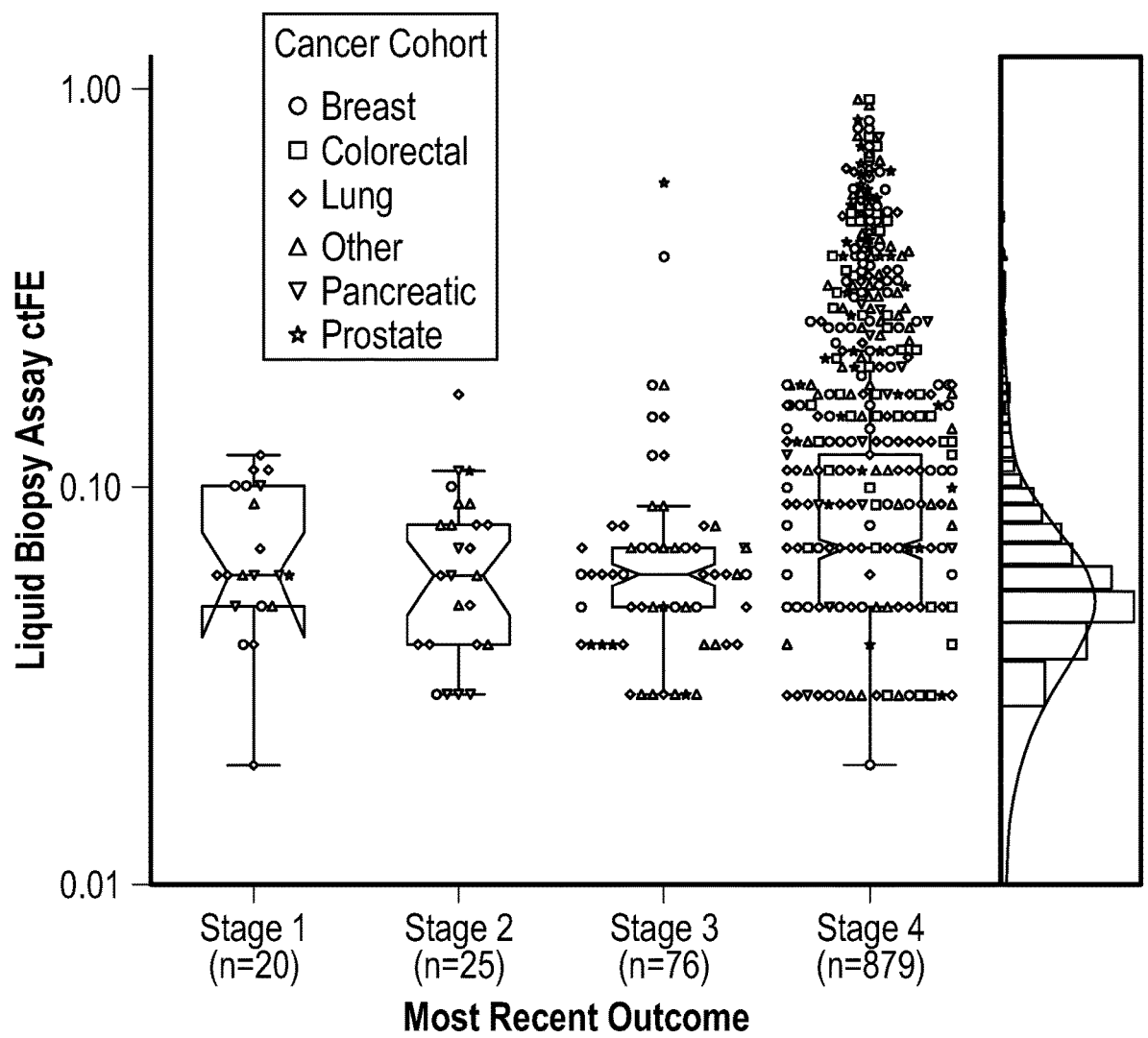
FIGS. 11A, 11B, and 11C collectively illustrate results of evaluating associations between ctFE and advanced disease states, in accordance with various embodiments of the present disclosure.
Figure 11B:
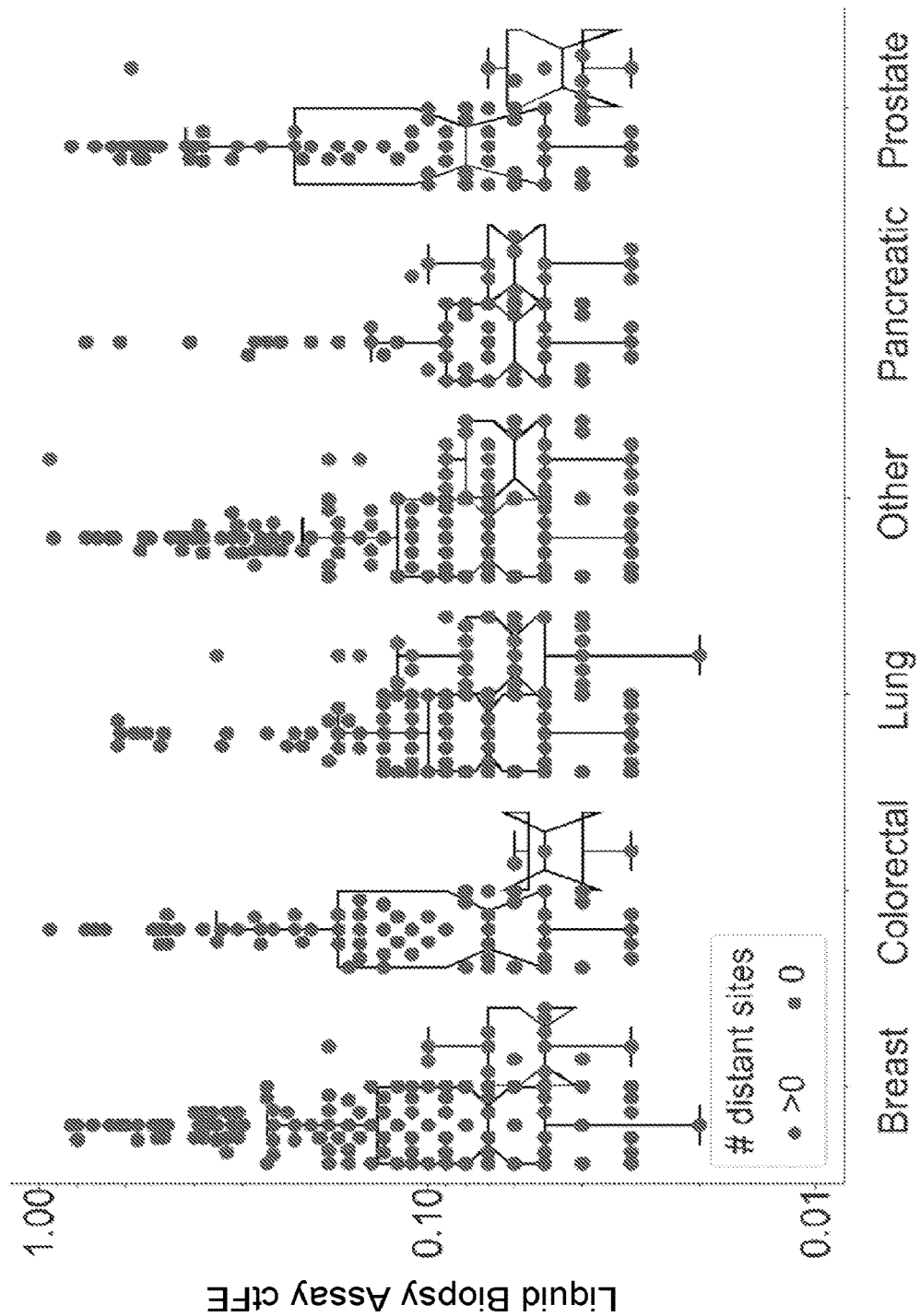
Figure 11C:
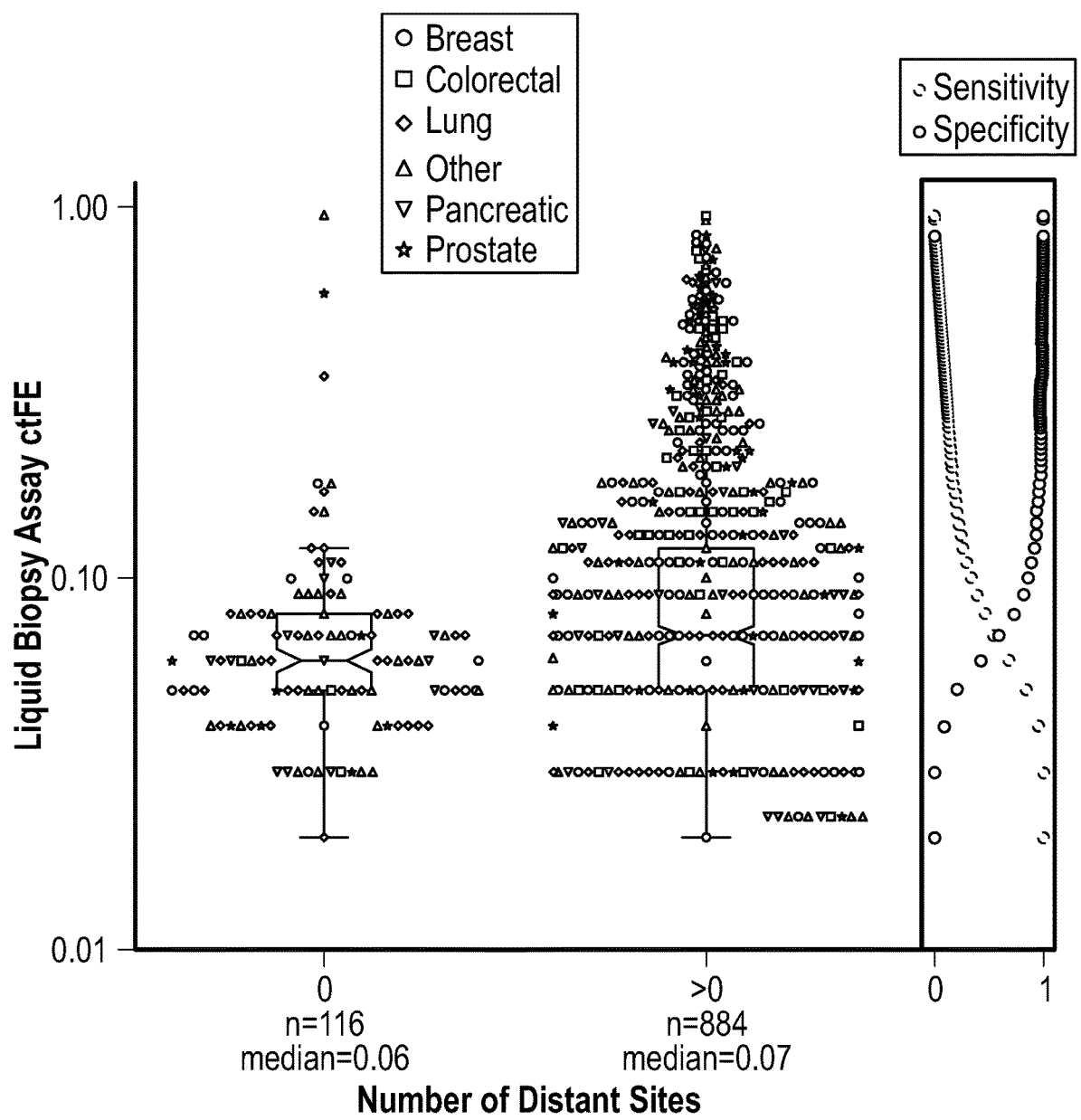

A goal of liquid biopsy assays of the present disclosure is to more efficiently monitor treatment response and predict disease progression in patients over time. To establish proof of concept, the association of ctFE with advanced disease states was investigated. Accordingly, referring to FIG. 11A, a significant difference in ctFE between stages (P=2.97e-5) was determined. However, since the majority of patients had advanced disease at the time of testing, more early stage samples are necessary to further verify these findings. Referring to FIG. 11B, ctFE in patients with metastatic disease was evaluated to determined that ctFE increases when distant sites are affected. Indeed, referring to FIG. 11C, patients with no metastatic lesions had a significantly lower ctFE than patients with one or more distant sites (P=4.77e-7), further highlighting the potential of ctFE for disease monitoring. Specifically, FIG. 11A illustrates circulating tumor fraction estimate (cfTE) according to stage and number of distant metastases among the liquid biopsy 1,000 cohort, in which there was a significant difference in ctFE between stages (Kruskal-Wallis P=2.97e-5). Accordingly, patients with stage 4 cancer (n=879, median ctFE=0.07) had a higher ctFE than those with stages 1 (n=20, median ctFE=0.06), 2 (n=25, median ctFE=0.06), or 3 (n=76, median ctFE=0.06). FIGS. 11B and 11C illustrate that ctFE increased with the number of metastatic distant sites (Mann-Whitney U test P=7.57e-7), and there was a significant difference in ctFE between patients with no metastatic lesions (n=116) and those with 1 or more distant sites affected (n=884, Mann-Whitney U test P=2.12e-5). The sensitivity and specificity shown to the right-hand side of the FIG. 11C represent the probability that a binary metastasis status prediction is correct at a given ctFE threshold. Accordingly, the model predicts metastasis with greater confidence at higher ctFE.

Estimated Tumor Fraction Correlates with Response to Treatment.

Figure 12A:
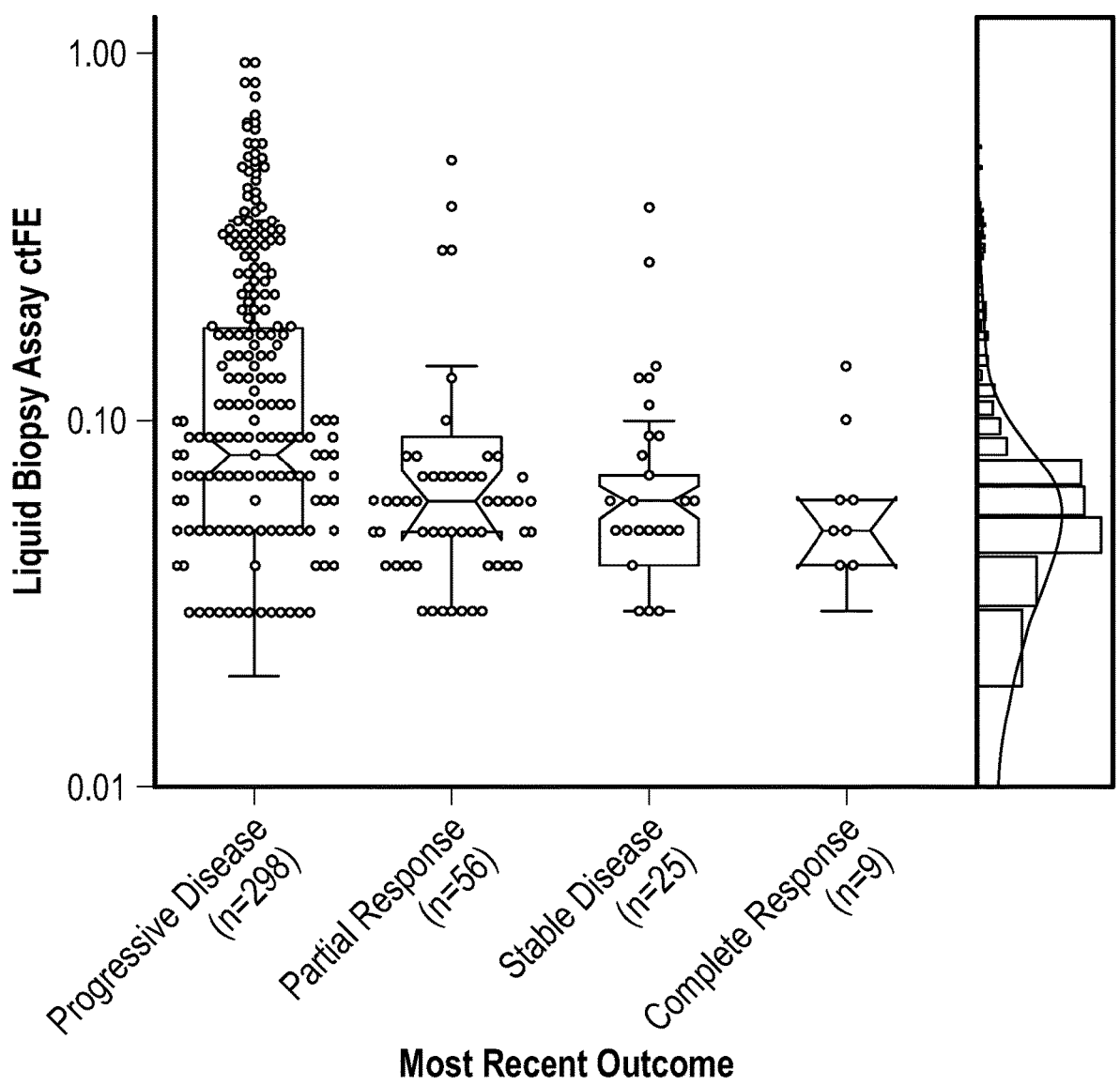
FIGS. 12A, 12B, and 12C collectively illustrate results of comparing ctFE with recent clinical response outcomes, in accordance with various embodiments of the present disclosure.
Figure 12B:
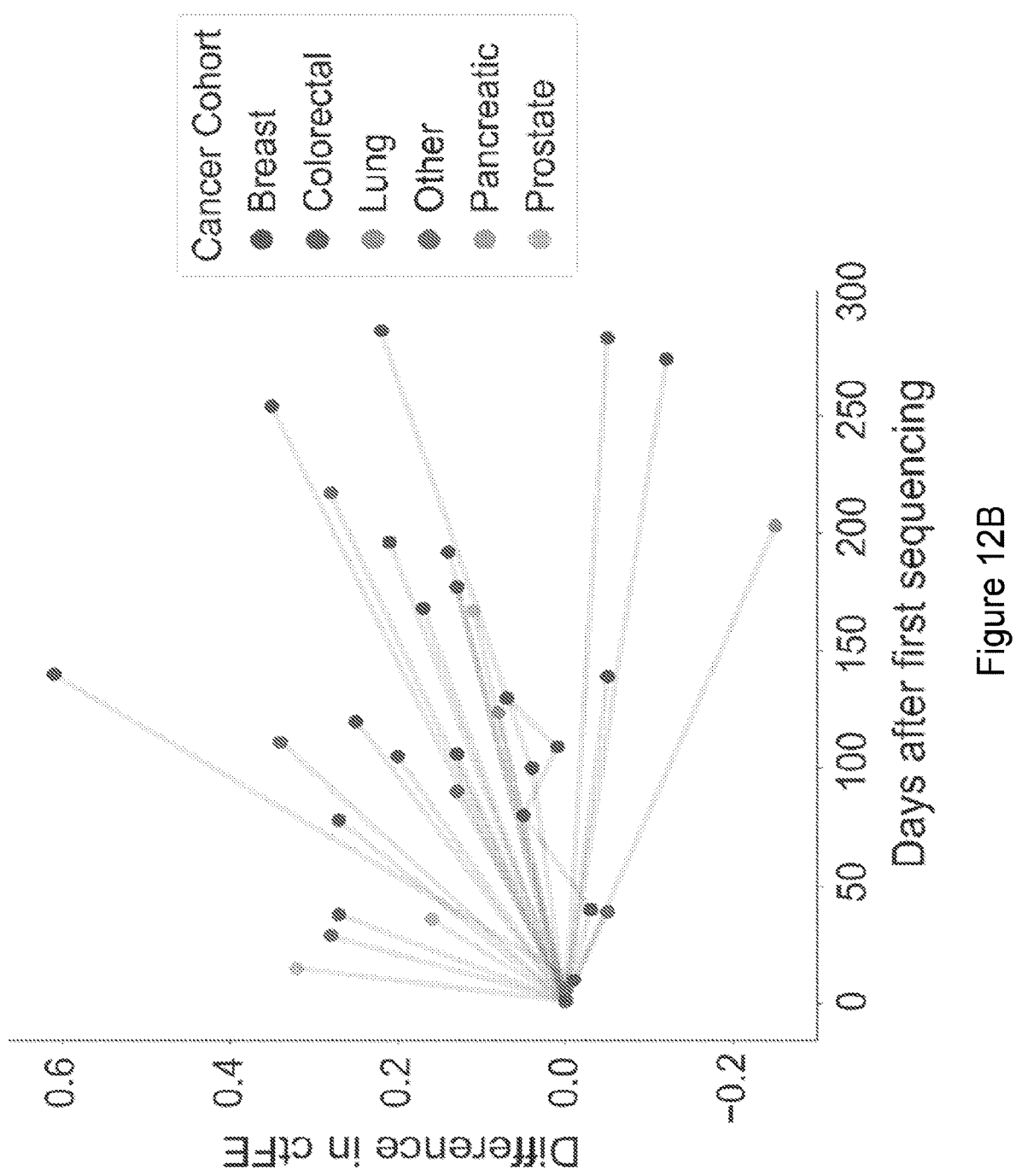
Figure 12C:
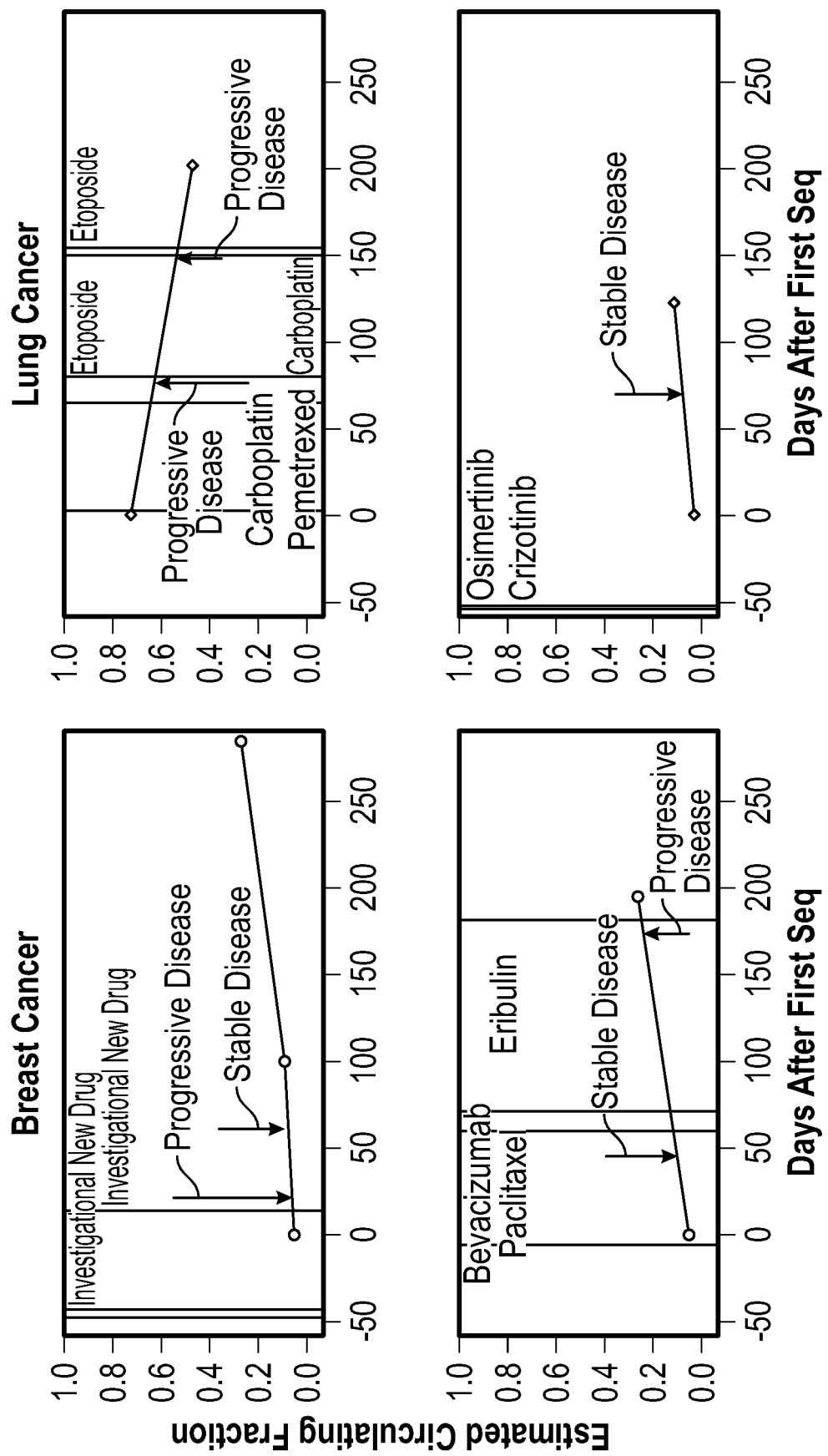

To determine how ctFE changes in response to treatment, comparisons between ctFE with the most recent clinical response outcome were determined. Accordingly, referring to FIG. 12A, patients classified as having complete response were determined to have a significantly lower median ctFE of 0.05, compared to 0.06, 0.06, and 0.08 in patients with stable disease, partial response, and progressive disease, respectively. Additionally, referring to FIG. 12B, patients with multiple liquid biopsy tests were determined to have large differences in ctFE between test dates. For example, referring to FIG. 12C, one breast cancer case had a ctFE of 0.05 at initial liquid biopsy testing. After treatment with bevacizumab and paclitaxel, clinical notes indicate the patient was classified as having stable disease. Eribulin treatment was started shortly after, but the patient was later diagnosed with progressive disease. A second liquid biopsy test, which was performed approximately 200 days after the initial liquid biopsy test, revealed a ctFE of 0.26, which supports the progressive disease diagnosis. Alternatively, in a breast cancer patient with progressive disease who was treated with investigational new drug therapies, the patient's status was updated to stable disease shortly after the first liquid biopsy test, which revealed a ctFE of 0.05. Approximately 100 days later, the patient's second liquid biopsy test revealed a ctFE of 0.09. The patient likely received no further treatment before the third liquid biopsy test, which revealed a ctFE of 0.27, suggesting this patient's disease had progressed. Specifically, FIG. 12A illustrates circulating tumor fraction estimate (cfTE) and abstracted clinical outcomes in a sub-cohort of the liquid biopsy 1000 (n=388) in which patients with complete response (n=9, ctFE=0.05) exhibited lower ctFE than those with progressive disease (n=298, ctFE=0.08), partial response (n=56, ctFE=0.06), or stable disease (n=25, ctFE=0.06). FIG. 12B illustrates that ctFE was also assessed temporally among a few randomly selected patients with multiple liquid biopsy tests throughout the course of treatment (n=26), with most patients showing large differences in ctFE between test dates. FIG. 12C illustrates four exemplary cases highlighting the utility of ctFE in relation to treatment course and disease status.

In the case of a lung cancer patient who underwent multiple rounds of treatment, including carboplatin, pemetrexed, and etoposide, a decrease in ctFE between liquid biopsy tests (0.72 to 0.47) was determined. However, the ctFE was still extremely high after treatment, making progressive disease likely. Indeed, the patient was classified as having progressive disease by their oncologist shortly before the second liquid biopsy test date. Alternatively, a patient who had undergone treatment with osimertinib and crizotinib approximately 50 days before the first liquid biopsy test showed very little change in ctFE between test dates (0.3-0.11) and was classified as stable shortly before the second liquid biopsy test. Referring to FIGS. 11A through 12C, while conclusions about the larger population based on these individual cases cannot be determined, the changes in ctFE in response to treatment is consistent with the above analyses showing that higher ctFEs are associated with advanced disease. Additionally, these results illustrate how serial testing can be beneficial for precision oncology in individual patients. These results further highlight the need for longitudinal studies with serial liquid biopsy testing in a larger cohort of patients.

While liquid biopsy is a promising tool for improving outcomes in precision oncology, there are challenges that must be overcome before it can replace large panel NGS tissue genotyping. For example, in early stage disease, when treatments have much higher success rates, many patients have low ctDNA fractions that may be below the LOD for liquid biopsies, limiting clinical utility because of the risk of false negatives. Bettegowda et al., 2014, "Detection of circulating tumor DNA in early- and late-stage human malignancies," Sci Transl Med, (6), pg. 224; Xue et al., 2019, "Early detection and monitoring of cancer in liquid biopsy: advances and challenges," Expert Rev Mol Diagn, (19), pg. 273; Hennigan et al., 2019, "Low Abundance of Circulating Tumor DNA in Localized Prostate Cancer," JCO Precis Oncol, (3), print; Abbosh et al., 2018, "Early stage NSCLC—challenges to implementing ctDNA-based screening and MRD detection," Nat Rev Clin Oncol, (15), pg. 577.

Consequently, most studies to date have focused on late stage patients for assay validation and research. Furthermore, while validation studies of existing liquid biopsy assays have shown high sensitivity and specificity, few studies have corroborated results with orthogonal methods, or between NGS testing platforms. Cheng et al., 2019, "Clinical Validation of a Cell-Free DNA Gene Panel," J Mol Diagn, (21), pg. 632; Hanibuchi et al., 2019, "Development, validation, and comparison of gene analysis methods for detecting EGFR mutation from non-small cell lung cancer patients-derived circulating free DNA," Oncotarget, (10), pg. 3654; Van Laar et al., 2018, "Development and validation of a plasma-based melanoma biomarker suitable for clinical use," Br J Cancer, (118), pg. 857; Odegaard et al., 2018, "Validation of a Plasma-Based Comprehensive Cancer Genotyping Assay Utilizing Orthogonal Tissue- and Plasma-Based Methodologies," Clin Cancer Res, (24), pg. 3539; Clark et al., 2018, "Analytical Validation of a Hybrid Capture-Based Next-Generation Sequencing Clinical Assay for Genomic Profiling of Cell-Free Circulating Tumor DNA," J Mol Diagn, (20), pg. 686; Plagnol et al., 2018, "Analytical validation of a next generation sequencing liquid biopsy assay for high sensitivity broad molecular profiling," PLoS One, (13), pg. 0193802. Kuderer et al. compared commercially available liquid and tissue NGS platforms and found only 22% concordance in genetic alterations. Kuderer et al., 2017, "Comparison of 2 Commercially Available Next-Generation Sequencing Platforms in Oncology," JAMA Oncol, (3), pg. 996. Other reports of liquid biopsy based studies are limited by comparison to non-comprehensive tissue testing algorithms including Sanger sequencing, small NGS hotspot panels, PCR and FISH, which may not contain all NCCN guideline genes in their reportable range, thus suffering in comparison to a more comprehensive liquid biopsy assay. Leighl et al., 2019. Since the 105 gene liquid biopsy assay is a subset of the 648 gene solid tumor tissue-based assay, the concordance data presented herein (74.31% for actionable variants) represents a direct comparison to a comprehensive NGS test which includes the entire reportable range of the liquid biopsy assay. Beaubier et al., 2019, "Integrated genomic profiling expands clinical options for patients with cancer," Nat Biotechnol, (37), pg. 1351. While this concordance is high relative previous reports, 25.69% of actionable variants would have been missed if only one of the tests were performed. Thus, liquid biopsies provide the greatest value to patients when used in combination with standard tissue genotyping. Furthermore, having both tests enabled additional analyses to exclude germline and CH variants, significantly improving specificity.

Accordingly, the systems and methods of the present disclosure provides analytical and clinical validation of the liquid biopsy assay. The systems and methods of the present disclosure provide high accuracy compared to orthogonal methods, including tissue biopsy, Avenio liquid biopsy, ddPCR, and LPWGS. The systems and methods of the present disclosure also provide improvements upon existing methodologies for estimating circulating tumor fraction. Notably, in combination with real-world clinical data, the systems and methods of the present disclosure demonstrate the value and suitability of liquid biopsy testing for monitoring disease progression, predicting objective measures of response, and assessing treatment outcomes. As such, the results obtained through validating the systems and methods of the present disclosure strongly support utilizing the liquid biopsy assay in routine monitoring of cancer patients with advanced disease.

References Cited and Alternative Embodiments

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of validating a somatic sequence variant in a cancerous tissue of a test subject having a cancer condition, the method comprising:

at a computer system having one or more processors, and memory storing one or more programs for execution by the one or more processors:

(A) obtaining, from a first sequencing reaction, a corresponding sequence of each cell-free DNA fragment in a plurality of cell-free DNA fragments in a liquid biopsy sample of the test subject, thereby obtaining a plurality of sequence reads, wherein:
the plurality of sequence reads comprises at least 100,000 sequence reads,
the plurality of sequence reads represents at least 100 genomic loci, and
the average length of respective sequence reads in the plurality of sequence reads is at least 50 nucleotides;

(B) aligning each respective sequence read in the plurality of sequence reads to a reference construct, wherein the reference construct represents at least 1 Mb of the genome for the species of the subject, thereby identifying a candidate somatic sequence variant mapping to a respective locus in the reference construct;

(C) determining for the candidate somatic sequence variant, (i) a respective variant allele fragment count for the first sequencing reaction, and (ii) a respective locus fragment count for the first sequencing reaction; and (D) comparing the respective variant allele fragment count for the candidate somatic sequence variant against a threshold for the respective locus in the reference construct, wherein the threshold is determined by comparing (i) a pre-test odds of a positive variant call for the respective locus based upon a prevalence of a plurality of variants in a genomic region that includes the respective locus in a cohort of training subjects having the cancer condition and (ii) a desired post-test odds of a positive variant call for the respective locus, accounting for an observed variant fraction for the candidate somatic sequence variant in the liquid biopsy sample, and:

when the respective variant allele fragment count for the candidate somatic sequence variant satisfies the threshold for the respective locus, not rejecting the presence of the candidate somatic sequence variant in the test subject, or when the variant allele fragment count for the candidate somatic sequence variant does not satisfy the threshold for the respective locus, rejecting the presence of the candidate somatic sequence variant in the test subject.

2. The method of claim 1, wherein the comparing further uses a sequencing error rate of the sequencing reaction.

3. The method of claim 2, wherein the sequencing error rate for the sequencing reaction is a trinucleotide sequencing error rate.

4. The method of claim 1, wherein the threshold is also based upon comparing further uses a background sequencing error rate determined for the locus.

5. The method of claim 1, wherein the comparing applies a variant detection sensitivity to the pre-test odds and desired post-test odds, wherein the variant detection sensitivity is selected from a distribution of variant detection sensitivities, wherein the distribution of variant detection sensitivities is based on a correlation between (i) a detection rate of a reference variant allele, in one or more sequencing reactions that are process-matched with the first sequencing reaction, for a plurality of cancer samples, and (ii) a plurality of variant allele fractions for the reference variant allele in the plurality of cancer samples.

6. The method of claim 5, wherein the correlation is established by determining, for each respective bin in a plurality of bins collectively representing a span of variant allele fractions represented in the plurality of cancer samples, wherein each respective bin corresponds to a respective contiguous span of variant allele fractions that does not overlap with any other respective bin in the plurality of bins, a corresponding sensitivity for detection of the reference variant alleles for a corresponding subset of cancer samples in the plurality of cancer sample having a variant allele fraction in the corresponding contiguous span of variant allele fractions of the respective bin.

7. The method of claim 5, wherein the applying the variant detection sensitivity to the pre-test odds and desired post-test odds is used to select a quantile of a beta-binomial distribution of the minimal variant allele fragment count required to support a positive variant call for the respective locus, thereby defining the threshold for the respective locus, wherein the beta-binomial distribution is defined by a sequencing error rate for the sequencing reaction and a background sequencing error rate determined for the locus.

8. The method of claim 1, wherein the pre-test odds of the positive variant call for the respective locus is based on the prevalence of the plurality of variants in the genomic region that includes the respective locus from a set of nucleic acids obtained from the cohort of training subjects having the cancer condition.

9. The method of claim 8, wherein, when the genomic region is associated with a mutation known to confer resistance against a therapy used to treat the cancer condition, the pre-test odds are boosted based on a pre-test-odds multiplier specific for the genomic region.

10. The method of claim 8, wherein the pre-test odds of a positive variant call for the respective locus is further based on a known or inferred effect of the plurality of variants, wherein:

when the known or inferred effect of a variant in the plurality of variants is loss-of-function of a gene that includes the locus, the genomic region used to compute the pre-test odds is the entire gene, and when the known or inferred effect of a variant in the plurality of variants is gain-of-function of the gene that includes the locus, the genomic region used to compute the pre-test odds is the exon, of the gene, that includes the locus.

11. The method of claim 10, wherein the effect of the plurality of variants is inferred by:

binning each respective variant of the plurality of variants in the genomic region that includes the locus from the set of nucleic acids obtained from the cohort of training subjects having the cancer condition into a respective bin, in a plurality of bins for the gene that include the locus, corresponding to the exon encompassing the respective variant in the gene, wherein each bin in the plurality of bins corresponds to a different exon of the respective gene; and determining whether any bin in the plurality of bins contains significantly more variants than the other bins in the plurality of bins, wherein:

when a bin contains significantly more variants than the other bins in the plurality of bins, the effect of the sequence variant is inferred to be a gain-of-function of the gene, and when no bin in the plurality of bins contains significantly more sequence variants than the other bins in the plurality of bins, the effect of the sequence variant is inferred to be a loss-of-function of the gene.

12. The method of claim 11, wherein determining whether any bin in the plurality of bins contains significantly more variants than the other bins in the plurality of bins comprises applying a rolling Poisson test of difference between bin counts corresponding to adjacent exons in the gene.

13. The method of claim 1, wherein the liquid biopsy sample is blood.

14. The method of claim 1, wherein the liquid biopsy sample comprises blood, whole blood, peripheral blood, plasma, serum, or lymph of the test subject.

15. The method of claim 1, wherein:

the first sequencing reaction is a panel-enriched sequencing reaction of a first plurality of enriched loci, and each respective locus in the plurality of enriched loci are sequenced at an average unique sequence depth of at least 250×.

16. The method of claim 15, wherein each respective locus in the plurality of enriched loci are sequenced at an average unique sequence depth of at least 1000×.

17. The method of claim 15, wherein the panel-enriched sequencing reaction uses a sequencing panel that enriches for at least 50 genes.

18. The method of claim 15, wherein the panel-enriched sequencing reaction uses a sequencing panel that enriches for at least 10 genes selected from the group consting of ALK, B2M, ERRFI1, IDH2, MSH6, PIK3R1, SPOP, FGFR2, BAP1, ESR1, JAK1, MTOR, PMS2, STK11, FGFR3, BRC1, EZH2, JAK2, MYCN, PTCH1, TERT, NTRK1, BRCA2, FBXW7, JAK3, NF1, PTEN, TP53, RET, BTK, FGR1, KDR, NF2, TSC1, TSC1, ROS1, CCND1, FGR4, KEAP1, NFE2L2, RAD51C, TSC2, BRAF, CCND2, FLT3, KIT, NOTCH1, RAF1, UGT1A1, AKT1, CCND3, FOXL2, KRAS, NPM1, RB1, VHL, AKT2, CHD1, GATA3, MAP2K1, NRAS, RHEB, CCNE1, APC, CDK4, GNA11, MAP2K2, PALB2, RHOA, CD274, AR, CDK6, CNAQ, MAPK1, PBRM1, RIT1, EGFR, ARAF, CDKN2A, GNAS, MLH1, PDCD1LG2, RNF43, ERBB2, ARID1A, CTNNB1, HNF1A, MPL, PDGFRA, SDHA, MET, ATM, DDR2, HRAS, MSH2, PDGFRB, SMAD4, MYC, ATR, DPYD, IDH1, MSH13, PIK3CA, SMO, and KMT2A.

19. The method of claim 15, wherein the panel-enriched sequencing reaction uses a sequencing panel that enriches for at least 10 genes selected from the group consting of AKT1 (14q32.33), ALK (2p23.2-23.1), APC (5q22.2), AR (Xq12), ARAF(Xp11.3), ARID1A (1p36.11), ATM (11q22.3), BRAF (7q34), BRCA1 (17q21.31), BRCA2 (13q13.1), CCND1 (11q13.3), CCND2 (12p13.32), CCNE1 (19q12), CDH1 (16q22.1),CDK4 (12q14.1), CDK6 (7q21.2), CDKN2A (9p21.3), CTNNB1 (3p22.1), DDR2 (1q23.3), EGFR (7p11.2), ERBB2 (17q12), ESR1 (6q25.1-25.2), EZH2 (7q36.1), FBXW7 (4q31.3), FGFR1 (8p11.23), FGFR2 (10q26.13), FGFR3 (4p16.3), GATA3 (10p14), GNA11 (19p13.3), GNAQ (9q21.2), GNAS (20q13.32), HNF1A (12q24.31), HRAS (11p15.5), IDH1 (2q34), IDH2 (15q26.1), JAK2 (9p24.1), JAK3 (19p13.11), KIT (4q12), KRAS (12p12.1), MAP2K1 (15q22.31), MAP2K2 (19p13.3), MAPK1 (22q11.22), MAPK3 (16p11.2), MET (7q31.2), MLH1 (3p22.2), MPL (1p34.2), MTOR (1p36.22), MYC (8q24.21), NF1 (17q11.2), NFE2L2 (2q31.2), NOTCH1 (9q34.3), NPM1 (5q35.1), NRAS (1p13.2), NTRK1 (1q23.1), NTRK3 (15q25.3), PDGFRA (4q12), PIK3CA (3q26.32), PTEN (10q23.31), PTPN11 (12q24.13), RAF1 (3p25.2), RB1 (13q14.2), RET (10q11.21), RHEB (7q36.1), RHOA (3p21.31), RIT1 (1q22), ROS1 (6q22.1), SMAD4 (18q21.2), SMO (7q32.1), STK11 (19p13.3), TERT (5p15.33), TP53 (17p13.1), TSC1 (9q34.13), and VHL (3p25.3).

20. The method of claim 15, wherein the panel-enriched sequencing reaction uses a sequencing panel that enriches for at least 10 genes selected from the group consting of ABL1, ACVR1B, AKT1, AKT2, AKT3, ALK, ALOX12B, AMER1 (FAM123B), APC, AR, ARAF, ARFRP1, ARID1A, ASXL1, ATM, ATR, ATRX, AURKA, AURKB, AXIN1, AXL, BAP1, BARD1, BCL2, BCL2L1, BCL2L2, BCL6, BCOR,BCORL1, BRAF, BRCA1, BRCA2, BRD4, BRIP1, BTG1, BTG2, BTK, C11orf30 (EMSY),C17orf39 (GID4), CALR, CARD11, CASP8, CBFB, CBL, CCND1, CCND2, CCND3, CCNE1, CD22, CD274 (PD-L1), CD70, CD79A, CD79B, CDC73, CDH1, CDK12, CDK4, CDK6, CDK8, CDKN1A, CDKN1B, CDKN2A, CDKN2B, CDKN2C, CEBPA, CHEK1, CHEK2, CIC, CREBBP, CRKL, CSF1R, CSF3R, CTCF, CTNNA1, CTNNB1, CUL3, CUL4A, CXCR4, CYP17A1, DAXX, DDR1, DDR2, DIS3, DNMT3A, DOT1L, EED, EGFR, EP300, EPHA3, EPHB1, EPHB4, ERBB2, ERBB3, ERBB4, ERCC4, ERG, ERRFI1 ESR1, EZH2, FAM46C, FANCA, FANCC, FANCG, FANCL, FAS, FBXW7, FGF10, FGF12, FGF14, FGF19, FGF23, FGF3, FGF4, FGF6, FGFR1, FGFR2, FGFR3, FGFR4, FH, FLCN, FLT1, FLT3, FOXL2, FUBP1, GABRA6, GATA3, GATA4, GATA6, GNA11, GNA13, GNAQ, GNAS, GRM3, GSK3B, H3F3A, HDAC1, HGF, HNF1A, HRAS, HSD3B1, ID3, IDH1, IDH2, IGF1R, IKBKE, IKZF1, INPP4B, IRF2, IRF4, IRS2, JAK1, JAK2, JAK3, JUN, KDM5A, KDM5C, KDM6A, KDR, KEAP1, KEL, KIT, KLHL6, KMT2A, KMT2D (MLL2), KRAS, LTK, LYN, MAF, MAP2K1 (MEK1), MAP2K2 (MEK2), MAP2K4, MAP3K1, MAP3K13, MAPK1, MCL1, MDM2, MDM4, MED12, MEF2B, MEN1, MERTK, MET, MITF, MKNK1, MLH1, MPL, MRE11A, MSH2, MSH3, MSH6, MST1R, MTAP, MTOR, MUTYH, MYC, MYCL (MYCL1), MYCN, MYD88, NBN, NF1, NF2, NFE2L2, NFKBIA, NKX2-1, NOTCH1, NOTCH2, NOTCH3, NPM1, NRAS, NSD3 (WHSC1L1), NT5C2, NTRK1, NTRK2, NTRK3, P2RY8, PALB2, PARK2, PARP1, PARP2, PARP3, PAXS, PBRM1, PDCD1 (PD-1), PDCD1LG2 (PD-L2), PDGFRA, PDGFRB, PDK1, PIK3C2B, PIK3C2G, PIK3CA, PIK3CB, PIK3R1, PIM1, PMS2, POLD1, POLE, PPARG, PPP2R1A, PPP2R2A, PRDM1, PRKAR1A, PRKCI, PTCH1, PTEN, PTPN11, PTPRO, QKI, RAC1, RAD21, RAD51, RAD51B, RAD51C, RAD51D, RAD52, RAD54L, RAF1, RARA, RB1, RBM10, REL, RET, RICTOR, RNF43, ROS1, RPTOR, SDHA, SDHB, SDHC, SDHD, SETD2, SF3B1, SGK1, SMAD2, SMAD4, SMARCA4, SMARCB1, SMO, SNCAIP, SOCS1, SOX2, SOX9, SPEN, SPOP, SRC, STAG2, STAT3, STK11, SUFU, SYK, TBX3, TEK, TERC, TERT, TET2, ncRNA, Promoter, TGFBR2, TIPARP, TNFAIP3, TNFRSF14, TP53, TSC1, TSC2, TYRO3, U2AF1, VEGFA, VHL, WHSC1, WT1, XPO1, XRCC2, ZNF217, and ZNF703.

21. The method of claim 1, wherein:
the first sequencing reaction is a whole genome sequencing reaction, and
the average sequencing depth of the reaction across the genome is at least 25×.

22. The method of claim 1, wherein the first plurality of sequence reads comprises at least 250,000 sequence reads.

23. The method of claim 1, wherein the cancer condition is a particular type and stage of cancer.

24. The method of claim 1, wherein the cohort of subjects having the cancer condition are matched to at least one personal characteristic of the subject.

25. The method of claim 1, further comprising validating the candidate variant when the variant allele fragment count for the candidate variant satisfies the threshold for the locus and all other variant filtering criteria are satisfied.

26. The method of claim 1, further comprising generating a report for the test subject comprising the identity of variant alleles having variant allele counts, in the first sequencing reaction, that each satisfy a threshold for the corresponding locus in the reference construct to which they map.

27. The method of claim 26, wherein the generated report further comprises therapeutic recommendations for the test subject based on the identity of one or more of the reported variant alleles.

28. A computer system comprising:
one or more processors;
a memory; and
one or more programs, wherein the one or more programs are stored in the memory and are configured to be executed by the one or more processors, wherein the one or more programs are for validating a somatic sequence variant in a cancerous tissue of a test subject having a cancer condition and comprise instructions for:
(A) obtaining, from a sequencing reaction, a corresponding sequence of each cell-free DNA fragment in a plurality of cell-free DNA fragments in a liquid biopsy sample of the test subject, thereby obtaining a plurality of sequence reads, wherein:
the plurality of sequence reads comprises at least 100,000 sequence reads,
the plurality of sequence reads represents at least 100 genomic loci, and
the average length of respective sequence reads in the plurality of sequence reads is at least 50 nucleotides;
(B) aligning each respective sequence read in the plurality of sequence reads to a reference construct, wherein the reference construct represents at least 1 Mb of the genome for the species of the subject, thereby identifying a candidate somatic sequence variant mapping to a respective locus in the reference construct;

(C) determining for the candidate somatic sequence variant, (i) a respective variant allele fragment count for the sequencing reaction, and (ii) a respective locus fragment count for the sequencing reaction; and (D) comparing the respective variant allele fragment count for the candidate somatic sequence variant against a threshold for the respective locus in the reference construct, wherein the threshold is determined by comparing (i) a pre-test odds of a positive variant call for the respective locus based upon a prevalence of a plurality of variants in a genomic region that includes the respective locus in a cohort of training subjects having the cancer condition and (ii) a desired post-test odds of a positive variant call for the respective locus, accounting for an observed variant fraction for the candidate somatic sequence variant in the liquid biopsy sample, and;

when the respective variant allele fragment count for the candidate somatic sequence variant satisfies the threshold for the respective locus, not rejecting the presence of the candidate somatic sequence variant in the test subject, or when the variant allele fragment count for the candidate somatic sequence variant does not satisfy the threshold for the respective locus, rejecting the presence of the candidate somatic sequence variant in the test subject.

29. A computer readable storage medium storing one or more programs, the one or more programs comprising instructions that, when executed by an electronic device with one or more processors and a memory, cause the electronic device to perform a method for validating a somatic sequence variant in a cancerous tissue of a test subject having a cancer condition, the method comprising:

(A) obtaining, from a sequencing reaction, a corresponding sequence of each cell-free DNA fragment in a plurality of cell-free DNA fragments in a liquid biopsy sample of the test subject, thereby obtaining a plurality of sequence reads, wherein:

the plurality of sequence reads comprises at least 100,000 sequence reads, the plurality of sequence reads represents at least 100 genomic loci, and the average length of respective sequence reads in the plurality of sequence reads is at least 50 nucleotides;

(B) aligning each respective sequence read in the plurality of sequence reads to a reference construct, wherein the reference construct represents at least 1 Mb of the genome for the species of the subject, thereby identifying a candidate somatic sequence variant mapping to a respective locus in the reference construct;

(C) determining for the candidate somatic sequence variant, (i) a respective variant allele fragment count for the sequencing reaction, and (ii) a respective locus fragment count for the sequencing reaction; and (D) comparing the respective variant allele fragment count for the candidate somatic sequence variant against a threshold for the respective locus in the reference construct, wherein the threshold is determined by comparing (i) a pre-test odds of a positive variant call for the respective locus based upon a prevalence of a plurality of variants in a genomic region that includes the respective locus in a cohort of training subjects having the cancer condition and (ii) a desired post-test odds of a positive variant call for the respective locus, accounting for an observed variant fraction for the candidate somatic sequence variant in the liquid biopsy sample, and;

when the respective variant allele fragment count for the candidate somatic sequence variant satisfies the threshold for the respective locus, not rejecting the presence of the candidate somatic sequence variant in the test subject, or when the variant allele fragment count for the candidate somatic sequence variant does not satisfy the threshold for the respective locus, rejecting the presence of the candidate somatic sequence variant in the test subject.

\* \* \* \* \*